United States Patent
Onder et al.

(10) Patent No.: US 9,670,463 B2
(45) Date of Patent: Jun. 6, 2017

(54) INHIBITION AND ENHANCEMENT OF REPROGRAMMING BY CHROMATIN MODIFYING ENZYMES

(71) Applicant: Children's Medical Center Corporation, Boston, MA (US)

(72) Inventors: Tamer T. Onder, Cambridge, MA (US); George Q. Daley, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/351,717

(22) PCT Filed: Oct. 14, 2012

(86) PCT No.: PCT/US2012/000514
§ 371 (c)(1),
(2) Date: Apr. 14, 2014

(87) PCT Pub. No.: WO2013/055397
PCT Pub. Date: Apr. 18, 2013

(65) Prior Publication Data
US 2014/0242046 A1    Aug. 28, 2014

Related U.S. Application Data

(60) Provisional application No. 61/547,404, filed on Oct. 14, 2011.

(51) Int. Cl.
*C12N 5/074* (2010.01)
(52) U.S. Cl.
CPC ...... *C12N 5/0696* (2013.01); *C12N 2501/065* (2013.01)
(58) Field of Classification Search
CPC ... C12N 5/0696; C12N 2501/065; C12N 5/00

USPC ................................................. 435/366, 377
See application file for complete search history.

(56) References Cited

U.S. PATENT DOCUMENTS

| 2011/0136145 A1 | 6/2011 | Song et al. |
| 2012/0207744 A1* | 8/2012 | Mendlein et al. ......... 424/130.1 |

FOREIGN PATENT DOCUMENTS

| EP | 1 437 404 A1 | 7/2004 |
| WO | WO 2009/102983 A2 | 8/2009 |
| WO | WO 2009143421 A2 * | 11/2009 |
| WO | WO 2010/033920 A2 | 3/2010 |
| WO | WO 2012075500 A2 * | 6/2012 |
| WO | WO 2012082436 A2 * | 6/2012 |

OTHER PUBLICATIONS

Invitation to Pay Additional Fees for PCT/US12/00514 mailed Jan. 16, 2013.
International Search Report and Written Opinion for PCT/US12/00514 mailed Mar. 22, 2013.
International Preliminary Report on Patentability for PCT/US12/00514 mailed Apr. 24, 2014.
Daigle et al., Selective killing of mixed lineage leukemia cells by a potent small-molecule DOT1L inhibitor. Cancer Cell. Jul. 12, 2011;20(1):53-65. doi: 10.1016/j.ccr.2011.06.009.
Onder et al., Chromatin-modifying enzymes as modulators of reprogramming. Nature. Mar. 4, 2012;483(7391):598-602. doi: 10.1038/nature10953.
Extended European Search Report for EP 12840683.2 mailed Jun. 1, 2015.

* cited by examiner

*Primary Examiner* — Janet Epps-Smith
(74) *Attorney, Agent, or Firm* — Wolf, Greenfield & Sacks, P.C.

(57) ABSTRACT

Methods and compositions are provided for the production of stem cells and induced pluripotent stem cells, and for uses thereof.

10 Claims, 19 Drawing Sheets

A

B

SEQUENCE LISTING

<160> NUMBER OF SEQ ID NOS: 127

<210> SEQ ID NO 1
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 1
gatggctgct cgagaaggta tattgctgtt gacagtgagc g      41

<210> SEQ ID NO 2
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 2
gtctagagga attccgaggc agtaggc      27

<210> SEQ ID NO 3
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 3
tgctgttgac agtgagcgag cgattgctcc aggaatttaa tagtgaagcc acagatgtat      60
taaattcctg gagcaatcgc ctgcctactg cctcgga      97

<210> SEQ ID NO 4
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 4
tgctgttgac agtgagcgcc gtgcccattc cctgtgtcaa tagtgaagcc acagatgtat      60
tgacacaggg aatgggcacg ttgcctactg cctcgga      97

<210> SEQ ID NO 5
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 5
tgctgttgac agtgagcgag gtgatgactt cagtctctac tagtgaagcc acagatgtag      60
tagagactga agtcatcacc ctgcctactg cctcgga      97

<210> SEQ ID NO 6
<211> LENGTH: 97
<212> TYPE: DNA
<213> ORGANISM: Artificial Sequence

```
<220> FEATURE:
<223> OTHER INFORMATION: Synthetic Oligonucleotide

<400> SEQUENCE: 6
tgctgttgac agtgagcgcg gatggagagg tgtactgcat tagtgaagcc acagatgtaa      60
tgcagtacac ctctccatcc ttgcctactg cctcgga                               97

<210> SEQ ID NO 7
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 7
tgctgttgac agtgagcgac gatgccagca gtcatgcaaa tagtgaagcc acagatgtat      60
ttgcatgact gctggcatcg ctgcctactg cctcgga                               97

<210> SEQ ID NO 8
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 8
tgctgttgac agtgagcgag cagcaacgga tacatcttaa tagtgaagcc acagatgtat      60
taagatgtat ccgttgctgc ctgcctactg cctcgga                               97

<210> SEQ ID NO 9
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 9
tgctgttgac agtgagcgac gatgccagca gtcatgcaaa tagtgaagcc acagatgtat      60
ttgcatgact gctggcatcg ctgcctactg cctcgga                               97

<210> SEQ ID NO 10
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 10
tgctgttgac agtgagcgag ggattcagat gtcaccttaa tagtgaagcc acagatgtat      60
taaggtgaca tctgaatccc gtgcctactg cctcgga                               97

<210> SEQ ID NO 11
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 11
tgctgttgac agtgagcgcc gagtgttata tttgtgaata tagtgaagcc acagatgtat      60
attcacaaat ataacactcg ttgcctactg cctcgga                               97
```

<210> SEQ ID NO 12
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 12
tgctgttgac agtgagcgcg cacctctgaa cttcagaata tagtgaagcc acagatgtat    60
attctgaagt tcagaggtgc atgcctactg cctcgga                            97

<210> SEQ ID NO 13
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 13
tgctgttgac agtgagcgag gacgggagct ccactgtgaa tagtgaagcc acagatgtat    60
tcacagtgga gctcccgtcc gtgcctactg cctcgga                            97

<210> SEQ ID NO 14
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 14
tgctgttgac agtgagcgcg gagctcacct ttgattacaa tagtgaagcc acagatgtat    60
tgtaatcaaa ggtgagctcc ttgcctactg cctcgga                            97

<210> SEQ ID NO 15
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 15
tgctgttgac agtgagcgac ctcggtatct ctaagaggaa tagtgaagcc acagatgtat    60
tcctcttaga gataccgagg gtgcctactg cctcgga                            97

<210> SEQ ID NO 16
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 16
tgctgttgac agtgagcgac gggccttcgt gtacatcaat tagtgaagcc acagatgtaa    60
ttgatgtaca cgaaggcccg ctgcctactg cctcgga                            97

<210> SEQ ID NO 17
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 17

```
tgctgttgac agtgagcgcg cccgttactg cttcagcaat tagtgaagcc acagatgtaa      60
ttgctgaagc agtaacgggc gtgcctactg cctcgga                              97

<210> SEQ ID NO 18
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 18
tgctgttgac agtgagcgcg cttagtatat gtgtacttaa tagtgaagcc acagatgtat      60
taagtacaca tatactaagc ttgcctactg cctcgga                              97

<210> SEQ ID NO 19
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 19
tgctgttgac agtgagcgac caaatcttca ggtgttcaat tagtgaagcc acagatgtaa      60
ttgaacacct gaagatttgg gtgcctactg cctcgga                              97

<210> SEQ ID NO 20
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 20
tgctgttgac agtgagcgcc ctgatagtca gcatgcgaat tagtgaagcc acagatgtaa      60
ttcgcatgct gactatcagg ttgcctactg cctcgga                              97

<210> SEQ ID NO 21
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 21
tgctgttgac agtgagcgcg ggctttcatg ttatctataa tagtgaagcc acagatgtat      60
tatagataac atgaaagccc atgcctactg cctcgga                              97

<210> SEQ ID NO 22
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 22
tgctgttgac agtgagcgac ctgaagagtc caatgatgat tagtgaagcc acagatgtaa      60
tcatcattgg actcttcagg gtgcctactg cctcgga                              97

<210> SEQ ID NO 23
<211> LENGTH: 97
<212> TYPE: DNA
```

```
<213> ORGANISM: Artificial Sequence
<220> FEATURE:
<223> OTHER INFORMATION: Synthetic Oligonucleotide

<400> SEQUENCE: 23
tgctgttgac agtgagcgca ggattctggc caaacagaaa tagtgaagcc acagatgtat    60
ttctgtttgg ccagaatcct tgcctactg cctcgga                              97

<210> SEQ ID NO 24
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 24
tgctgttgac agtgagcgac ggagggccaa gcactataaa tagtgaagcc acagatgtat    60
ttatagtgct tggccctccg gtgcctactg cctcgga                             97

<210> SEQ ID NO 25
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 25
tgctgttgac agtgagcgaa ccggttaaga gattcttatt tagtgaagcc acagatgtaa    60
ataagaatct cttaaccggt ctgcctactg cctcgga                             97

<210> SEQ ID NO 26
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 26
tgctgttgac agtgagcgcg gcattatgct tgttgtacaa tagtgaagcc acagatgtat    60
tgtacaacaa gcataatgcc atgcctactg cctcgga                             97

<210> SEQ ID NO 27
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 27
tgctgttgac agtgagcgac cattgtaagt gttgtttcta tagtgaagcc acagatgtat    60
agaaacaaca cttacaatgg gtgcctactg cctcgga                             97

<210> SEQ ID NO 28
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 28
tgctgttgac agtgagcgag gaaagaatat gcatagaata tagtgaagcc acagatgtat    60
attctatgca tattctttcc gtgcctactg cctcgga                             97
```

-continued

<210> SEQ ID NO 29
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 29
tgctgttgac agtgagcgcc ggaactcaac cattaagcaa tagtgaagcc acagatgtat    60
tgcttaatgg ttgagttccg ttgcctactg cctcgga                             97

<210> SEQ ID NO 30
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 30
tgctgttgac agtgagcgcg ggactgcaat tattcagtat tagtgaagcc acagatgtaa    60
tactgaataa ttgcagtccc ttgcctactg cctcgga                             97

<210> SEQ ID NO 31
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 31
tgctgttgac agtgagcgac cagtggccag ttcactgtat tagtgaagcc acagatgtaa    60
tacagtgaac tggccactgg ctgcctactg cctcgga                             97

<210> SEQ ID NO 32
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 32
tgctgttgac agtgagcgag cagttacatg catacttcaa tagtgaagcc acagatgtat    60
tgaagtatgc atgtaactgc ctgcctactg cctcgga                             97

<210> SEQ ID NO 33
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 33
tgctgttgac agtgagcgcg ctctgtaatc tcgtttcaaa tagtgaagcc acagatgtat    60
ttgaaacgag attacagagc atgcctactg cctcgga                             97

<210> SEQ ID NO 34
<211> LENGTH: 97
<212> TYPE: DNA
<213> ORGANISM: Artificial Sequence
<220> FEATURE:
<223> OTHER INFORMATION: Synthetic Oligonucleotide

```
<400> SEQUENCE: 34
tgctgttgac agtgagcgcc ctcctgatta ttcagaatat tagtgaagcc acagatgtaa    60
tattctgaat aatcaggagg ttgcctactg cctcgga                             97

<210> SEQ ID NO 35
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 35
tgctgttgac agtgagcgac gaagagctct tctttgatta tagtgaagcc acagatgtat    60
aatcaaagaa gagctcttcg ctgcctactg cctcgga                             97

<210> SEQ ID NO 36
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 36
tgctgttgac agtgagcgcg ccagtaacaa gaaagagaaa tagtgaagcc acagatgtat    60
ttctctttct tgttactggc atgcctactg cctcgga                             97

<210> SEQ ID NO 37
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 37
tgctgttgac agtgagcgac ctgcatcatg actcagaatt tagtgaagcc acagatgtaa    60
attctgagtc atgatgcagg gtgcctactg cctcgga                             97

<210> SEQ ID NO 38
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 38
tgctgttgac agtgagcgcc aacattatgg gcatcgagaa tagtgaagcc acagatgtat    60
tctcgatgcc cataatgttg ttgcctactg cctcgga                             97

<210> SEQ ID NO 39
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 39
tgctgttgac agtgagcgac gagctacaaa gcatgggaaa tagtgaagcc acagatgtat    60
ttcccatgct ttgtagctcg gtgcctactg cctcgga                             97

<210> SEQ ID NO 40
<211> LENGTH: 97
```

```
<212> TYPE: DNA
<213> ORGANISM: Artificial Sequence
<220> FEATURE:
<223> OTHER INFORMATION: Synthetic Oligonucleotide

<400> SEQUENCE: 40
tgctgttgac agtgagcgac gtccgcagga acttaactta tagtgaagcc acagatgtat      60
aagttaagtt cctgcggacg ctgcctactg cctcgga                              97

<210> SEQ ID NO 41
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 41
tgctgttgac agtgagcgcc ctgaggataa ctcaatataa tagtgaagcc acagatgtat      60
tatattgagt tatcctcagg ttgcctactg cctcgga                              97

<210> SEQ ID NO 42
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 42
tgctgttgac agtgagcgcc cgggaacaga gaatgtttaa tagtgaagcc acagatgtat      60
taaacattct ctgttcccgg ttgcctactg cctcgga                              97

<210> SEQ ID NO 43
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 43
tgctgttgac agtgagcgcg gtctcaggcg ccagtggaaa tagtgaagcc acagatgtat      60
ttccactggc gcctgagacc atgcctactg cctcgga                              97

<210> SEQ ID NO 44
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 44
tgctgttgac agtgagcgcg cctagtaaat tacagaagaa tagtgaagcc acagatgtat      60
tcttctgtaa tttactaggc atgcctactg cctcgga                              97

<210> SEQ ID NO 45
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 45
tgctgttgac agtgagcgcg cttctaggca gagttgctta tagtgaagcc acagatgtat      60
```
aagcaactct gcctagaagc ttgcctactg cctcgga                                    97

<210> SEQ ID NO 46
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 46
tgctgttgac agtgagcgac gcatatattt gcagtatgaa tagtgaagcc acagatgtat          60
tcatactgca aatatatgcg ctgcctactg cctcgga                                   97

<210> SEQ ID NO 47
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 47
tgctgttgac agtgagcgac cgtcccgtgg agtcgctaaa tagtgaagcc acagatgtat          60
ttagcgactc cacgggacgg gtgcctactg cctcgga                                   97

<210> SEQ ID NO 48
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 48
tgctgttgac agtgagcgcg ccctccctgt cctttccaga tagtgaagcc acagatgtat          60
ctggaaagga cagggagggc ttgcctactg cctcgga                                   97

<210> SEQ ID NO 49
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 49
tgctgttgac agtgagcgcc gccagccttc gcttctgaaa tagtgaagcc acagatgtat          60
ttcagaagcg aaggctggcg ttgcctactg cctcgga                                   97

<210> SEQ ID NO 50
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 50
tgctgttgac agtgagcgcg agcttcatgg gattggtaaa tagtgaagcc acagatgtat          60
ttaccaatcc catgaagctc atgcctactg cctcgga                                   97

<210> SEQ ID NO 51
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 51
tgctgttgac agtgagcgaa cctttccagc catagagatt tagtgaagcc acagatgtaa      60
atctctatgg ctggaaaggt gtgcctactg cctcgga                              97

<210> SEQ ID NO 52
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 52
tgctgttgac agtgagcgcg ctttcaagct catctgttat tagtgaagcc acagatgtaa      60
taacagatga gcttgaaagc ttgcctactg cctcgga                              97

<210> SEQ ID NO 53
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 53
tgctgttgac agtgagcgaa cagttggatt ctttagagaa tagtgaagcc acagatgtat      60
tctctaaaga atccaactgt ctgcctactg cctcgga                              97

<210> SEQ ID NO 54
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 54
tgctgttgac agtgagcgac gagagagtta gctgacttta tagtgaagcc acagatgtat      60
aaagtcagct aactctctcg gtgcctactg cctcgga                              97

<210> SEQ ID NO 55
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 55
tgctgttgac agtgagcgac ctgattatat ccagtaacac tagtgaagcc acagatgtag      60
tgttactgga tataatcagg gtgcctactg cctcgga                              97

<210> SEQ ID NO 56
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 56
tgctgttgac agtgagcgcg cccaaggtca aggagattat tagtgaagcc acagatgtaa      60
taatctcctt gaccttgggc ttgcctactg cctcgga                              97

<210> SEQ ID NO 57

```
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 57
tgctgttgac agtgagcgcg gcatccactg tgaatgataa tagtgaagcc acagatgtat      60
tatcattcac agtggatgcc atgcctactg cctcgga                              97

<210> SEQ ID NO 58
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 58
tgctgttgac agtgagcgcg ctgtctctct tgatggaat tagtgaagcc acagatgtaa      60
ttccatcaaa gagagacagc atgcctactg cctcgga                              97

<210> SEQ ID NO 59
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 59
tgctgttgac agtgagcgcg cctgcaagga catggttaaa tagtgaagcc acagatgtat      60
ttaaccatgt ccttgcaggc ttgcctactg cctcgga                              97

<210> SEQ ID NO 60
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 60
tgctgttgac agtgagcgac gcacctactc caagttcaaa tagtgaagcc acagatgtat      60
ttgaacttgg agtaggtgcg ctgcctactg cctcgga                              97

<210> SEQ ID NO 61
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 61
tgctgttgac agtgagcgcc gagtctggct ttgagagtta tagtgaagcc acagatgtat      60
aactctcaaa gccagactcg ttgcctactg cctcgga                              97

<210> SEQ ID NO 62
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 62
tgctgttgac agtgagcgag ccatggaaat gctatcaatg tagtgaagcc acagatgtac      60
```

```
attgatagca tttccatggc ctgcctactg cctcgga                              97
```

<210> SEQ ID NO 63
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 63

```
tgctgttgac agtgagcgca gatggaagat gatatagata tagtgaagcc acagatgtat   60
atctatatca tcttccatct ttgcctactg cctcgga                              97
```

<210> SEQ ID NO 64
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 64

```
tgctgttgac agtgagcgcc caaatcttct cctgtcagta tagtgaagcc acagatgtat   60
actgacagga gaagatttgg atgcctactg cctcgga                              97
```

<210> SEQ ID NO 65
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 65

```
tgctgttgac agtgagcgaa gagattattt ctcaagatga tagtgaagcc acagatgtat   60
catcttgaga ataatctct ctgcctactg cctcgga                               97
```

<210> SEQ ID NO 66
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 66

```
tgctgttgac agtgagcgca gagggaaagt gtatgataaa tagtgaagcc acagatgtat   60
ttatcataca ctttccctct ttgcctactg cctcgga                              97
```

<210> SEQ ID NO 67
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 67

```
tgctgttgac agtgagcgcg gaaagaacgg aaatcttaaa tagtgaagcc acagatgtat   60
ttaagatttc cgttctttcc atgcctactg cctcgga                              97
```

<210> SEQ ID NO 68
<211> LENGTH: 97
<212> TYPE: DNA
<213> ORGANISM: Artificial Sequence
<220> FEATURE:

<223> OTHER INFORMATION: Synthetic Oligonucleotide

<400> SEQUENCE: 68
tgctgttgac agtgagcgcg cagttatgct cttaatgctt tagtgaagcc acagatgtaa    60
agcattaaga gcataactgc ttgcctactg cctcgga    97

<210> SEQ ID NO 69
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 69
tgctgttgac agtgagcgcg catgcatgac tttaatctta tagtgaagcc acagatgtat    60
aagattaaag tcatgcatgc ttgcctactg cctcgga    97

<210> SEQ ID NO 70
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 70
tgctgttgac agtgagcgaa acatgtgtaa gctgcggccc tagtgaagcc acagatgtag    60
ggccgcagct tacacatgtt ctgcctactg cctcgga    97

<210> SEQ ID NO 71
<211> LENGTH: 97
<212> TYPE: DNA
<213> ORGANISM: Artificial Sequence
<220> FEATURE:
<223> OTHER INFORMATION: Synthetic Oligonucleotide

<400> SEQUENCE: 71
tgctgttgac agtgagcgaa aggatgtggt ccgagtgtgg tagtgaagcc acagatgtac    60
cacactcgga ccacatcctt ctgcctactg cctcgga    97

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
tgaagtgtga cgtggacatc    20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
ggaggagcaa tgatcttgat    20

<210> SEQ ID NO 74
<211> LENGTH: 23
<212> TYPE: DNA
<213> ORGANISM: Artificial Sequence

```
<220> FEATURE:
<223> OTHER INFORMATION: Synthetic Oligonucleotide

<400> SEQUENCE: 74
gaatctcttg cacgaatttc tgc                                              23

<210> SEQ ID NO 75
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 75
catgagcacc gttctccaag g                                                21

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
ccgatgctgg ggacaagaat                                                  20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
cccgtcatcc accaagacac                                                  20

<210> SEQ ID NO 78
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 78
gcggaggaat atgtccgaga g                                                21

<210> SEQ ID NO 79
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 79
agaggtctgg attgctgttc t                                                21

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
atgggccaga ctgggaagaa                                                  20
```

<210> SEQ ID NO 81
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 81
tggaaaatcc aagtcactgg tc                                           22

<210> SEQ ID NO 82
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 82
agttgtccaa taaggcaagt tcc                                          23

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 83
acgagtcact ctaaatagca acg                                          23

<210> SEQ ID NO 84
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 84
catttccgca tgagtgatga tgt                                          23

<210> SEQ ID NO 85
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 85
caggccacct cctgagttc                                               19

<210> SEQ ID NO 86
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 86
ttaccccagg tgaagcaaga g                                            21

<210> SEQ ID NO 87
<211> LENGTH: 22
<212> TYPE: DNA
<213> ORGANISM: Artificial Sequence
<220> FEATURE:
<223> OTHER INFORMATION: Synthetic Oligonucleotide

```
<400> SEQUENCE: 87
ccaatacggg agaagtcagg ac                                            22

<210> SEQ ID NO 88
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 88
cccacaacga atgaatgaac agc                                           23

<210> SEQ ID NO 89
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 89
tgaagacctt tgggtagttc ca                                            22

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
ctgggagagg gaagaagtgc                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
cggaagtcga aggtgctcag                                               20

<210> SEQ ID NO 92
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 92
agcagagaca tcagaagggt c                                             21

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
cggccagatt tcctttgctt                                               20

<210> SEQ ID NO 94
```

```
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 94
gctgccggtc tacgataaac a                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 95
agcttgagat ccgggatttc t                                              21

<210> SEQ ID NO 96
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 96
atatccagac tcagagagca cc                                             22

<210> SEQ ID NO 97
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 97
cagctccctt tctaagtcct tg                                             22

<210> SEQ ID NO 98
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 98
tggatgacaa aagatgtgag tgg                                            23

<210> SEQ ID NO 99
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 99
ccatatttgg acgtgtcctg ag                                             22

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 100
```
gccctacagt aagcactatc ct                                          22

<210> SEQ ID NO 101
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 101
agtctcccta gcttcaacca c                                           21

<210> SEQ ID NO 102
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 102
ccacctgatg tgtgtgcttt g                                           21

<210> SEQ ID NO 103
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 103
ttcagtagtg gtctggtctt gt                                          22

<210> SEQ ID NO 104
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 104
tcagaactca tgtgccctat ct                                          22

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
gcaggtagga cactccttgt                                             20

<210> SEQ ID NO 106
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 106
agaagagcgg caagaagagt t                                           21

<210> SEQ ID NO 107
<211> LENGTH: 23
<212> TYPE: DNA

```
<213> ORGANISM: Artificial Sequence
<220> FEATURE:
<223> OTHER INFORMATION: Synthetic Oligonucleotide

<400> SEQUENCE: 107
caaccactgt ctcatggtca ata                                             23

<210> SEQ ID NO 108
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 108
tcaatgaagc ctgtgagtgg a                                               21

<210> SEQ ID NO 109
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 109
caatgcaact gtgttcagtg ac                                              22

<210> SEQ ID NO 110
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 110
caggccagta cgcactcac                                                  19

<210> SEQ ID NO 111
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 111
tgttctcgat gcccataatg ttg                                             23

<210> SEQ ID NO 112
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 112
ccccaccgtc acctctagt                                                  19

<210> SEQ ID NO 113
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 113
gtagcaccaa actgagcaga a                                               21
```

<210> SEQ ID NO 114
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 114
ggctaaacaa aggatagctc tgc                                           23

<210> SEQ ID NO 115
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 115
tgaaagaagc aatctgtgca tga                                           23

<210> SEQ ID NO 116
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 116
caacgccgta gacagcgag                                                19

<210> SEQ ID NO 117
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 117
ctccccgtcc ttattgtcga g                                             21

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
ccctagggga tgttccagat                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
tgaagctttt ccctcttcca                                               20

<210> SEQ ID NO 120
<211> LENGTH: 20
<212> TYPE: DNA
<213> ORGANISM: Artificial Sequence
<220> FEATURE:

```
<223> OTHER INFORMATION: Synthetic Oligonucleotide

<400> SEQUENCE: 120
agcttggtgg tggatgaaac                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
ccctcttcag caaagcagac                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
ctagaccgtg ggttttgcat                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
tgggttaagt gcccctgtag                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
acccagttca tagcggtgac                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
caattgtcat gggattgcag                                               20

<210> SEQ ID NO 126
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 126
atggaaactc tattaaagtg aacctg                                        26
```

```
<210> SEQ ID NO 127
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 127
tagacctcat actcagcatt ccagt                                              25
```

INHIBITION AND ENHANCEMENT OF REPROGRAMMING BY CHROMATIN MODIFYING ENZYMES

RELATED APPLICATIONS

This application is a national stage filing under 35 U.S.C. 371 of International Application PCT/US2012/000514, filed Oct. 14, 2012, which claims the benefit under 35 U.S.C. §119(e) of U.S. provisional application Ser. No. 61/547,404 filed Oct. 14, 2011, entitled "INHIBITION AND ENHANCEMENT OF REPROGRAMMING BY CHROMATIN MODIFYING ENZYMES", the contents of both of which are incorporated by reference in their entirety. International Application PCT/US2012/000514 was published under PCT Article 21(2) in English.

GOVERNMENT SUPPORT

This invention was made with government support under Grant No. R01 DK70055 from the National Institutes of Health. The Government has certain rights in this invention.

FIELD OF THE INVENTION

The field of invention relates to methods and compositions for the production of stem cells.

BACKGROUND OF THE INVENTION

A variety of methods are available for reprogramming adult cells to obtain induced pluripotent stem cells. However, the methods currently available suffer from low efficiency and incomplete programming. In addition, some of the methods currently available result in the upregulation of oncogenes, thereby increasing the risk of tumor formation. New methods for the production of induced pluripotent stem cells are needed therefore.

SUMMARY OF THE INVENTION

Aspects of the disclosure provide compositions and methods for reprogramming differentiated cells to produce pluripotent cells (e.g., stem cells). In some embodiments, certain enzyme inhibitors enhance cellular reprogramming by accelerating the reprogramming process and/or by simplifying the process (for example, by reducing the number and type of factors required for cellular reprogramming). For example, in some embodiments, methods and compositions described herein can be used to reprogram differentiated cells without using transcription factors that can have unwanted side effects such as oncogenesis. In some embodiments, inhibiting one or more of Dot1L (a histone H3 methyltransferase), YY1 (a transcriptional repressor protein), and/or SUV39H1 (a histone-lysine N-methyltransferase) helps promote the reprogramming of differentiated cells. One or more of these enzymes can be inhibited using any appropriate technique, including, for example, by inhibiting expression (e.g., transcription, translation, and/or modification) and/or activity of the enzyme(s).

Pluripotent (e.g., induced pluripotent stems cells—iPSCs) produced methods and compositions described herein are useful for therapeutic and research applications.

Accordingly, in some embodiments the disclosure provides methods and compositions for the production of stem cells. In certain embodiments, the disclosure provides stem cells (for example induced pluripotent stem cells) and methods and compositions for their use.

In some embodiments, a method of producing induced pluripotent stem cells includes inhibiting of Dot1L, YY1, and/or SUV39H1 in a differentiated cell (e.g., in a preparation containing one or more differentiated cell types). In some embodiments, the method also includes culturing the differentiated cell(s) under one or more reprogramming conditions. In some embodiments, the inhibition of Dot1L, YY1, and/or SUV39H1 occurs under the cell reprogramming conditions. However, in some embodiments, inhibition of Dot1L, YY1, and/or SUV39H1 is initiated prior to exposing the cell(s) to reprogramming conditions.

In some embodiments, the act of inhibiting includes inhibiting the activity of Dot1L, YY1, and/or SUV39H1 (e.g., inhibiting the methyltransferase activity of Dot1L). In some embodiments, the activity is inhibited by contacting a differentiated cell with a composition comprising one or more enzyme inhibitors (e.g., one or more enzyme inhibitors specific for Dot1L, YY1, and/or SUV39H1).

In some embodiments, the act of inhibiting includes knocking down the expression of Dot1L, YY1, and/or SUV39H1 (e.g., by inhibiting transcription and/or translation of the Dot1L, YY1, and/or SUV39H1 gene). In some embodiments, a differentiated cell is contacted with one or more RNAi (e.g., shRNA) molecules that specifically inhibit Dot1L, YY1, and/or SUV39H1 expression.

In some embodiments, the reprogramming conditions include using a cocktail containing one or more reprogramming factors (e.g., one or more reprogramming transcription factors). In some embodiments, the reprogramming cocktail includes Oct4 and/or Sox2. In some embodiments, the reprogramming cocktail consists essentially of Oct4 and Sox2. In some embodiments, the reprogramming cocktail includes Klf4 and/or c-Myc (e.g., in addition to Oct4 and/or Sox2). However, in some embodiments, the reprogramming cocktail does not include Klf4 or c-Myc. In some embodiments, an inhibitor (e.g., a Dot1L inhibitor) is added to the transcription factor(s) in the reprogramming cocktail.

In some embodiments, the differentiated cell is a somatic cell (e.g., a somatic cell obtained from a subject) or a cultured cell. In some embodiments, the differentiated cell is a fibroblast (e.g., an adult fibroblast). In some embodiments, the differentiated cell is a human cell (e.g., dH1fs, IMR-90 or MRC-5), or a mouse cell.

In some embodiments, the presence of induced pluripotent stem cells is determined (e.g., by detecting one or more markers characteristic of an induced pluripotent stem cell) after cellular reprogramming. In some embodiments, the presence of induced pluripotent stem cells is determined by evaluating the presence of one or more markers selected from the group consisting of SSEA4, SSEA3, Tra-1-81, Oct4, Sox2 and Nanog. In some embodiments, induced pluripotent stem cells are isolated after reprogramming of one or more differentiated cell types.

In some embodiments, the production of induced pluripotent stem cells is accelerated by inhibiting Dot1L, YY1, and/or SUV39H1 in a differentiated cell. In some embodiments, the production of induced pluripotent stem cells is more efficient when Dot1L, YY1, and/or SUV39H1 are inhibited in a differentiated cell. Inhibition can occur (e.g., be initiated) before, during, or after culturing the differentiated cell under reprogramming conditions. A reduction in time and/or increase in efficiency can be obtained relative to a reprogramming of the differentiated cell in which Dot1L, YY1, and/or SUV39H1 are not inhibited.

In some embodiments, a method of producing induced pluripotent stem cells includes upregulating the expression of Nanog and/or Lin28 in a differentiated cell. In some embodiments, these cells are cultured (e.g., before, concurrently, and/or subsequently) under reprogramming conditions to produce induced pluripotent stem cells. In some embodiments, the expression of Nanog and Lin28 is upregulated by inhibiting Dot1L.

In some embodiments, a preparation of induced pluripotent stem cells is provided wherein the stem cells were produced as described herein. In some embodiments, a preparation of induced pluripotent stem cells includes one or more inhibitors of Dot1L, YY1, and/or SUV39H1 (e.g., one or more expression and/or activity inhibitors). In some embodiments, the inhibitors are present in trace amounts. In some embodiments, the induced pluripotent stem cells are human cells.

In some embodiments, the induced pluripotent stems cell can differentiate (e.g., be differentiated using appropriate factors and/or conditions) into ectoderm, mesoderm and/or endoderm cells.

In some embodiments, a preparation of induced pluripotent stem cells is administered to a subject. In some embodiments, a preparation of differentiated stem cells (e.g., induced pluripotent stem cells that were differentiated ex vivo) is administered to a subject. In some embodiments, the subject is a patient (e.g., a human or animal patient) in need of treatment with pluripotent stem cells and/or differentiated cells. In some embodiments, a subject in need of treatment is patient having brain damage (e.g., associated with a neurodegenerative disorder such as Parkinson's disease), cancer, spinal cord injury, heart damage, baldness, deafness, diabetes, neuronal defects, blindness, amyotrophic lateral sclerosis, a genetic disorder, infertility, and/or unhealed wounds. It should be appreciated that the pluripotent and differentiated cell populations described herein may be used in a variety of in vivo methods including but not limited to therapeutic or cosmetic applications.

In some embodiments, one or more inhibitors of Dot1L, YY1, and/or SUV39H1 is administered to a subject to promote stem cell growth or development (e.g., locally at or near the site of local administration, or systemically). In some embodiments, one or more inhibitors may be administered in combination with one or more other factors, including but not limited to, one or more transcription factors (e.g., 2, 3, 4 or more transcription factors such as those described herein), for example in the form of a transcription factor expressing vector (e.g., for inducing local stem cell populations).

In some aspects, the disclosure provides kits, compositions, and methods for identifying enhancers and/or inhibitors of cell reprogramming. In some aspects, the disclosure provides kits, compositions, and methods for producing or isolating induced pluripotent stem cells and/or differentiated cells obtained from the stem cells.

These and other aspects and embodiments of the invention are described in greater detail below.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

DETAILED DESCRIPTION OF THE INVENTION

Figure 1:
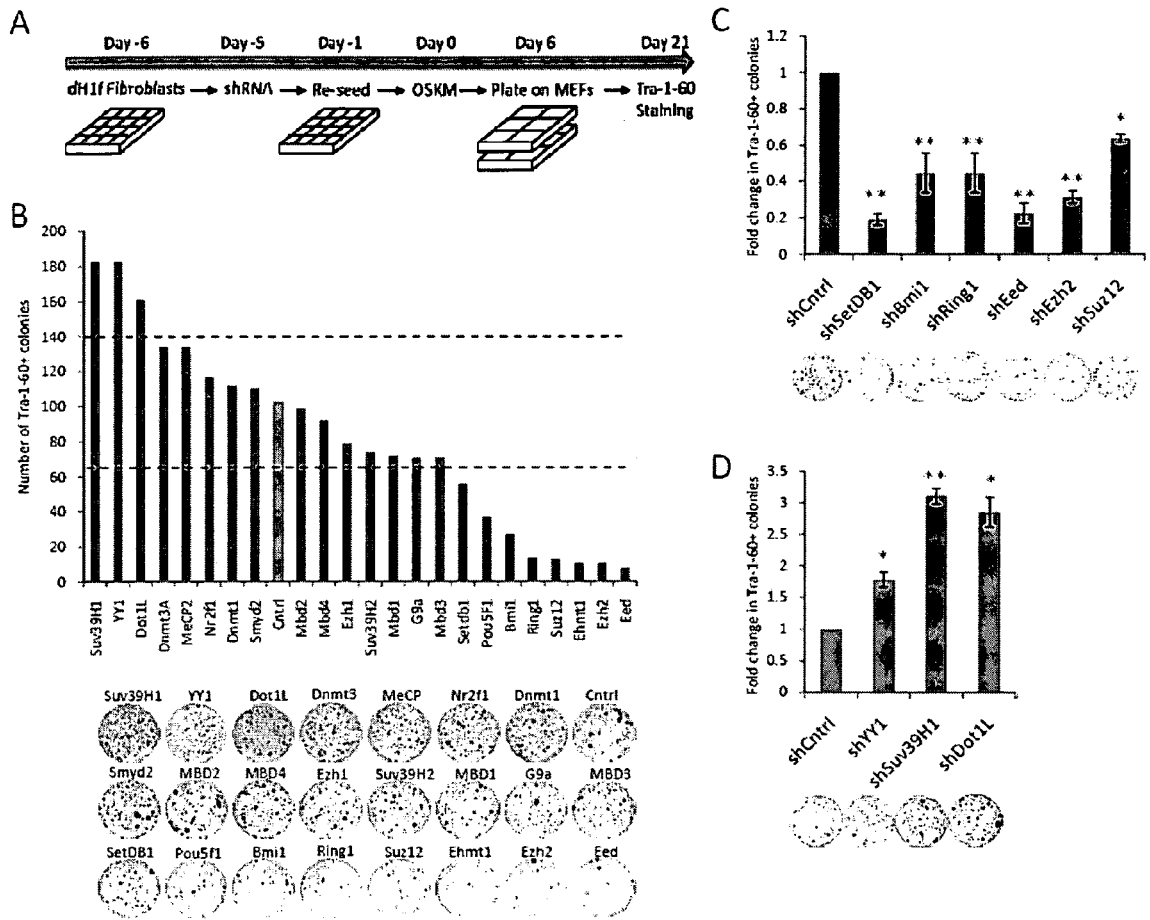
FIG. 1 illustrates a non-limiting example of a screen for inhibitors and enhancers of cellular reprogramming.

In one aspect, the disclosure provides methods and compositions that are useful in the production of stem cells (e.g., induced pluripotent stem cells—iPSC) from differentiated cells. In some embodiments, the inhibition of Dot1L, SUV39H1, and/or YY1 during at least a portion of a cell reprogramming technique increases the efficiency of and/or accelerates the reprogramming process. In some embodiments, the inhibition of one or more of these proteins also can be used to reduce the number of transcription factors required for a cell reprogramming procedure.

Stem cells produced using compositions and methods described herein are useful in therapeutic and/or research applications. In addition, methods and compositions of promoting stems cell production can be used for therapeutic and/or research purposes.

Methods and compositions described herein can simplify the process of reprogramming a somatic cell. In general, the production of induced pluripotent stem cells (iPSCs) from differentiated cell types by somatic cell reprogramming involves resetting the epigenetic states of the differentiated cells. Typical reprogramming techniques involve exposing cells to several transcription factors, some of which can have undesirable side-effects (e.g., they can be oncogenic). Surprisingly, inhibiting one or more of Dot1L, SUV39H1, and/or YY1 during at least a portion of a reprogramming technique allows for the use of fewer transcription factors, thereby reducing the risks associated with certain transcription factors, in addition to enhancing the efficiency and speed of the overall reprogramming procedure.

In some aspects, the disclosure also provides compositions and methods for identifying genes and proteins that are negative or positive regulators in the reprogramming of differentiated cells. While several proteins are known to regulate chromatin marks associated with the distinct epigenetic states of cells before and after reprogramming, how chromatin-modifying proteins influence the reprogramming process remains largely unknown. By identifying negative or positive regulators of iPSC generation, techniques for controlling the process of iPSC generation can be further developed or refined by inhibiting or increasing the expression and/or activity of one or more of the negative or positive regulators.

In some embodiments, inhibition of the core components of the polycomb repressive complex 1 and 2, including the histone 3 lysine 27 methyltransferase Ezh2, reduced reprogramming efficiency. However, surprisingly, inhibition of SUV39H1, YY1, and Dot1L, increased reprogramming. In contrast to genes whose functions appear to be required for reprogramming, inhibition of these three genes enhanced reprogramming (see FIG. 1D). YY1 is a transcription factor that activates or represses transcription in a context-dependent manner[10,11], whereas Suv39H1 is a histone H3K9 methyltransferase implicated in heterochromatin formation[12], and Dot1L is a H3K79 histone methyl-transferase.

In some embodiments, inhibition of Dot1L, the H3K79 histone methyl-transferase, either by RNAi or by a small molecule inhibitor accelerated reprogramming, significantly increased the yield of iPSC colonies, and substituted for Klf4 and c-Myc in a reprogramming cocktail. In some embodiments, inhibition of Dot1L functions early in the reprogramming process can be used to markedly induce two alternative reprogramming factors, Nanog and Lin28. Furthermore, in loss-of-function experiments, it was shown that Nanog and Lin28 play essential functional roles in the enhancement of reprogramming by Dot1L-inhibition in some embodiments.

As shown herein, suppression of Dot1L expression using shRNAs or inhibition of its catalytic activity using a small molecule both accelerates and increases the yield of iPSCs and substitutes for both Klf4 and Myc in the reprogramming process. These effects are primarily mediated through induction of two key pluripotency factors, Nanog and Lin28, whose activation normally occurs during the later stages of reprogramming[20,21,22,23]. Accordingly, in some embodiments, cell reprogramming can be promoted (e.g., ex vivo) by inhibiting Dot1L and/or stimulating Nanog and/or Lin28 expression and/or activity.

Genome-wide analysis of K79me2 distribution revealed that fibroblast-specific, epithelial to mesenchymal transition-associated genes start to lose K79me2 in the initial phases of reprogramming and Dot1L inhibition facilitates the loss of this mark from such genes that eventually get repressed in the pluripotent state. Accordingly, in some embodiments these marks can be used to evaluate and/or monitor the effectiveness of Dot1L inhibition in a cell reprogramming procedure that is used to generate induced pluripotent stems cells.

It should be appreciated that in some embodiments, stem cells can be generated from cultured somatic cell lines. However, in some embodiments, methods and compositions described herein can be used to generate "personalized" stem cells (e.g., for autologous cell therapy) by obtaining one or more somatic cells from a subject and reprogramming the cell(s) ex vivo as described herein. These personalized stem cells can be useful to produce cell preparations (e.g., containing undifferentiated stem cells and/or differentiated stem cells) that can be reintroduced to the subject (e.g., to treat a disease or disorder) with a low risk of host rejection of the reimplanted cells.

In some embodiments, inhibition of Dot1L can be used to prepare cells for a reprogramming procedure by inhibiting Dot1L prior to exposing the cells to a reprogramming cocktail (e.g., containing one or more transcription factors that are useful to promote reprogramming). However, in some embodiments, Dot1L inhibition can be initiated during reprogramming. In some embodiments, one or more Dot1L inhibitors are provided along with one or more transcription factors in a reprogramming cocktail. In some embodiments, one or more Dot1L inhibitors are added to a reprogramming cocktail that contains one or more transcription factors. Accordingly, it should be appreciated that cells being reprogrammed can be contacted with (e.g., incubated with) one or more Dot1L inhibitors (and/or one or more YY1 inhibitors and/or one or more SUV39H1 inhibitors) prior to, along with, and/or after incubation with one or more transcription factors in an incubation cocktail. The presence of the inhibitor(s) can be useful to increase the efficiency of the reprogramming, accelerate the reprogramming (e.g., reduce the incubation time with the reprogramming cocktail), and/or reduce the number of transcription factors required in the incubation cocktail.

Stem cells described herein can be used for therapeutic and research applications. In some embodiments, stem cells can be administered to a subject (e.g., a human subject). In some embodiments, stem cells can be differentiated into one or more somatic cell types of interest prior to administration to a subject. In some embodiments, stem cells can be used to produce artificial tissue or organs ex vivo (e.g., for organ transplantation purposes). Techniques for differentiating stem cells into different types of cell types (e.g., prior to administration to a subject or for use in generating artificial tissue or organs) are known in the art.

Although a cell reprogramming technique typically occurs ex vivo using isolated cells that are obtained from a cell bank or a subject, methods and compositions described herein also can be used in vivo to promote stem cell production and or maintenance in a subject. For example, in some embodiments one or more inhibitors described herein can be administered to a subject (e.g., using any suitable route) to promote or maintain stem cell populations in the subject. In some embodiments, the inhibitor(s) may be administered systemically. In some embodiments, the inhibitor(s) may be administered locally (e.g., to provide local stimulation or maintenance of a stem cell population). In some embodiments, one or more inhibitors may be administered in combination with one or more other factors, including but not limited to, one or more transcription factors (e.g., 2, 3, 4 or more transcription factors such as those described herein). In some embodiments, the transcription factors are provided in the form of a transcription factor expressing vector that expresses one or more transcription factors in vivo after administration. In some embodiments, a vector can include one or more expression regulators to limit expression of the transcription factor(s) to particular tissue or cell types. In some embodiments, the inhibitor(s) and transcription factor(s) are administered locally. Accordingly, methods and compositions described herein can be used to induce local stem cell populations.

In some embodiments, one or more small molecule inhibitors of Dot1L, YY1 and/or SUV39H1 are provided to cells (e.g., ex vivo, or in vivo) in an amount sufficient to inhibit protein function. In some embodiments, the cells are exposed to 0.01 uM, 0.1 uM, 1 uM or 10 uM of inhibitor for a time sufficient to inhibit the protein during a reprogramming procedure. In some embodiments, the cells are exposed to the inhibitor for several hours or several days (e.g., 1-10 days, for example about 5 days) before, during, or after incubation with a reprogramming cocktail.

In some embodiments, one or more of the inhibitors described herein (for example one or more inhibitors of Formula I, II, III, or IV) may be used to inhibit Dot1L in vivo or in vitro. In some embodiments, an inhibitor of structure:

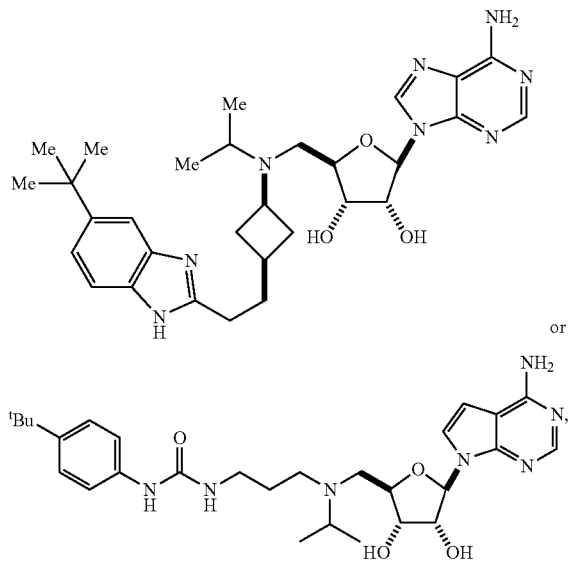

pharmaceutically acceptable salt thereof (e.g.,

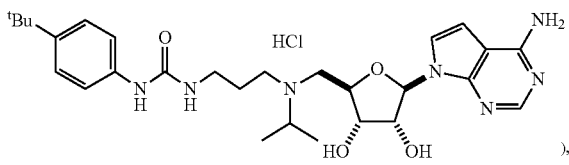

may be used to inhibit Dot1L in vitro (e.g., contacted to differentiated cells in vitro, for example alone or in combination with one or more transcription factors or other agents described herein, to promote iPSC generation in vitro) or in vivo (e.g., administered to a subject in vivo, for example alone or in combination with one or more transcription factors or other agents described herein, to promote iPSC generation in vivo, for example to promote local stem cell production or to support local stem cell growth or maintenance).

In some embodiments, Dot1L, YY1 and/or SUV39H1 is inhibited by contacting a differentiated cell with one or more nucleic acids that prevent production of the protein(s). In some embodiments, Dot1L, YY1 and/or SUV39H1 is inhibited by an shRNA that knocks down expression. Non-limiting embodiments of shRNAs that knock down expression are provided in the Examples section.

Nucleic acids that prevent Dot1L, YY1 and/or SUV39H1 expression can be provided to the cells in a variety of formats including dsRNA, siRNA and shRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. "Short interfering RNA" (siRNA), also referred to herein as "small interfering RNA" is defined as a nucleic acid-comprising agent which functions to inhibit expression of a target gene, by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be encoded by plasmids, retroviruses, and lentiviruses and expressed from, for example, the pol III U6 promoter, or another promoter (see, e.g., Stewart, et al., RNA April; 9(4):493-501 (2003), incorporated by reference herein in its entirety).

It is envisioned that inhibitors of Dot1L, YY1 and/or SUV39H1 are used in effective amounts. In some embodiments, an effective amount of Dot1L inhibitor (e.g., small molecule or RNAi molecule) is an amount sufficient to inhibit the transferase activity (e.g., by at least 25%, at least 50%, at least 75%, at least 80%, at least 85%, at least 90%, at least 95%, at least 99%, or more) in the targeted cells (e.g., cells growing in vitro, or targeted cells types in a subject). In some embodiments, an effective amount of YY1 inhibitor is an amount sufficient to inhibit the activity (e.g., by at least 25%, at least 50%, at least 75%, at least 80%, at least 85%, at least 90%, at least 95%, at least 99%, or more) in the targeted cells (e.g., cells growing in vitro, or targeted cells types in a subject). In some embodiments, an effective amount of SUV39H1 inhibitor is an amount sufficient to inhibit the activity (e.g., by at least 25%, at least 50%, at least 75%, at least 80%, at least 85%, at least 90%, at least 95%, at least 99%, or more) in the targeted cells (e.g., cells growing in vitro, or targeted cells types in a subject).

In some embodiments, a subject may be evaluated to determine whether Dot1L is overexpressed. Certain genetic abnormalities associated with Dot1L (e.g., the Dot1L regulatory pathway) result in Dot1L overexpression. Assays for detecting genetic abnormalities associated with Dot1L overexpression are known in the art and can include, but are not limited to, molecular assays (e.g., hybridization or sequencing) or in situ or chromosomal assays (e.g., FISH) or other chromosomal assays. Depending on the level of Dot1L in the subject (or in cells obtained from the subject) the amount of Dot1L inhibitor that is used (e.g., in vivo or in vitro) may be adjusted. One of ordinary skill can perform assays to determine suitable levels of Dot1L inhibitor to use in order to inhibit Dot1L levels that are present in a subject (for example in vivo or in vitro in cells isolated from the subject).

Reprogramming

In some embodiments, inhibiting Dot1L, YY1 and/or SUV39H1 can be used to promote cellular reprogramming (e.g., ex vivo or in vivo). During development, individual cells become specified to adopt distinct fates through the activation of lineage-specific gene expression programs. Under normal circumstances, these gene expression programs are stably inherited throughout mitotic divisions, thereby maintaining cell identity. At the molecular level, this cellular identity is largely controlled at the chromatin level whereby genes appropriate for a given lineage are embedded in a chromatin structure that supports their transcriptional activity, whereas genes specifying other lineages are sequestered in repressive chromatin structures resulting in transcriptional silencing[1]. Differentiated cells such as fibroblasts can be converted into induced pluripotent stem cells (iPSCs) upon overexpression of critical transcriptional regulators of embryonic stem cells (ESCs)[2,3,4].

In some embodiments, the effect of inhibition of one or more proteins on reprogramming was evaluated in dH1fs cells. The dH1fs cells were transfected with shRNA pools (at high multiplicity of infection to ensure all cells received an shRNA vector) followed by super-infection with reprogramming vectors expressing Oct4, Sox2, Klf4 and c-Myc (OSKM), and the resulting iPSCs were identified by Tra-1-60 staining.

In one aspect, the disclosure provides a method of producing induced pluripotent stem cells, by inhibiting Dot1L (and/or YY1 and/or SUV39H1) in a differentiated cell and culturing the differentiated cell under reprogramming conditions to produce induced pluripotent stem cells. In some embodiments, the reprogramming conditions comprise the presence of a reprogramming cocktail. In some embodiments, the reprogramming cocktail comprises Oct4 and/or Sox2. In some embodiments, the reprogramming cocktail includes Klf4 and/or c-Myc. In some embodiments, the reprogramming cocktail does not include Klf4 and/or c-Myc. In some embodiments, the reprogramming cocktail consists essentially of Oct4 and Sox2. In some embodiments, Dot1L (and/or YY1 and/or SUV39H1) is inhibited at the same time as providing the reprogramming cocktail.

Reprogramming, when relating to cells, generally refers to the process of changing a cell from a first phenotype to a second phenotype. In particular, and as used herein, reprogramming refers to the process of changing a differentiated cell into an induced pluripotent stem cell.

Reprogramming conditions as used herein refers to the conditions that allow a differentiated cell to transform into an induced pluripotent stem cell. Reprogramming conditions include culture media, culture components (e.g., buffer, pH, salt) and the duration of the culturing of the cells.

In some embodiments, the reprogramming conditions comprise the presence of a reprogramming cocktail. A reprogramming cocktail as used herein refers to the combination of specific agents (e.g., Sox2, Oct 4, Klf4, c-Myc, or a combination of any 2 or 3 thereof, or all 4, and/or one or more additional transcription factors) that is required to reprogram a cell from a differentiated cell into an induced pluripotent stem cell. In some embodiments, the reprogramming cocktail comprises Oct4 and Sox2. In some embodiments, the reprogramming cocktail consists essentially of Oct4 and Sox2. A reprogramming cocktail that consists essentially of Oct4 and Sox2, refers to a reprogramming cocktail that does not include any other specific agents (e.g., transcription factors) that could be used to reprogram a differentiated cell. However, in some embodiments, a reprogramming cocktail (e.g., a cocktail that consists essentially of specified transcription factors) may include buffers, salts, sugars, and other components that may be useful to support the growth and reprogramming of the differentiated cells.

The production of induced pluripotent stem cells is generally achieved by the introduction of nucleic acid sequences encoding stem cell-associated genes into a somatic cell. In general, these nucleic acids are introduced using retroviral vectors and expression of the gene products results in cells that are morphologically and biochemically similar to pluripotent stem cells (e.g., embryonic stem cells). This process of altering a cell phenotype from a somatic cell or progenitor cell phenotype to a stem cell-like phenotype is termed "reprogramming".

It was surprisingly found herein that inhibiting DotL1 provides an alternative route for reprogramming cell, eliminating the need for one or more cell transforming factors (e.g., c-Myc) that are associated with oncogenesis.

In some embodiments, reprogramming can be achieved by introducing a combination of stem cell-associated genes including, for example Oct3/4 (Pouf51), Sox1, Sox2, Sox3, Sox 15, Sox 18, NANOG, Klf1, Klf2, Klf4, Klf5, c-Myc, 1-Myc, n-Myc and LIN28. In general, successful reprogramming is accomplished by introducing Oct-3/4, a member of the Sox family, a member of the Klf family, and a member of the Myc family to a somatic or progenitor cell. In some embodiments, the nucleic acid sequences of Oct-4, Sox2, c-MYC, and Klf4 are delivered using a viral vector, such as an adenoviral vector, a lentiviral vector or a retroviral vector. However, while it is understood that reprogramming is usually accomplished by viral delivery of stem-cell associated genes, it is also contemplated herein that reprogramming can be induced using other delivery methods.

In one aspect, the disclosure provides a method of accelerating the production of induced pluripotent stem cells, the method comprising inhibiting Dot1L (and/or YY1 and/or SUV39H1) in a differentiated cell and culturing the differentiated cell under reprogramming conditions to accelerate the production of induced pluripotent stem cells, wherein the production of induced pluripotent stem cells is accelerated compared to a differentiated cell in which Dot1L is not inhibited. Thus, as provided herein, in some embodiments, a differentiated cell can be reprogrammed into an induced pluripotent stem cells by using a known combination of cell-associated genes (e.g., Oct-4, Sox2, c-MYC, and Klf4 or a subset thereof). It was unexpectedly shown herein that the addition of Dot1L to the combination of cell-associated genes resulted in the acceleration of the production of induced pluripotent stem cells.

The efficiency of reprogramming (e.g., the number of reprogrammed cells) can be enhanced by the addition of various small molecules as shown by Shi, Y., et al (2008) Cell-Stem Cell 2:525-528, Huangfu, D., et al (2008) Nature Biotechnology 26(7):795-797, Marson, A., et al (2008) Cell-Stem Cell 3:132-135, which are incorporated herein by reference in their entirety. It is contemplated that the methods described herein can also be used in combination with a single small molecule (or a combination of small molecules) that enhances the efficiency of induced pluripotent stem cell production. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), trichostatin (TSA), and inhibitors of the TGF-β signaling pathway, among others. It is also contemplated herein that inhibitors can be used alone or in combination with other small molecule(s) to replace one or more of the reprogramming factors used for the production of induced pluripotent stem cells.

In some embodiments, a method of producing pluripotent stem cells includes upregulating the expression of Nanog and/or Lin28 in a differentiated cell and culturing the differentiated cell under reprogramming conditions to produce induced pluripotent stem cells. In some embodiments, Nanog and/or Lin28 are upregulated by inhibiting Dot1L. In some embodiments, Nanog and/or Lin28 are upregulated by introducing agents that stimulate expression of Nanog and/or Lin28, and/or by introducing agents that suppress removal of Nanog and/or Lin28 from the cell (e.g., by protease action). In some embodiments, promoters are introduced into the genome of the cell that result in the upregulation of the expression of Nanog and/or Lin28.

In some embodiments, a method of producing pluripotent stem cells includes inhibiting SUV39H1 in a differentiated cell and culturing the differentiated cell under reprogramming conditions to produce induced pluripotent stem cells. Histone-lysine N-methyltransferase SUV39H1 is a member of the suppressor of variegation 3-9 homolog family and encodes a protein with a chromodomain and a C-terminal SET domain. This nuclear protein moves to the centromeres during mitosis and functions as a histone methyltransferase, methylating Lys-9 of histone H3 Histone-lysine N-methyltransferase SUV39H1. It was surprisingly shown herein that inhibiting SUV39H1 provides a novel pathway for producing induced pluripotent stem cells. In some embodiments, SUV39H1 is inhibited by providing the cell with an siRNA, shRNA (or other RNAi) against SUV39H1. In some embodiments, SUV39H1 is inhibited by providing the cell with an SUV39H1 inhibitor (e.g., a small molecule inhibitor such as Chaetocin, see Greiner et al. Nat Chem Biol. 2005 August; 1(3):143-5).

In some embodiments, a method of producing pluripotent stem cells includes inhibiting YY1 in a differentiated cell and culturing the differentiated cell under reprogramming conditions to produce induced pluripotent stem cells. Transcriptional repressor protein YY1 is a ubiquitously distributed transcription factor belonging to the GLI-Kruppel class of zinc finger proteins. The protein is involved in repressing and activating a diverse number of promoters. YY1 may direct histone deacetylases and histone acetyltransferases to a promoter in order to activate or repress the promoter, thus implicating histone modification in the function of YY1. It was surprisingly shown herein that inhibiting YY1 provides a novel pathway for producing induced pluripotent stem cells. In some embodiments, YY1 is inhibited by providing the cell with an siRNA, shRNA (or other RNAi) against YY1. In some embodiments, YY1 is inhibited by providing the cell with an YY1 inhibitor (e.g., a small molecule inhibitor).

Differentiated Cells

Methods described herein embrace the use of any differentiated cell (e.g., somatic cell). In some embodiments, the differentiated cell is a fibroblast, epithelial, endothelial, neuronal, adipose, cardiac, skeletal muscle, immune cells, hepatic, splenic, lung, circulating blood, gastrointestinal, renal, bone marrow, or pancreatic cell. The differentiated cell can be a primary cell isolated from any somatic tissue including, but not limited to brain, liver, lung, gut, stomach, intestine, fat, muscle, uterus, skin, spleen, endocrine organ, bone, etc., Methods for isolating differentiated cells from a body are known in the art.

In some embodiments, the differentiated cell is a fibroblast. In some embodiments, the differentiated cell is an adult fibroblast.

The differentiated cell used according to the methods provided herein can be from any mammalian species, with non-limiting examples including a murine, bovine, simian, porcine, equine, ovine, or human cell.

In some embodiments, the differentiated cell is a human cell. In some embodiments, the differentiated cell is dH1fs, IMR-90 or MRC-5.

In some embodiments, the differentiated cell is a mouse cell.

The differentiated cells used in the methods provided herein, and prior to being reprogrammed, can be maintained under in vitro conditions using conventional tissue culture.

In some embodiments, one or more differentiated cells are obtained from a subject that will subsequently be treated by reimplanting induced pluripotent stem cells obtained from the differentiated cells and/or by reimplanting redifferentiated cells, tissue, or organs obtained from the stem cells.

Induced Pluripotent Stem Cells

In one aspect, the disclosure provides methods for producing stem cells. In some embodiments, the cells are induced pluripotent stem cells. The term "pluripotent," as used in the context of cells, describes the developmental capacity of a cell or cell population and refers to cells that are capable of self-renewal and have the capacity to differentiate into cells of any of the three germ layers (endoderm, mesoderm, and ectoderm). Examples of pluripotent cells are embryonic stem cells (ES-cells), embryonic carcinoma cells (EC cells), and induced pluripotent stem cells (iPS cells). A pluripotent cell has the potential to give rise to any fetal or adult cell type. However, pluripotent cells cannot contribute to extraembryonic tissue, such as, the placenta. This distinguishes pluripotent cells from totipotent cells, which can give rise to all fetal, adult, and extraembryonic cell types.

In one aspect of the methods provided herein, the presence of induced pluripotent stem cells is determined. In some embodiments, the presence of induced pluripotent stem cells is determined by evaluating the presence of one or more markers selected from the group consisting of SSEA4, SSEA3, Tra-1-81, Oct4, Sox2 and Nanog.

In humans and mice, the transcription factors Oct-4, Sox2, and Nanog are biomarkers that are specific for pluripotent cells (see, e.g., Looijenga, L. H. et al. (2003) Cancer Res 63, 2244-50; Peske, M. and Scholer, H. R. (2001) Stem Cells 19, 271-8; Pan, G. and Thomson, J. A. (2007) Cell Res 17, 42-9; the entire contents of each of which are incorporated herein by reference). Additional biomarkers specific for human pluripotent cells include stage specific embryonic antigens SSEA3 and SSEA4, as well as the podocalyxin antigens TRA 1-81 and TRA 1-60 (see, e.g., Schopperle et al. (2007) Stem Cells 25(3):723-30. Epub 2006 Nov. 22; Henderson, J. K. et al. (2002) Stem Cells 20, 329-37; and Draper, J. S. et al. (2002) J Anat 200, 249-58; the entire contents of each of which are incorporated herein by reference). Additional biomarkers for mouse pluripotent stem cells include SSEA1, which is specific for pluripotent cells, and the less stringent marker alkaline phosphatase, which is indicative, but not specific for pluripotent cells (see, e.g., Brambrink, T. et al. (2008) Cell Stem Cell 2(2):151-9; the entire contents of which are incorporated herein by reference). Expression of these pluripotency markers decreases and is eventually lost during differentiation, corresponding to a restriction in developmental potential and, thus, a loss of pluripotency (see, e.g., Schopperle, W. M. and DeWolf, W. C. (2007) Stem Cells 25, 723-30; the entire contents of which are incorporated herein by reference). Table 1 below lists some additional biomarkers useful for the identification of pluripotent stem cells from mouse, human, and other mammals, as well as their expression spectrum among pluripotent cell types.

TABLE 1 stem cell markers

| Biomarker | Expressed in | Remarks |
|---|---|---|
| Alkaline phosphatase | ES, EC | Elevated expression of this enzyme is associated with undifferentiated pluripotent stem cell (PSC) |
| Cluster designation 30 (CD30) | ES, EC | Surface receptor molecule found specifically on PSC |
| Cripto (TDGF-1) | ES, cardiomyocyte | Growth factor expressed by ES cells, primitive ectoderm, and developing cardiomyocyte |
| GCTM-2 | ES, EC | Extracellular-matrix antigen that is synthesized by undifferentiated PSCs |
| Genesis | ES, EC | Transcription factor expressed by PSCs |
| Germ cell nuclear factor | ES, EC | Transcription factor expressed by PSCs |
| OCT4/ POU5F1 | ES, EC | Transcription factor unique to PSCs |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |

In some embodiments, methods provided herein include a step of isolating the produced induced pluripotent stem cells. In some embodiments, the induced pluripotent stem cells are isolated from a mixed population cells comprising pluripotent cells and cells that have not yet or only partially been reprogrammed. Methods for isolating induced pluripotent stem cells are known in the art and are generally based on moieties that bind to markers that are uniquely expressed on induced pluripotent stem cells (e.g., SSEA-1).

In some embodiments, methods described herein include a step of evaluating the developmental capacity of the induced pluripotent stem cells. In some embodiments, the compositions of induced pluripotent stem cells provided herein can be evaluated for their developmental capacity. In some embodiments, the induced pluripotent stem cells are evaluated for their capacity to differentiate into ectoderm, mesoderm and endoderm cells. In some embodiments, the developmental capacity of the induced pluripotent stem cells is evaluated in a teratoma assay.

The developmental capacity of a cell or a cell population can be tested by assays well known to those of skill in the art. One test for pluripotency of a mouse cell or a population of mouse cells, is diploid blastocyst complementation, in which one or more of the cells in question are injected into a host blastocyst, which is then transferred to a foster mouse. If the injected cell(s) are pluripotent, contribution to all three germ layers, and to the germ line, will be observed in the resulting pup, which will typically be a chimera comprising cells derived from the host blastocyst and from the injected cell(s). The most stringent test for the developmental capacity of a pluripotent mouse cell, e.g., an ES or iPS cell is the tetraploid blastocyst complementation assay, which is well known to those of skill in the art (see, e.g., Eggan et al., PNAS, 2001 (May) 6209-6214; and Li et al., Reproduction, 2005 130:53-59; the entire contents of which are incorporated herein by reference). In this assay, a cell or a plurality of cells is injected into a tetraploid host blastocyst. The cells of the tetraploid host blastocyst can contribute to extra-embryonic tissues, e.g., the placenta, but cannot give rise to fetal or adult cell types. Accordingly, a tetraploid blastocyst alone cannot give rise to a live pup at birth, because it cannot generate the required fetal tissues. However, if a pluripotent cell or a plurality of such cells is injected into a tetraploid blastocyst, thus creating a complemented tetraploid blastocyst, the pluripotent cell(s) can give rise to the cell types required for embryonic development, if the injected cells exhibit a high developmental capacity. Tetraploid blastocyst complementation is a more stringent test for developmental capacity than the derivation of chimeric mice after diploid blastocyst injection, because any defect in developmental capacity of the injected cell(s) cannot be compensated by cells of the host blastocyst. A pup resulting from a complemented tetraploid blastocyst typically consists of cells derived from the injected cell(s).

Additional tests for developmental capacity or pluripotency include teratoma formation assays, also sometimes referred to as teratocarcinoma assays (see. e.g., Wesselschmidt, R. L. (2011) *Methods Mol Biol.* 767:231-41, the entire contents of which are incorporated herein by reference). Typically, a population of cells to be tested is injected subcutaneously into an immunocompromised host animal, e.g., a SCID mouse. If the cell population comprises pluripotent cells, a solid tumor will form at the site of injection. Teratocarcinomas derived from pluripotent cells will contain differentiated cell types of all three germ layers. This assay is an in vivo assay for differentiation capacity that can be used for all pluripotent cells, including cells that cannot be tested by blastocyst complementation (e.g., human cells).

In some embodiments, methods described herein include a step of promoting the development and/or differentiation one or more of the induced pluripotent stem cells.

In some embodiments, the iPSCs produced as described herein may be differentiated in vitro, partially or completely. Methods of promoting the development or differentiation of stem cells are known in the art. For example, differentiation protocols are known in the art and include those described in U.S. Pat. No. 7,326,572 (endoderm differentiation), U.S. Pat. No. 7,282,366 (hepatocyte differentiation), U.S. Pat. No. 7,250,294 (neural differentiation), and U.S. Pat. No. 7,033,831 (islet cell differentiation). In some embodiments, Embryoid Body differentiation, or in vitro directed differentiation using cytokines, growth factors, and/or co-culture with mature cell types may be used. A variety of differentiation factors that can act on pluripotent stem cells and their precursor progeny are known in the art. For example, members of the BMP family of factors have been used to differentiate pluripotent stem cells such. These include the use of BMP-4 and BMP-7 to generate endoderm-like differentiation. (Xu et al. Nat Biotechnol 20:1261-1264, 2002; Pera et al. J Cell Sci 117:1269-1280, 2004.) Activin A can be used to differentiate pluripotent stem cells into definitive endoderm using monolayers or three dimensional (e.g., EB) culture systems. (D'Amour et al. Nat Biotechnol 23:1534-1541, 2005.) Nervous system cells have been observed as a result of culture with epidermal growth factor and fibroblast growth factor (resulting in the generation of neurospheres that comprise neural stem cells), subsequent removal of these factors (resulting in the generation of astrocyte-like cells) or supplementation with nerve growth factor (resulting in the generation of neurons and glial cells). (Kim et al. Nature 418:50-6, 2002; Lee et al. Nat Biotechnol 18:675-9, 2000.) Dopaminergic neurons, useful in Parkinson's disease, may be formed through culture or contact with FGF20 and FGF2. Bjorklund et al. (PNAS 2002, 99:2344-2349) provides additional methods for differentiating ES cells into dopaminergic neurons. Hepatic cell differentiation may be induced through contact and/or culture with an insulin, dexamethasone, and collagen type I (via EB formation) combination; a sodium butyrate and DMSO combination; an FGF4, HGF and collagen type I combination; an aFGF, HGF, oncostatin M, dexamethasone and collagen type I combination; and a bFGF, variant HGF, DMSO and dexamethasone combination in the presence of poly-amino-urethane coated non-woven polytetrafluoroethylene fabric. (Shirahashi et al. Cell Transplant 13:197-211, 2004; Rambhatla et al. Cell Transplant 12:1-11, 2003; Schwartz et al. Stem Cells Dev 14:643-655, 2005; Baharvand et al. Int J Dev Biol 50:645-652, 2006; Soto-Gutierrez et al. Cell Transplant 15:335-341, 2006.) Hepatic differentiation may also occur spontaneously. (Lavon et al. Differentiation 72:230-238, 2004.) Pancreatic differentiation, including differentiation towards beta-islet cells, can be induced using Activin A, retinoic acid, FGF2 and FGF10, betacellulin, HGF, Exendin 4, DKK1 and DKK3. (Gu et al. Mech Dev 120:35-43, 2003; Grapin-Botton et al. Trends Genet 16:124-130, 2000; D'Amour et al. Nat Biotechnol 23:1534-1541, 2005a; D'Amour et al. published US application US2005-0266554A1.) Endothelial differentiation may be induced in the presence of ECM proteins such as collagen type IV, optionally in the presence of VEGF and bFGF. (Gerecht-Nir et al. Lab Invest 83:1811-1820, 2003.) Further reference may be made to published PCT application WO2009/007852 for a review of various differentiative procedures known in the art and applicable to the differentiation of the immature and precursor cells of the invention. Such teachings, and in particular those found on pages 57-61 (under the subheading "Cell Differentiation") of WO2009/007852, are incorporated by reference herein. Still other references include West and Daley, 2004, Curr Opin Cell Biol 16:688-692; U.S. Pat. No. 6,534,052 B1; Kehat and Gepstein, 2003, 8:229-236; Nir et al., 2003, 58:313-323; and U.S. Pat. Nos. 6,613,568 and 6,833,269.

In some embodiments, the disclosure provides compositions comprising a population of induced pluripotent stem cells (e.g., human induced pluripotent stem cells) produced according to the methods provided herein. In some embodiments, the disclosure provides compositions comprising a population of differentiated stem cells (e.g., human differentiated stem cells) obtained from stem cells produced according to the methods provided herein. In some embodiments, a composition, in addition to the population of induced pluripotent stem cells and/or differentiated stem cells, may include cell culture and cell culture components needed for cell viability. In some embodiments, the compositions include pharmaceutical excipients allowing for the administration of the induced pluripotent stem cells.

It should be appreciated that differentiated cells (e.g., obtained from a subject), induced pluripotent stem cells, and/or differentiated iPSCs referred to herein may be isolated cells (e.g., in the form of preparations of isolated cells). As used herein, isolated cells are cells which have been physically separated from their environment. If the cells are naturally occurring, then isolation implies that the cells are physically separated from the naturally occurring environment from which they derive. In some instances, isolated cells are additionally or alternatively physically separated, in whole or in part, from an in vitro environment. Thus, as used herein, the term isolated means that a molecule, cell, cell population and the like is physically separated from an environment in which it normally exists, or in which it originally or previously existed. Isolation may refer to physical separation of cells from a culture condition (e.g., a differentiation culture), from a naturally occurring environment or source, and the like. A differentiated cell population may be isolated from a differentiation culture condition, for example, by harvesting the cells and removing the culture medium (e.g., by centrifugation). Isolating may also involve washing the cells. Typically, the cells are resuspended in fresh medium. Isolation of the differentiated cell population from the differentiation culture therefore can serve to remove factors or stimuli used to differentiated the pluripotent stem cells towards one or more lineages.

In some embodiments, cells described herein (e.g., original differentiated cells, iPSCs, and or subsequently differentiated cells) may be genetically manipulated (e.g., they may be transfected) or they may not be genetically manipulated. Transfection refers to genetic manipulation of cells to introduce and typically express an exogenous nucleic acid. The exogenous nucleic acid may be a reporter such as green fluorescent protein (GFP) or it may be a selection marker such as thymidine kinase or it may be a transcription factor or other factor that is used to promote reprogramming or subsequent redifferentiation. It will be understood that in some instances reporters such as GFP may also serve as selection markers, particularly if their expression is controlled by pluripotent gene promoters such as an Oct4 promoter.

It should be appreciated that techniques described herein may be used with cells obtained from different species, including for example, human, and various animal species including household species such as dogs and cats, agricultural species such as cows, pigs, and horses, laboratory species such as mice and rats, and the like, or other species.

In Vivo Uses

In some embodiments, the disclosure provides methods of treatment using the induced pluripotent stem cells or differentiated cells (e.g., obtained from iPSCs) provided herein. In some embodiments, the methods of treatment comprise administering to a person in need thereof a composition comprising induced pluripotent stem cells and/or differentiated stems cells produced according to the methods provided herein.

In some embodiments, a person in need of treatment with a composition comprising induced pluripotent stem cells or differentiated cells is a person having brain damage, cancer, spinal cord injury, heart damage, baldness, deafness, diabetes, neuronal defects, blindness, amyotrophic lateral sclerosis, a genetic disorder, infertility, or unhealed wounds. In some embodiments, cells obtained as described herein also may be used to treat hematological malignancies, immunodeficiencies, age related macular degeneration, and other conditions. For example cell populations (e.g., differentiated cell populations) can be used in transplant settings in the treatment or prevention of various conditions including but not limited to Parkinson's disease (dopaminergic neurons), Alzheimer's disease (neural precursors), Huntington's disease (GABAergic neurons), blood disorders such as leukemia, lymphoma myeloma and anemia (hematopoietic cells), side-effects of radiation e.g., in transplant patients (hematopoietic precursors), cardiovascular disease, myocardial infarction, ischemic cardiac tissue or heart-failure (partially- or fully-differentiated cardiomyocytes), muscular dystrophy (skeletal muscle cells), liver cirrhosis or failure (hepatocytes), chronic hepatitis (hepatocytes), diabetes including type I diabetes (insulin-producing cells such as islet cells), ischemic brain damage (neurons), spinal cord injury (glial progenitor cells and motor neurons), amyotrophic lateral sclerosis (ALS) (motor neurons), orthopedic tissue injury (osteoblasts), kidney disease (kidney cells), corneal scarring (corneal stem cells), cartilage damage (chondrocytes), bone damage (osteogenic cells including osteocytes), osteoarthritis (chondrocytes), myelination disorders such as Pelizaeus-Merzbacher disease, multiple sclerosis, adenoleukodystrophies, neuritis and neuropathies (oligodendrocytes), and hair loss.

Pluripotent or differentiated cell populations may be provided as pharmaceutical compositions that are sterile and appropriate for in vivo use, optionally together with a pharmaceutically acceptable carrier. As used herein, a pharmaceutically-acceptable carrier means a non-toxic material that does not interfere with the effectiveness of the biological activity of the active ingredients. Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. Cell populations may be formulated for local or systemic administration including as part of an implant. Cells may be used alone or together with another agent, whether active or inactive, including but not limited to a scaffold, a matrix, and the like. These cells may further be included in a kit that additionally comprises at a minimum instructions for use of the cells, and optionally comprises one or more other agents whether active or inactive. The cells may be provided as a frozen aliquot of cells, a culture of cells, or a liquid suspension of cells.

Cells may be administered in numbers effective to produce a desired result, including but not limited to a short-term or long-term therapeutic result. Such result may include an improvement in or complete eradication of symptoms associated with a particular condition.

The cell numbers to be administered will depend on a number of factors including the weight and age of the subject, the type of condition being treated, the desired effect (e.g., short-term or long-term), and the like. Some treatments therefore may require as few as $10^3$ cells, while others may require $10^4$, $10^5$, $10^6$, $10^7$, $10^8$, $10^9$ or more cells.

In Vitro Uses

Cell populations produced as described herein may be studied for gene expression profiles and/or responses to various external stimuli in order to understand differentiation or other processes more fully. In some embodiments, disease-specific iPS cells may be used to model diseases (e.g., ALS or other diseases). In some embodiments, cells may be used in methods for screening and/or identifying agents (e.g., therapeutic agents such as inhibitors) being used or to be used clinically. These assays may measure the therapeutic efficacy and/or toxicity of the candidate agent, among other things. The readouts from such in vitro assays are correlative of the in vivo toxicity or efficacy such agents would exhibit in subjects. Thus, the effect of the agent on the differentiated cells generated according to the invention in vitro is a form of surrogate marker or readout for how the agent will function in vivo in a subject. The agents to be tested include those used clinically as well as experimental agents. In some more common embodiments, such testing will focus on the toxicity of agents including drugs in particular differentiated progeny. Accordingly, in these assays, the readout would be cell death (or conversely cell viability). These in vitro assays may employ suspensions of pluripotent or differentiated cells, adherent populations of pluripotent or differentiated cells, or three dimensional structures comprised of pluripotent or differentiated cells (e.g., in vitro organ tissues, matrices and architectures).

Administration of Cell Preparations

In one aspect, the disclosure provides methods for administering induced pluripotent stem cells or differentiated cells produced according to methods provided herein.

Cells can be administered to hosts by a variety of methods as discussed elsewhere herein. In certain embodiments the cells are administered by injection, such as by intravenous injection. In some embodiments cells are encapsulated for administration. In some embodiments the cells are administered in situ. In some embodiments of the invention, cells are administered in doses measured by the ratio of cells to body mass (weight). Alternatively, iPSCs can be administered in doses of a fixed number of cells.

In some embodiments the purity of cells for administration to a subject is about 100%. In other embodiments it is 95% to 100%. In some embodiments it is 85% to 95%. Particularly in the case of admixtures with other cells, the percentage of IPSCs or differentiated cells can be 25%-30%, 30%-35%, 35%-40%, 40%-45%, 45%-50%, 60%-70%, 70%-80%, 80%-90%, or 90%-95%.

The number of iPSCs or differentiated cells in a given volume can be determined by well known and routine procedures and instrumentation. The percentage of iPSCs or differentiated cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering cells for a given application will depend on a variety of factors. Prominent among these will be the species of subject, the nature of the disorder, dysfunction, or disease being treated and its state and distribution in the subject, the nature of other therapies and agents that are being administered, the optimum route for administration of the cells, survivability of cells via the route, the dosing regimen, and other factors that will be apparent to those skilled in the art. In particular, for instance, the choice of suitable carriers and other additives will depend on the exact route of administration and the nature of the particular dosage form, for example, liquid dosage form (e.g., whether the composition is to be formulated into a solution, a suspension, gel or another liquid form, such as a time release form or liquid-filled form).

Examples of compositions comprising iPSCs and/or differentiated cells include liquid preparations, including suspensions and preparations for intramuscular or intravenous administration (e.g., injectable administration), such as sterile suspensions or emulsions. Such compositions may comprise an admixture of cells with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Typically, the compositions will be isotonic, for example, they will have the same osmotic pressure as blood and lacrimal fluid when properly prepared for administration. The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

A pharmaceutically acceptable preservative or cell stabilizer can be employed to increase the life of cellular compositions. If such preservatives are included, it is well within the purview of the skilled artisan to select compositions that will not affect the viability or efficacy of the cells.

Sterile injectable solutions can be prepared by incorporating the cells utilized in practicing the present invention in the required amount of the appropriate solvent with various amounts of the other ingredients, as desired.

For any composition to be administered to an animal or human, and for any particular method of administration, it is preferred to determine therefore: toxicity, such as by determining the lethal dose (LD) and LD50 in a suitable animal model, e.g., rodent such as mouse or rat; and, the dosage of the composition(s), concentration of components therein, and timing of administering the composition(s), which elicit a suitable response. Such determinations do not require undue experimentation from the knowledge of the skilled artisan, this disclosure, and the documents cited herein. And, the time for sequential administrations can be ascertained without undue experimentation.

Order of administration, formulations, doses, frequency of dosing, and routes of administration of factors (such as the cytokines discussed herein) and IPSCs generally will vary with the disorder or disease being treated, its severity, the subject, other therapies that are being administered, the stage of the disorder or disease, and prognostic factors, among others. General regimens that have been established for other treatments provide a framework for determining appropriate dosing in cell-mediated direct or adjunctive therapy. These, together with the additional information provided herein, will enable the skilled artisan to determine appropriate administration procedures in accordance with embodiments of the invention, without undue experimentation.

It should be appreciated that iPSCs or differentiated cells described herein can be administered to a subject by any of a variety of routes known to those skilled in the art that may be used to administer cells to a subject.

Among methods that may be used in this regard in embodiments of the invention are methods for administering cells by a parenteral route. Parenteral routes of administration useful in various embodiments of the invention include, among others, administration by intravenous, intraarterial, intracardiac, intraspinal, intrathecal, intraosseous, intraarticular, intrasynovial, intracutaneous, intradermal, subcutaneous, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

Cells may be administered to the subject through a hypodermic needle by a syringe in some embodiments of the invention. In various embodiments, cells are administered to the subject through a catheter. In a variety of embodiments, cells are administered by surgical implantation. Further in this regard, in various embodiments, cells are administered to the subject by implantation using an arthroscopic procedure. In some embodiments cells are administered to the subject in or on a solid support, such as a polymer or gel. In various embodiments, cells are administered to the subject in an encapsulated form.

In additional embodiments of the invention, cells are suitably formulated for oral, rectal, epicutaneous, ocular, nasal, and/or pulmonary delivery and are administered accordingly.

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

Kits

In some embodiments, the disclosure provides kits for the production of induced pluripotent stem cells. In some embodiment, the kits include a Dot1L inhibitor. In some embodiments, the kits include a Dot1L inhibitor and a reprogramming cocktail (e.g., Sox2 and/or Oct4). In some embodiments, the kits include instructions for the production of induced pluripotent stem cells. In some embodiment, the kits include a YY1 inhibitor. In some embodiment, the kits include an SUV39H1 inhibitor.

In some embodiments, the disclosure provides a kit for the production of induced pluripotent stem cells. In some embodiments, the kit includes one or more Dot1L inhibitors. In some embodiments, the Dot1L inhibitor is a compound of Formula I, II, III or IV (for example one or more of the embodiments described herein), or a pharmaceutically acceptable salt thereof. In some embodiments, the Dot1L inhibitor is an expression inhibitor such as an RNAi inhibitor, for example one or more of the shRNA molecules provided herein.

In some embodiments, the kit includes one or more YY1 inhibitors and/or one or more SUV39H1 inhibitors. In some embodiments, the YY1 and/or SUV39H1 inhibitors are small molecule inhibitors or expression inhibitors such as RNAi inhibitors, for example one or more of the shRNA molecules provided herein.

In some embodiments, the kits include a reprogramming cocktail, or one or more moieties that can be used to generate a reprogramming cocktail. In some embodiments, the kit includes nucleic acids for the introduction of one or more stem cell-associated genes into cells, including, for example Oct3/4 (Pouf51), Sox1, Sox2, Sox3, Sox 15, Sox 18, NANOG, Klf1, Klf2, Klf4, Klf5, c-Myc, 1-Myc, n-Myc and LIN28. In some embodiments, the kit includes nucleic acids for the introduction of Oct-4, Sox2, c-MYC, and Klf4 into a cell. In some embodiments, the kit includes nucleic acids for the introduction of Oct-4, and Sox2 into a cell. In some embodiments, the nucleic acids are in delivery vehicle such as a viral vector, such as an adenoviral vector, a lentiviral vector or a retroviral vector.

In some embodiments, this kit includes one or more agents that enhance reprogramming efficiency including, for example, soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), trichostatin (TSA), and inhibitors of the TGF-β signaling pathway.

In some embodiments, this kit includes one or more agents that can bind markers to detect the presence of induced pluripotent stem cells. Such markers include SSEA4, SSEA3, Tra-1-81, Oct4, Sox2 and Nanog. Agents that bind such markers include antibodies and compounds that selectively bind the markers.

In some embodiments, the kit includes one or more elements useful in establishing a reprogramming cocktail, including buffers, salts, sugars, and other components that may be useful to support the growth and reprogramming of the differentiated cells.

In some embodiments, the kit includes one or more components for administering the induced pluripotent stem cells or differentiated cells. These components include pharmaceutical carriers for systemic and/or local administration of the cells.

In some embodiments, the kit includes separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another.

Dot1L

In one aspect, the disclosure provides methods of promoting the production of induced pluripotent stem cells. In some embodiments, the methods of producing induced pluripotent stem cells include inhibiting Dot1L in a differentiated cell. In some embodiments, the differentiated cell is cultured under reprogramming conditions to produce induced pluripotent stem cells. In some embodiments, the methods of producing induced pluripotent stem comprise inhibiting the methyltransferase activity of Dot1L.

In some embodiments, the methods of producing induced pluripotent stem comprise inhibiting Dot1L in a differentiated cell. Dot1L is a histone methyl transferase (HMT) known to methylate lysine 79 of histone H3 ("H3K79") in vivo (Feng et al. (2002) Curr. Biol. 12: 1052-1058). Similar to other HMTs, Dot1L contains a 5-adenosylmethionine (SAM) binding site and uses SAM as a methyl donor. Dot1L nucleic acid and polypeptides have previously been described (see, e.g., U.S. Patent Application Publication No. 2005-0048634 A1 (incorporated by reference); Feng et al. (2002) Curr. Biol. 12: 1052-1058; and Okada et al. (2005) Cell 121: 167-78). The human Dot1L homolog has been cloned, isolated, and has been designated as hDot1L (human Dot i-like protein). The sequences of the human nucleic acid and protein have been deposited under GenBank Accession No. AF509504, while the mouse homolog is GenBank Accession No. XP125730). Additional hDot1L homologs are known as well (See e.g., WO2012075500). The 2.5 angstrom resolution structure of a fragment of the hDot1L protein containing the catalytic domain (amino acids 1-416) has been solved; and the atomic coordinates for amino acids 1-416 of hDot1L have been determined and deposited in the RCSB database under ID code 1NW3 and described in the scientific literature (see Min, et al. (2003) Cell 112:711-723).

In some embodiments, Dot1L is inhibited by contacting Dot1l, or a cell expressing Dot1L with one or more of the compounds provided herein. In some embodiments, Dot1l is inhibited by contacting a cell expressing Dot1l with a nuclei acid that "knocks down" Dot1L, thereby inhibiting Dot1L. It should be appreciated that inhibiting Dot1L activity as used herein included both complete (i.e., about 100%) and partial inhibition. In some embodiments, partial inhibition results in 90% or less, 80% or less, 70% or less, 60% or less, 50% or less, 40% or less, 30% or less, 20% or less, 10% or less, 5% or less, 2% or less, or 1% or less up to complete inhibition of Dot1L. Dot1L inhibition in a cell can be achieved both by suppressing one more biological functions of Dot1L (e.g., by contacting the cell with a compound that binds the active site of Dot1L), or by "knocking down" Dot1L (e.g., by contacting the cell with a nucleic acid that prevents production of Dot1L in the cell. In some embodiments, Dot1L is inhibited by inhibiting the catalytic function of Dot1L.

In one aspect, the disclosure provides methods of producing induced pluripotent stem comprise inhibiting Dot1L in a differentiated cell. In some embodiments inhibiting Dot1L comprises inhibiting the methyltransferase activity of Dot1L. In some embodiments, Dot1L is inhibited by contacting the cell with one or more small molecules that inhibit Dot1L activity. Small molecules that inhibit Dot1L are described for instance in WO2012/075500, WO2012/082436, WO2012/075381, and WO2012/075492.

In some embodiments, Dot1L is inhibited by contacting the differentiated cell with a composition comprising a compound of formula I:

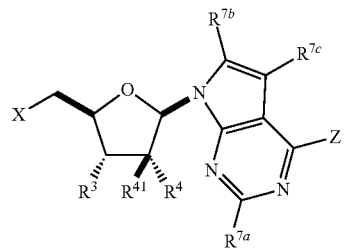

or a pharmaceutically acceptable salt, hydrate, enantiomer or stereoisomer thereof, wherein independently for each occurrence, X is

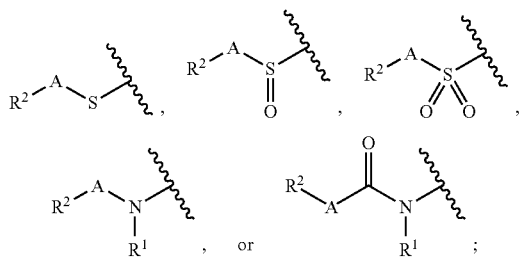

$R^1$ is hydrogen, alkyl, cycloalkyl, alkylcycloalkyl, alkylaryl, haloalkyl, formyl, heterocyclyl, heterocyclylalkyl,

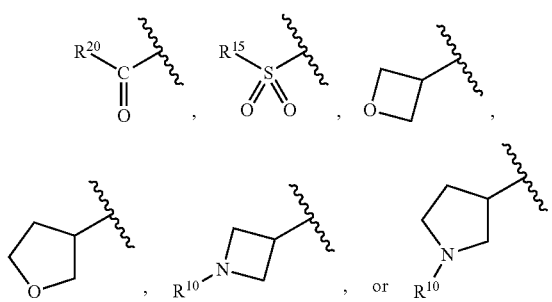

or ($C_2$-$C_4$) alkyl substituted with

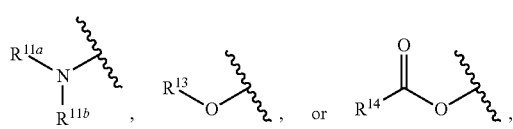

except that when X is

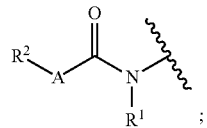

$R^1$ is not

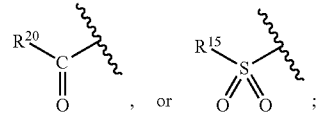

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl, or silyl;
$R^{14}$ is hydrogen, alkyl, aryl, heteroaryl, aralkyl, or heteroaralkyl;
$R^{15}$ is alkyl, cycloalkyl, or cycloalkylalkyl;
$R^{20}$ is hydrogen, alkyl, cycloalkyl, or cycloalkylalkyl;

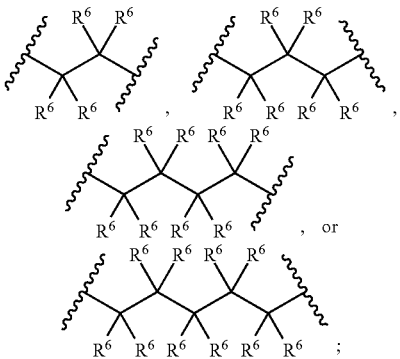

$R^2$ is

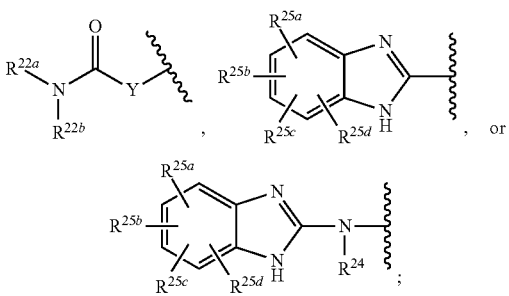

Y is —NH—, —N(alkyl)-, —O—, or —$CR^6{}_2$—;
$R^{22a}$ is aryl, heteroaryl, aralkyl, heteroaralkyl, fused bicyclyl, biaryl, aryloxyaryl, heteroaryloxyaryl, aryloxyheteroaryl, or heteroaryloxyheteroaryl;

$R^{22b}$ is hydrogen or alkyl;

$R^{24}$ is hydrogen or alkyl;

$R^{25a}$, $R^{25b}$, $R^{25c}$, and $R^{25d}$ independently are -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $R_{S4}$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R^3$ is hydrogen, halogen, hydroxy, alkyloxy, aralkyloxy, alkylcarbonyloxy, or silyloxy;

$R^4$ is hydrogen, halogen, hydroxy, alkyloxy, aralkyloxy, alkylcarbonyloxy, or silyloxy;

$R^{41}$ is hydrogen, alkyl, or alkynyl;

Z is hydrogen or

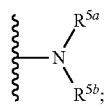

$R^{5a}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl, or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl, and heteroaryl;

$R^{5b}$ is hydrogen, alkyl, haloalkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl, or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl, and heteroaryl; or taken together with $R^{5a}$ and the nitrogen to which it is attached forms a 4- to 8-membered heterocyclyl comprising 0 or 1 additional heteroatoms;

$R^6$ is hydrogen, alkyl, or halo; or two geminal $R^6$ taken together are ethylene, propylene, or butylene;

$R^{7a}$ is hydrogen, lower alkyl, lower haloalkyl, cyano, halo, lower alkoxy, or $C_3$-$C_5$ cycloalkyl, optionally substituted with 1, 2, or 3 substituents independently selected from the group consisting of cyano, lower alkoxy, and halo;

$R^{7b}$ is hydrogen, lower alkyl, lower haloalkyl, cyano, halo, lower alkoxy, or $C_3$-$C_5$ cycloalkyl, optionally substituted with 1, 2, or 3 substituents independently selected from the group consisting of cyano, lower alkoxy, and halo; and $R^{7c}$ is hydrogen, lower alkyl, lower haloalkyl, cyano, halo, lower alkoxy, or $C_3$-$C_5$ cycloalkyl, optionally substituted with 1, 2, or 3 substituents independently selected from the group consisting of cyano, lower alkoxy, and halo.

Compounds of formula I, methods of making thereof, and methods of use thereof can be found in WO 2012/075500, which is incorporated herein by reference.

In certain embodiments, X is

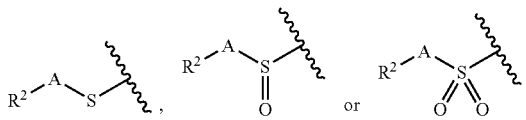

In certain embodiments, X is

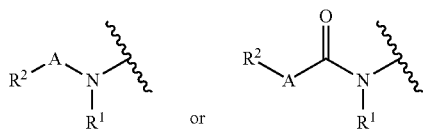

In certain embodiments, $R^2$ is H

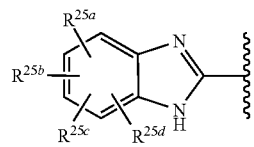

In certain embodiments, $R^2$ is

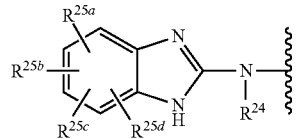

In certain embodiments, $R^{24}$ is hydrogen or alkyl. In certain embodiments, $R^{24}$ is hydrogen.

In certain embodiments, $R^{25a}$ is hydrogen, alkyl, —O-alkyl, halogen, trifluoroalkyl, —O— trifluoromethyl, or —$SO_2$-trifluoromethyl. In certain embodiments, $R^{25b}$ is hydrogen, alkyl, halogen, or trifluoroalkyl. In certain embodiments, $R^{25c}$ is hydrogen, alkyl, or halogen. In certain embodiments, $R^{25c}$ is hydrogen or halogen.

In certain embodiments, $R^2$ is

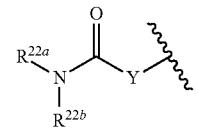

In certain embodiments, Y is —NH— or —N(alkyl)-. In certain embodiments, Y is —NH—. In certain embodiments, Y is —N(CH_3)—. In certain embodiments Y is —O—. In certain embodiments, Y is —$CH_2$—.

In certain embodiments, $R^{22a}$ is aryl or aralkyl. In certain embodiments, $R^{22a}$ is substituted phenyl or substituted benzyl. In certain embodiments, $R^{22a}$ is one of the following:

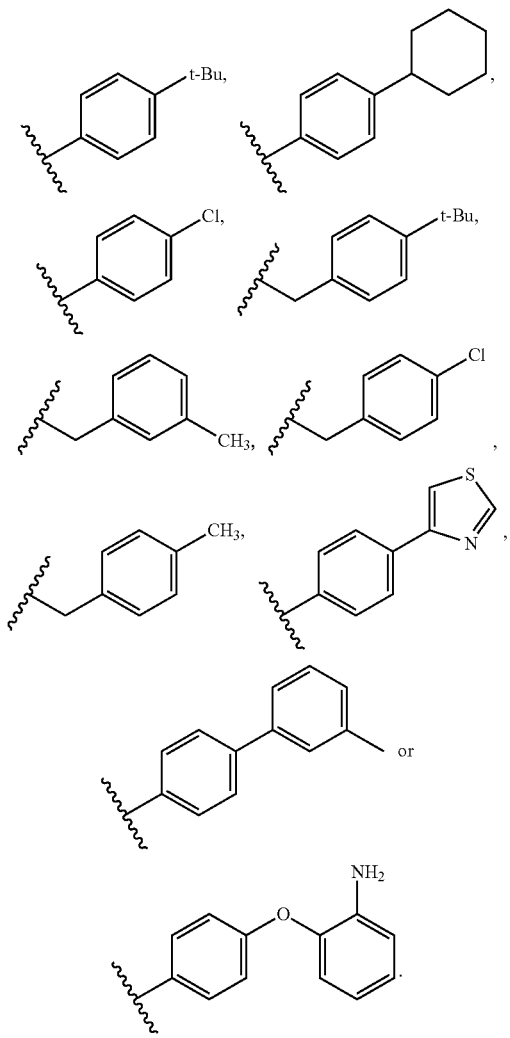

In certain embodiments, $R^{22a}$ is one of the following:

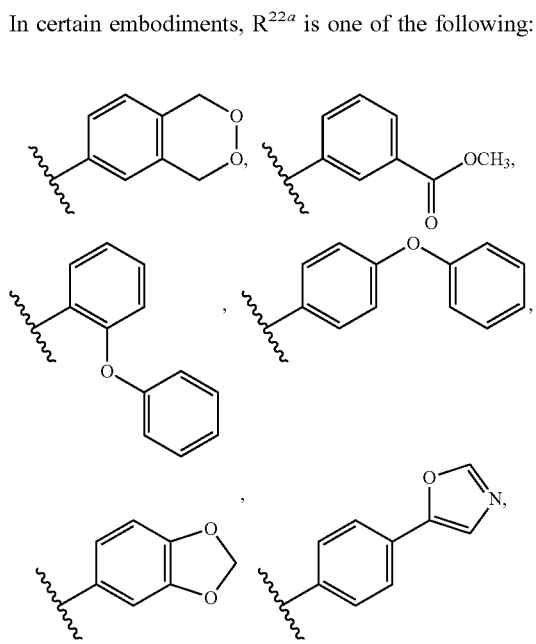

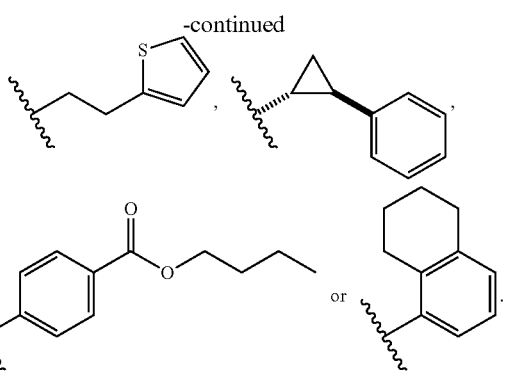

In certain embodiments, $R^{22b}$ is hydrogen. In certain embodiments, $R^{22b}$ is methyl.

In certain embodiments, $R^1$ is hydrogen. In certain embodiments, $R^1$ is alkyl. In certain embodiments, $R^1$ is —CH$_3$, —CH$_2$CH$_3$, —CH$_2$CH(CH$_3$)$_2$ or —CH$_2$CH$_2$CH(CH$_3$)$_2$. In certain embodiments, $R^1$ is $C_3$-$C_7$ cycloalkyl. In certain embodiments, $R^1$ is cyclopropyl, cyclopropylmethyl, 2-cyclopropylethyl, cyclobutyl, cyclobutylmethyl, 2-cyclobutylethyl, cyclopentyl, cyclopentylmethyl, or 2-cyclopentylethyl. In certain embodiments, $R^1$ is

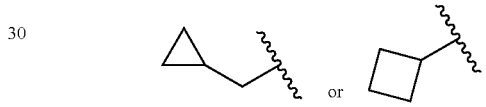

In certain embodiments, $R^1$ is —CH$_2$CF$_3$. In certain embodiments, $R^1$ is —CH$_2$Ph. In certain embodiments, $R^1$ is —C(=O)H. In certain embodiments, $R^1$ is —C(=O)CH$_3$. In certain embodiments, $R^1$ is heterocyclyl or heterocyclylalkyl. In certain embodiments, $R^1$ is

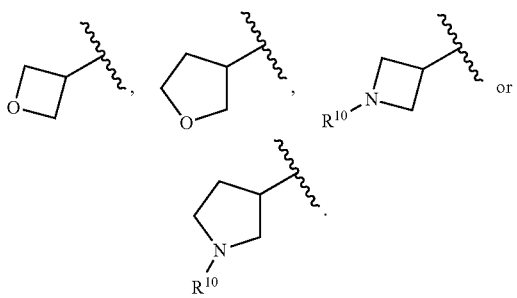

In certain embodiments, $R^1$ is

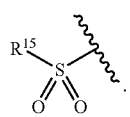

In certain embodiments, $R^{15}$ is alkyl. In certain embodiments, $R^{15}$ is cycloalkyl. In certain embodiments, $R^{15}$ is cycloalkylalkyl.

In certain embodiments, $R^1$ is ($C_2$-$C_4$) alkyl substituted with

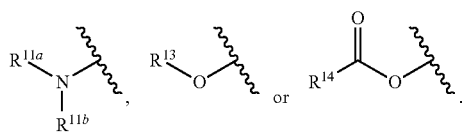

In certain embodiments, $R^1$ is

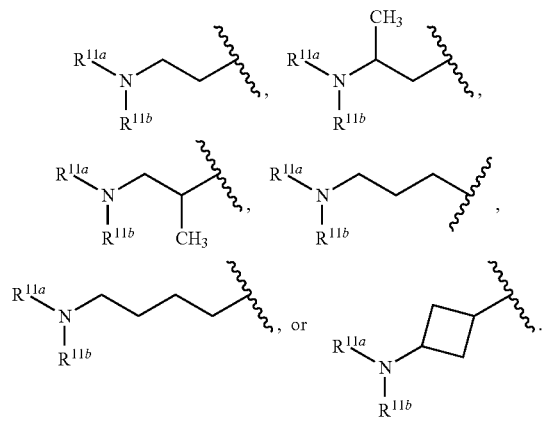

In certain embodiments, $R^{11a}$ is hydrogen, alkyl, or alkyl-cycloalkyl. In certain embodiments, $R^{11a}$ is hydrogen, methyl, or i-propyl. In certain embodiments, $R^1$ is

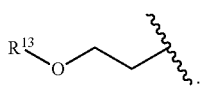

In certain embodiments, $R^{13}$ is hydrogen.

In certain embodiments, $R^1$ is

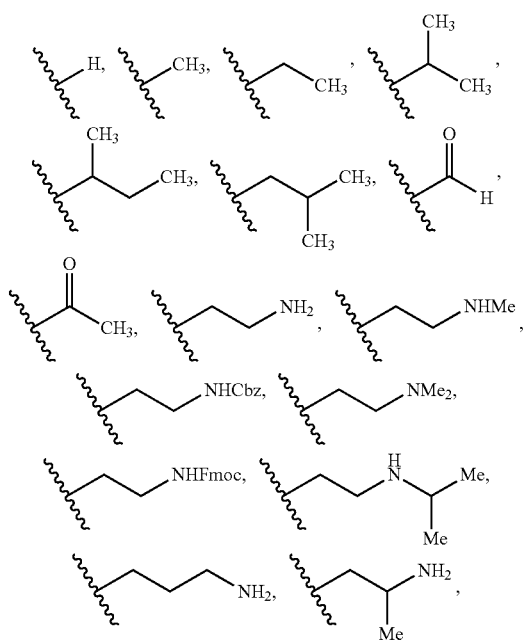

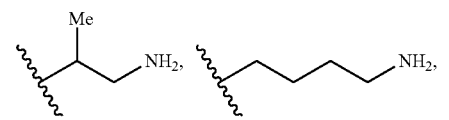

In certain embodiments, A is

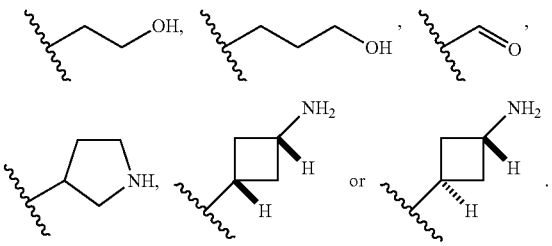

In certain embodiments, A is

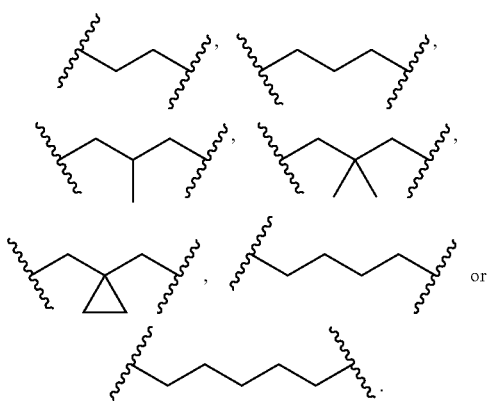

In certain embodiments, A is

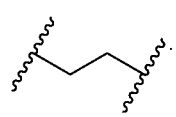 [SMILES: *CC*]

In certain embodiments, A is

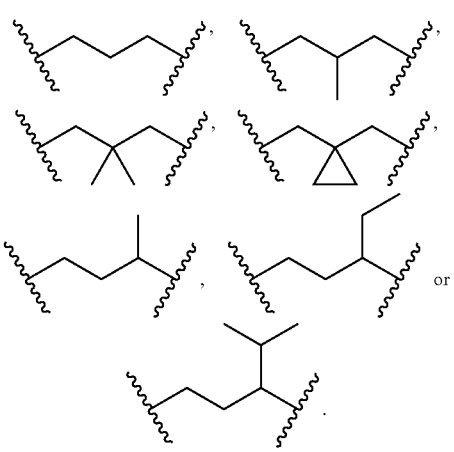

In certain embodiments, A is

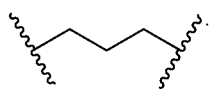 [SMILES: *CCC*]

In certain embodiments, A is

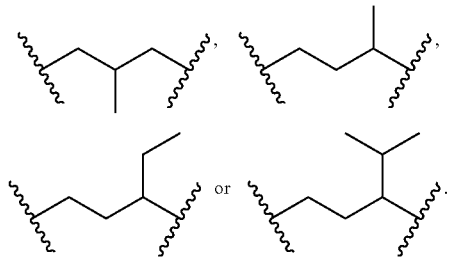

certain embodiments, A is

In certain embodiments, A is

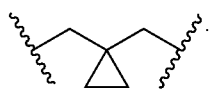

In certain embodiments, A is

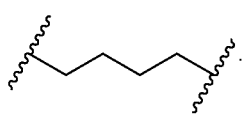 [SMILES: *CCCC*]

In certain embodiments, A is

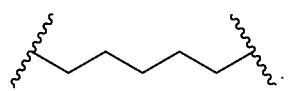 [SMILES: *CCCCC*]

In certain embodiments, A is

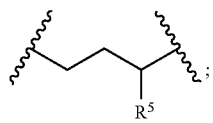

and $R^6$ is alkyl. In certain embodiments, A is

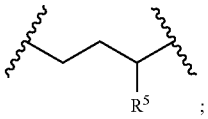

and $R^6$ is methyl, ethyl, or isopropyl.

In certain embodiments, $R^3$ is hydroxyl. In certain embodiments, $R^3$ is hydrogen. In certain embodiments, $R^4$ is hydroxyl. In certain embodiments, $R^4$ is hydrogen. In certain embodiments, $R^{41}$ is hydrogen. In certain embodiments, $R^{41}$ is methyl. In certain embodiments, $R^3$ is hydroxyl; and $R^4$ is hydroxyl. In certain embodiments, $R^3$ is hydroxyl; $R^4$ is hydroxyl; and $R^{41}$ is hydrogen. In certain embodiments, $R^3$ is hydroxyl; $R^4$ is hydroxyl; and $R^{41}$ is methyl. In certain embodiments, $R^3$ is hydrogen; and $R^4$ is hydroxyl. In certain embodiments, $R^3$ is hydrogen; $R^4$ is hydroxyl; and $R^{41}$ is hydrogen. In certain embodiments, $R^3$ is hydrogen; $R^4$ is hydroxyl; and $R^{41}$ is methyl. In certain embodiments, $R^3$ is hydroxyl; and $R^4$ is hydrogen. In certain embodiments, $R^3$ is hydroxyl; $R^4$ is hydrogen; and $R^{41}$ is hydrogen. In certain embodiments $R^3$ is hydroxyl; $R^4$ is hydrogen; and $R^{41}$ is methyl.

In certain embodiments, Z is hydrogen or

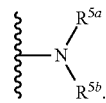

In certain embodiments, Z is hydrogen. In certain embodiments, Z is

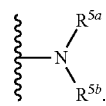

In certain embodiments, $R^{5a}$ is hydrogen, alkyl, carbocyclyl, heterocyclyl, aryl, heteroaryl, carbocyclylalkyl, heterocyclylalkyl, aralkyl, or heteroaralkyl. In certain embodiments, $R^{5a}$ is hydrogen, aralkyloxyalkyl, alkyl, aryl, aralkyl, aminoalkyl or hydroalkyl. In certain embodiments, $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH. In certain embodiments, $R^{5b}$ is hydrogen, alkyl, carbocyclyl, heterocyclyl, aryl, heteroaryl, carbocyclylalkyl, heterocyclylalkyl, aralkyl, or heteroaralkyl. In certain embodiments, $R^{5b}$ is hydrogen, aralkyloxyalkyl, alkyl, aryl, aralkyl, aminoalkyl or hydroalkyl. In certain embodiments, $R^{5b}$ is hydrogen. In certain embodiments, $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH; and R is —H.

In certain embodiments, $R^{7a}$ is hydrogen or lower alkyl. In certain embodiments, $R^{7a}$ is hydrogen. In certain embodiments, $R^{7b}$ is hydrogen or lower alkyl. In certain embodiments, $R^{7b}$ is hydrogen. In certain embodiments, $R^{7c}$ is hydrogen or lower alkyl. In certain embodiments, $R^{7c}$ is hydrogen.

In some embodiments, Dot1L is inhibited by contacting the differentiated cell with a composition comprising a compound of formula II:

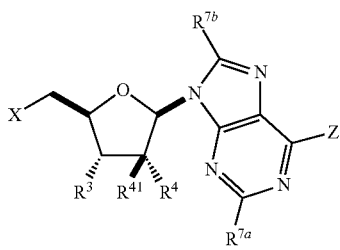

or a pharmaceutically acceptable salt, hydrate, enantiomer or stereoisomer thereof, wherein independently for each occurrence, X is

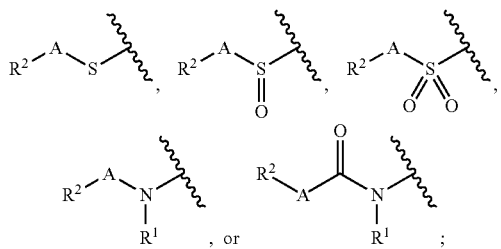

$R^1$ is hydrogen, alkyl, cycloalkyl, alkylcycloalkyl, alkylaryl, haloalkyl, formyl, heterocyclyl, heterocyclylalkyl,

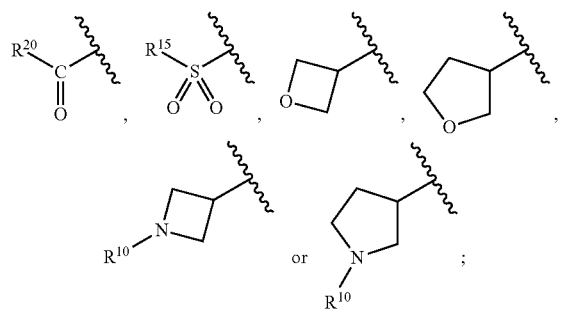

$(C_2-C_4)$alkyl substituted with

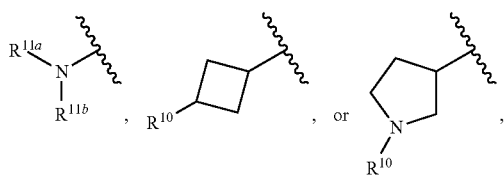

except that when X is

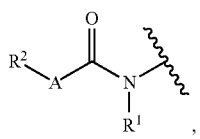

$R^1$ is not

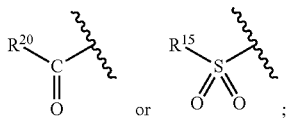

$R^{10}$ is hydrogen or alkyl;
$R^{11a}$ is hydrogen, alkyl, or alkyl-cycloalkyl;
$R^{11b}$ is hydrogen or alkyl; or taken together with $R^{11a}$ and the nitrogen to which it is attached forms a 4- to 8-membered heterocyclyl comprising 0 or 1 additional heteroatoms;
$R^{13}$ is hydrogen, alkyl, aryl, heteroaryl, aralkyl, heteroaralkyl or silyl;
$R^{14}$ is hydrogen, alkyl, aryl, heteroaryl, aralkyl or heteroaralkyl;
$R^{15}$ is alkyl, cycloalkyl or cycloalkylalkyl;
$R^{20}$ is hydrogen, alkyl, cycloalkyl or cycloalkylalkyl;
A is

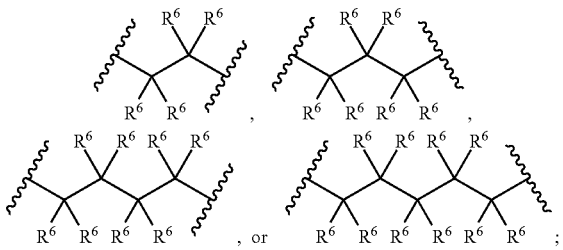

$R^2$ is

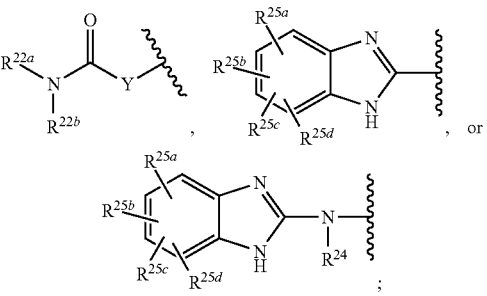

Y is —NH—, —N(alkyl)-, —O—, or —$CR^6_2$;
$R^{22a}$ is aryl, heteroaryl, aralkyl, heteroaralkyl, fused bicyclyl, biaryl, aryloxyaryl, heteroaryloxyaryl, aryloxyheteroaryl or heteroaryloxyheteroaryl;
$R^{22b}$ is hydrogen or alkyl;
$R^{24}$ is hydrogen or alkyl;
$R^{25a}$, $R^{25b}$, $R^{25c}$, $R^{25d}$ are independently -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $Rs_4$, $Rs_4$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, 1, and $Rs_4$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alky lamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R^3$ is hydrogen, halogen, hydroxy, alkyloxy, aralkyloxy, alkylcarbonyloxy or silyloxy;

$R^4$ is hydrogen, halogen, hydroxy, alkyloxy, aralkyloxy, alkylcarbonyloxy or silyloxy;

$R^{41}$ is hydrogen, alkyl or alkynyl;

Z is hydrogen or

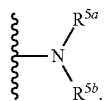

$R^{5a}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylarhinoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl;

$R^{5b}$ is hydrogen, alkyl, alkenyl, alkynyl, carbocyclyl, heterocyclyl, aryl, heteroaryl, biaryl, alkenylalkyl, alkynylalkyl, carbocyclylalkyl, heterocyclylalkyl, aralkyl, heteroaralkyl, alkylcarbonylaminoalkyl, arylcarbonylaminoalkyl, aralkylcarbonylaminoalkyl, arylsulfonylaminoalkyl, alkylthioalkyl, aralkylthioalkyl or heteroaralkylthioalkyl; or alkyl substituted with 1, 2 or 3 substituents independently selected from the group consisting of hydroxy, halo, carboxy, alkyoxy, aryloxy, aralkyloxy, nitro, amino, amido, aryl and heteroaryl; or taken together with $R^{5a}$ and the nitrogen to which it is attached forms a 4- to 8-membered heterocyclyl comprising 0 or 1 additional heteroatoms;

$R^6$ is hydrogen, alkyl or halo; or two geminal $R^6$ taken together are ethylene, propylene or butylene; and $R^{7a}$ is hydrogen, lower alkyl, lower haloalkyl, cyano, halo, lower alkoxy, or $C_3$-$C_5$ cycloalkyl, optionally substituted with 1, 2, or 3 substituents independently selected from the group consisting of cyano, lower alkoxy and halo; and $R^{7b}$ is hydrogen, lower alkyl, lower haloalkyl, cyano, halo, lower alkoxy, or $C_3$-$C_5$ cycloalkyl, optionally substituted with 1, 2, or 3 substituents independently selected from the group consisting of cyano, lower alkoxy and halo.

Compounds of formula II, methods of making thereof, and methods of use thereof can be found in WO 2012/082436, which is incorporated herein by reference.

In certain embodiments, X is

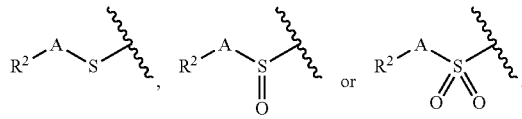

In certain embodiments, X is

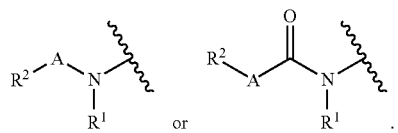

In certain embodiments, $R^2$ is

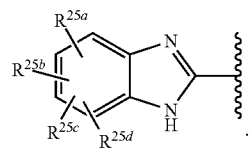

In certain embodiments, $R^2$ is

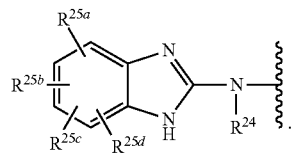

In certain embodiments, $R^{24}$ is hydrogen or alkyl. In certain embodiments, $R^{2a}$ is hydrogen. In certain embodiments, $R^{25a}$ is hydrogen, alkyl, —O-alkyl, halogen, trifluoroalkyl, —O-trifluoromethyl, or —$SO_2$-trifluoromethyl. In certain embodiments, $R^{25b}$ is hydrogen, alkyl, halogen, or trifluoroalkyl. In certain embodiments, $R^{25c}$ is hydrogen, alkyl, or halogen. In certain embodiments, $R^{25c}$ is hydrogen or halogen.

In certain embodiments, $R^2$ is

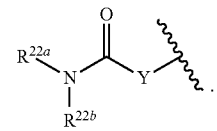

In certain embodiments, Y is —NH— or —N(alkyl)-. In certain embodiments, Y is —NH—. In certain embodiments, Y is —N($CH_3$)—. In certain embodiments, Y is —O—. In certain embodiments, Y is —$CH_2$—. In certain embodiments, $R^{22a}$ is aryl or aralkyl. In certain embodiments, $R^{22a}$ is substituted phenyl or substituted benzyl. In certain embodiments, $R^{22a}$ is one of the following:

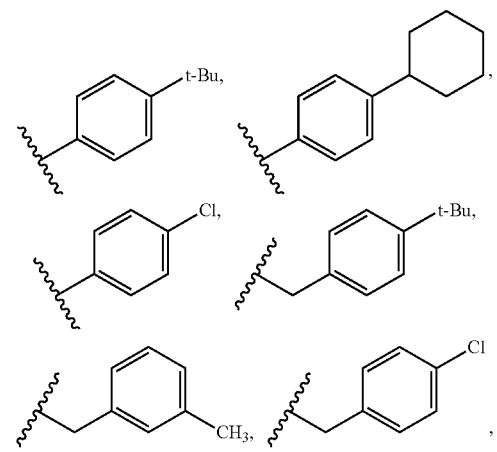

In certain embodiments, R¹ is hydrogen. In certain embodiments, R¹ is alkyl. In certain embodiments, R¹ is —CH₃, —CH₂CH₃, —CH₂CH(CH₃)₂ or —CH₂CH₂CH(CH₃)₂. In certain embodiments, R¹ is

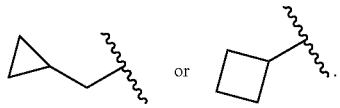 [SMILES: *CC1CC1 ; *C1CCC1]

In certain embodiments, R¹ is —CH₂CF₃. In certain embodiments, R¹ is —CH₂Ph. In certain embodiments, R¹ is —C(=O)H. In certain embodiments, R¹ is —C(=O)CH₃. In certain embodiments, R¹ is heterocyclyl or heterocyclylalkyl. In certain embodiments, R¹ is

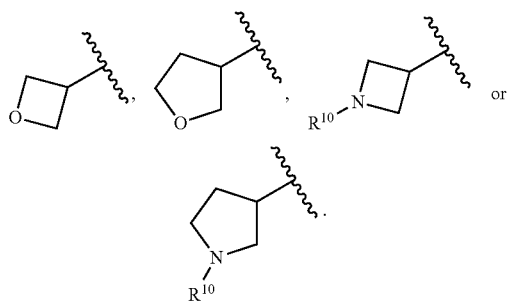

In certain embodiments, R¹ is

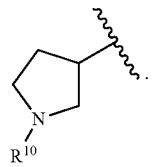

In certain embodiments, R is

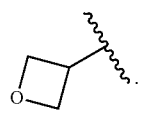

In certain embodiments, R¹ is

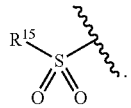

In certain embodiments, R¹⁵ is alkyl. In certain embodiments, R¹⁵ is methyl. In certain embodiments, R¹⁵ is cycloalkyl. In certain embodiments, R¹⁵ is cycloalkylalkyl.

In certain embodiments, R¹ is (C₂-C₄)alkyl substituted with

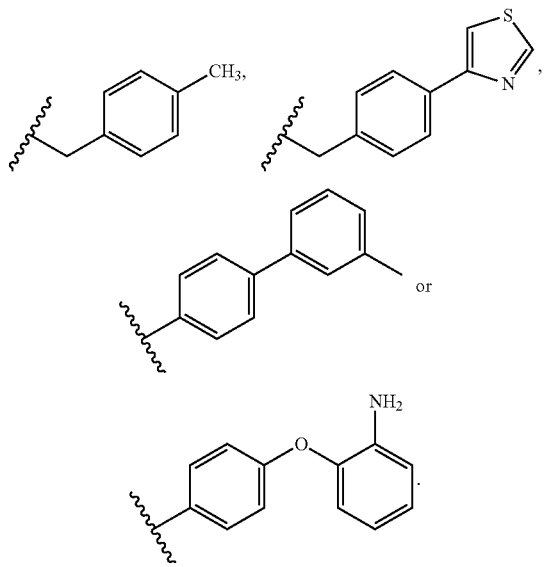

In certain embodiments, R²²ᵃ is one of the following:

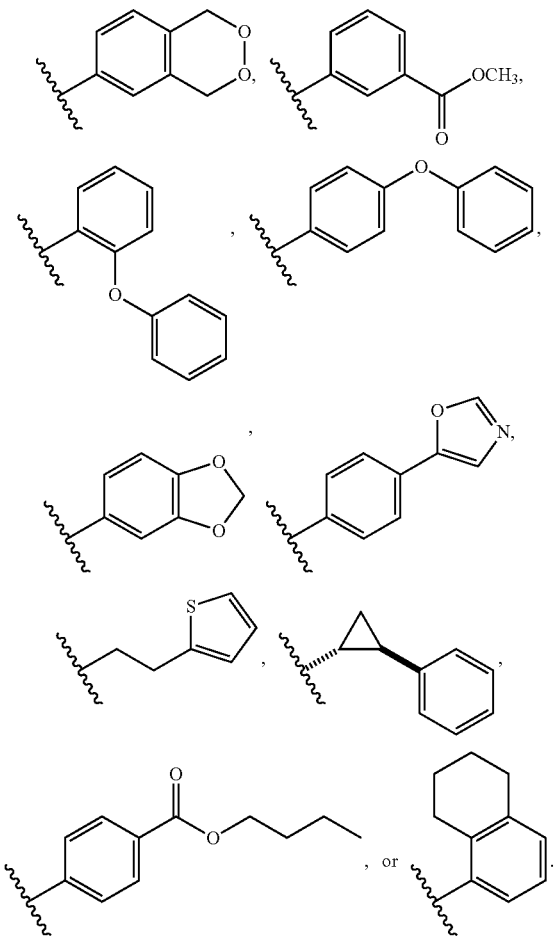

In certain embodiments, R²²ᵇ is hydrogen. In certain embodiments, R²²ᵇ is methyl.

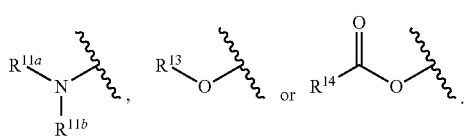

In certain embodiments, R¹ is

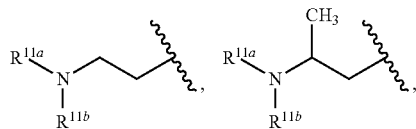

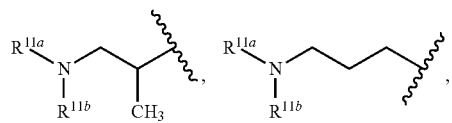

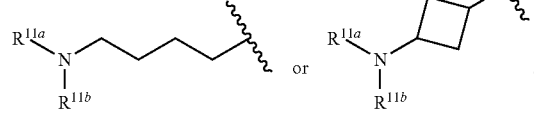

In certain embodiments, $R^{11a}$ is hydrogen, alkyl, or alkylcycloalkyl. In certain embodiments, $R^{11a}$ is hydrogen, methyl, or i-propyl. In certain embodiments, $R^{22a}$ is heteroaryl. In certain embodiments, $R^{22a}$ is substituted phenyloxyphenyl, substituted 4-(phenyl)phenyl or optionally substituted 4-(heteroaryl)phenyl.

In certain embodiments, $R^{22a}$ is one of the following:

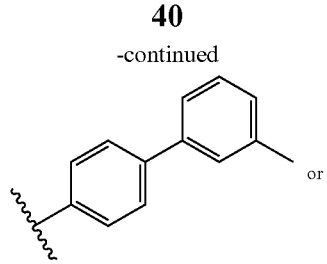

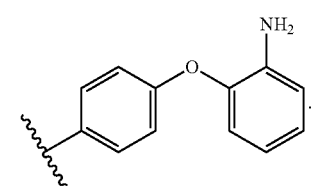

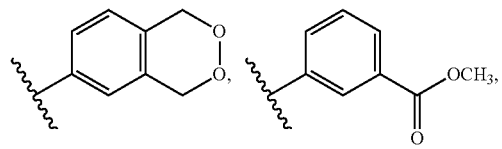

-continued

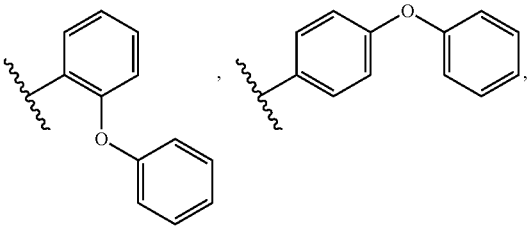

In certain embodiments, $R^{22a}$ is one of the following:

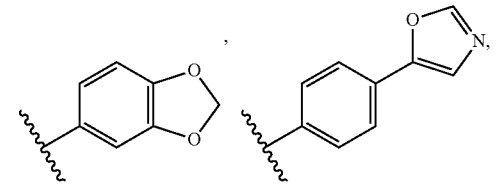

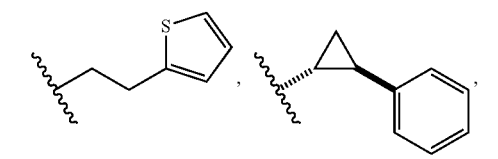

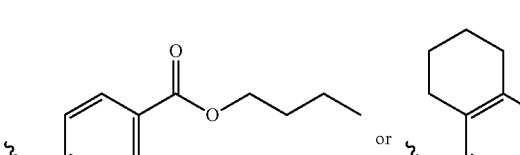

In certain embodiments, $R^{11a}$ is hydrogen. In certain embodiments, $R^{11b}$ is hydrogen. In certain embodiments, $R^{11b}$ is methyl.

In certain embodiments, $R^1$ is
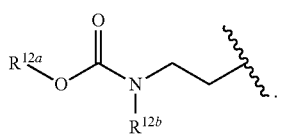
In certain embodiments, $R^1$ is
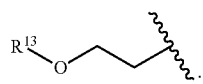
In certain embodiments, $R^{13}$ is hydrogen.
In certain embodiments, $R^1$ is
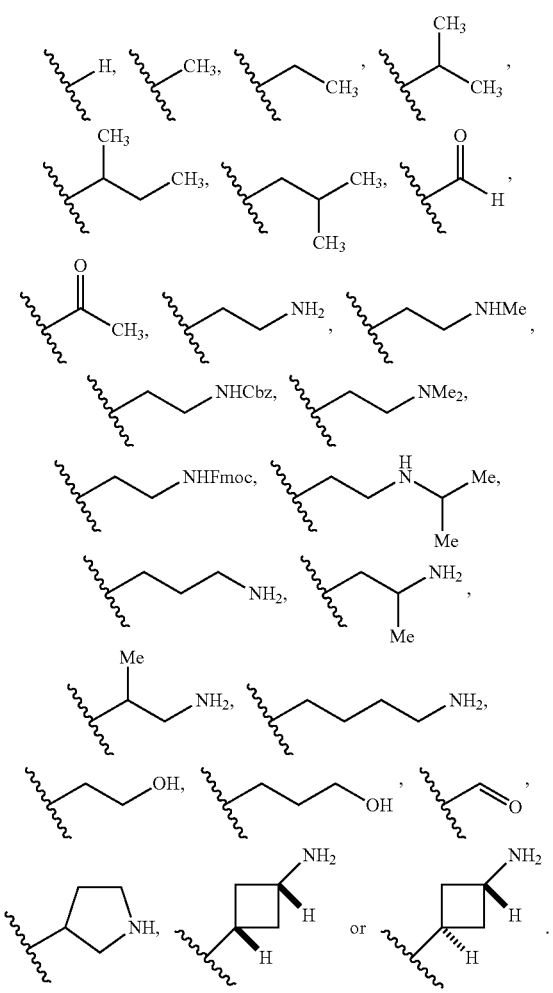
In certain embodiments, A is
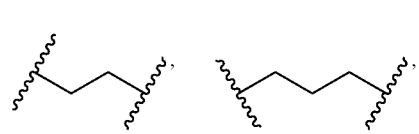
-continued
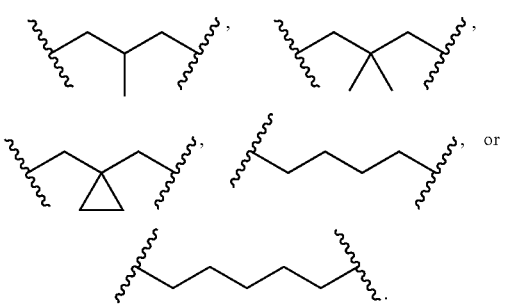
In certain embodiments, A is
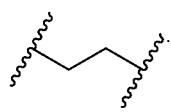 [SMILES: *CC*]
In certain embodiments, A is
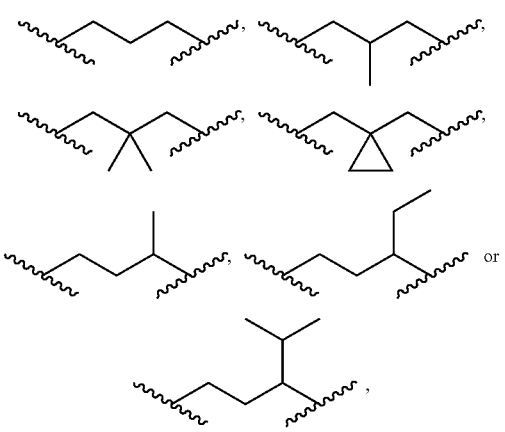
In certain embodiments, A is
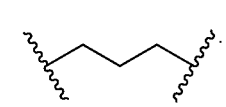
In certain embodiments, A is
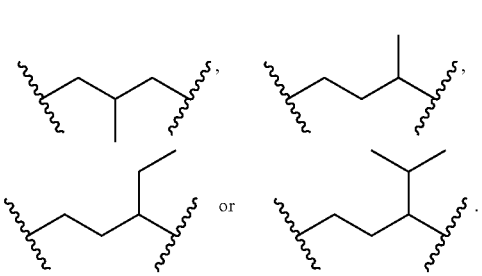

In certain embodiments, A is

In certain embodiments, A is

In certain embodiments, A is

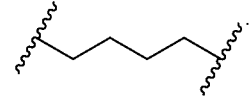 [SMILES: *CCCC*]

In certain embodiments, A is

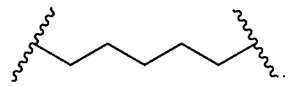 [SMILES: *CCCCC*]

In certain embodiments, A is

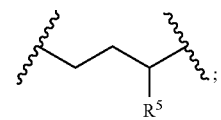

and $R^6$ is alkyl. In certain embodiments, A is

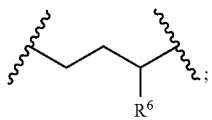

and $R^6$ is methyl, ethyl, or isopropyl.

In certain embodiments, $R^3$ is hydroxyl. In certain embodiments, $R^3$ is hydrogen. In certain embodiments, $R^3$ is hydroxyl. In certain embodiments, $R^3$ is hydrogen. In certain embodiments, $R^{41}$ is hydrogen. In certain embodiments, $R^{41}$ is methyl. In certain embodiments, $R^3$ is hydroxyl; and $R^4$ is hydroxyl. In certain embodiments, $R^3$ is hydroxyl; $R^4$ is hydroxyl; and $R^{41}$ is hydrogen. In certain embodiments, $R^3$ is hydroxyl; $R^4$ is hydroxyl; and $R^{41}$ is methyl. In certain embodiments, $R^3$ is hydrogen; and $R^4$ is hydroxyl. In certain embodiments, $R^3$ is hydrogen; $R^4$ is hydroxyl; and $R^{41}$ is hydrogen. In certain embodiments $R^3$ is hydrogen; $R^4$ is hydroxyl; and $R^{41}$ is methyl. In certain embodiments, $R^3$ is hydroxyl; $R^4$ is hydrogen; and $R^{41}$ is hydrogen. In certain embodiments, $R^3$ is hydroxyl; $R^4$ is hydrogen; and $R^{41}$ is methyl. In certain embodiments, Z is hydrogen or

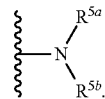

In certain embodiments, Z is hydrogen. In certain embodiments, Z is

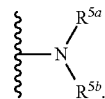

In certain embodiments, $R^{5a}$ is hydrogen, alkyl, carbocyclyl, heterocyclyl, aryl, heteroaryl, carbocyclylalkyl, heterocyclylalkyl, aralkyl, or heteroaralkyl. In certain embodiments, $R^{5a}$ is hydrogen, aralkyloxyalkyl, alkyl, aryl, aralkyl, aminoalkyl or hydroxyalkyl. In certain embodiments, $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH. In certain embodiments, $R^{5b}$ is hydrogen, alkyl, carbocyclyl, heterocyclyl, aryl, heteroaryl, carbocyclylalkyl, heterocyclylalkyl, aralkyl, or heteroaralkyl. In certain embodiments, $R^{5b}$ is hydrogen, aralkyloxyalkyl, alkyl, aryl, aralkyl, aminoalkyl or hydroalkyl. In certain embodiments, $R^{5b}$ is hydrogen. In certain embodiments, $R^{5a}$ is —H, —CH$_2$CH$_2$OCH$_2$Ph, —CH$_2$CH$_3$, —CH(CH$_3$)$_2$, -Ph, —CH$_2$CH(CH$_3$), —CH$_3$, —CH$_2$Ph, —CH$_2$CH$_2$NH$_2$, —CH$_2$(cyclohexyl) or —CH$_2$CH$_2$OH; and $R^{5b}$ is —H.

In certain embodiments, $R^{7a}$ is hydrogen or lower alkyl. In certain embodiments, $R^{7a}$ is hydrogen. In certain embodiments, $R^{7b}$ is hydrogen or lower alkyl. In certain embodiments, $R^{7b}$ is hydrogen.

In some embodiments, Dot1L is inhibited by contacting the differentiated cell with a composition comprising a compound of formula III:

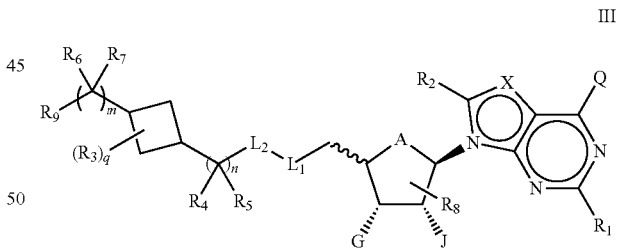

III or pharmaceutically acceptable salt or ester thereof, wherein:

A is O or CH$_2$;

each of G and J, independently, is H, halo, C(O)OH, C(O)O—C$_1$-C$_6$ alkyl or OR$_a$, R$_a$ being H, C$_1$-C$_6$ alkyl or C(O)—C$_1$-C$_6$ alkyl, wherein C(O)O—C$_1$-C$_6$ alkyl, C$_1$-C$_6$ alkyl or C(O)—C$_1$-C$_6$ alkyl is optionally substituted with one or more substituents selected from the group consisting of halo, cyano, hydroxyl, carboxyl, C$_1$-C$_6$ alkoxyl, amino, mono-C$_1$-C$_6$ alkylamino, di-C$_1$-C$_6$ alkylamino, and C$_3$-C$_8$ cycloalkyl;

Q is H, NH$_2$, NHR$_b$, NR$_b$R$_c$, R$_b$, or OR$_b$, in which each of R$_b$ and R$_c$ independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 7-membered heterocycloalkyl, 5 to 10-membered heteroaryl, or -M₁-T₁ in which Mt is a bond or $C_1$-$C_6$ alkyl linker optionally substituted with halo, cyano, hydroxyl or $C_1$-$C_6$ alkoxyl and $T_1$ is $C_3$-$C_8$ cycloalkyl, $C_6$-$C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $Rs_1$, $Rs_1$ being amino, $C_1$-$C_6$ alkoxyl, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_{S1}$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 6-membered heterocycloalkyl, or 5 to 6-membered heteroaryl, and $R_d$ being optionally substituted with one or more substituents selected from the group consisting of $C_1$-$C_6$ alkyl, $C_2$-$C_6$ alkenyl, $C_2$-$C_6$ alkynyl, halo, hydroxyl, carboxyl, cyano, $C_1$-$C_6$ alkoxyl, $C_1$-$C_6$ alkylsulfonyl, amino, mono-$C_1$-$C_6$ alkylamino, di-$C_1$-$C_6$ alkylamino, $C_3$-$C_5$ cycloalkyl, $C_6$-$C_{10}$ aryl, 4 to 6-membered heterocycloalkyl, and 5 to 6-membered heteroaryl and with $C_3$-$C_8$ cycloalkyl, $C_6$-$C_{10}$ aryl, 4 to 6-membered heterocycloalkyl, or 5 to 6-membered heteroaryl further optionally substituted with $C_1$-$C_6$ alkyl, $C_2$-$C_6$ alkenyl, $C_2$-$C_6$ alkynyl, halo, hydroxyl, carboxyl, C(O)OH, C(O)O—$C_1$-$C_6$ alkyl, OC(O)—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, or 5 to 6-membered heteroaryl;

each of $R_1$, $R_2$, $R_3$, $R_4$, $R_5$, $R_6$, and $R_7$, independently, is H, halo, hydroxyl, carboxyl, cyano, $Rs_2$, $Rs_2$ being amino, $C_1$-$C_6$ alkoxyl, $C_1$-$C_6$ alkyl, $C_2$-$C_6$ alkenyl, or $C_2$-$C_6$ alkynyl, and each $Rs_2$ being optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl;

$R_8$ is H, halo or $Rs_3$, $Rs_3$ being $C_1$-$C_6$ alkyl, $C_2$-$C_6$ alkenyl, or $C_2$-$C_6$ alkynyl, and $Rs_3$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

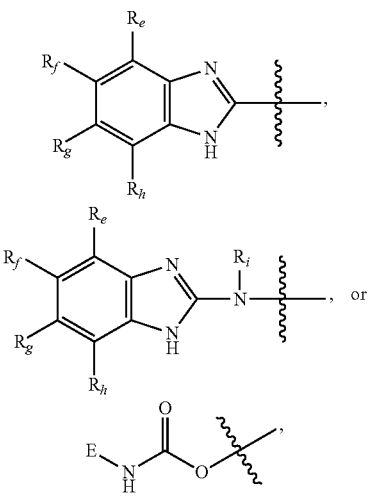

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $Rs_4$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

q is 0, 1, 2, 3, or 4;

m is 0, 1, or 2; and n is 0, 1, or 2.

Compounds of formula III, methods of making thereof, and methods of use thereof can be found in WO 2012/075500, which is incorporated herein by reference.

In certain embodiments, the sum of m and n is at least 1. In certain embodiments, m is 1 or 2 and n is 0. In certain embodiments, m is 2 and n is 0.

In certain embodiments, A is $CH_2$. In certain embodiments, A is O.

In certain embodiments, $L_1$ is N(Y). In certain embodiments, $L_1$ is SO or $SO_2$.

In certain embodiments, Y is Rj.

In certain embodiments, $R_d$ is $C_1$-$C_6$ alkyl.

In certain embodiments, $L_2$ is absent.

In certain embodiments, each of G and J independently is $OR_a$. In certain embodiments, $R_a$ is hydrogen.

In certain embodiments, $R_9$ is

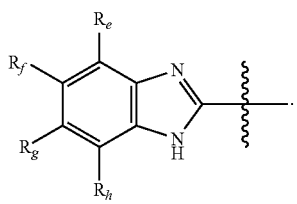

In certain embodiments, $R_9$ is

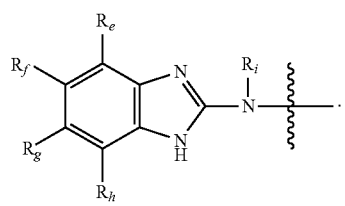

In certain embodiments, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$). In certain embodiments, Rj is H or $C_1$-$C_6$ alkyl (e.g., methyl, ethyl, n-propyl, i-propyl, n-butyl, s-butyl, t-butyl, n-pentyl, s-pentyl and n-hexyl).

In certain embodiments,

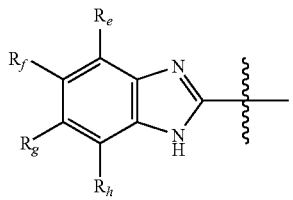

is unsubstituted benzimidazolyl or one of the following groups:

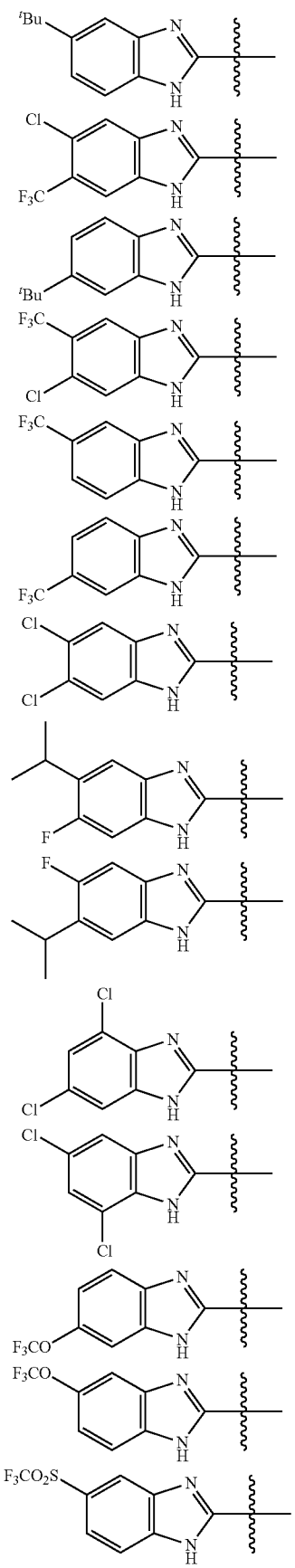

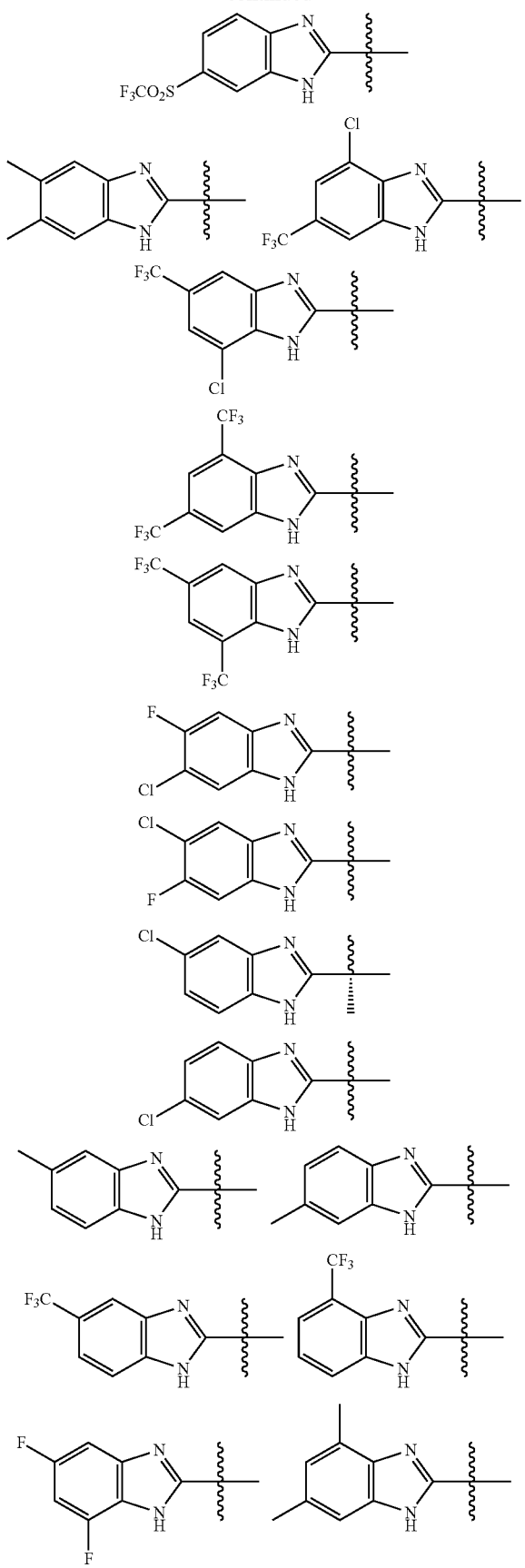

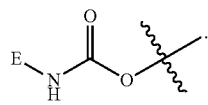

In certain embodiments, $R_9$ is

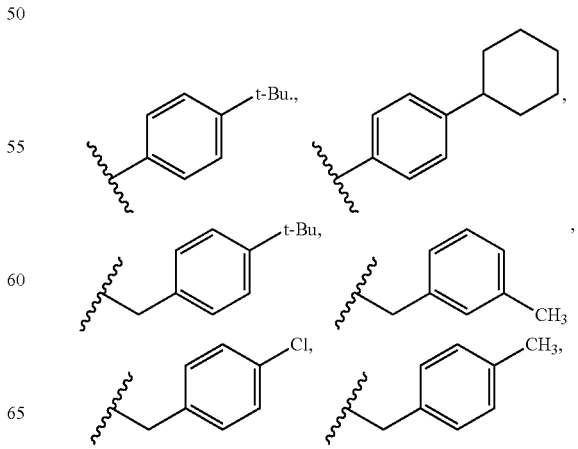

In certain embodiments, D is O. In certain embodiments, D is $NR_j$. In certain embodiments, $R_j$ is H. In certain embodiments, D is $CR_jR_k$. In certain embodiments, each of $R_j$ and $R_k$ is hydrogen. In certain embodiments, E is $-M_3-T_3$, in which $M_3$ is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl. In certain embodiments, $T_3$ is phenyl optionally substituted with one or more substituents selected from the group consisting of halo, hydroxyl, carboxyl, cyano, nitro, $C_1$-$C_6$ alkyl (e.g. methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl.

In certain embodiments, E is

51
-continued
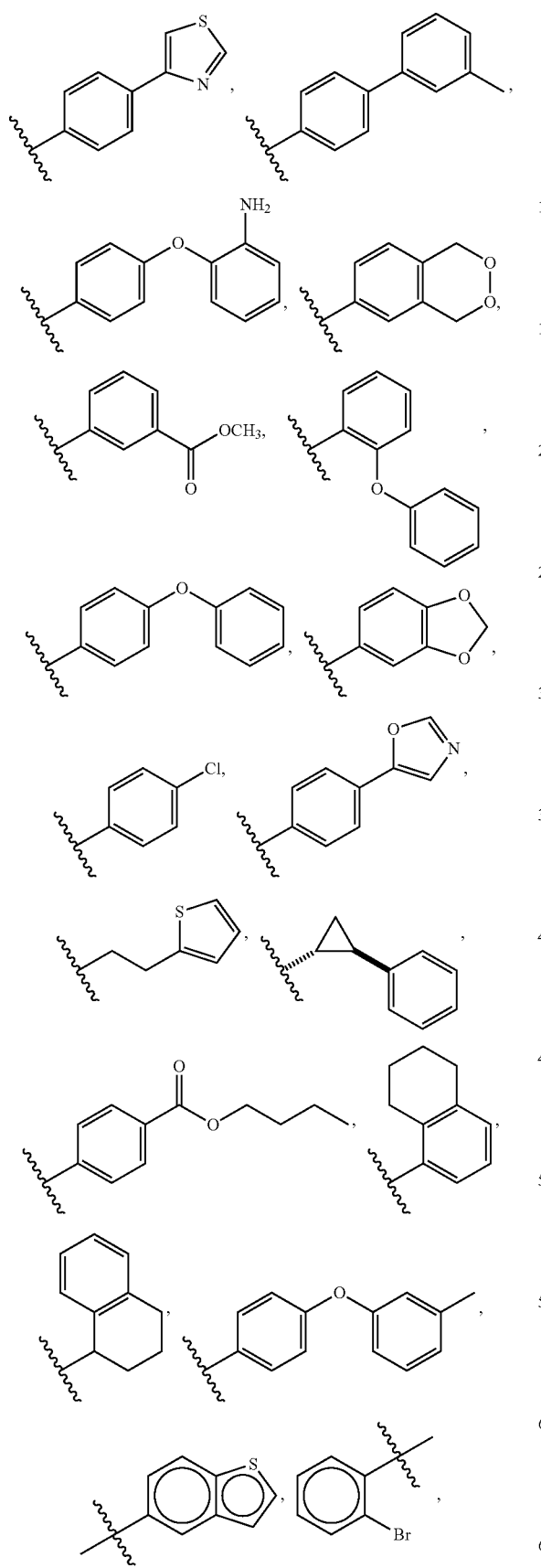
52
-continued
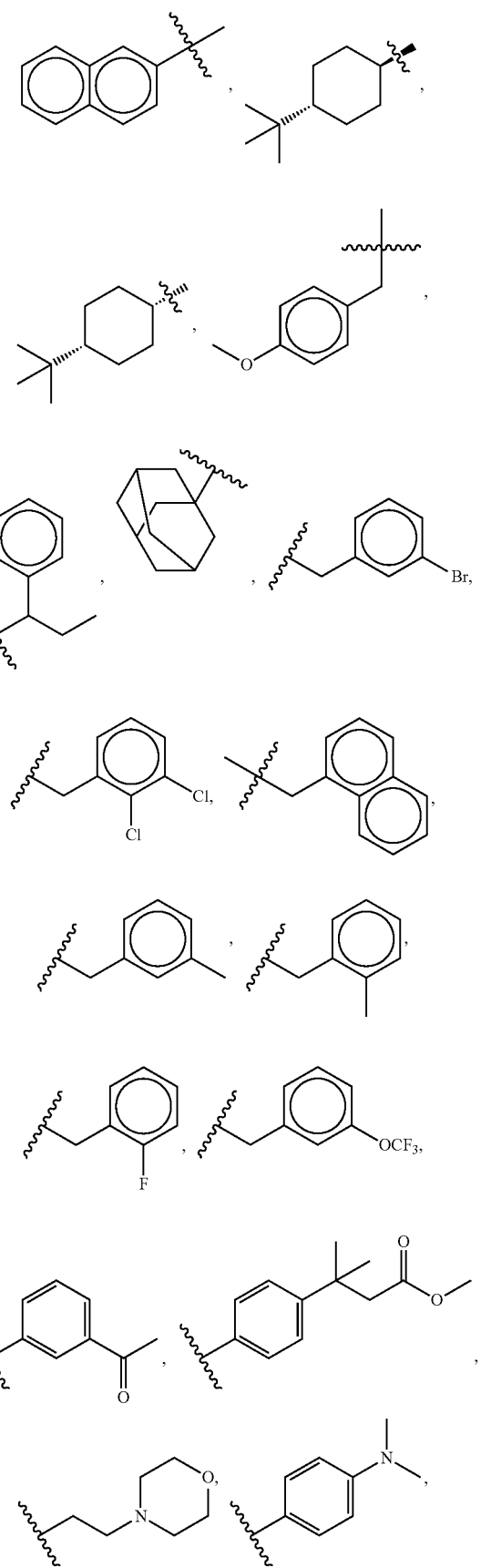

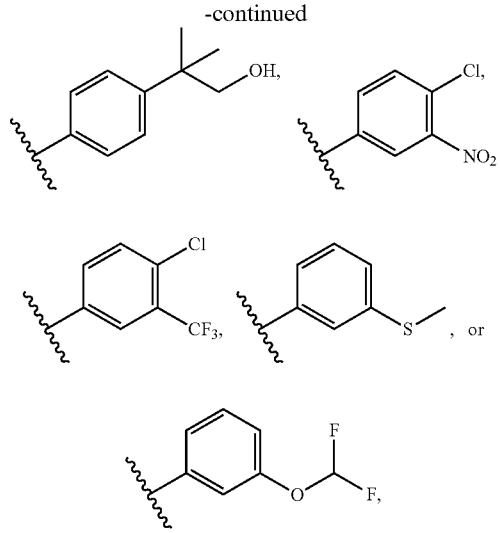

In certain embodiments, the compound is of formula III-a:

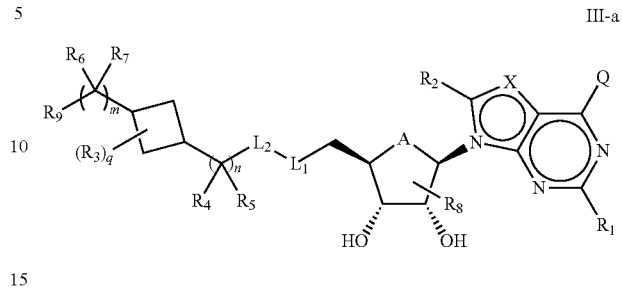

III-a or pharmaceutically acceptable salt or ester thereof, wherein A, Q, X, $L_1$, $L_2$, $R_1$, $R_2$, $R_3$, $R_4$, $R_5$, $R_6$, $R_7$, $R_8$, $R_9$, q, m, and n are as described herein for formula III.

In certain embodiments, the compound is of formula III-b or III-c:

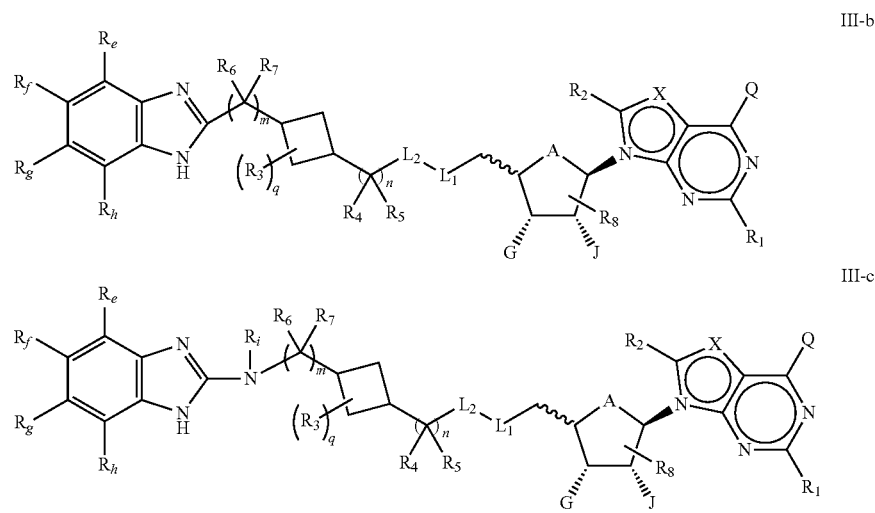

III-b

III-c

In certain embodiments, X is N. In certain embodiments, X is $CR_x$. In certain embodiments, X is CH.

In certain embodiments, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl. In certain embodiments, Q is H.

In certain embodiments, $R_1$, $R_2$, $R_3$, $R_4$, $R_5$, $R_6$, $R_7$, and $R_8$ are each H.

In certain embodiments, when $R_8$ is halo and is attached to the same carbon atom as J, then J is not hydroxyl. In certain embodiments, when $R_8$ is halo and is attached to the same carbon atom as G, then G is not hydroxyl. In certain embodiments, $T_2$ is not halo when $M_2$ is $SO_2$, SO, S, CO or O.

In certain embodiments, $T_2$ is a 4-8 membered heterocycloalkyl which is bound to $M_2$ via a heteroatom. In certain embodiments, $T_2$ is a 4-8 membered heterocycloalkyl which is bound to $M_2$ via a N atom. In certain embodiments, $T_2$ is a 4-8 membered heterocycloalkyl which is bound to $M_2$ via a C atom.

or pharmaceutically acceptable salt or ester thereof, wherein A, Q, X, $L_1$, $L_2$, $R_1$, $R_2$, $R_3$, $R_4$, $R_5$, $R_6$, $R_7$, $R_8$, $R_e$, $R_f$, $R_g$, $R_h$, $R_i$, q, m, and n are as described herein for formula III.

In certain embodiments, the compound is of formula III-d:

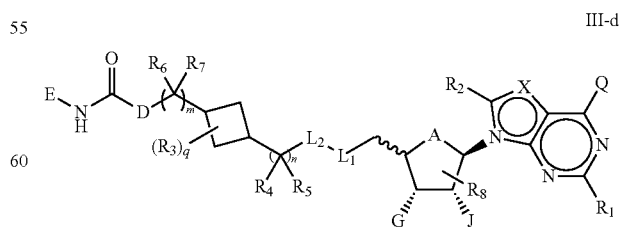

III-d or pharmaceutically acceptable salt or ester thereof, wherein A, Q, X, G, J, $L_1$, $L_2$, $R_1$, $R_2$, $R_3$, $R_4$, $R_5$, $R_6$, $R_7$, $R_8$, D, E, q, m, and n are as described herein for formula III.

In certain embodiments, the compound is of formula III-e:

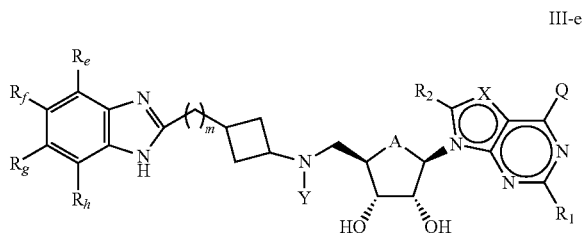

III-e or its N-oxide, or a pharmaceutically acceptable salt or ester thereof, wherein A, Q, X, Y, $R_1$, $R_2$, $R_e$, $R_f$, $R_g$, $R_h$, and m are as described herein for formula III.

In certain embodiments, A is O. In certain embodiments, A is O and m is 2. In certain embodiments, X is N. In certain embodiments, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl. In certain embodiments, $R_1$ and $R_2$ are each H. In certain embodiments, Y is $R_d$. In certain embodiments, $R_d$ is $C_1-C_6$ alkyl optionally substituted with $C_3-C_8$ cycloalkyl or halo. In certain embodiments, $R_d$ is $C_3-C_8$ cycloalkyl optionally substituted with $C_1-C_6$ alkyl or halo. In certain embodiments, at least one of $R_e$, $R_f$, $R_g$, and R is halo, $C_1-C_6$ alkoxyl optionally substituted with one or more halo; $C_1-C_6$ alkylsulfonyl optionally substituted with one or more halo; $C_1-C_6$ alkyl optionally substituted with one or more substituents selected from CN, halo, $C_3-C_8$ cycloalkyl, hydroxy, and $C_1-C_6$ alkoxyl; $C_3-C_8$ cycloalkyl optionally substituted with one or more $C_1-C_6$ alkyl or CN; or 4 to 8-membered heterocycloalkyl optionally substituted with one or more substituents selected from CN, halo, hydroxy, $C_1-C_6$ alkyl and $C_1-C_6$ alkoxyl. In certain embodiments, at least one of $R_e$, $R_f$, $R_g$, and $R_h$ is selected from F; Cl; Br; $CF_3$; $OCF_3$; $SO_2CF_3$; oxetanyl optionally substituted with one or more substituents selected from CN, halo, hydroxy, $C_1-C_6$ alkyl and $C_1-C_6$ alkoxyl; $C_3-C_8$ cycloalkyl optionally substituted with one or more substituents selected from $C_1-C_4$ alkyl; and $C_1-C_4$ alkyl optionally substituted with one or more substituents selected from halo, $C_3-C_8$ cycloalkyl, hydroxy and $C_1-C_6$ alkoxyl. In certain embodiments, at least one of $R_f$ and $R_g$ is alkyl, optionally substituted with hydroxyl. In certain embodiments, at least one of $R_f$ and $R_g$ is i-butyl substituted with hydroxyl.

In some embodiments, Dot1L is inhibited by contacting the differentiated cell with a composition comprising a compound of formula IV:

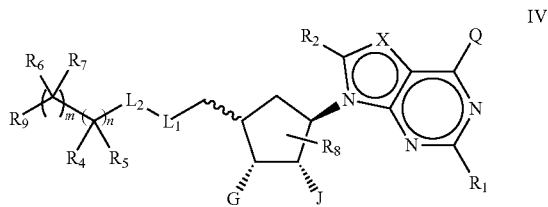

IV or a pharmaceutically acceptable salt or ester thereof, wherein:

each of G and 1, independently, is H, halo, C(O)OH, C(O)O—$C_1-C_6$ alkyl or $OR_a$, $R_a$ being H, $C_1-C_6$ alkyl or C(O)—$C_1-C_6$ alkyl, wherein C(O)O—$C_1-C_6$ alkyl, $C_1-C_6$ alkyl or C(O)—$C_1-C_6$ alkyl is optionally substituted with one or more substituents selected from the group consisting of halo, cyano hydroxyl, carboxyl, $C_1-C_6$ alkoxyl, amino, mono-$C_1-C_6$ alkylamino, di-$C_1-C_6$ alkylamino, and $C_3-C_8$ cycloalkyl;

Q is H, $NH_2$, $NHR_b$, $NR_bR_c$, $R_b$, or $OR_b$, in which each of $R_b$ and $R_c$ independently is $C_1-C_6$ alkyl, $C_2-C_6$ alkenyl, $C_2-C_6$ alkynyl, $C_3-C_8$ cycloalkyl, $C_6-C_{10}$ aryl, 4 to 7-membered heterocycloalkyl, 5 to 10-membered heteroaryl, or $-M_1-T_1$ in which $M_1$ is a bond or $C_1-C_6$ alkyl linker optionally substituted with halo, cyano, hydroxyl or $C_1-C_6$ alkoxyl and $T_1$ is $C_3-C_8$ cycloalkyl, $C_6-C_{10}$ aryl, 4 to 6-membered heterocycloalkyl, or 5 to 10-membered heteroaryl, or $R_b$ and $R_c$, together with the N atom to which they attach, form 4 to 7-membered heterocycloalkyl having 0 or 1 additional heteroatoms to the N atom optionally substituted with $C_1-C_6$ alkyl, $C_2-C_6$ alkenyl, $C_2-C_6$ alkynyl, halo, hydroxyl, carboxyl, C(O)OH, C(O)O—$C_1-C_6$ alkyl, OC(O)—$C_1-C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, or 5 to 6-membered heteroaryl, and each of $R_b$, $R_c$, and $T_1$ is optionally substituted with one or more substituents selected from the group consisting of $C_1-C_6$ alkyl, $C_2-C_6$ alkenyl, $C_2-C_6$ alkynyl, halo, hydroxyl, carboxyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl;

X is N or $CR_x$, in which $R_x$ is H, halo, hydroxyl, carboxyl, cyano, or $R_{S1}$, $Rs_1$ being amino, $C_1-C_6$ alkoxyl, $C_1-C_6$ alkyl, $C_2-C_6$ alkenyl, $C_2-C_6$ alkynyl, $C_3-C_5$ cycloalkyl, $C_6-C_{10}$ aryl, 4 to 6-membered heterocycloalkyl, or 5 to 6-membered heteroaryl, and $Rs_1$ being optionally substituted with one or more substituents selected from the group consisting of halo, hydroxyl, carboxyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl;

$L_1$ is N(Y), S, SO, or $SO_2$;

$L_2$ is CO or absent when $L_1$ is N(Y) or is absent when $L_1$ is S, SO, or $SO_2$, in which Y is H, $R_d$, $SO_2R_d$, or $COR_d$ when $L_2$ is absent, or Y is H or $R_d$ when $L_2$ is CO, $R_d$ being $C_1-C_6$ alkyl, $C_2-C_6$ alkenyl, $C_2-C_6$ alkynyl, $C_3-C_8$ cycloalkyl, $C_6-C_{10}$ aryl, 4 to 6-membered heterocycloalkyl, or 5 to 6-membered heteroaryl, and $R_d$ being optionally substituted with one or more substituents selected from the group consisting of $C_1-C_6$ alkyl, $C_2-C_6$ alkenyl, $C_2-C_6$ alkynyl, halo, hydroxyl, carboxyl, cyano, $C_1-C_6$ alkoxyl, $C_1-C_6$ alkylsulfonyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl and with $C_3-C_8$ cycloalkyl, $C_6-C_{10}$ aryl, 4 to 6-membered heterocycloalkyl, or 5 to 6-membered heteroaryl further optionally substituted with $C_1-C_6$ alkyl, $C_2-C_6$ alkenyl, $C_2-C_6$ alkynyl, halo, hydroxyl, carboxyl, C(O)OH, C(O)O—$C_1-C_6$ alkyl, OC(O)—$C_1-C_6$ alkyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, or 5 to 6-membered heteroaryl;

each of $R_1$, $R_2$, $R_4$, $R_5$, $R_6$, and $R_7$, independently, is H, halo, hydroxyl, carboxyl, cyano, $R_{S2}$, $Rs_2$ being amino, $C_1-C_6$ alkoxyl, $C_1-C_6$ alkyl, $C_2-C_6$ alkenyl, or $C_2-C_6$ alkynyl, and each $Rs_2$ being optionally substituted with one or more substituents selected from the group consisting of halo, hydroxyl, carboxyl, cyano, $C_1-C_6$ alkoxyl, amino, mono-$C_1-C_6$ alkylamino, di-$C_1-C_6$ alkylamino, $C_3-C_8$ cycloalkyl, $C_6-C_{10}$ aryl, 4 to 6-membered heterocycloalkyl, and 5 to 6-membered heteroaryl;

$R_8$ is H, halo or $Rs_3$, $Rs_3$ being $C_1$-$C_6$ alkyl, $C_2$-$C_6$ alkenyl, or $C_2$-$C_6$ alkynyl, and $Rs_3$ being optionally substituted with one or more substituents selected from the group consisting of halo, hydroxyl, carboxyl, cyano amino, $C_1$-$C_6$ alkoxyl, mono-$C_1$-$C_6$ alkylamino, di-$C_1$-$C_6$ alkylamino, and $C_3$-$C_8$ cycloalkyl;

$R_9$ is

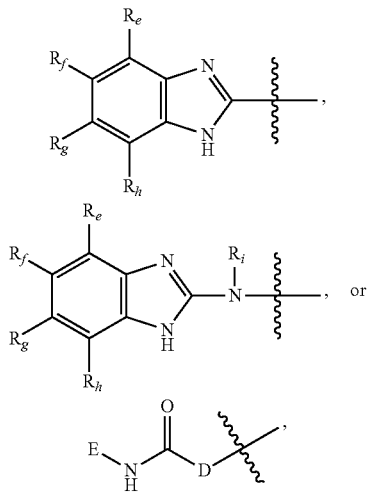

in which each of $R_e$, $R_f$, $R_g$, and $R_h$, independently is -$M_2$-$T_2$, in which $M_2$ is a bond, $SO_2$, SO, S, CO, $CO_2$, O, O—$C_1$-$C_4$ alkyl linker, $C_1$-$C_4$ alkyl linker, NH, or N($R_t$), $R_t$ being $C_1$-$C_6$ alkyl, and $T_2$ is H, halo, or $R_{S4}$, $Rs_4$ being $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl, and each of O—$C_1$-$C_4$ alkyl linker, $C_1$-$C_4$ alkyl linker, $R_t$, and $R_{S4}$ being optionally substituted with one or more substituents selected from the group consisting of halo, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl, $R_i$ is H or $C_1$-$C_6$ alkyl optionally substituted with one or more substituents selected from the group consisting of halo, hydroxyl, carboxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl; D is O, $NR_j$, or $CR_jR_k$, each of $R_j$ and $R_k$ independently being H or $C_1$-$C_6$ alkyl, or $R_j$ and $R_k$ taken together, with the carbon atom to which they are attached, form a $C_3$-$C_{10}$ cycloalkyl ring, and E is -$M_3$-$T_3$, $M_3$ being a bond or $C_1$-$C_6$ alkyl linker optionally substituted with halo or cyano, $T_3$ being $C_3$-$C_{10}$ cycloalkyl, $C_6$-$C_{10}$ aryl, 5 to 10-membered heteroaryl, or 4 to 10-membered heterocycloalkyl, and $T_3$ being optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ haloalkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with halo, $C_1$-$C_4$ alkyl, $C_1$-$C_4$ haloalkyl, 5 to 6-membered heteroaryl optionally substituted with halo, $C_1$-$C_4$ alkyl, and $C_1$-$C_6$ alkyl that is substituted with hydroxy, halo, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl optionally further substituted with halo, hydroxyl, or $C_1$-$C_6$ alkoxyl;

m is 1 or 2; and n is 1 or 2.

Compounds of formula IV, methods of making thereof, and methods of use thereof can be found in WO 2012/075492, which is incorporated herein by reference.

In certain embodiments, at least one of m and n is 2.

In certain embodiments, each of G and J independently is $OR_a$. In certain embodiments, each of G and J is OH.

In certain embodiments, $L_1$ is N(Y). In certain embodiments, $L_1$ is SO or $SO_2$.

In certain embodiments, Y is $R_d$. In certain embodiments, $R_d$ is $C_1$-$C_6$ alkyl.

In certain embodiments, $L_2$ is absent.

In certain embodiments, $R_9$ is

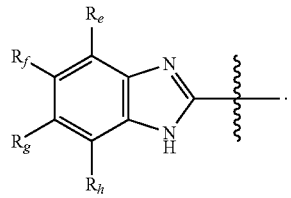

In certain embodiments, $R_9$ is

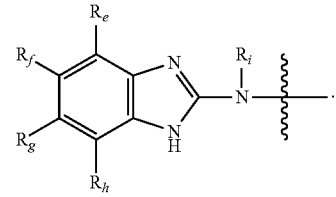

In certain embodiments, $R_i$ is H or $C_1$-$C_6$ alkyl (e.g., methyl, ethyl, n-propyl, i-propyl, n-butyl, s-butyl, t-butyl, n-pentyl, s-pentyl and n-hexyl).

In certain embodiments, at least one of $R_e$, $R_f$, $R_g$, and $R_h$ is halo (such as F, Cl, and Br), $C_1$-$C_6$ alkoxyl optionally substituted with one or more halo (such as $OCH_3$, $OCH_2CH_3$, O-iPr, and $OCF_3$), $C_1$-$C_6$ alkylsulfonyl optionally substituted with one or more halo (such as $SO_2CF_3$), or $C_1$-$C_6$ alkyl optionally substituted with one or more halo (such as $CH_3$, i-propyl, n-butyl, and $CF_3$). In certain embodiments, at least one of $R_e$, $R_f$, $R_g$, and $R_h$ is selected from the group consisting of F, Cl, $CF_3$, $OCF_3$, $C_1$-$C_4$ alkyl, and $C_1$-$C_4$ alkoxyl.

In certain embodiments,

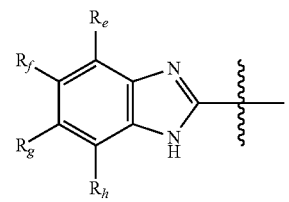

is unsubstituted benzimidazolyl or one of the following groups:
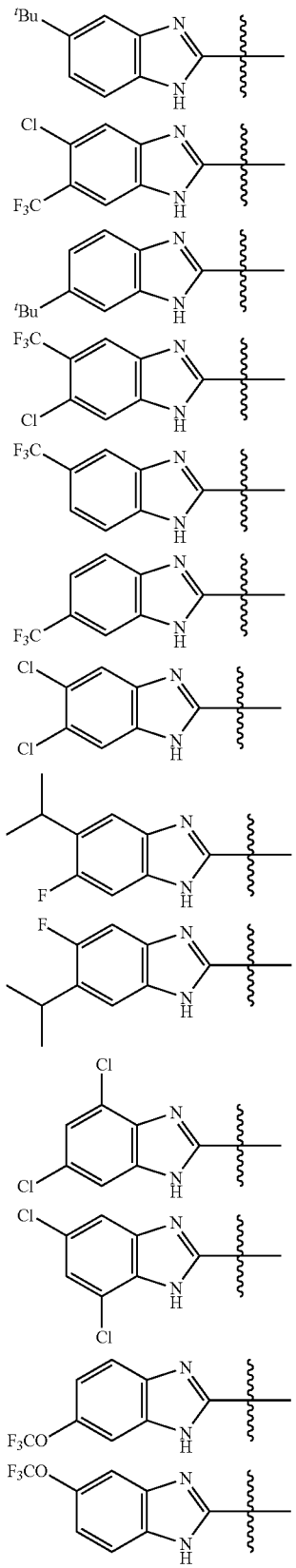
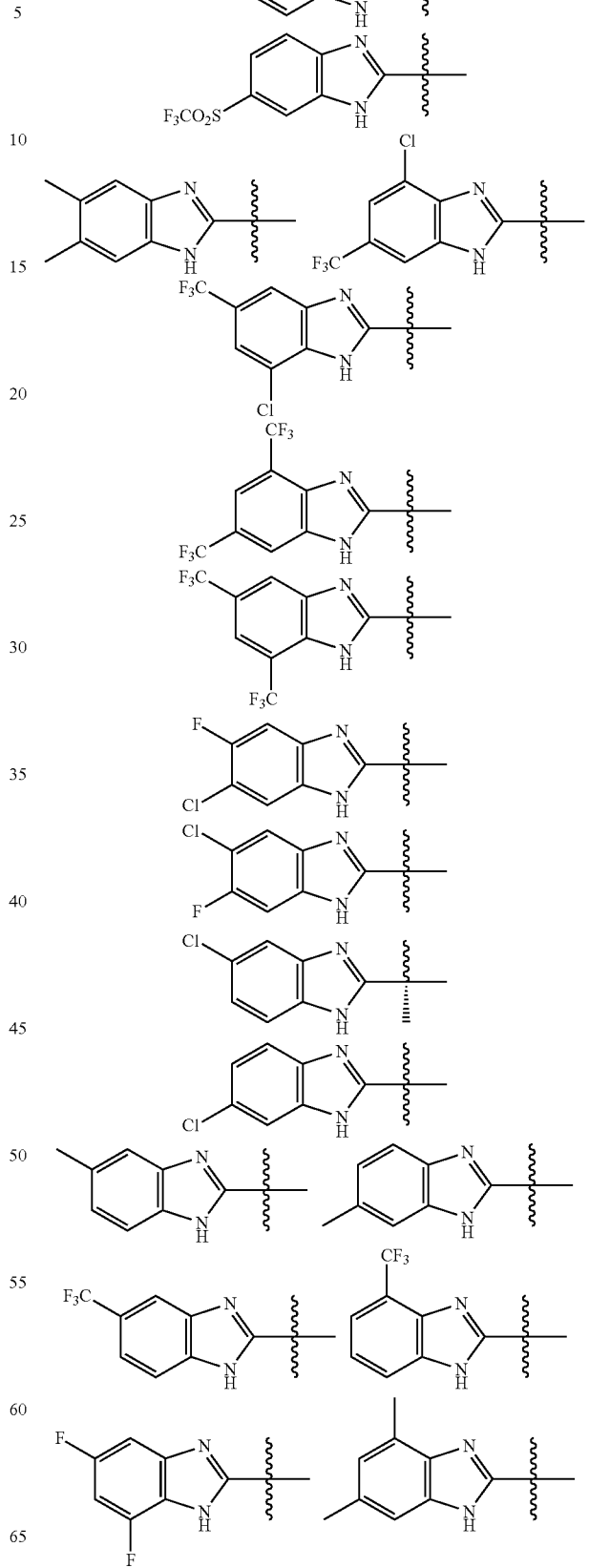

-continued

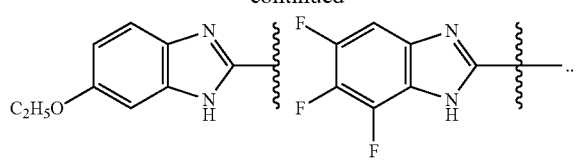

In certain embodiments, $R_9$ is

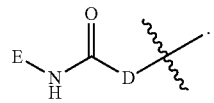

In certain embodiments, D is NRj. In certain embodiments, $R_j$ is H. In certain embodiments, D is $CR_jR_k$. In certain embodiments, each of $R_j$ and $R_k$ is H.

In certain embodiments, E is -$M_3$-$T_3$, in which Ms is a bond or $C_1$-$C_3$ alkyl linker, $T_3$ is phenyl, naphthyl, thienyl, cyclopropyl, or cyclohexyl, and $T_3$ is optionally substituted with one or more substituents selected from the group consisting of halo, hydroxyl, thiol, carboxyl, cyano, nitro, $C_1$-$C_6$ alkyl, $C_2$-$C_6$ alkenyl, $C_2$-$C_6$ alkynyl, $C_1$-$C_6$ alkoxyl, $C_1$-$C_6$ haloalkyl, $C_1$-$C_6$ haloalkoxyl, $C_1$-$C_6$ alkylthio, $C_1$-$C_6$ alkylsulfonyl, $C_1$-$C_6$ alkylcarbonyl, $C_1$-$C_6$ alkoxycarbonyl, oxo, amino, mono-$C_1$-$C_6$ alkylamino, di-$C_1$-$C_6$ alkylamino, $C_3$-$C_8$ cycloalkyl, $C_4$-$C_{12}$ alkylcycloalkyl, $C_6$-$C_{10}$ aryl, $C_6$-$C_{10}$ aryloxyl, $C_7$-$C_{14}$ alkylaryl, $C_6$-$C_{10}$ aminoaryloxyl, $C_6$-$C_{10}$ arylthio, 4 to 6-membered heterocycloalkyl optionally substituted with $C_1$-$C_4$ alkyl, 5 to 6-membered heteroaryl optionally substituted with $C_1$-$C_4$ alkyl, and $C_1$-$C_6$ alkyl that is substituted with hydroxy, $C_1$-$C_6$ alkoxycarbonyl, $C_3$-$C_8$ cycloalkyl, $C_6$-$C_{10}$ aryl, 4 to 6-membered heterocycloalkyl, or 5 to 6-membered heteroaryl. In certain embodiments, $T_3$ is phenyl optionally substituted with one or more substituents selected from the group consisting of halo, hydroxyl, carboxyl, cyano, nitro, $C_1$-$C_6$ alkyl (e.g., methyl, ethyl, n-propyl, i-propyl, n-butyl, s-butyl, t-butyl, n-pentyl, s-pentyl and n-hexyl), $C_1$-$C_6$ alkoxyl, $C_1$-$C_6$ haloalkyl, $C_1$-$C_6$ haloalkoxyl, $C_1$-$C_6$ alkylsulfonyl, $C_6$-$C_{10}$ aryl (e.g., phenyl or naphthyl), and $C_6$-$C_{10}$ aryloxyl, and $C_7$-$C_{14}$ alkylaryl. In certain embodiments, E is

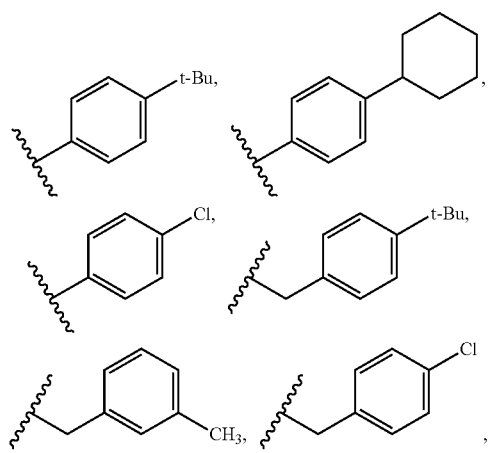

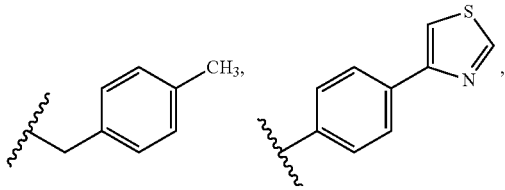

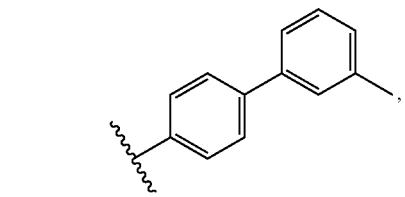

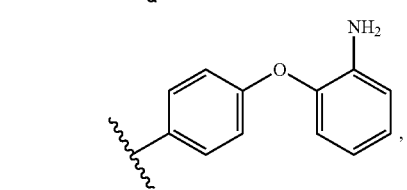

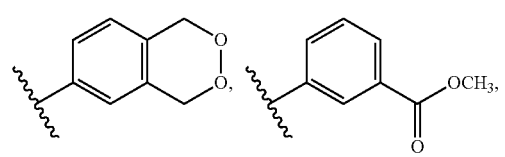

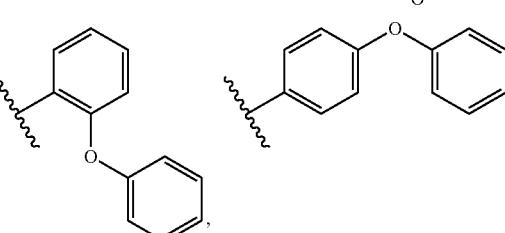

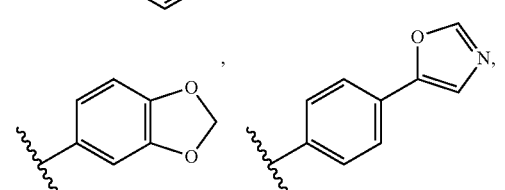

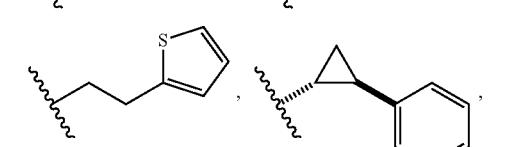

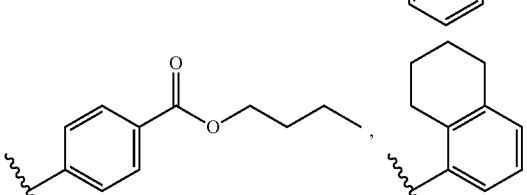

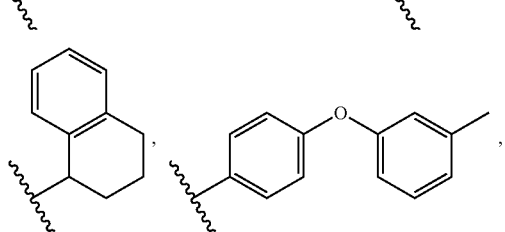

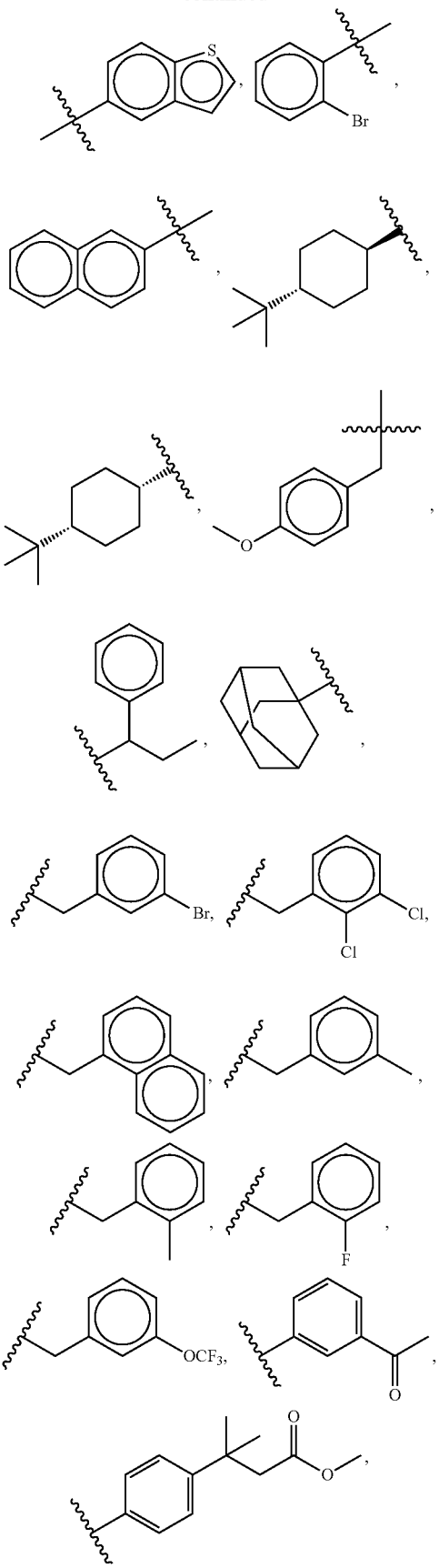

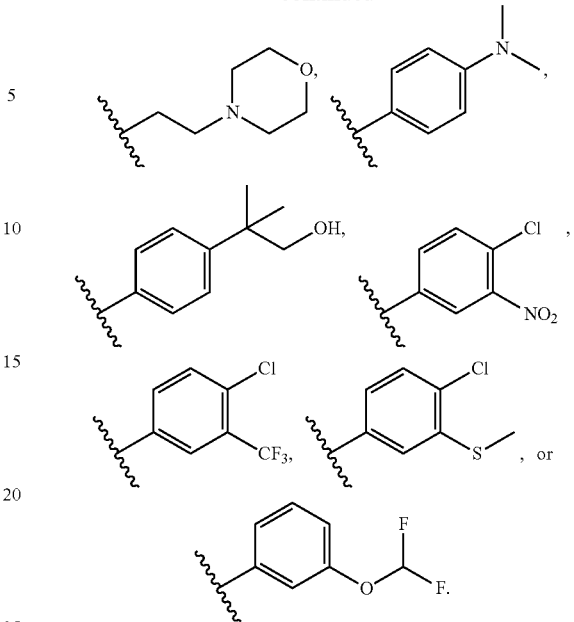

In certain embodiments, X is N. In certain embodiments, X is $CR_X$. In certain embodiments, X is CH.

In certain embodiments, Q is $NH_2$ or $NHR_b$, in which $R_b$ is $-M_1-T_1$, $M_1$ being a bond or $C_1-C_6$ alkyl linker and $T_1$ being $C_3-C_8$ cycloalkyl. In certain embodiments, Q is H.

In certain embodiments, $R_1$, $R_2$, $R_4$, $R_5$, $R_6$, $R_7$, and $R_8$ are each H.

In certain embodiments, when $R_8$ is halo and is attached to the same carbon atom as J, then J is not hydroxyl. In certain embodiments, when $R_8$ is halo and is attached to the same carbon atom as G, then G is not hydroxyl. In certain embodiments, $T_2$ is not halo when $M_2$ is $SO_2$, SO, S, CO or O.

In certain embodiments, $T_2$ is a 4-8 membered heterocycloalkyl which is bound to $M_2$ via a heteroatom. In certain embodiments, $T_2$ is a 4-8 membered heterocycloalkyl which is bound to $M_2$ via a N atom. In certain embodiments, $T_2$ is a 4-8 membered heterocycloalkyl which is bound to $M_2$ via a C atom.

In certain embodiments, the compound is of formula IV-a:

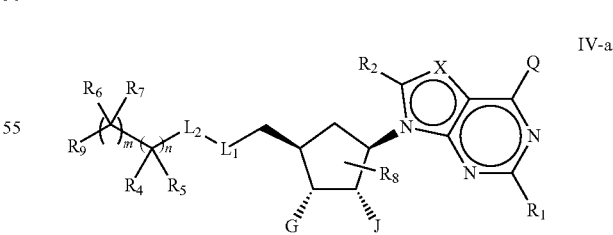

IV-a or a pharmaceutically acceptable salt or ester thereof, wherein G, J, Q, X, $L_1$, $L_2$, $R_1$, $R_2$, $R_4$, $R_5$, $R_6$ $R_7$, $R_8$, $R_9$, m, and n are as described herein for compounds of formula IV.

In certain embodiments, the compound is of the formula IV-b or IV-c:

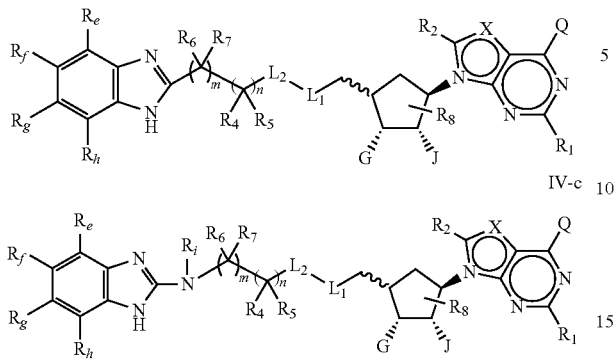

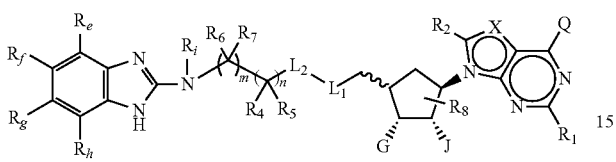

pharmaceutically acceptable salt or ester thereof, wherein G, J, Q, X, $L_1$, $L_2$, $R_1$, $R_2$, $R_4$, $R_5$, $R_6$, $R_7$, $R_8$, $R_e$, $R_f$, $R_g$, $R_h$, $R_i$, m and n are as described herein for compounds of formula IV.

In certain embodiments, the compound is of formula IV-d:

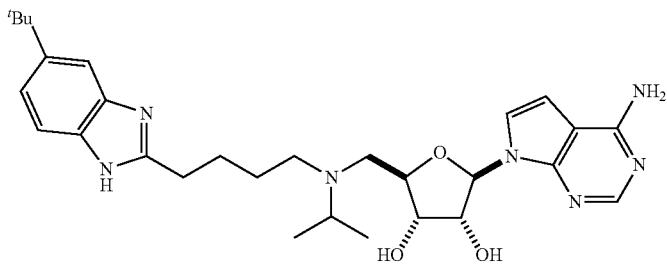

pharmaceutically acceptable salt or ester thereof, wherein G, J, Q, X, $L_1$, $L_2$, $R_1$, $R_2$, $R_4$, $R_5$, $R_6$, $R_7$, $R_8$, D, E, m, and n are as described herein for formula IV.

Exemplary compound useful in methods described include:

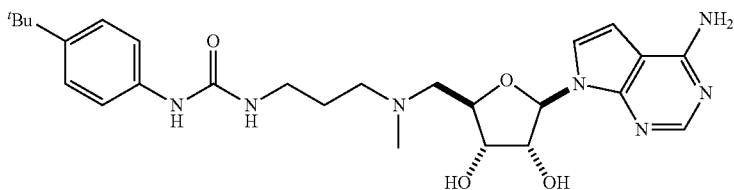

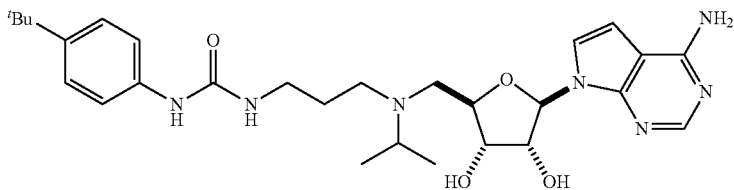

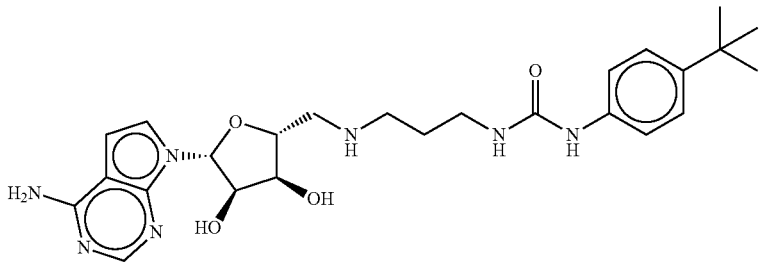

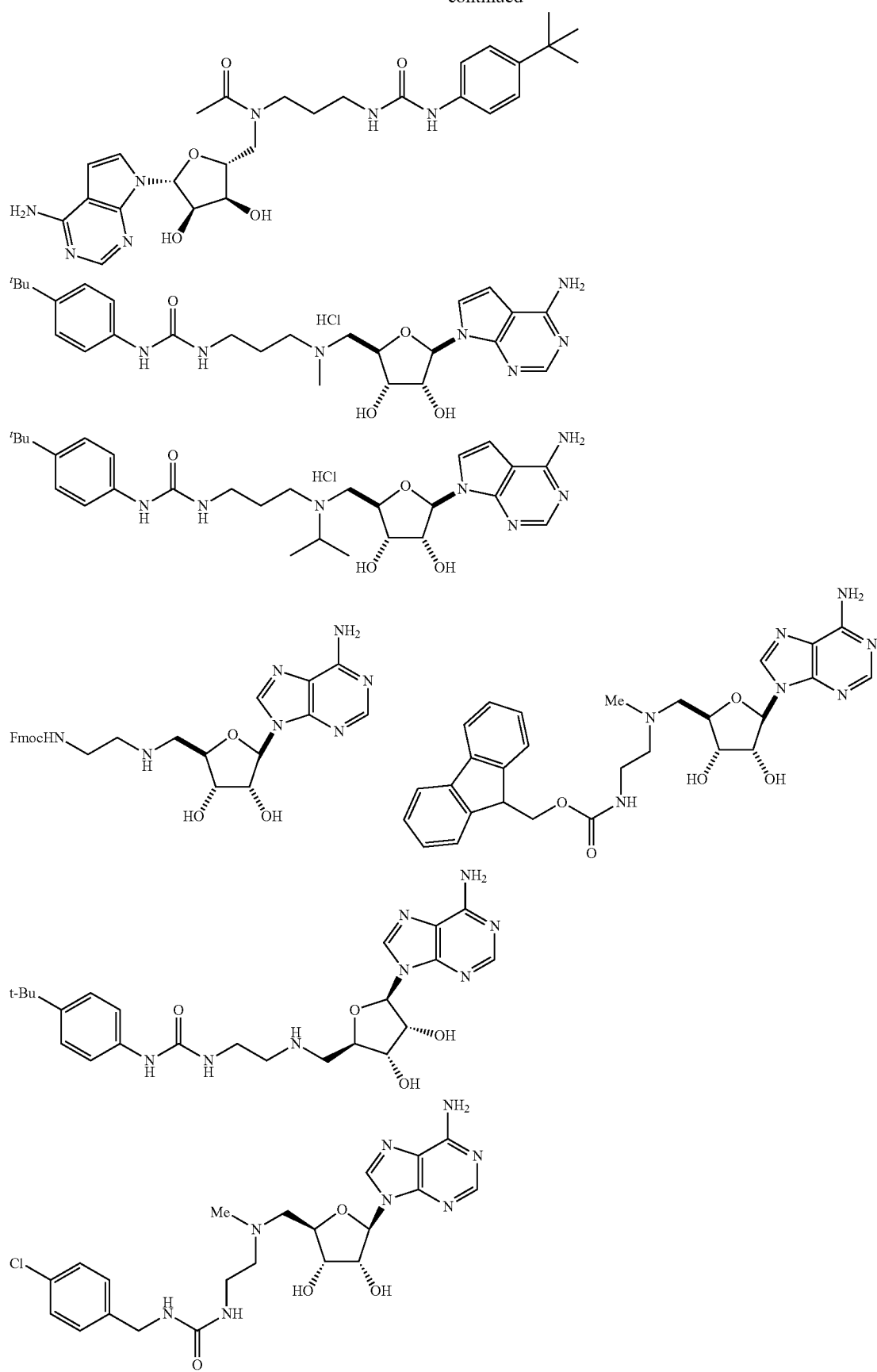

69
-continued
70
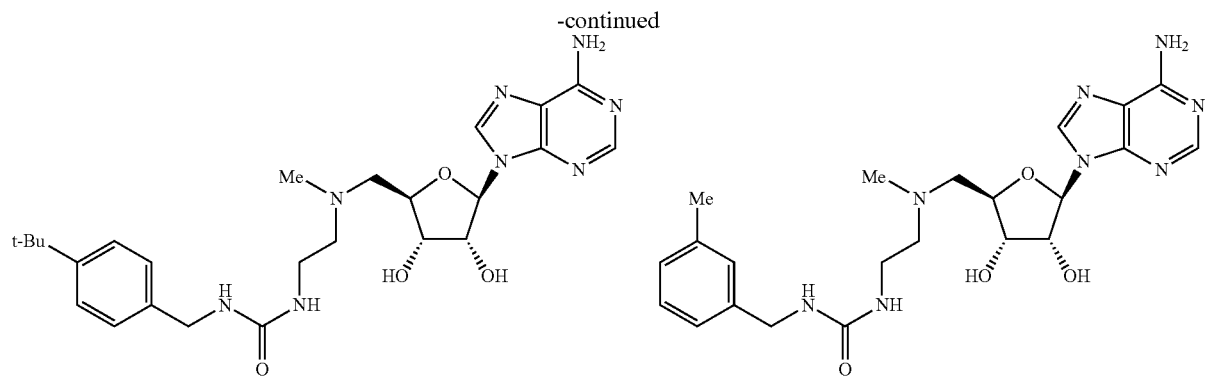
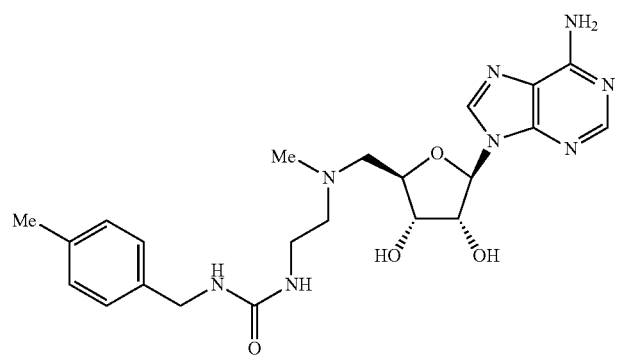
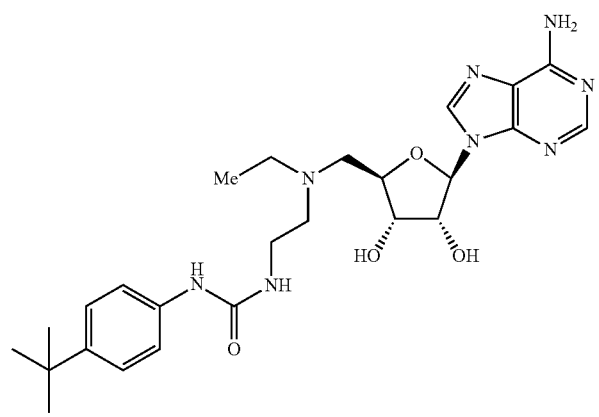
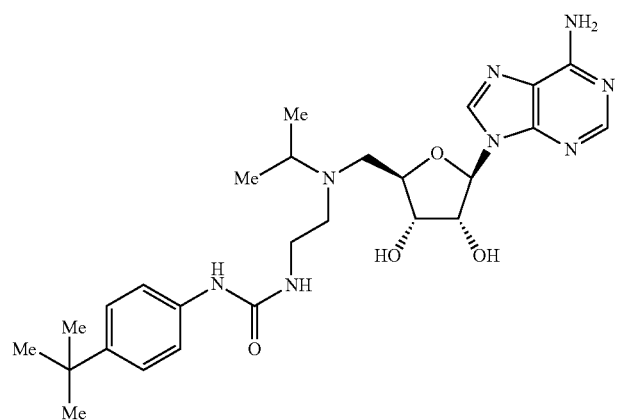

-continued
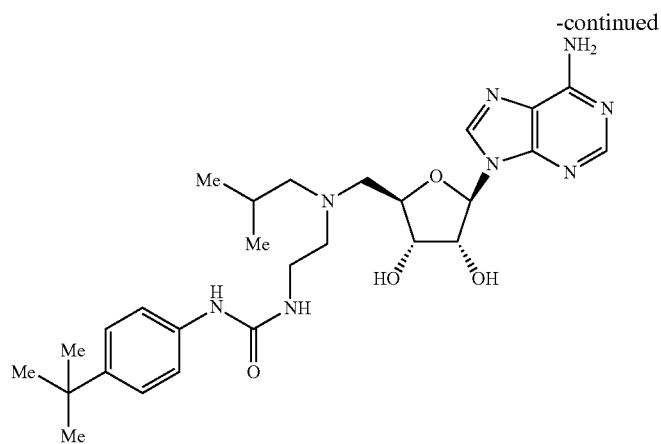
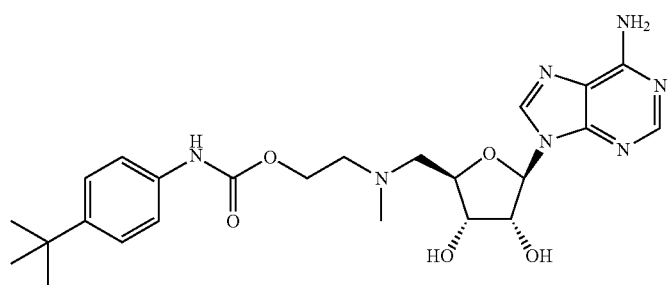
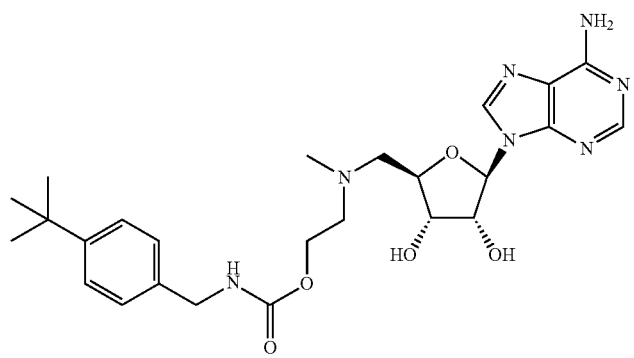
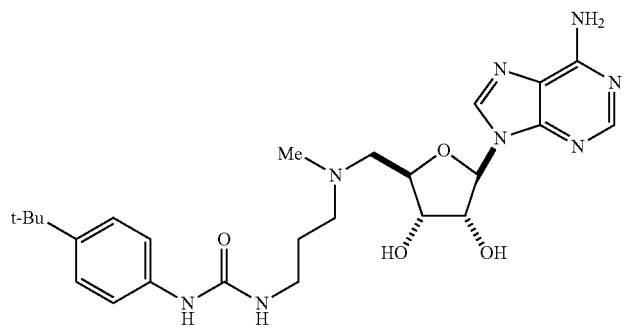

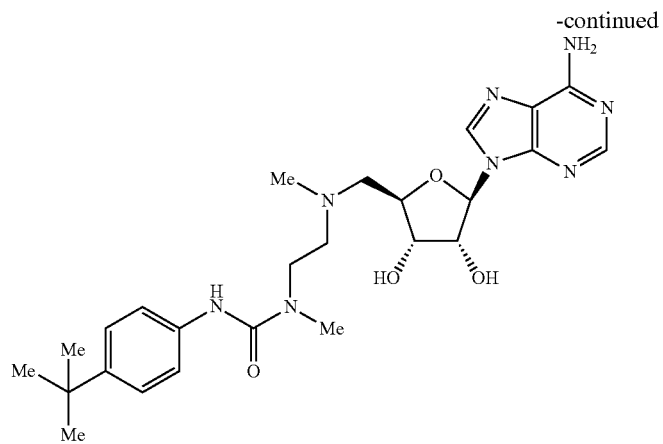
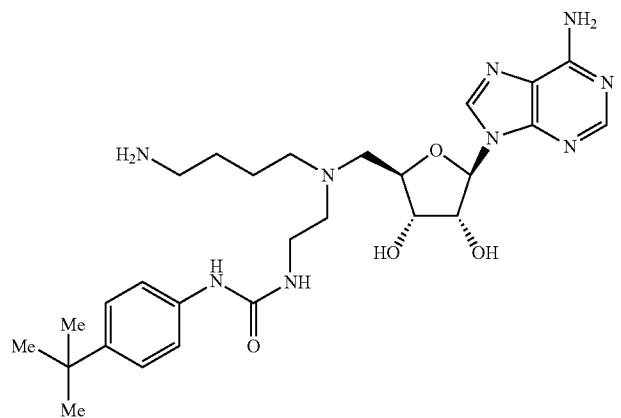
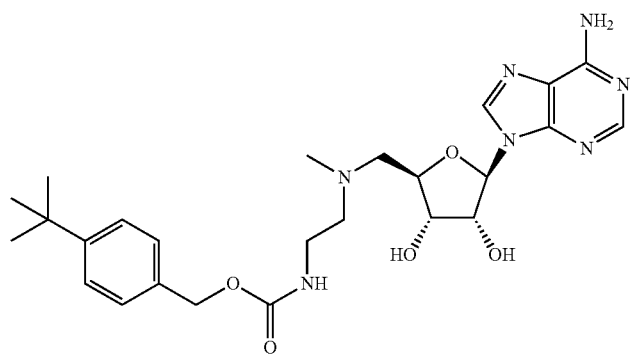
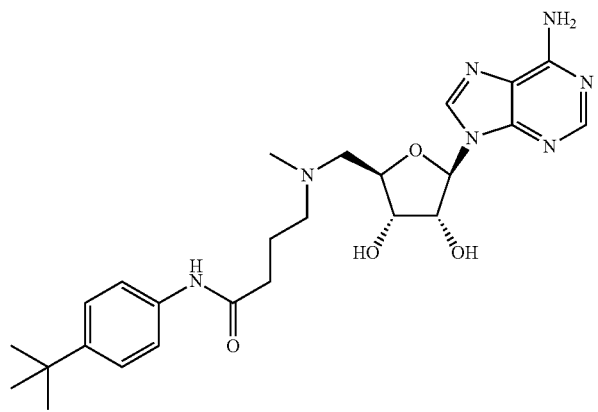

-continued
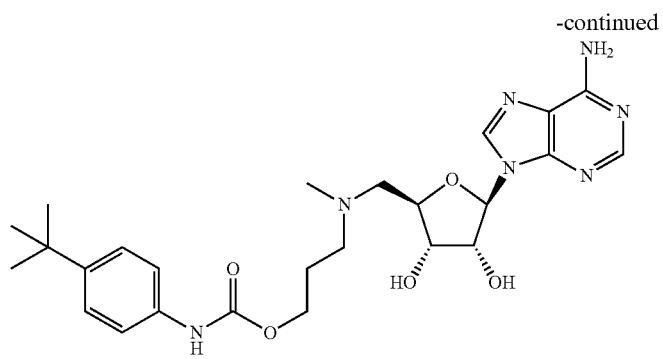
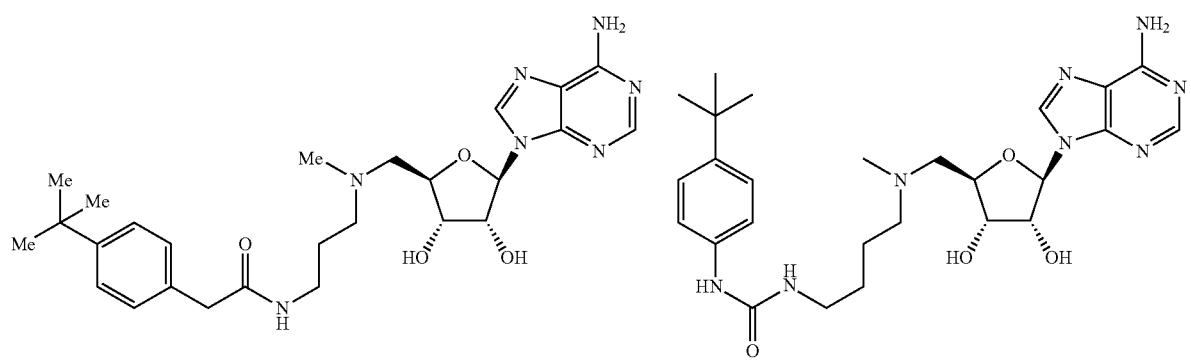
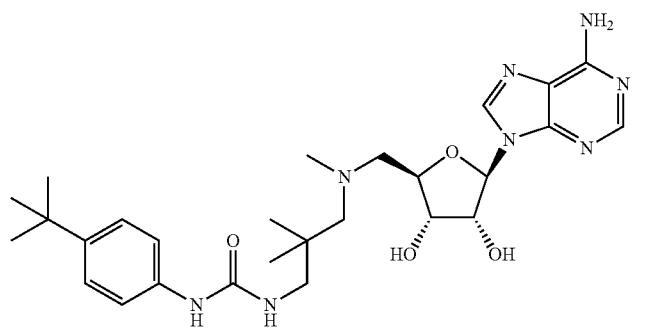
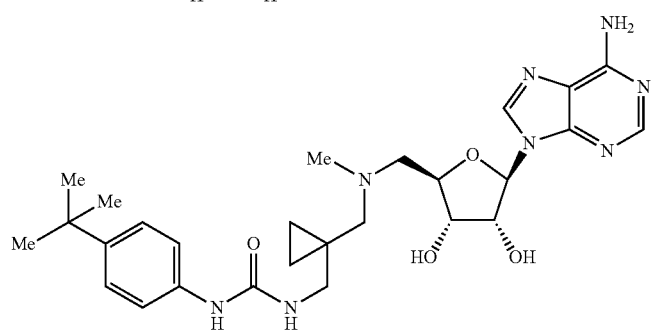
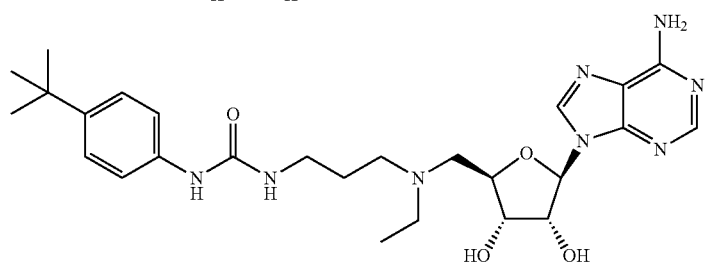

-continued
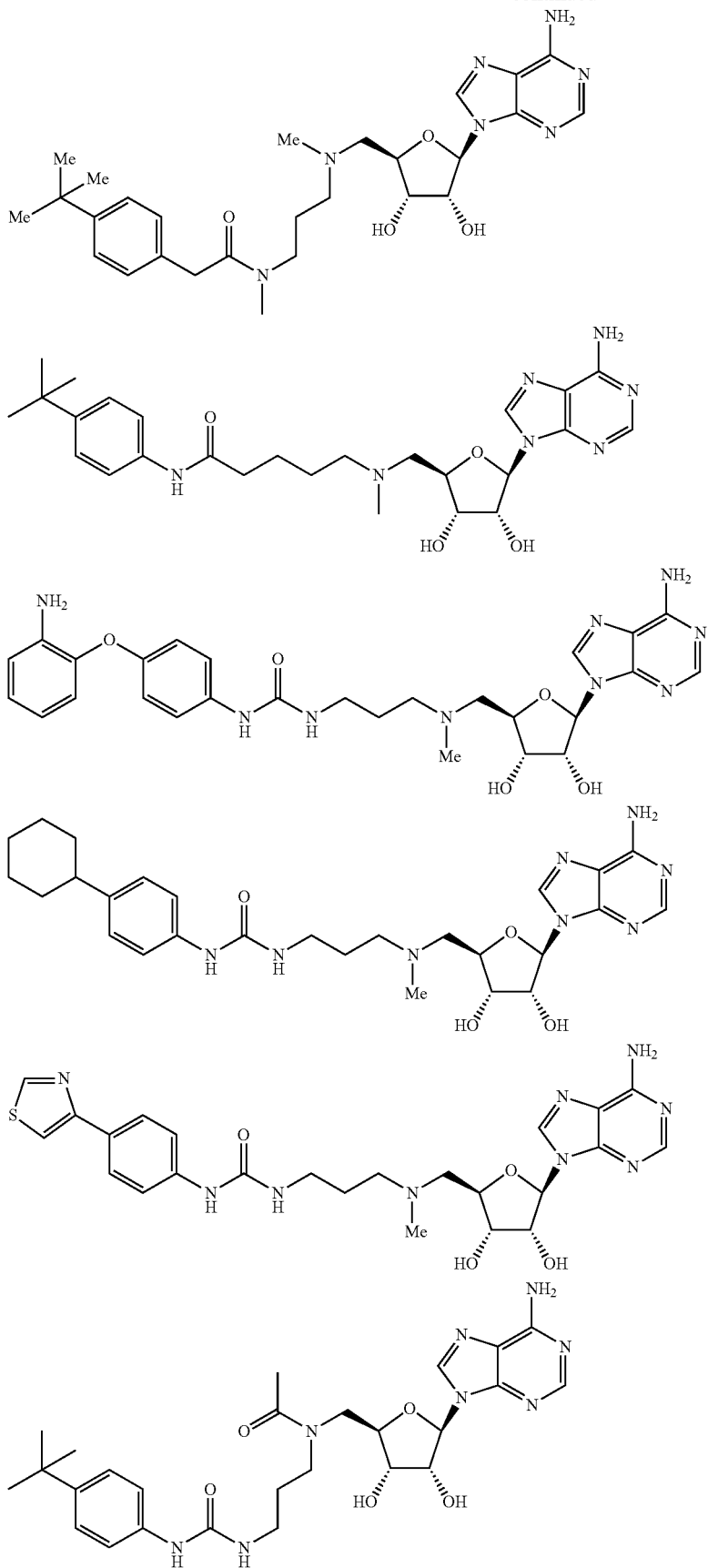

-continued
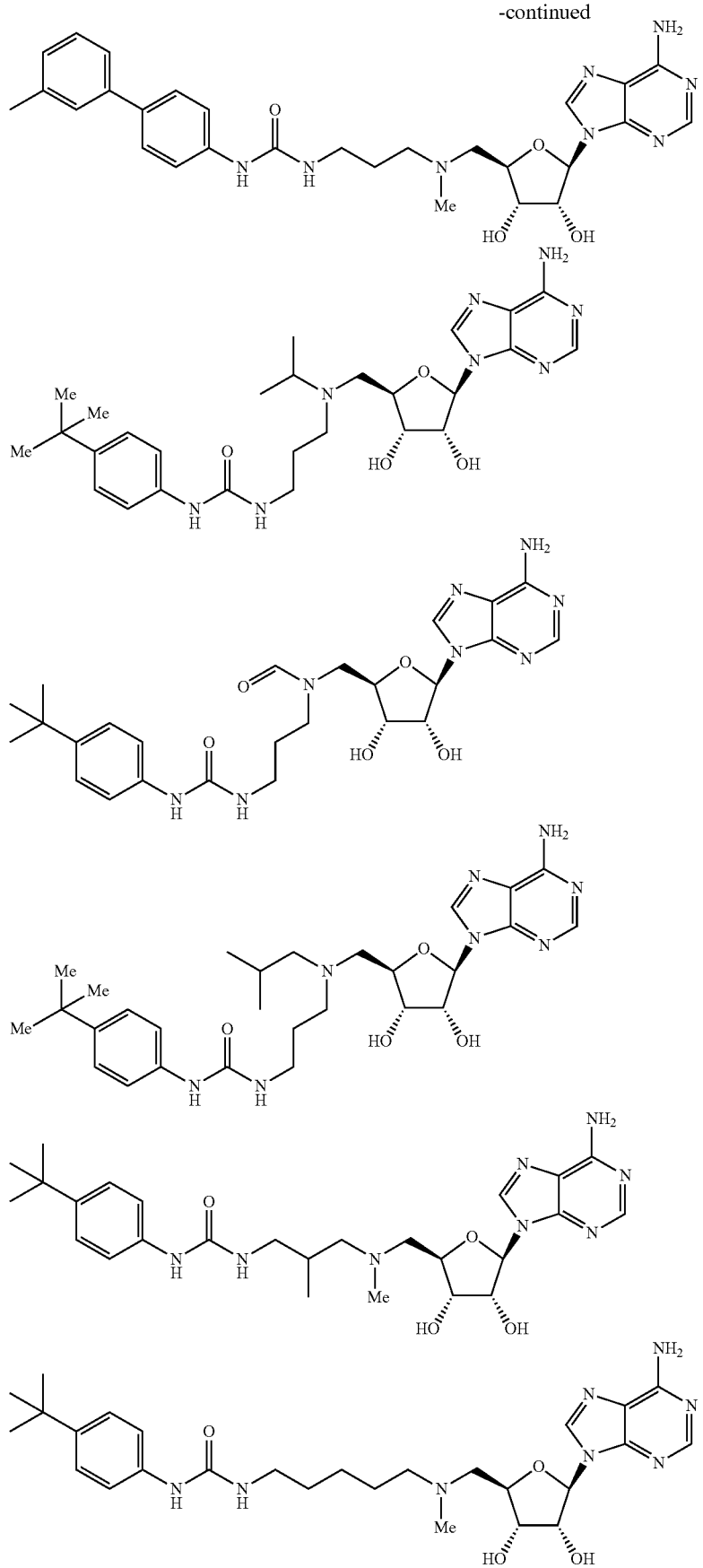

-continued
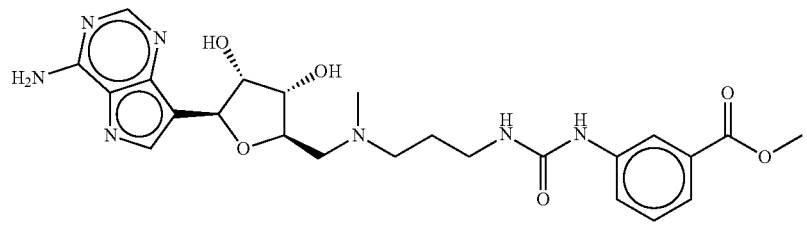
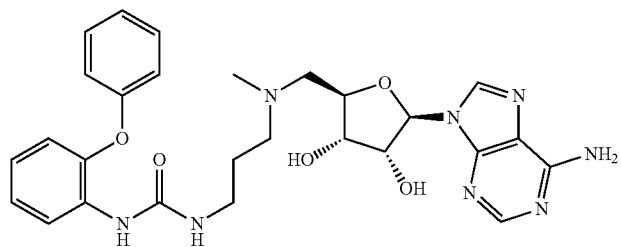
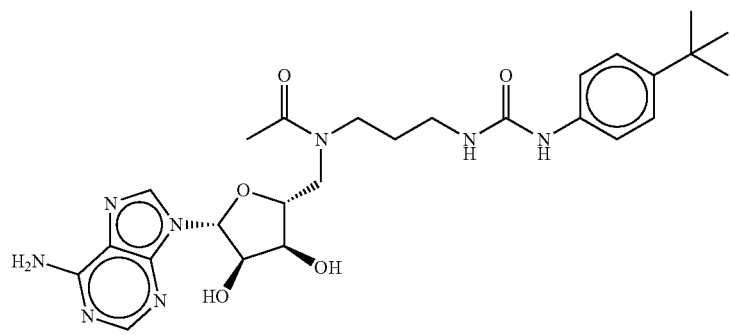
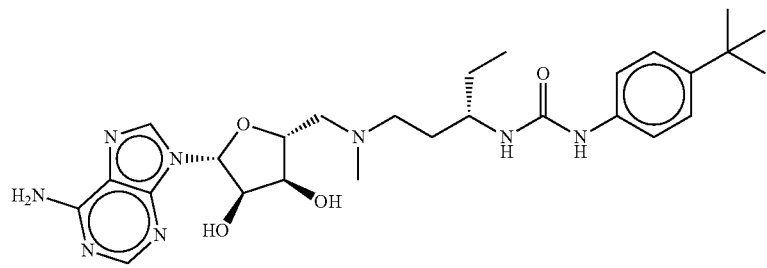
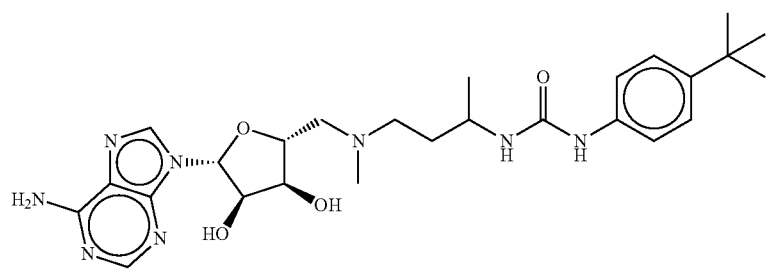
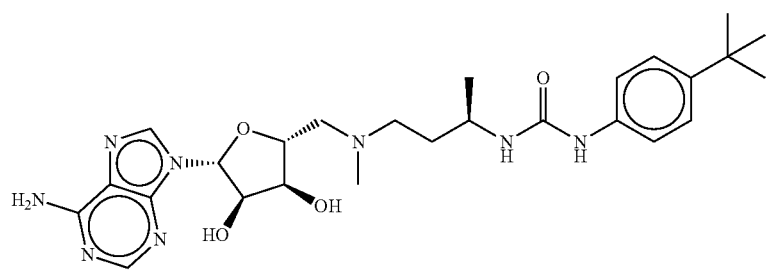

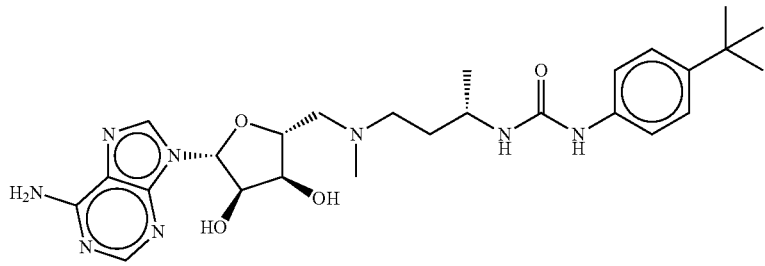
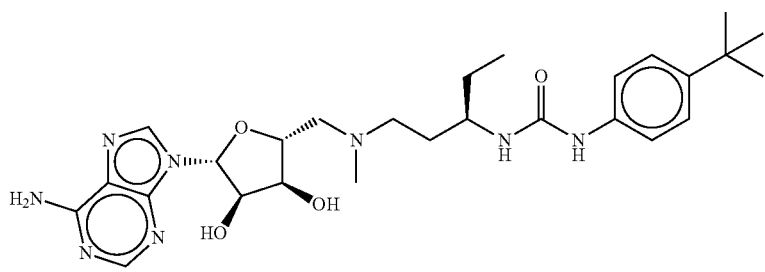
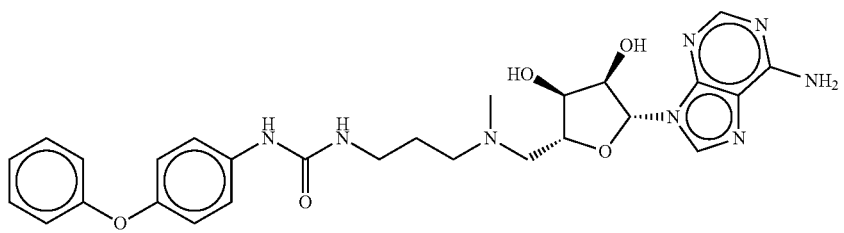
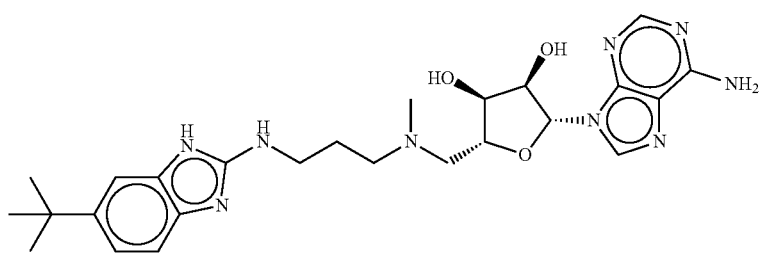
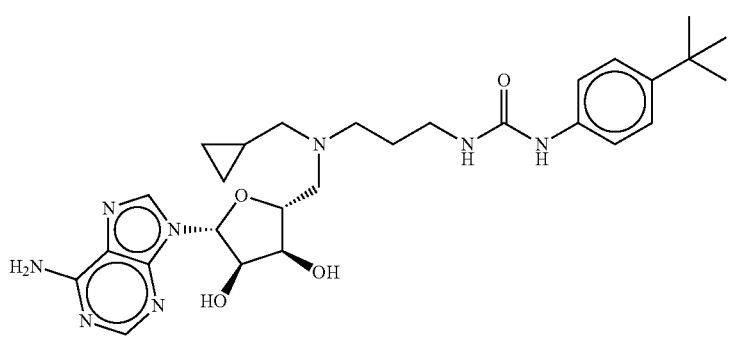
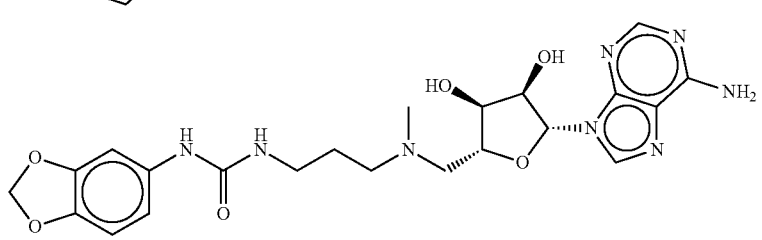

-continued
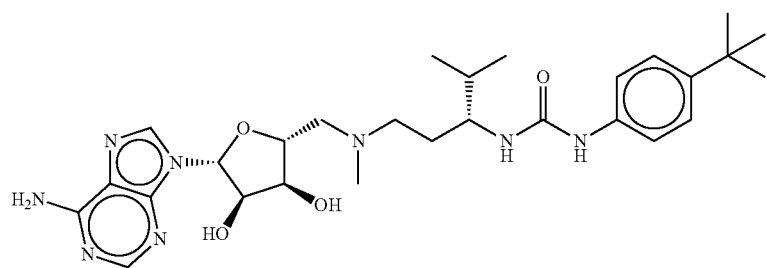
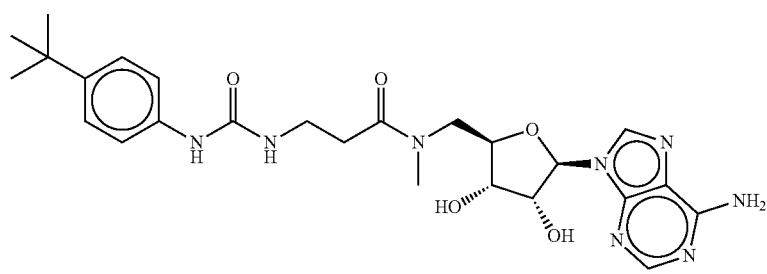
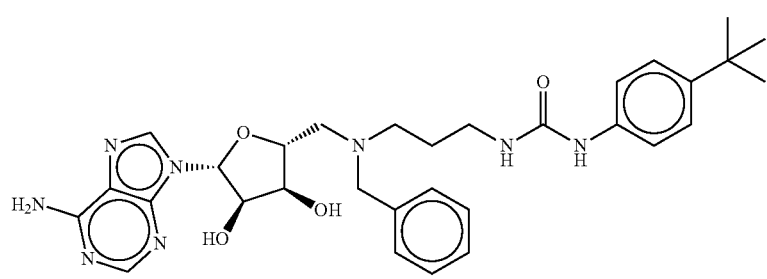
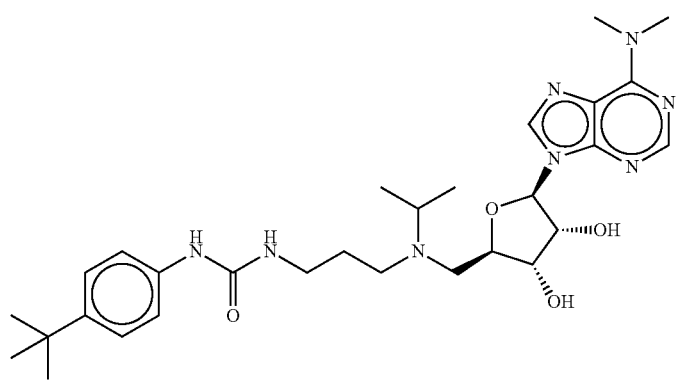
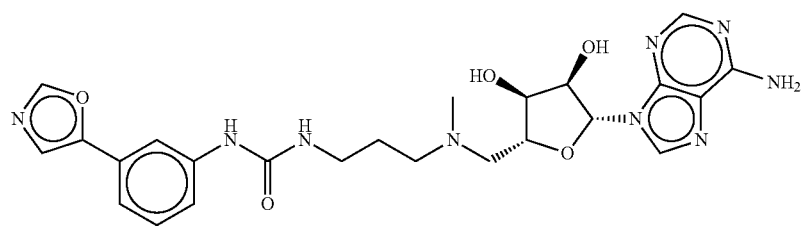
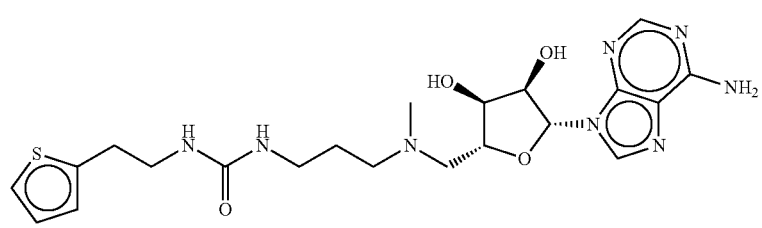

-continued
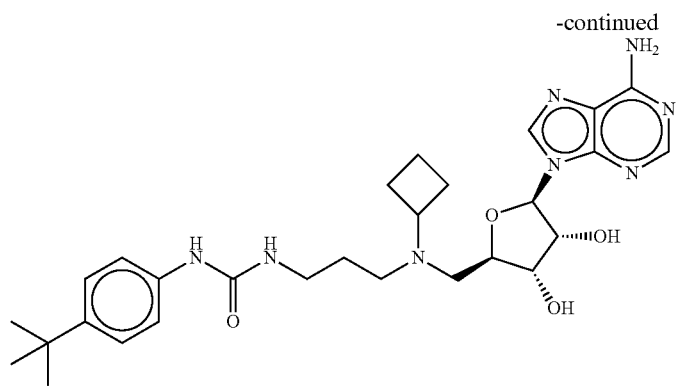
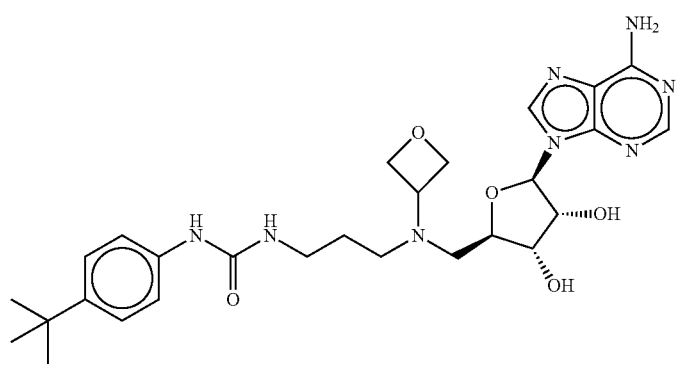
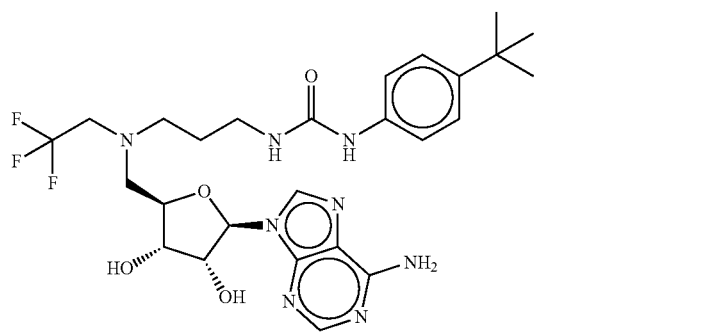
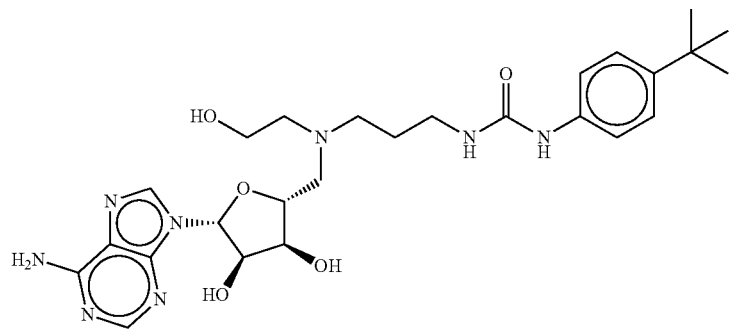
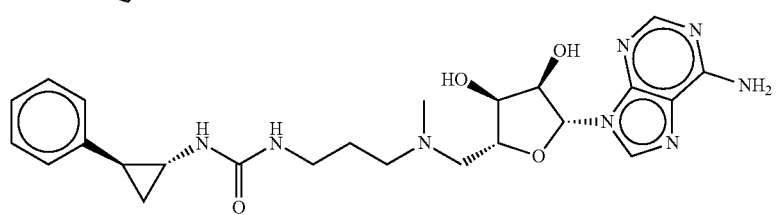

-continued
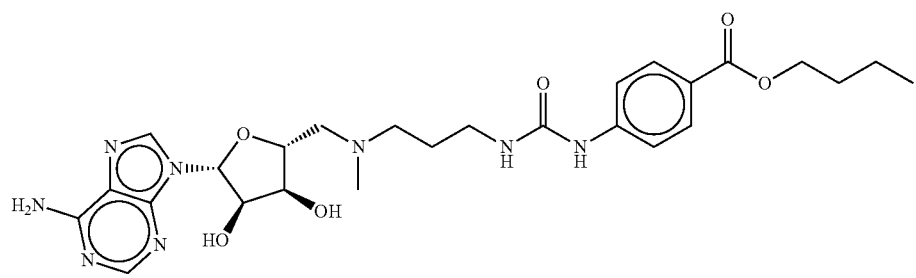
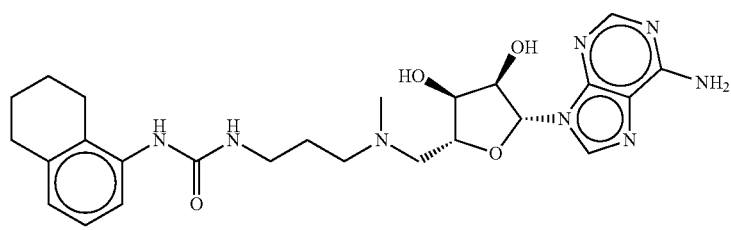
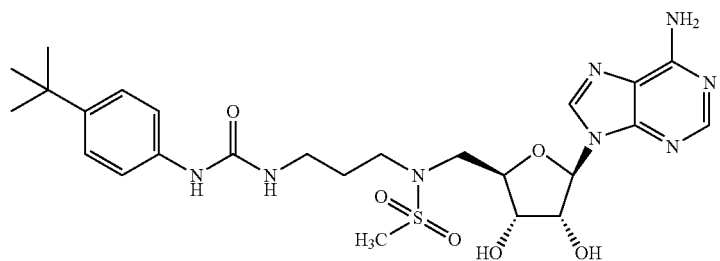
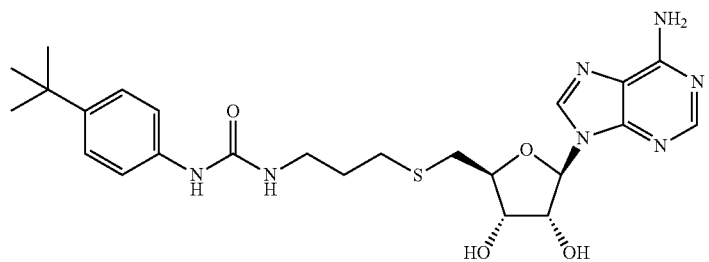
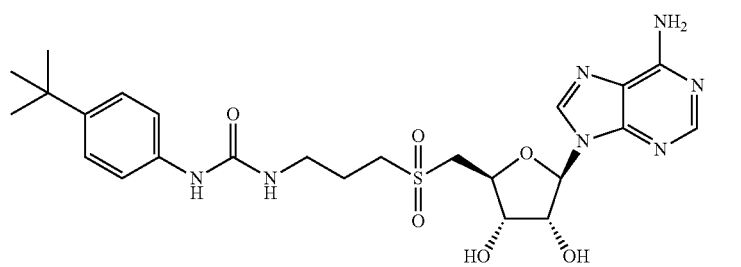
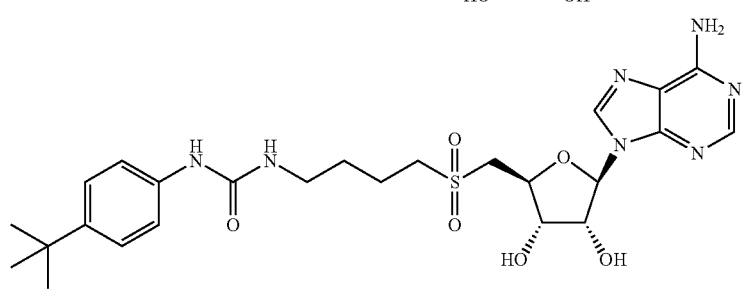

-continued
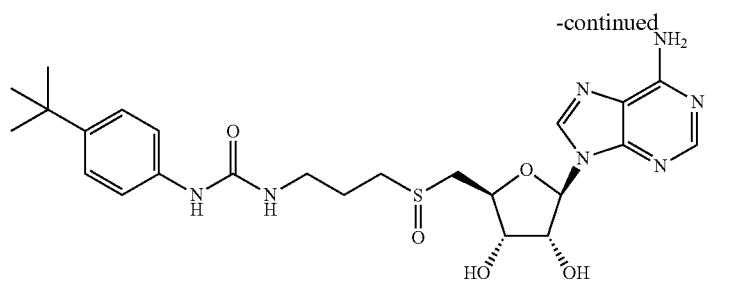
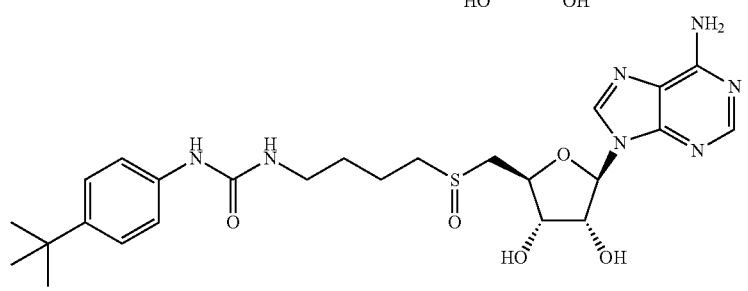
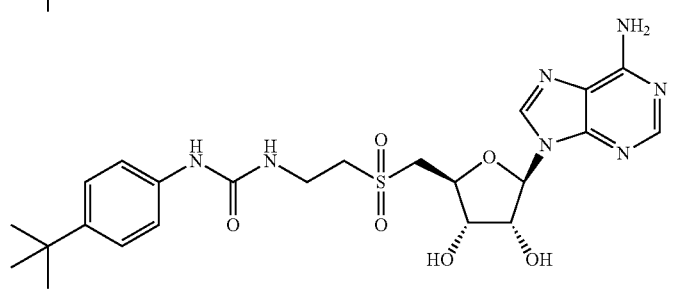
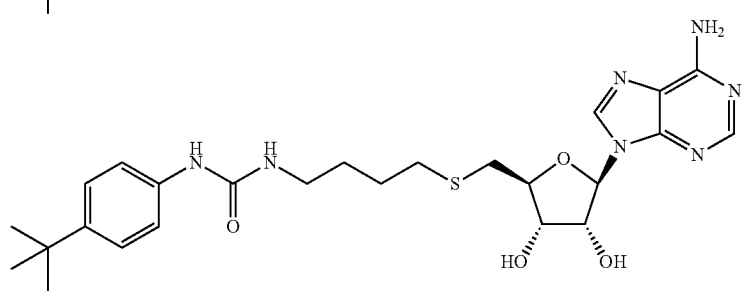
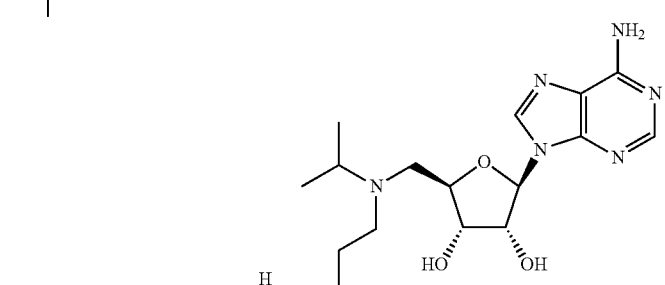
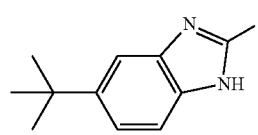
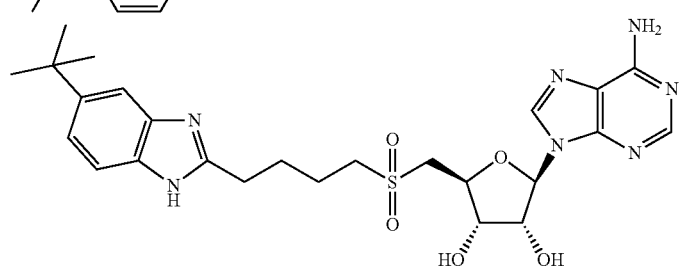

93
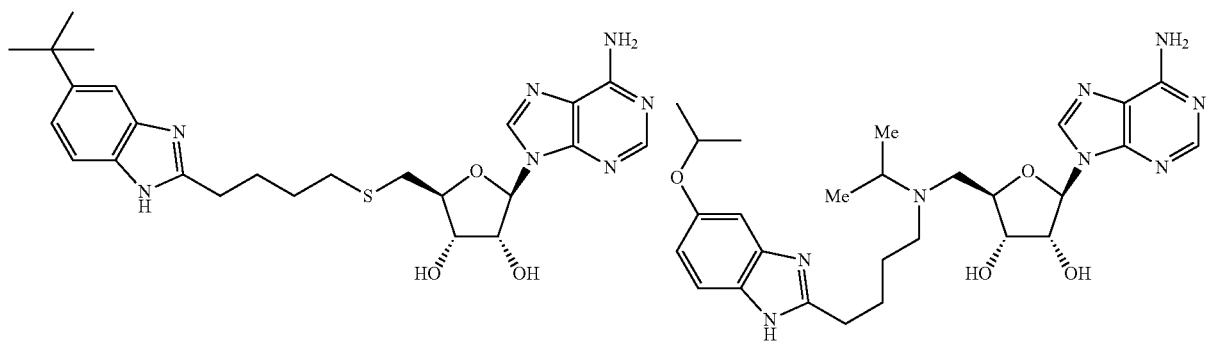
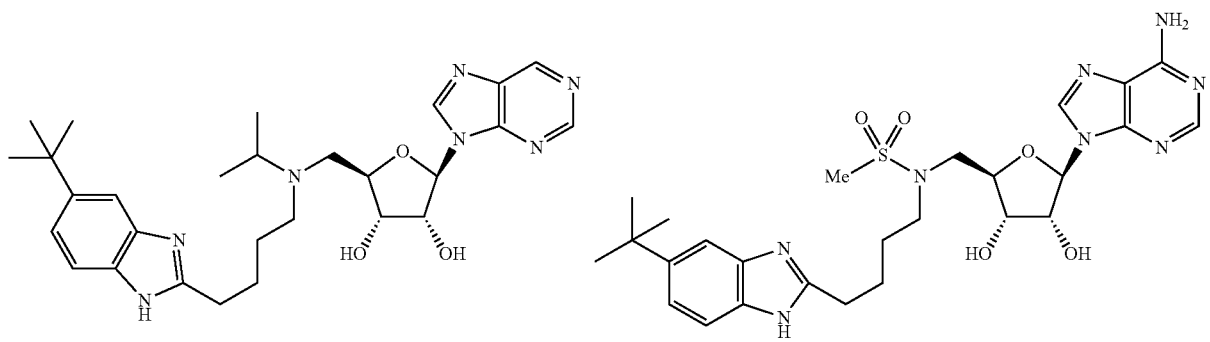
94
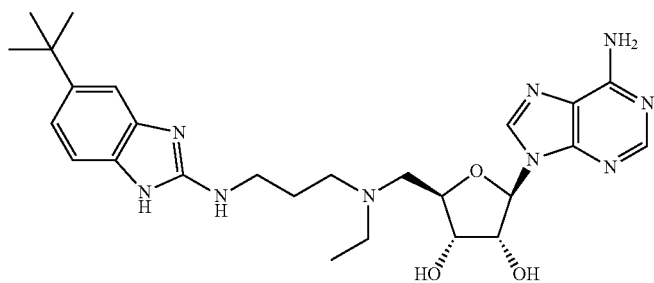
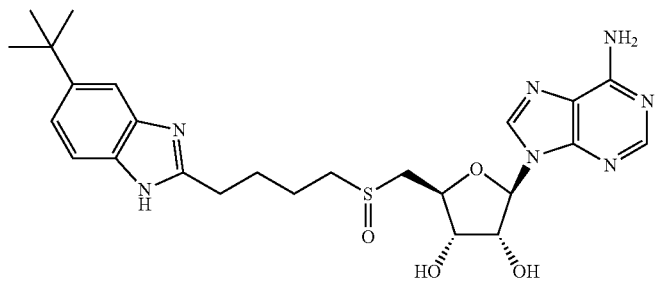
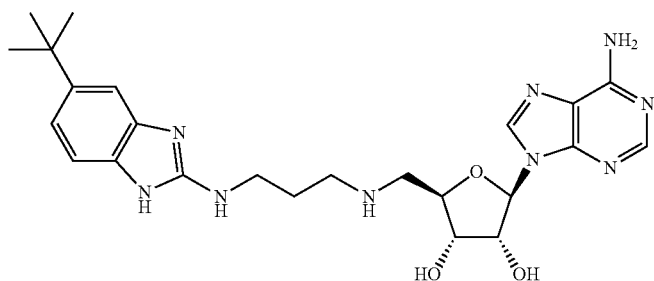

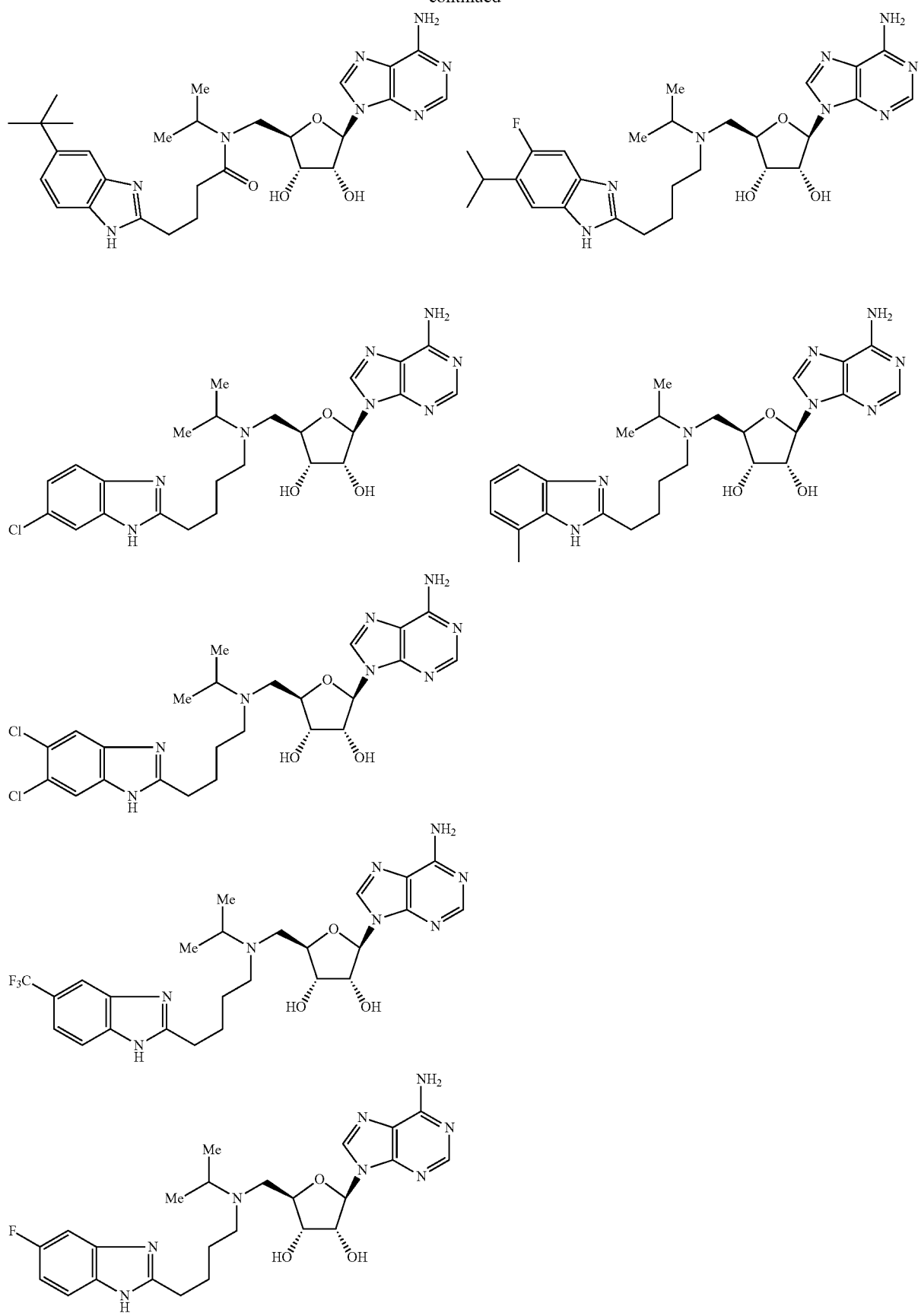

-continued
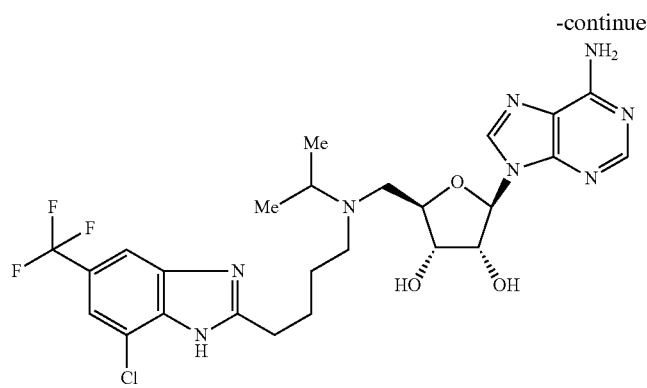
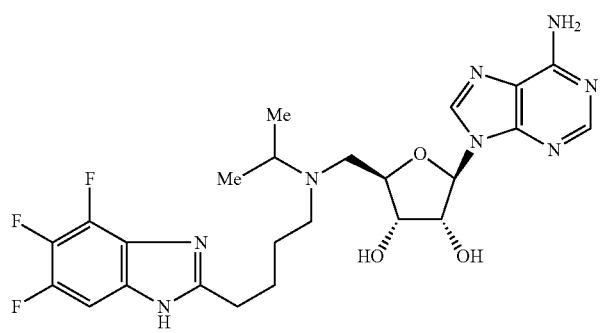
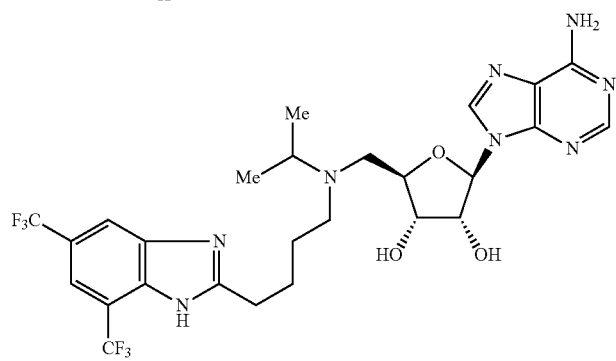
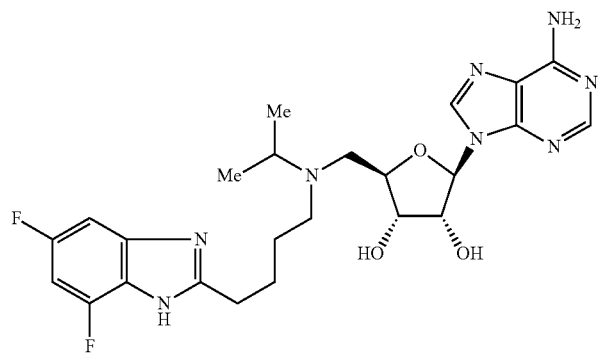
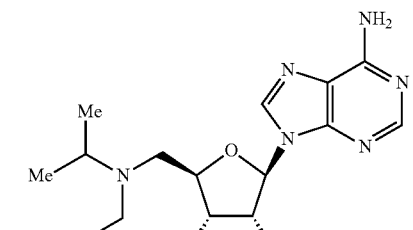
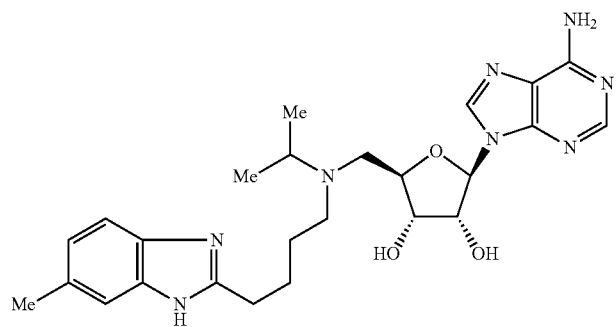

-continued
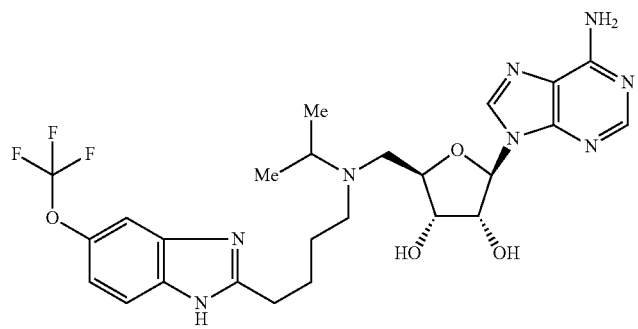
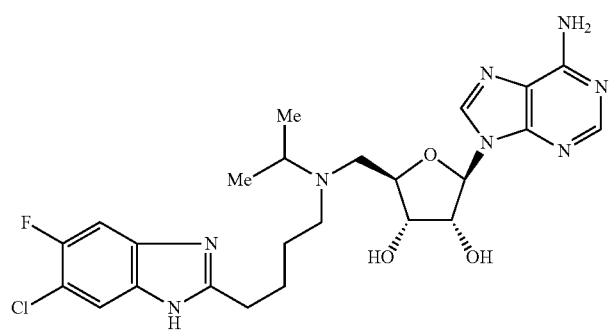
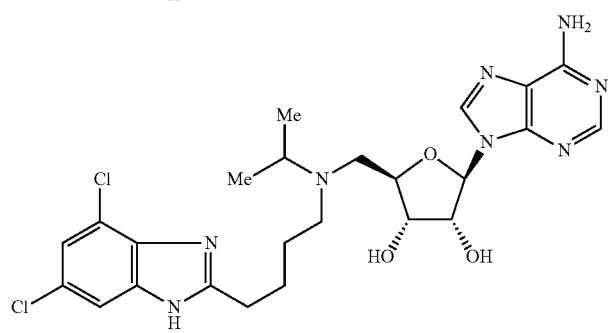
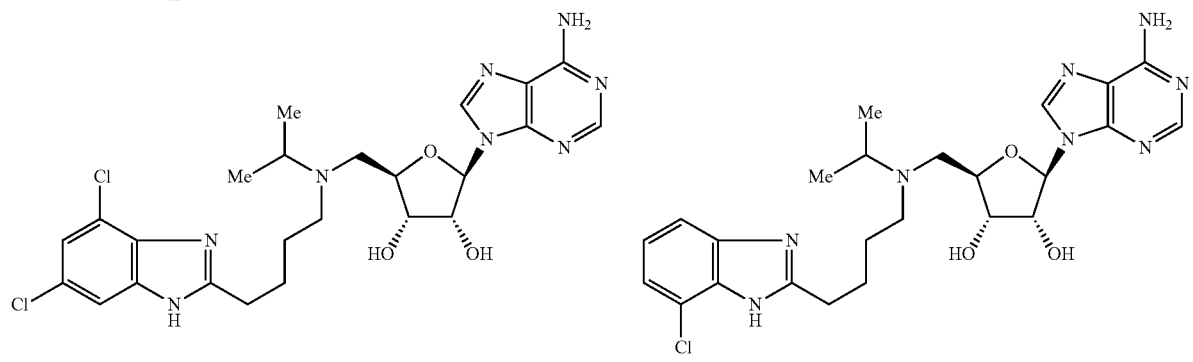
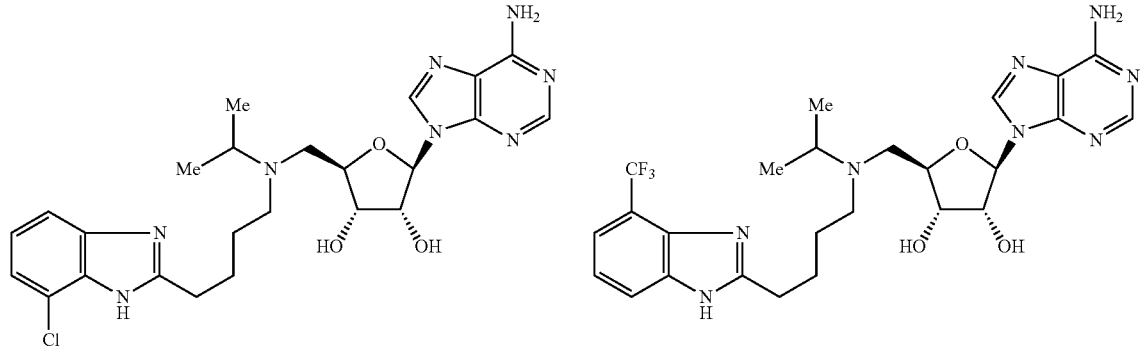

-continued
| 101 | 102 |
|---|---|
| 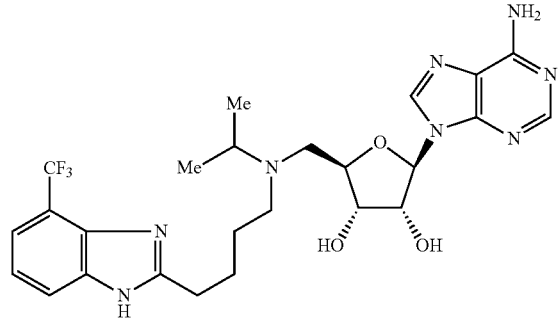 | 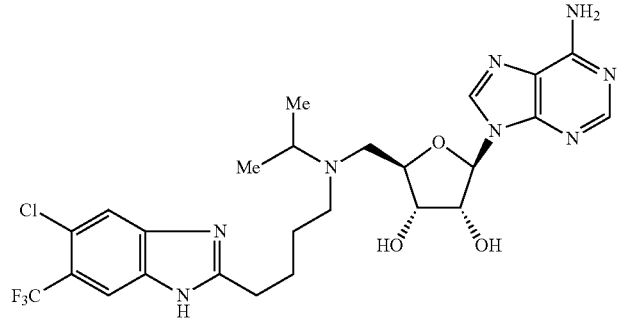 |
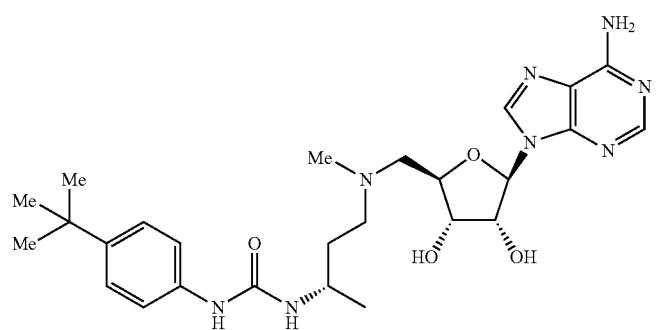
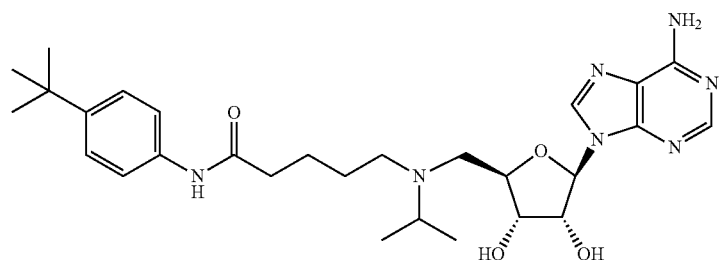
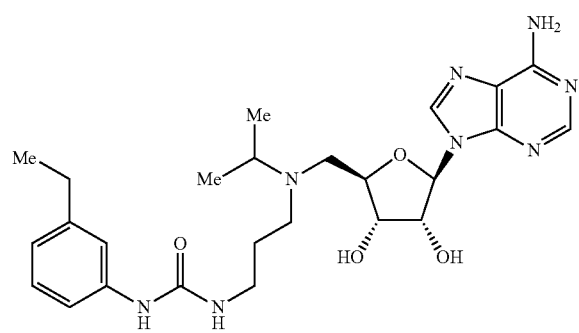 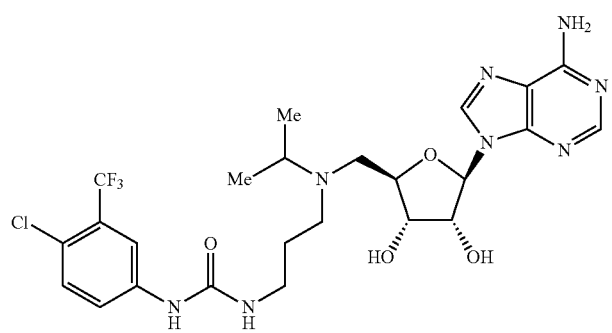
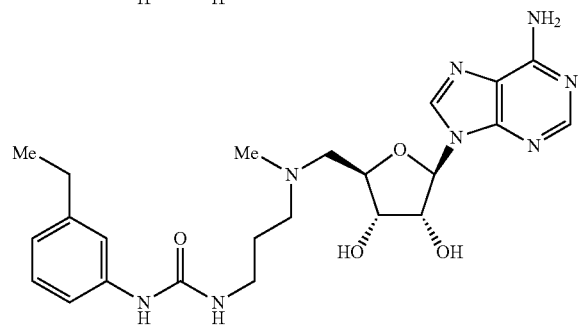 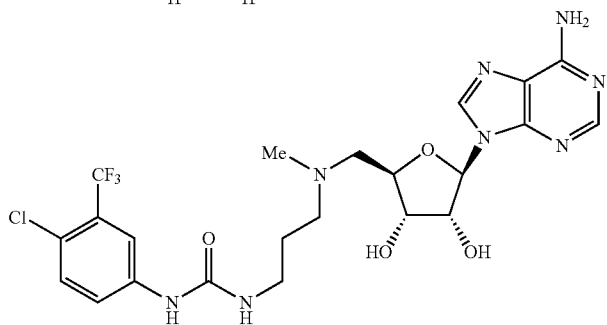

-continued
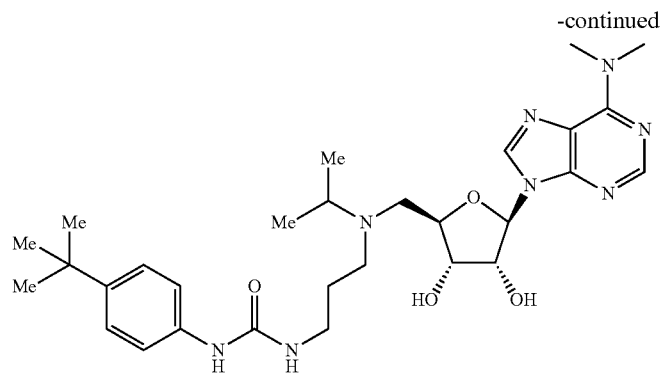
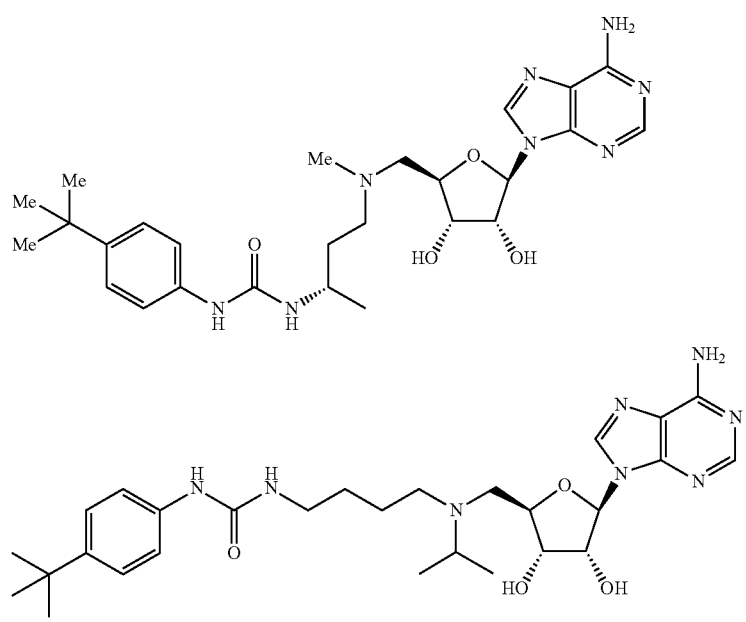
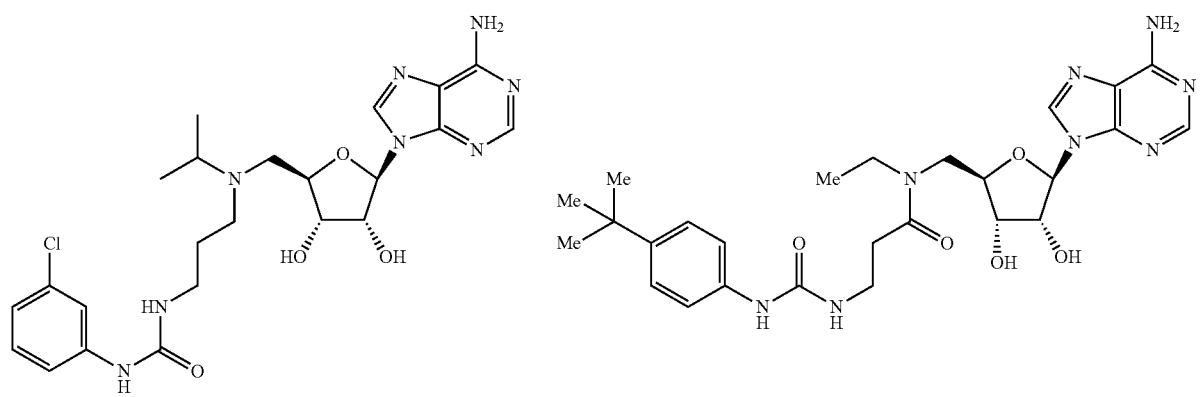
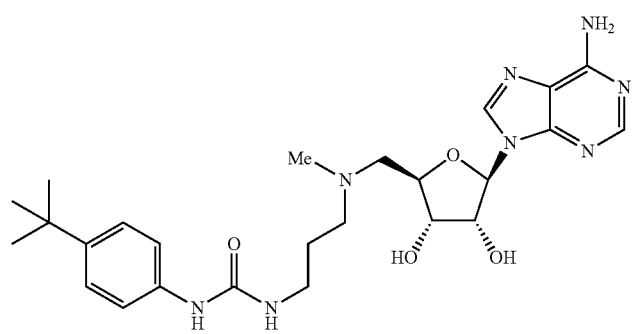

-continued
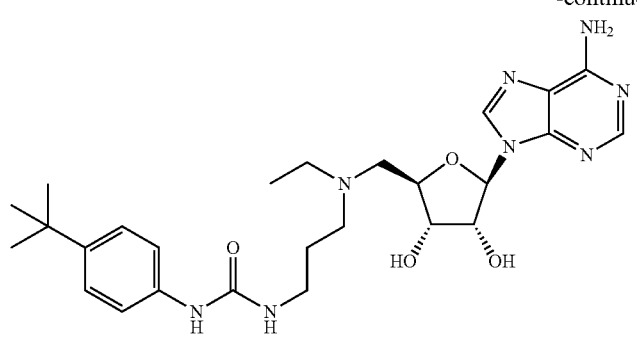
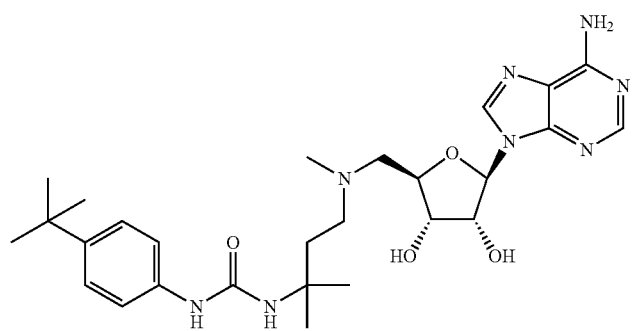
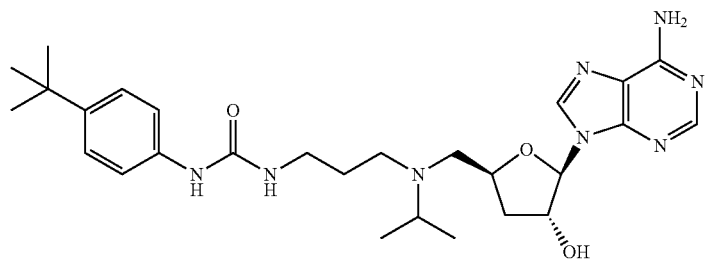
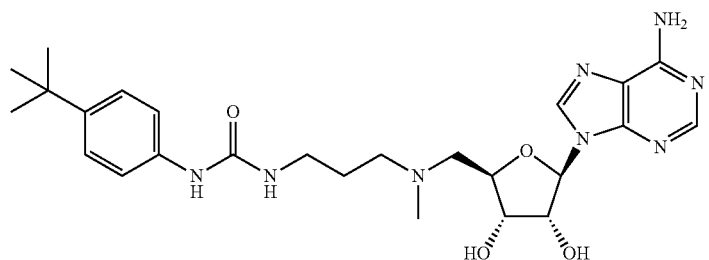
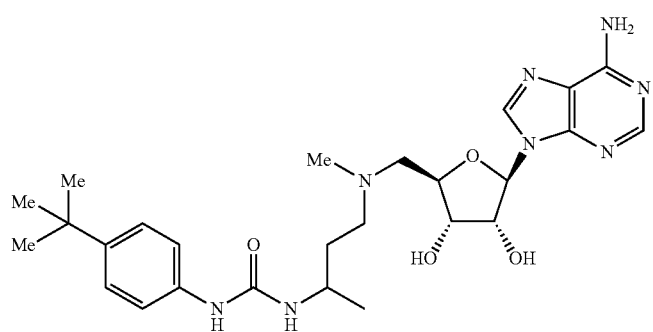

-continued
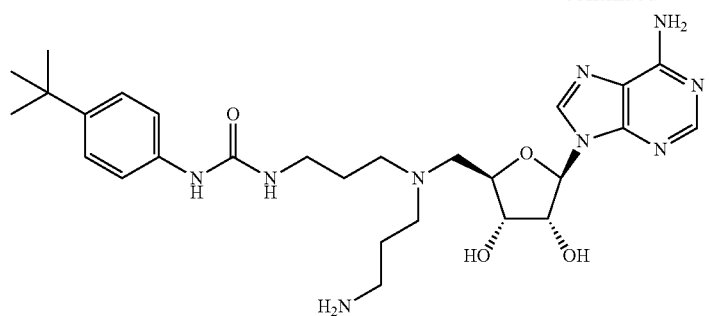
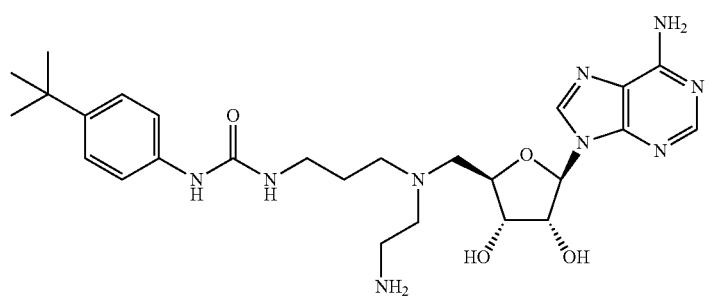
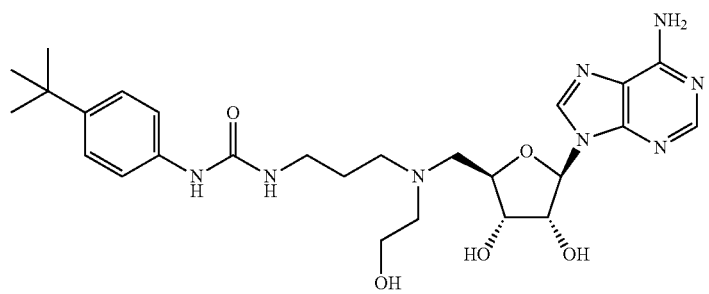
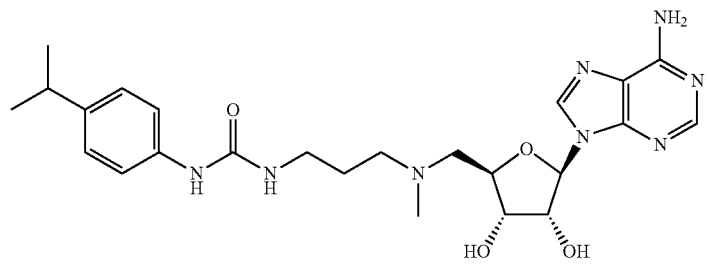
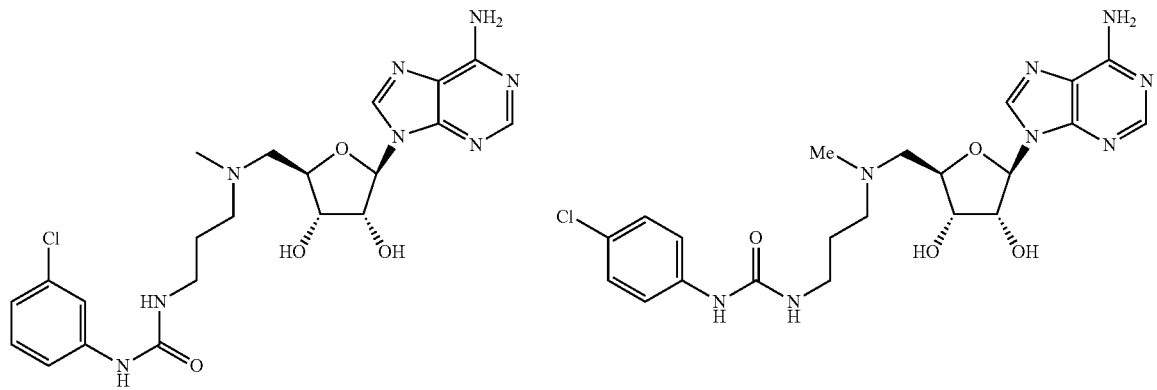

109 110
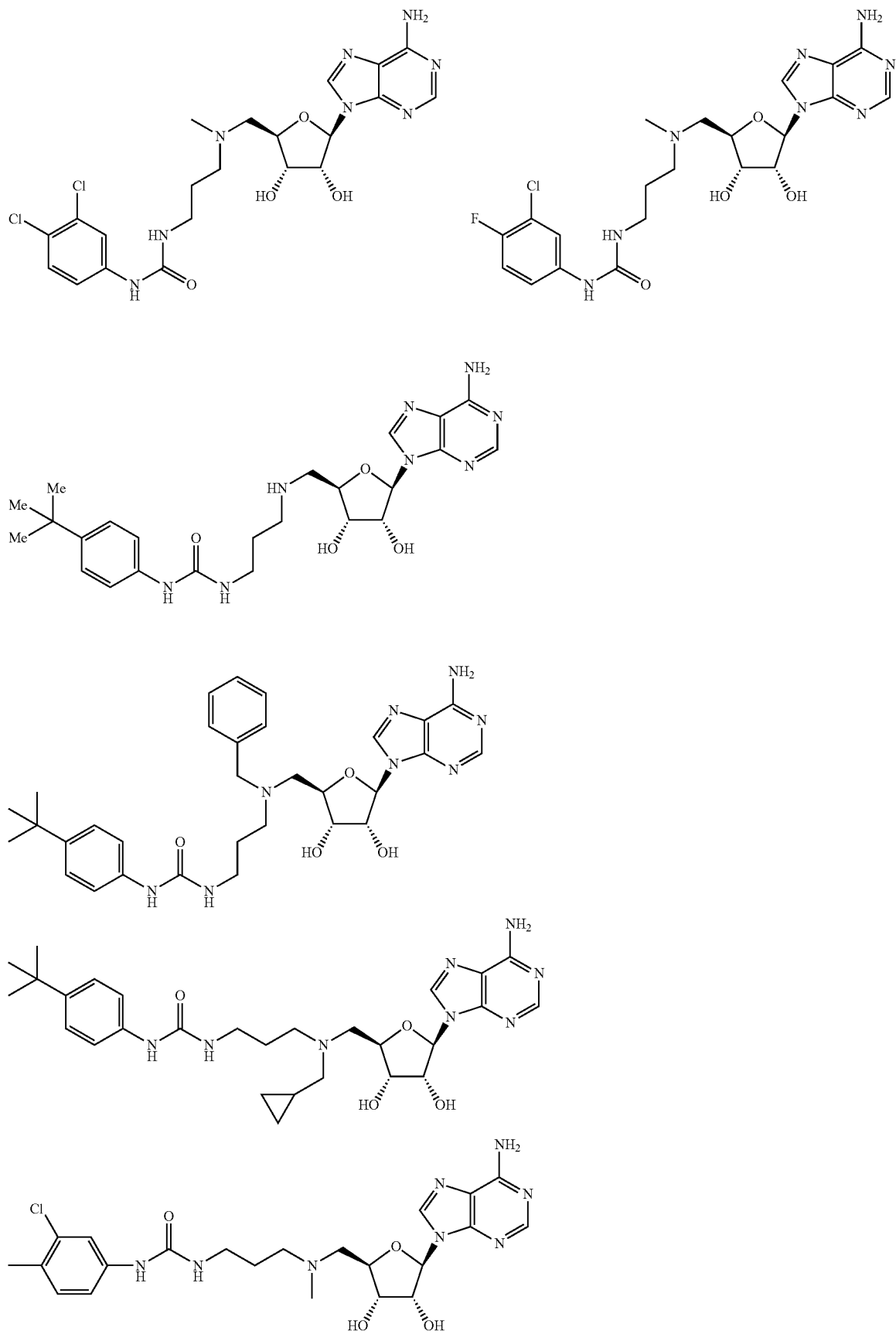
-continued

-continued
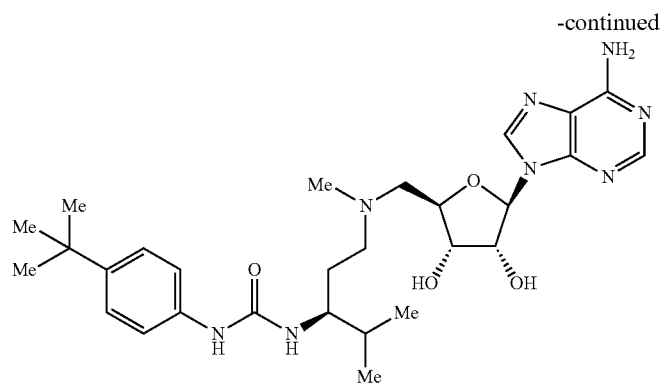
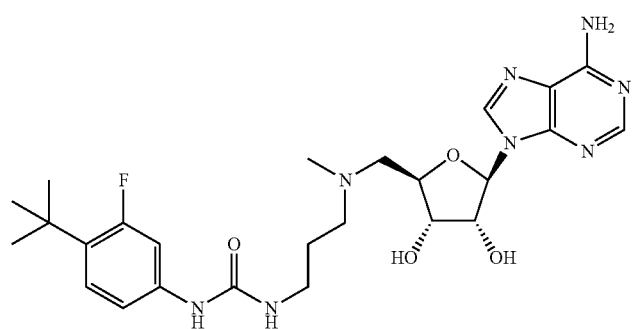
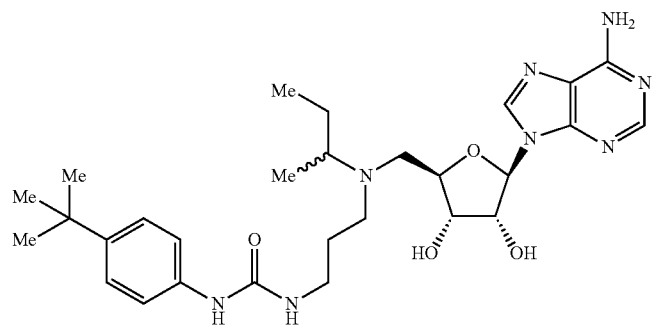
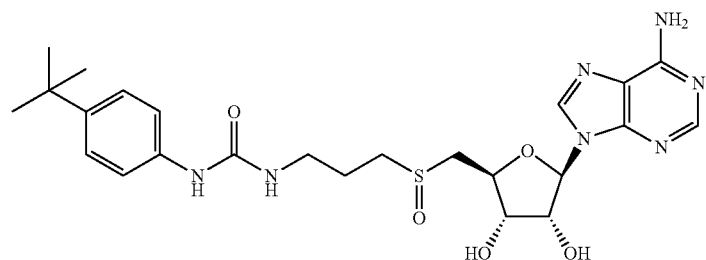
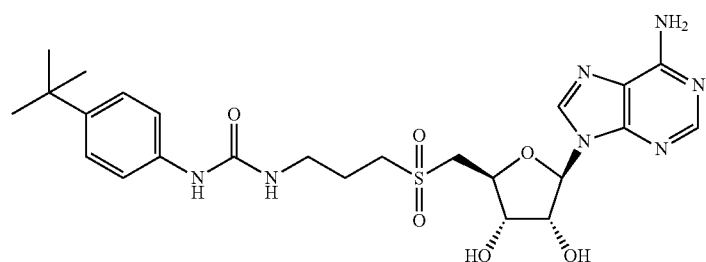

-continued
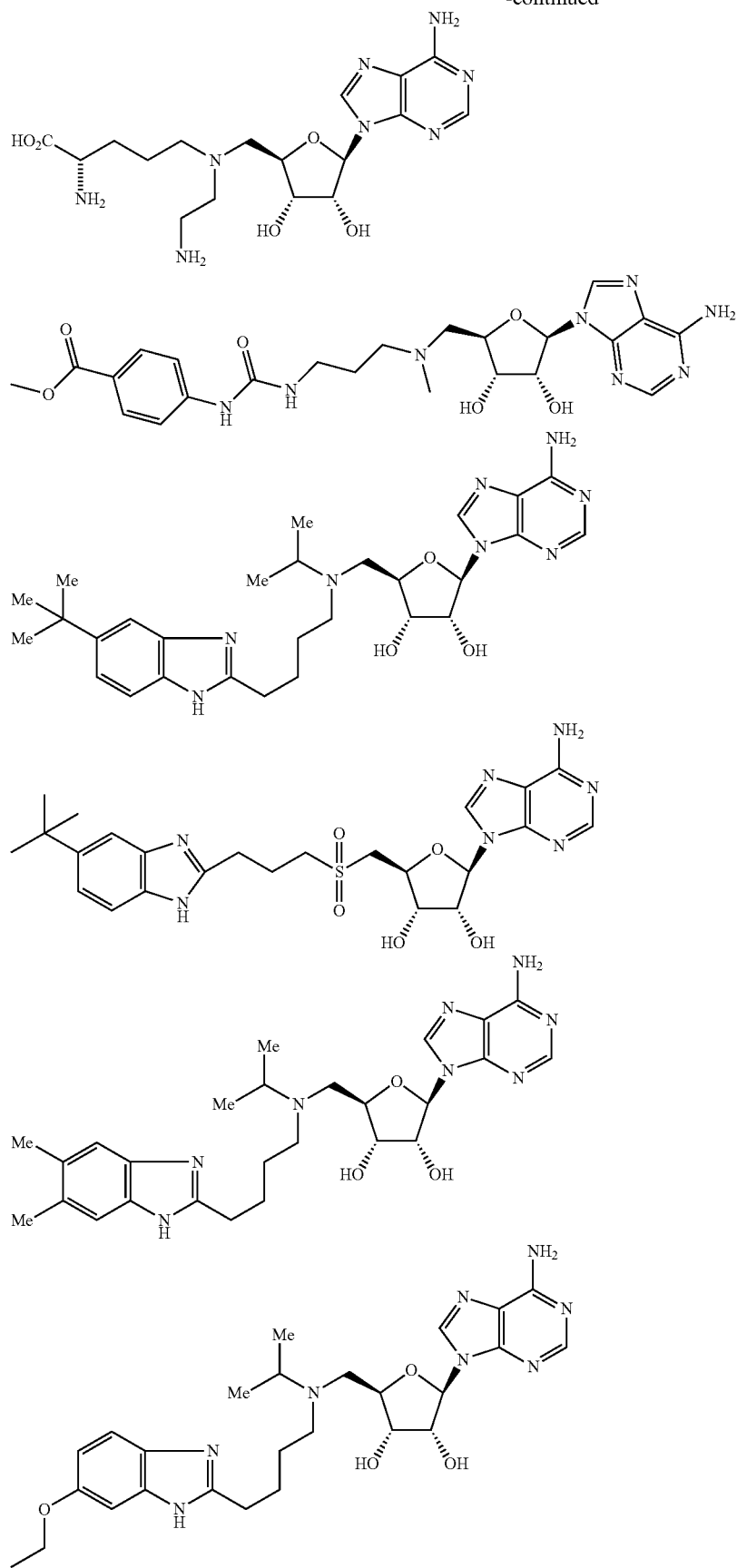

-continued
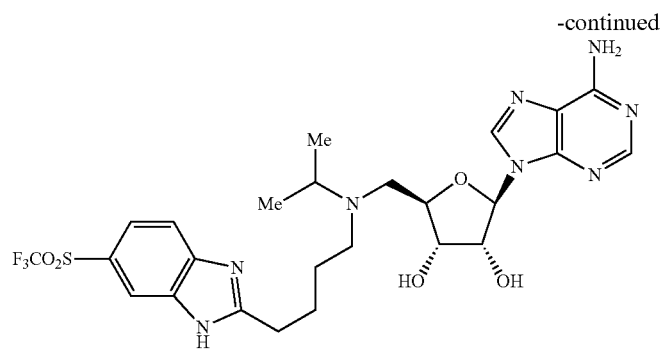
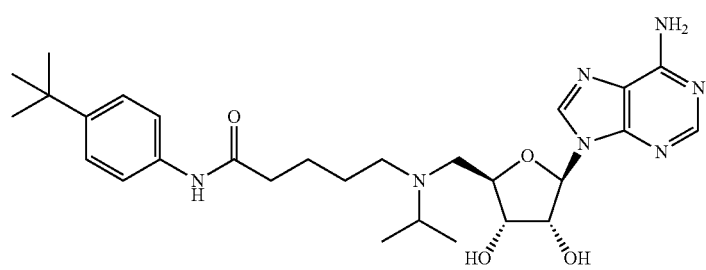
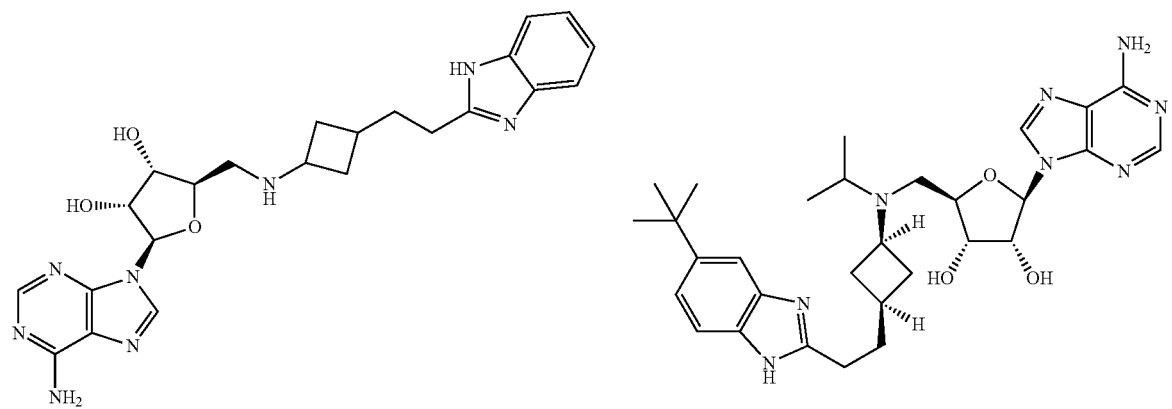
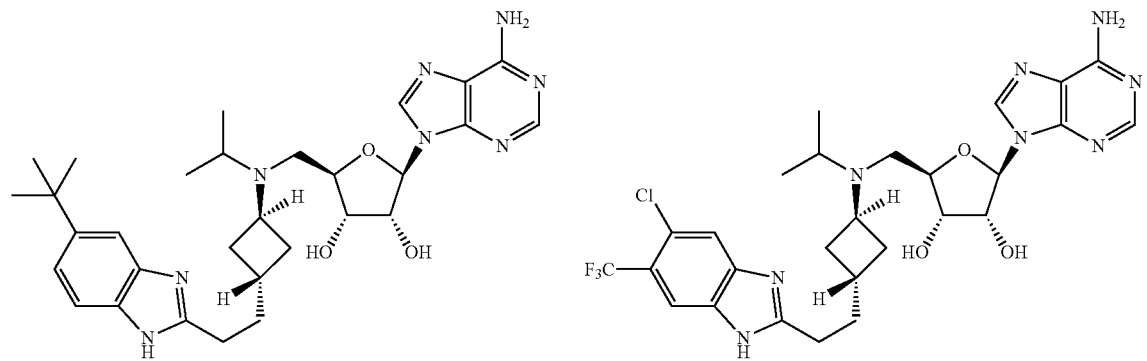

117 118
-continued
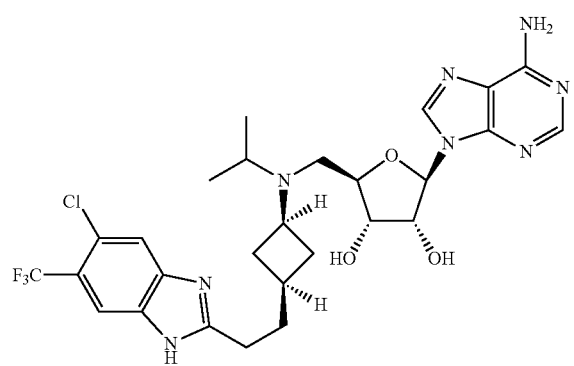
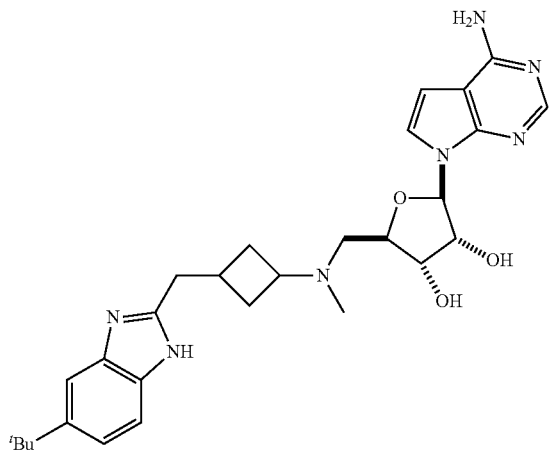
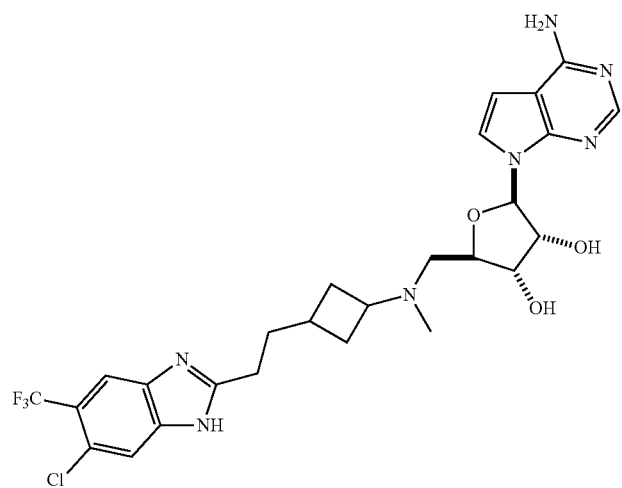
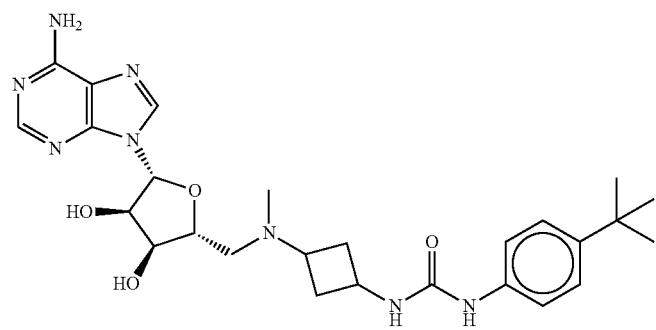
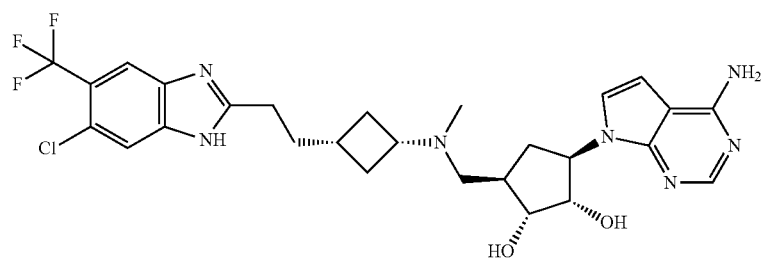

-continued
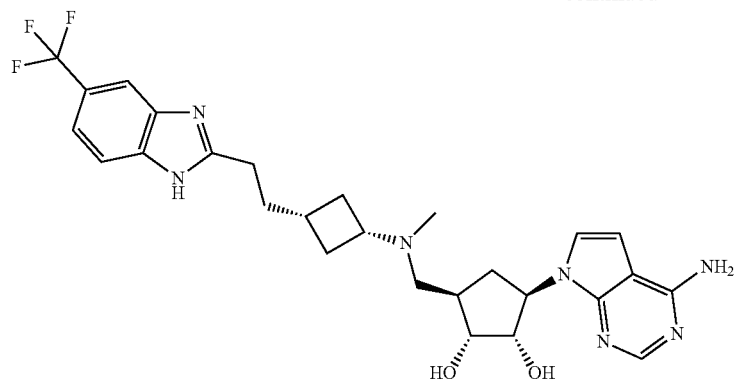
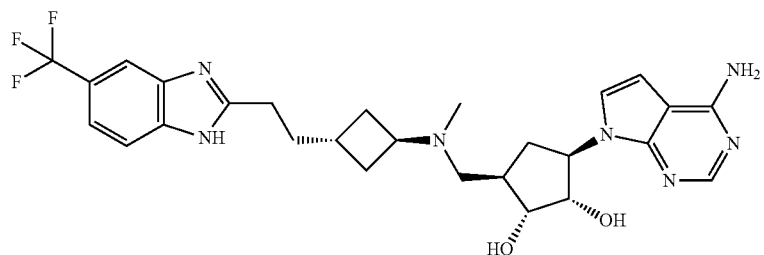
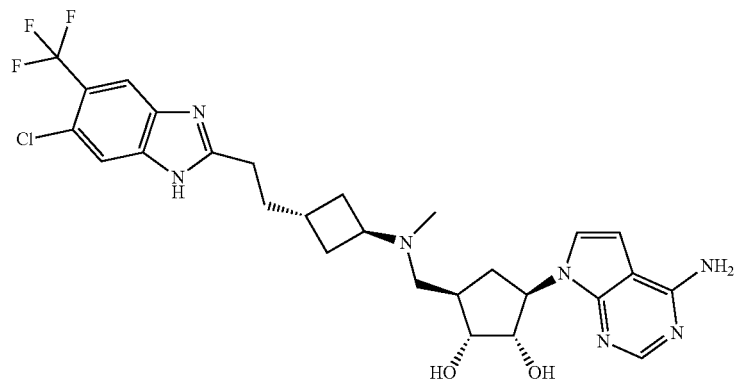
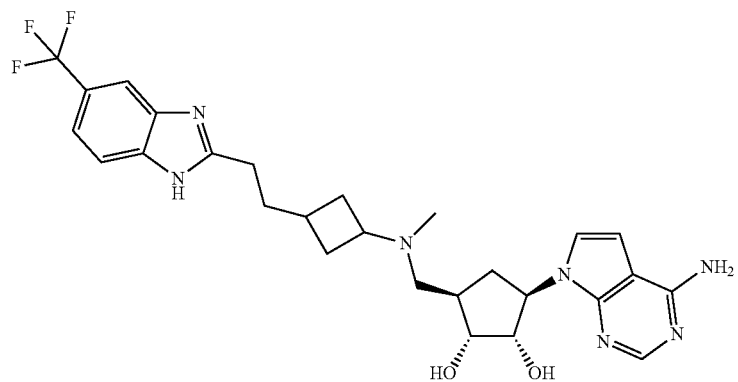

-continued
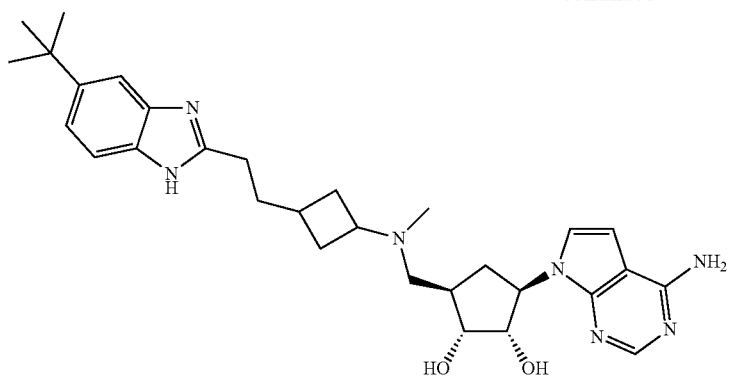
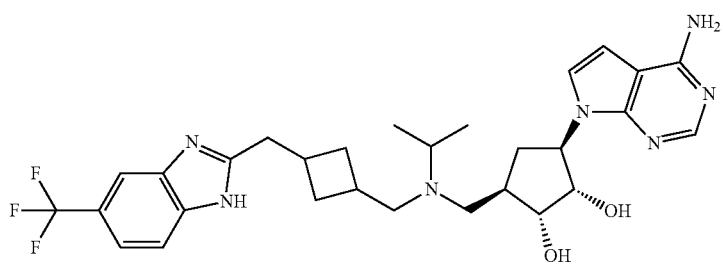
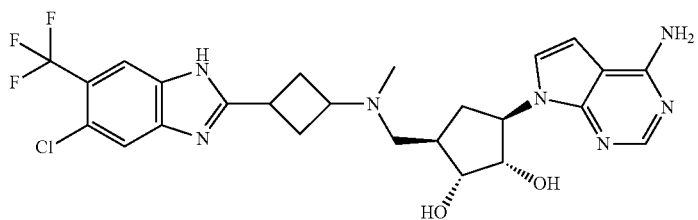
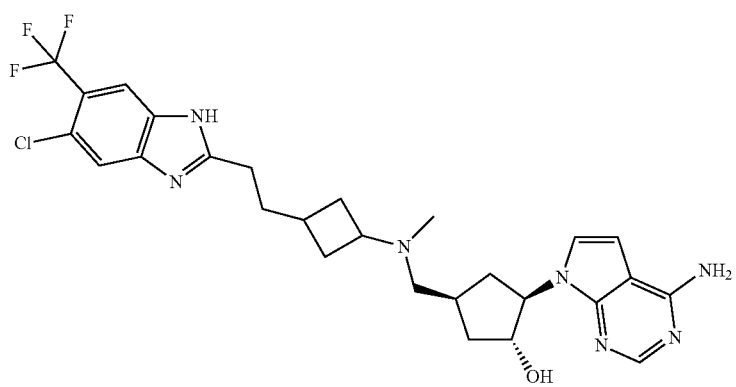
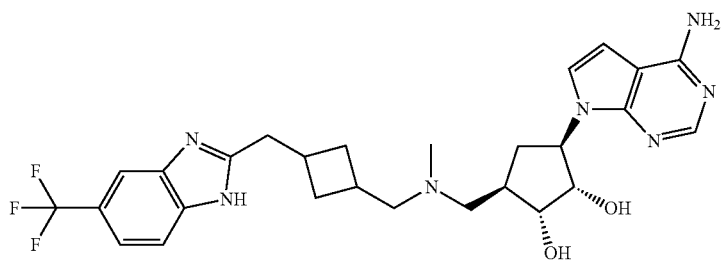

-continued
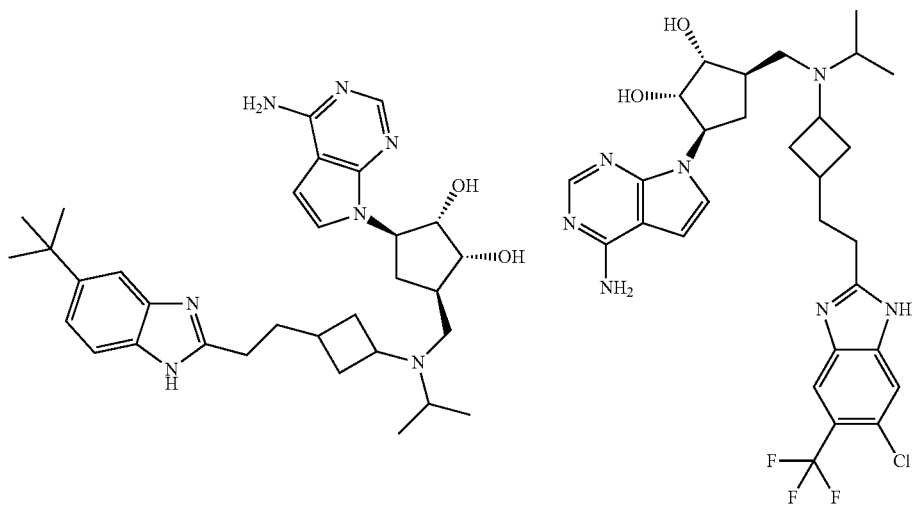
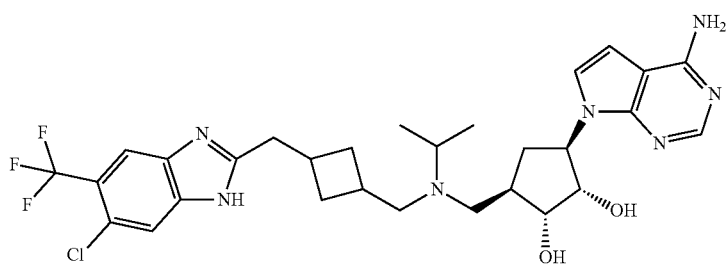
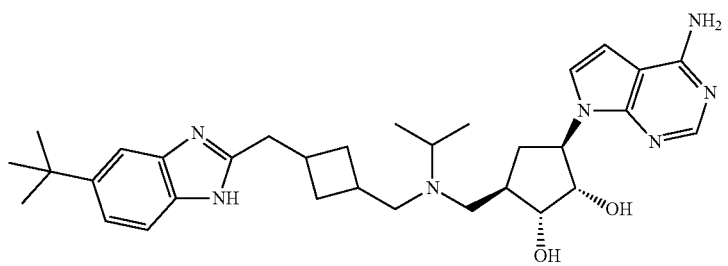
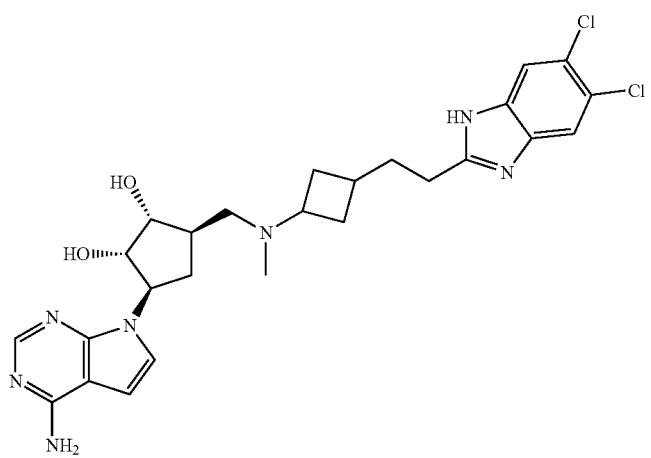

125
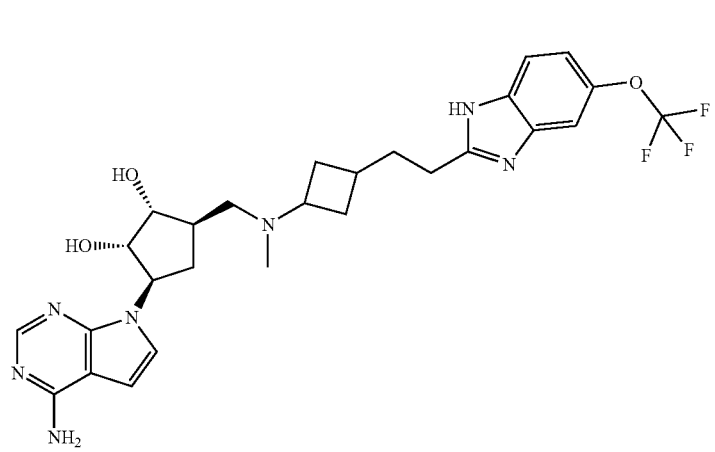
126
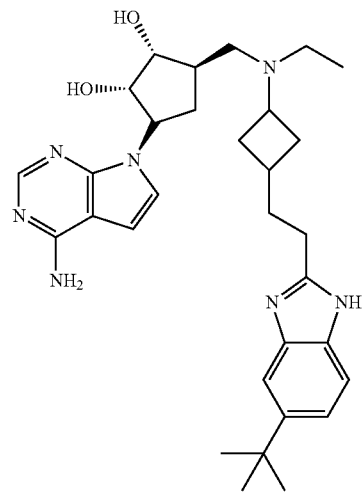
-continued
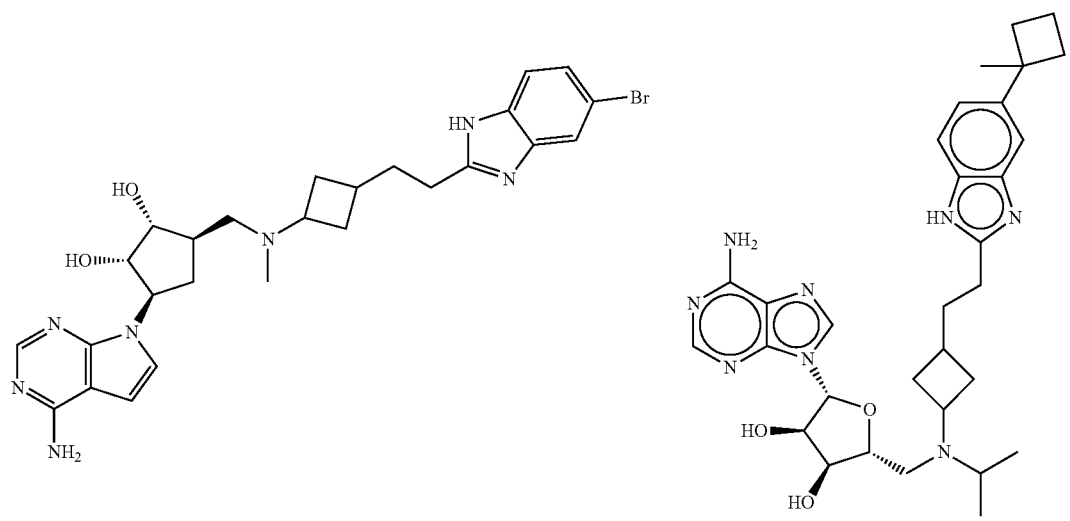
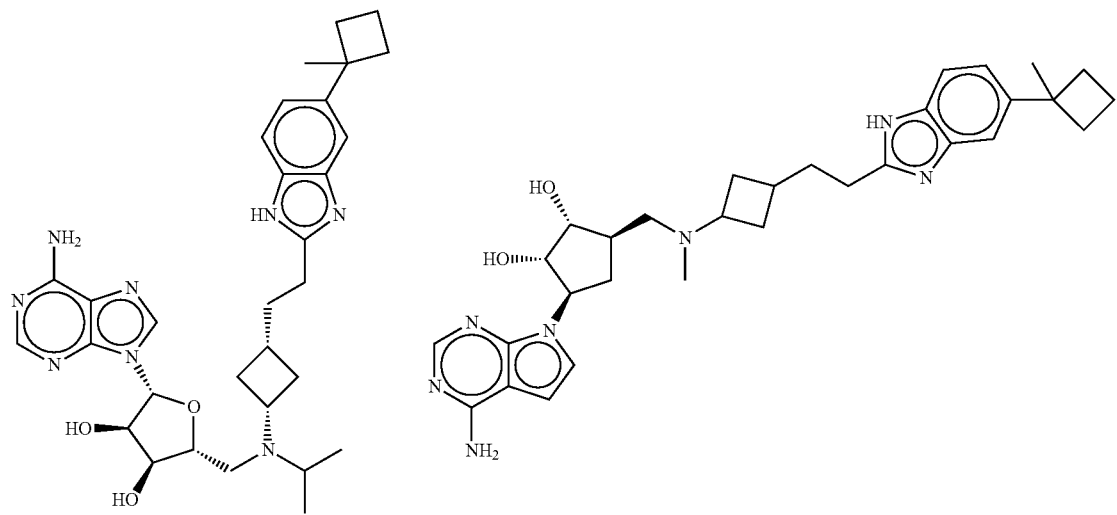

127
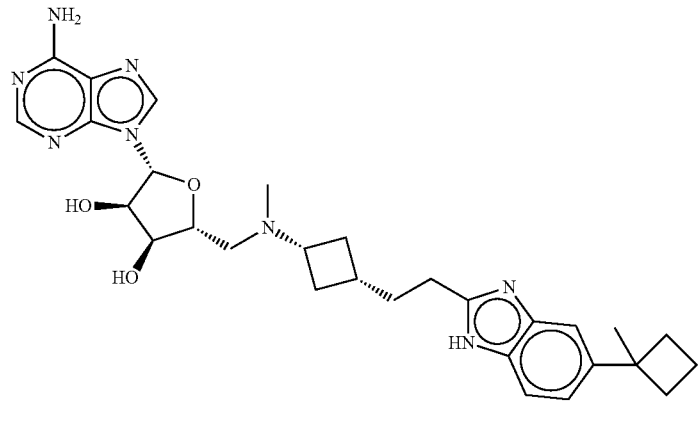
128
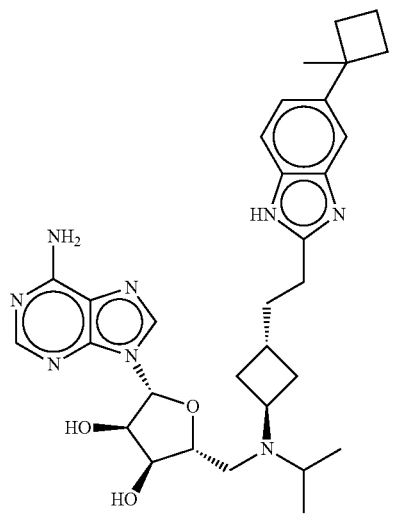
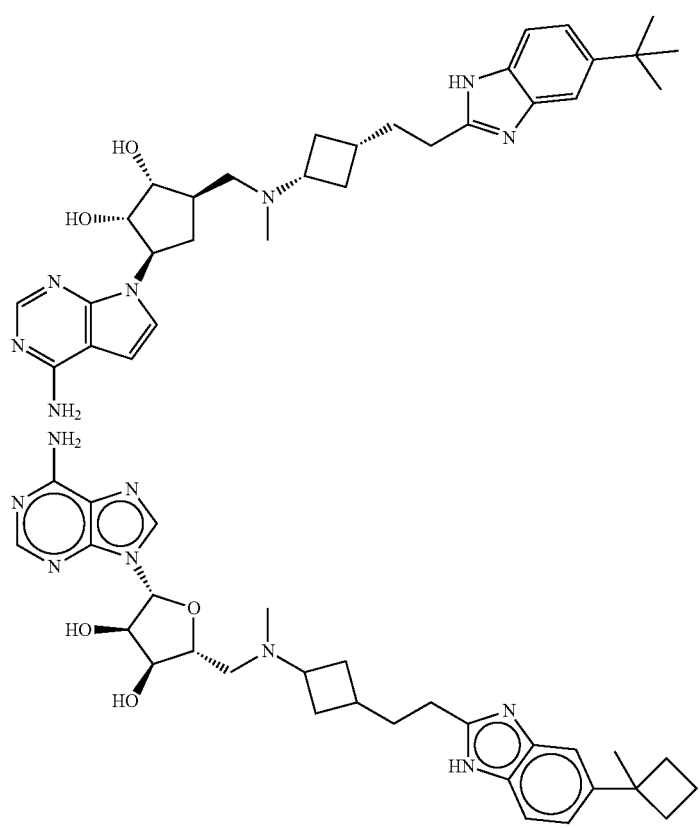
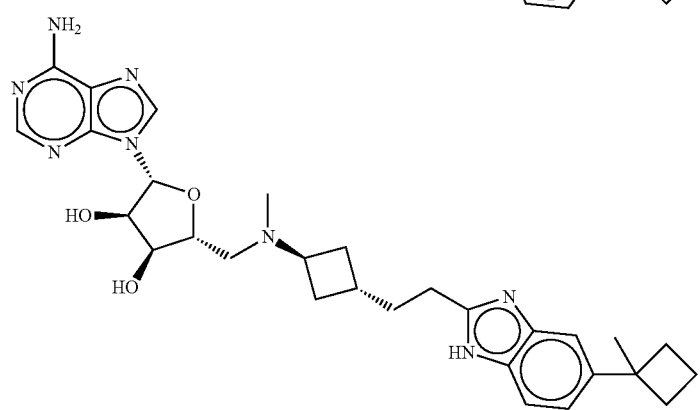

-continued
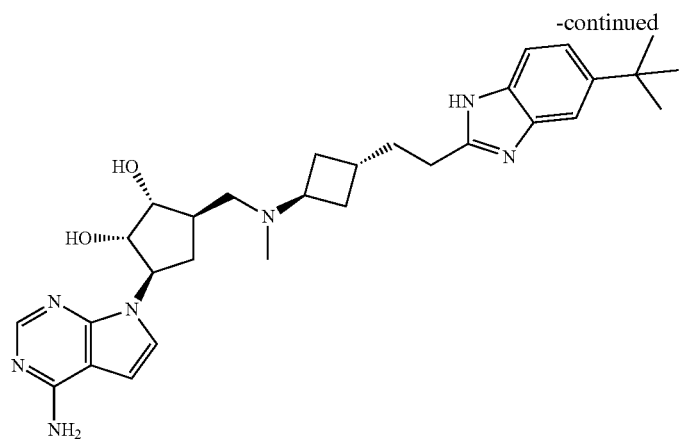
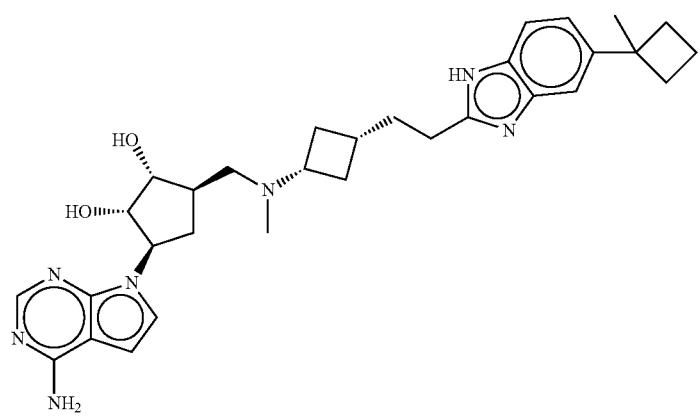
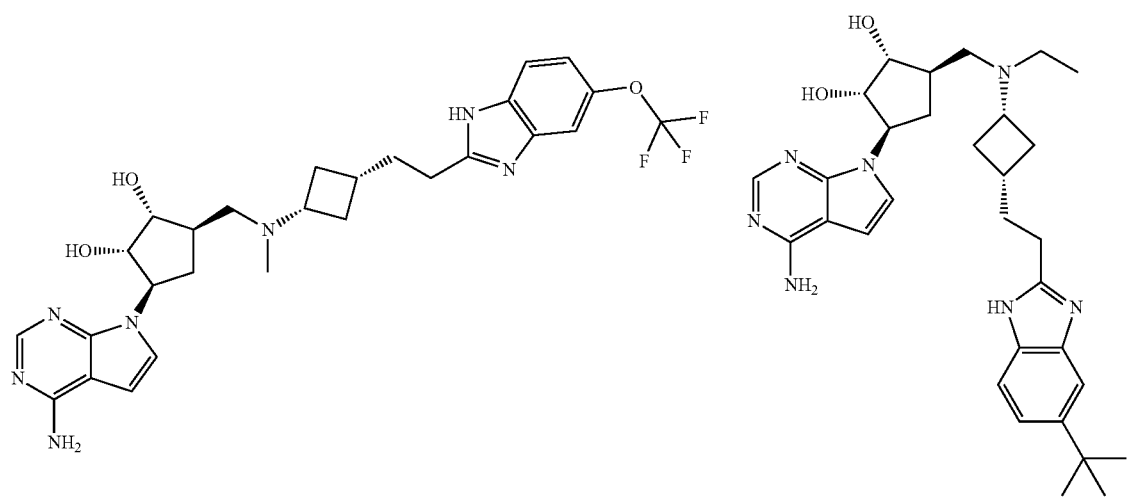

131
132
-continued
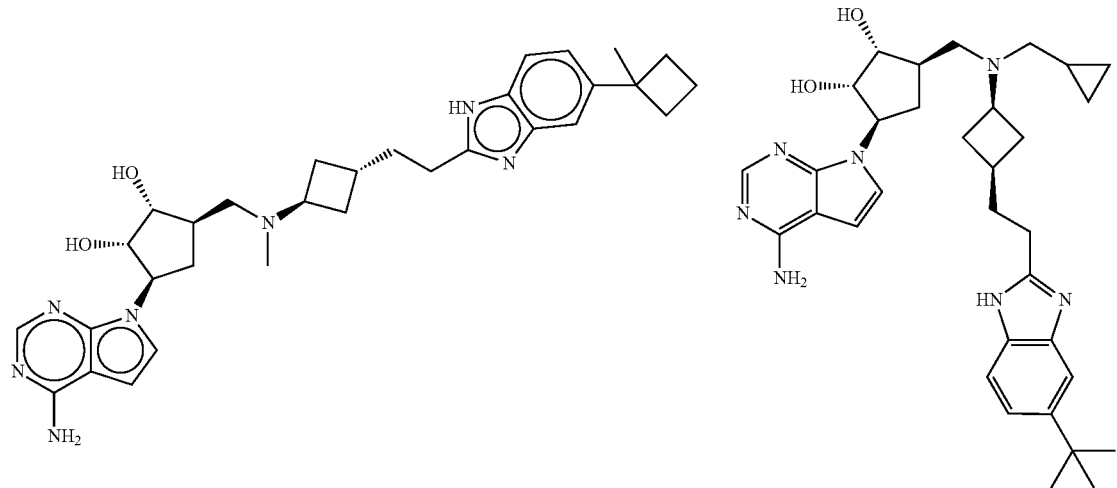
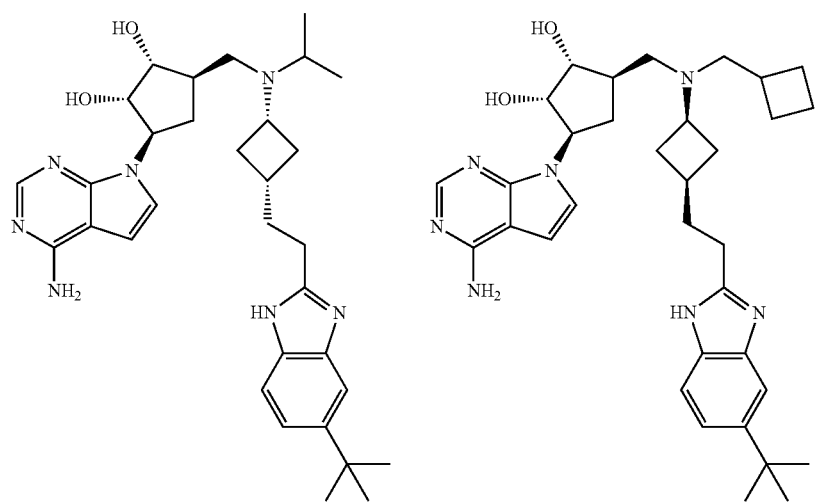
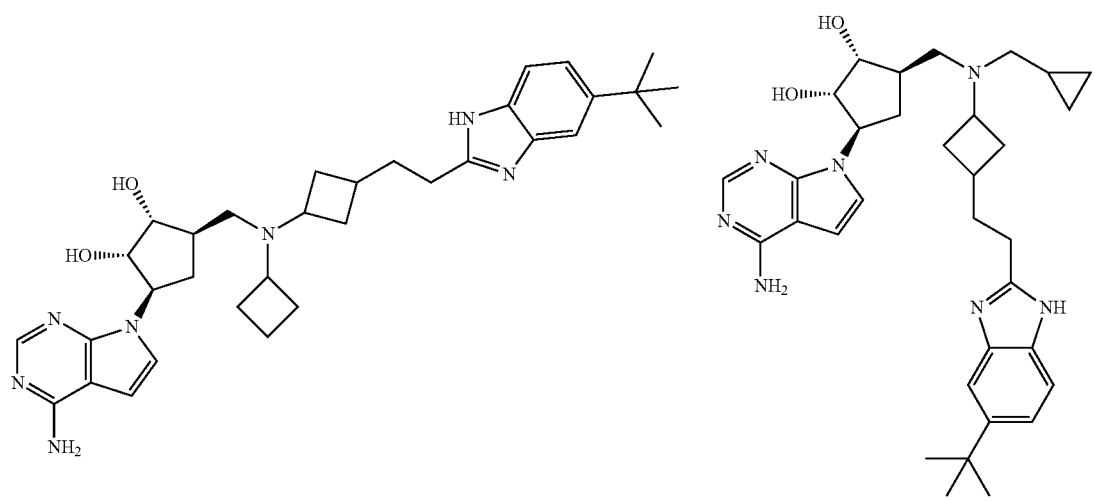

133
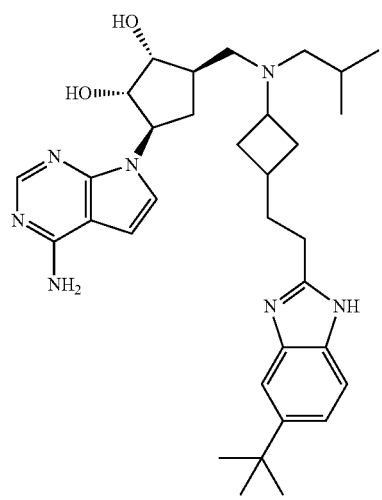
134
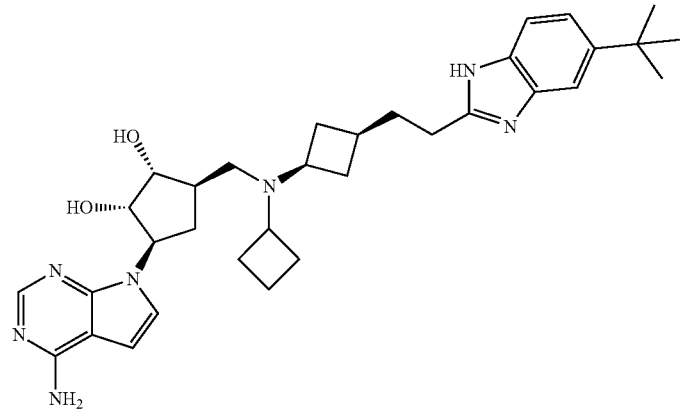
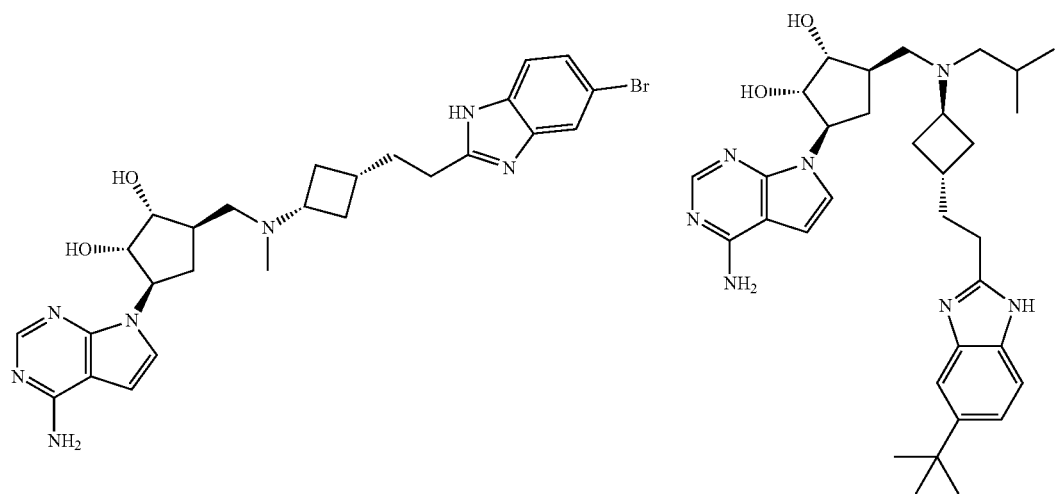
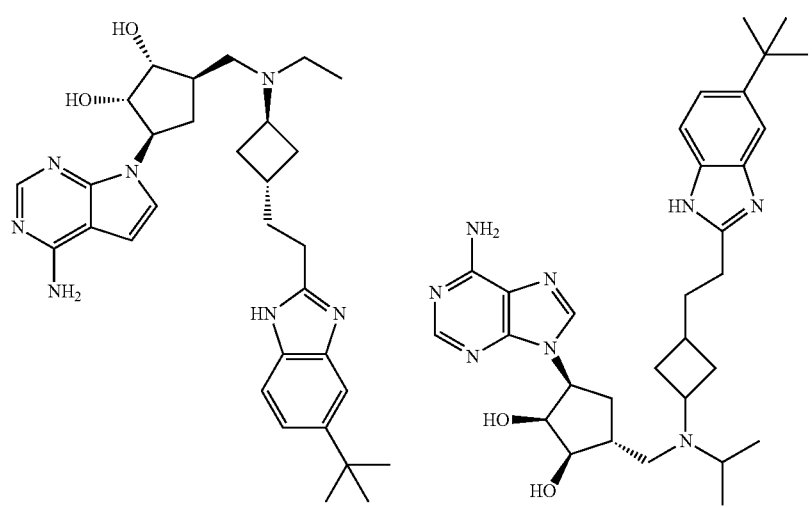

-continued
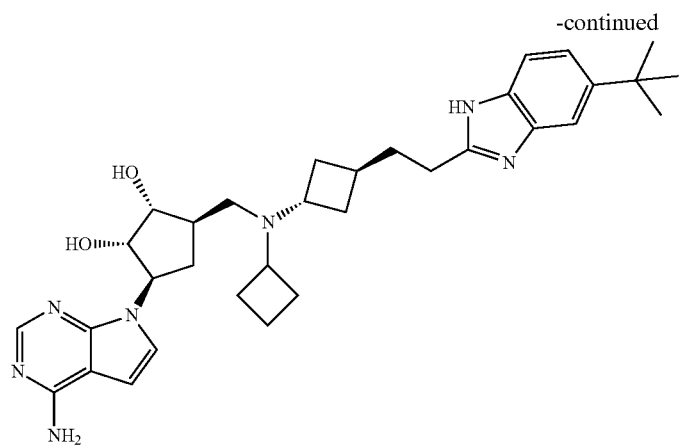
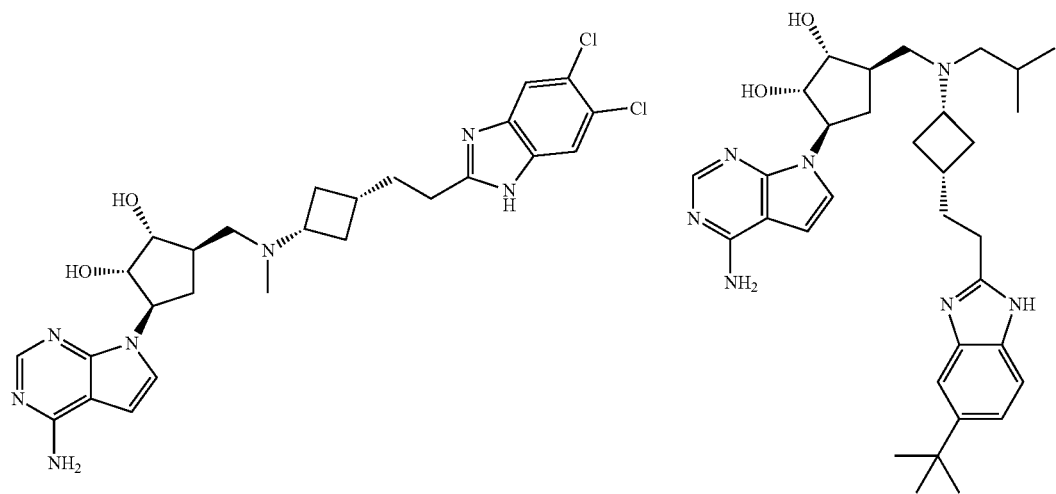
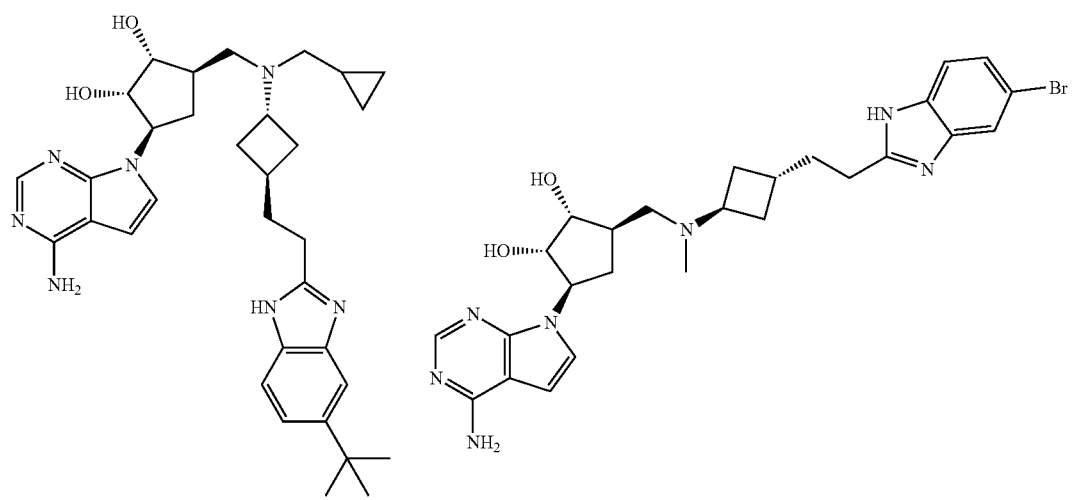

137
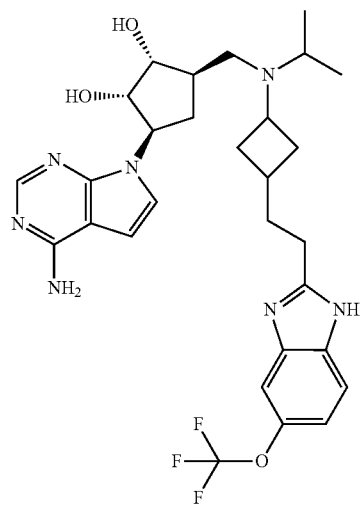
138
-continued
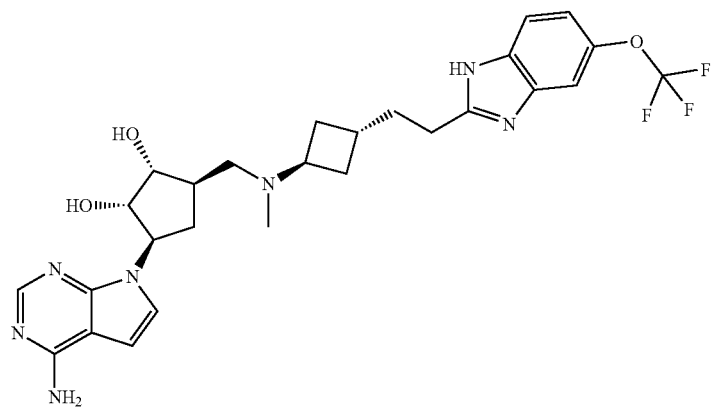
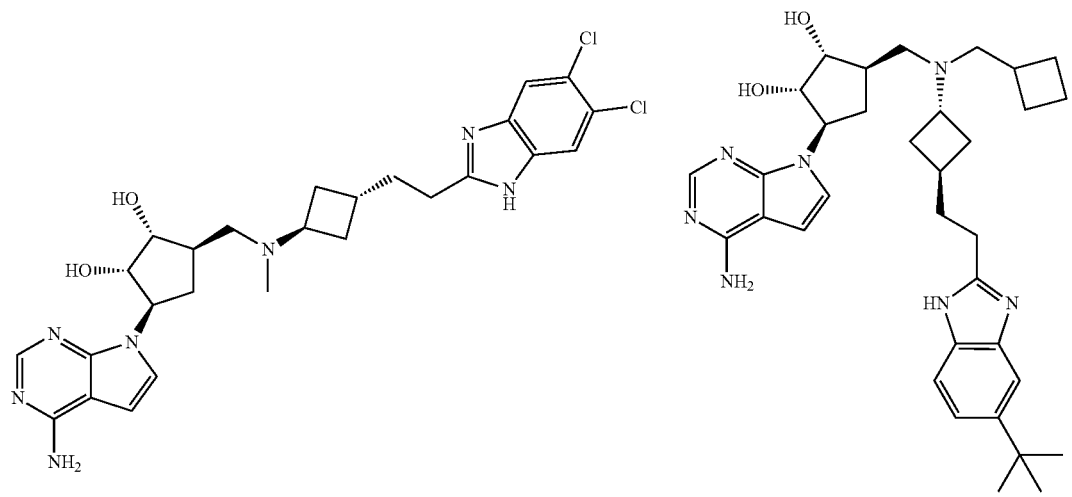
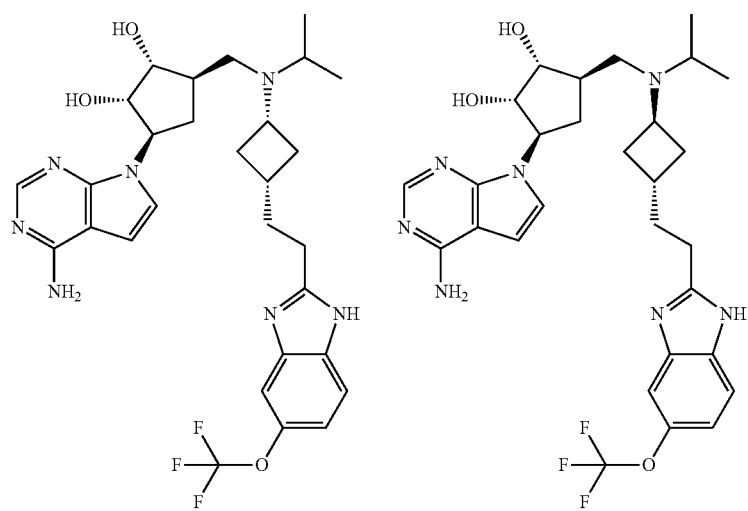

139
-continued
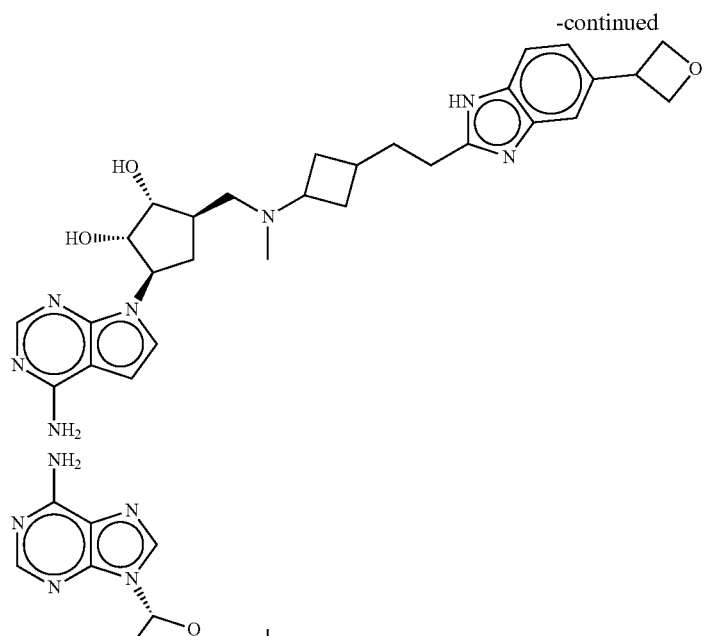
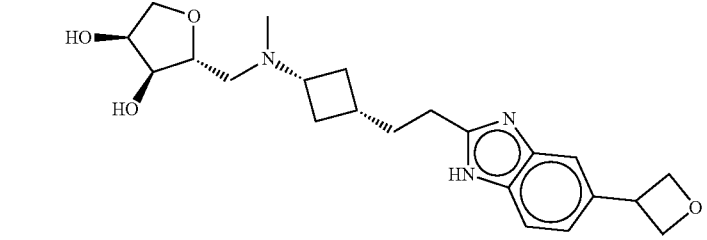
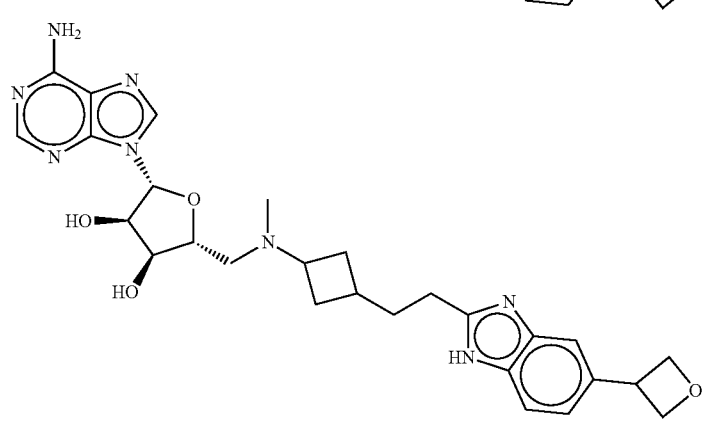
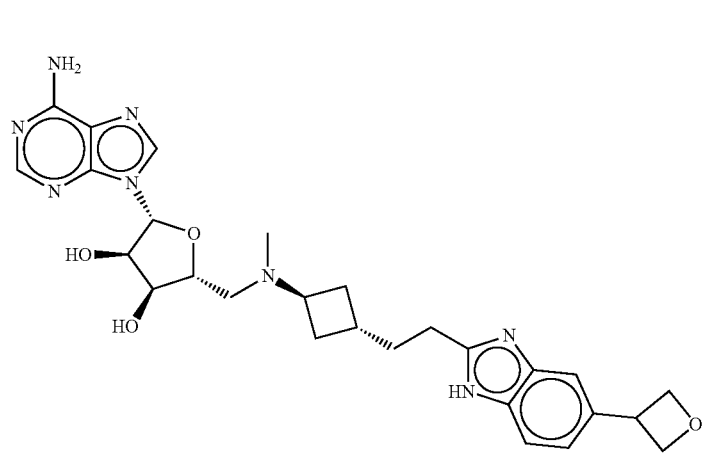
140
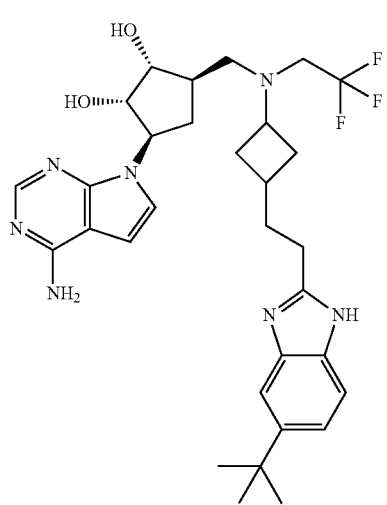

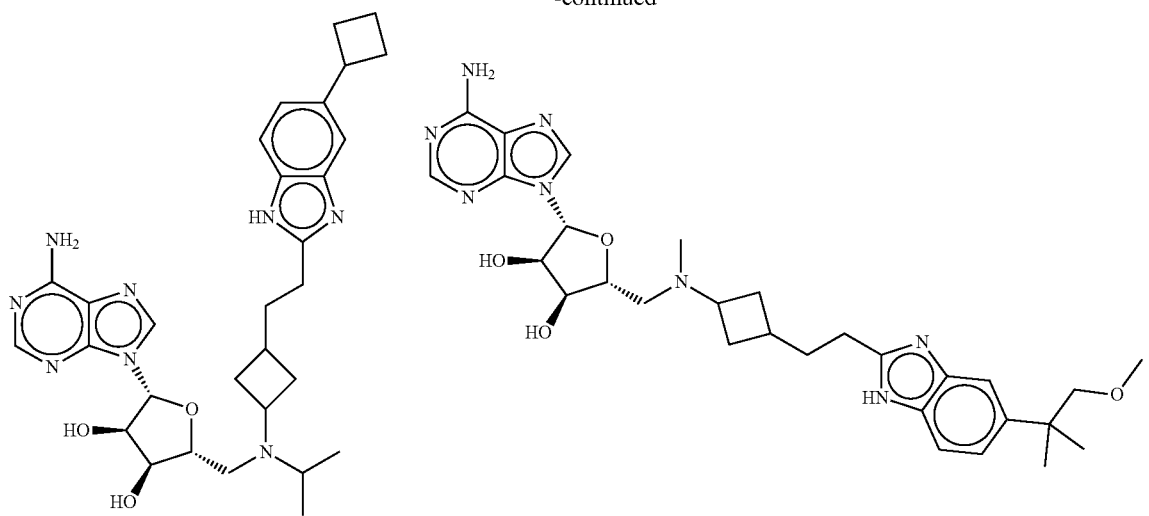
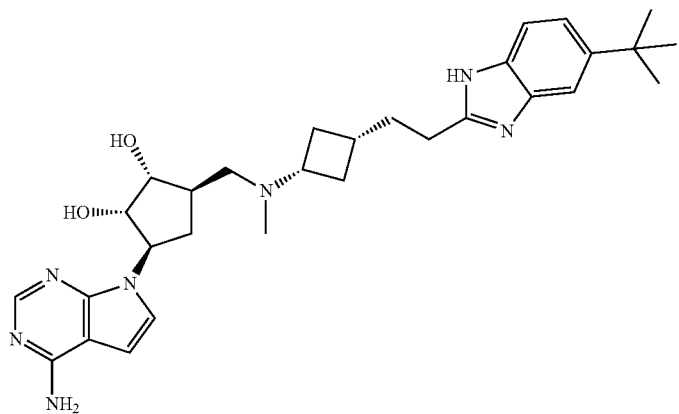
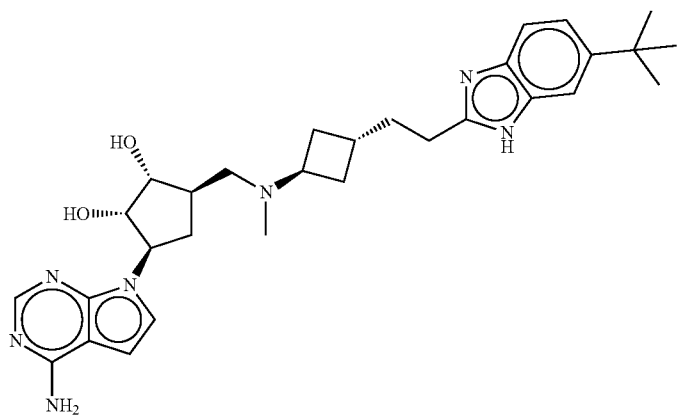

-continued
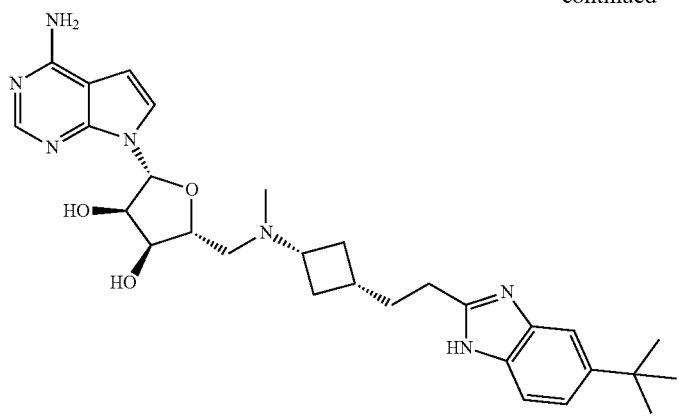
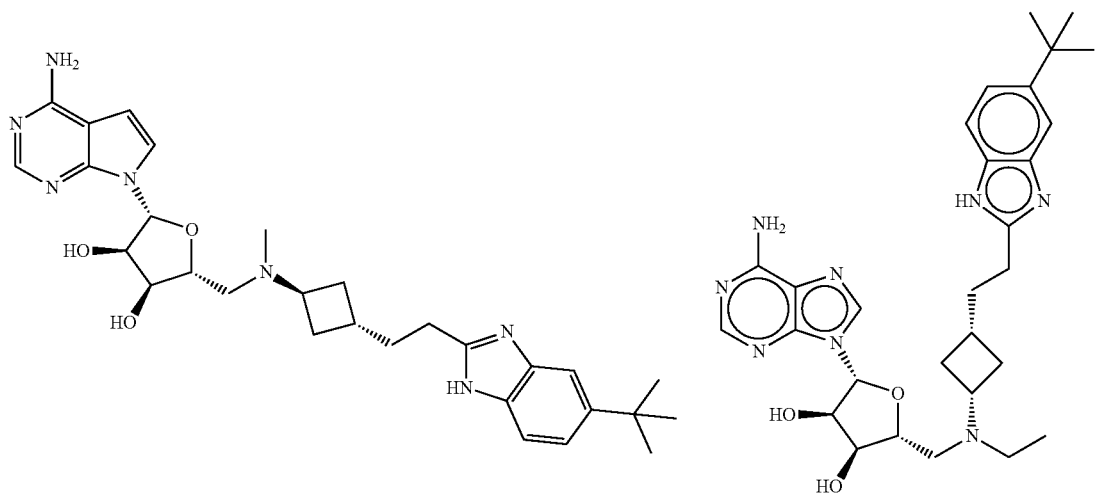
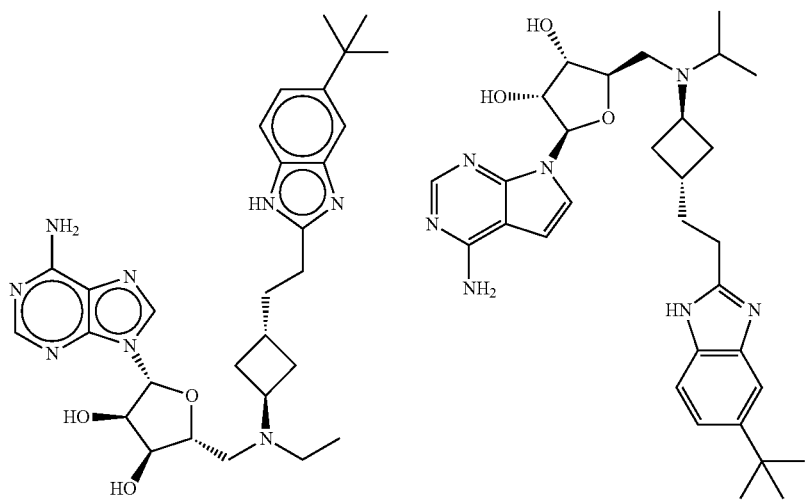

145
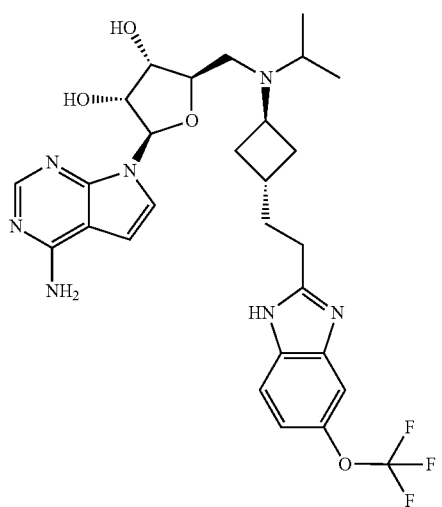
-continued
146
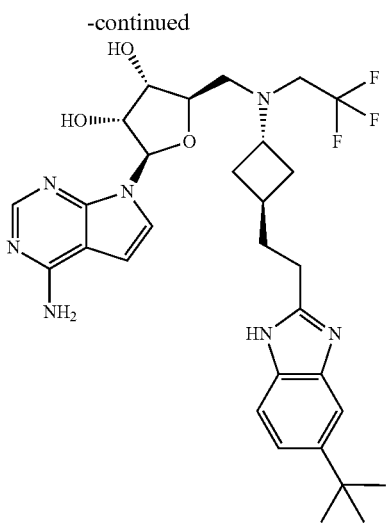
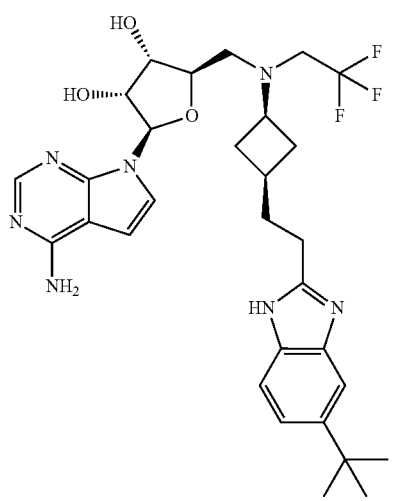
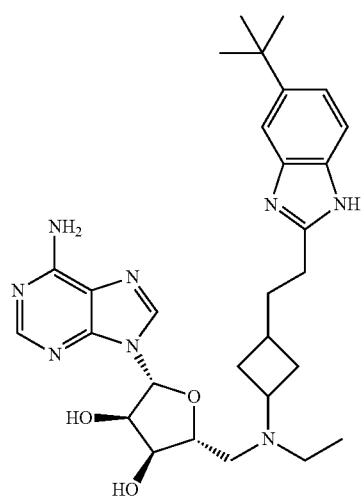
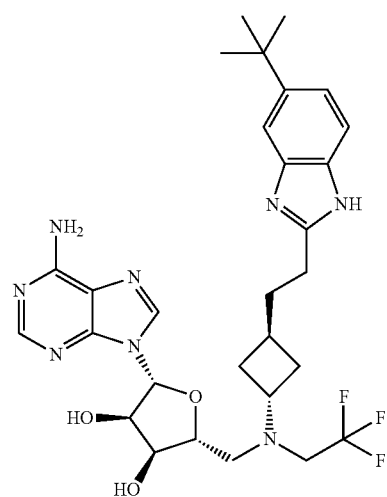
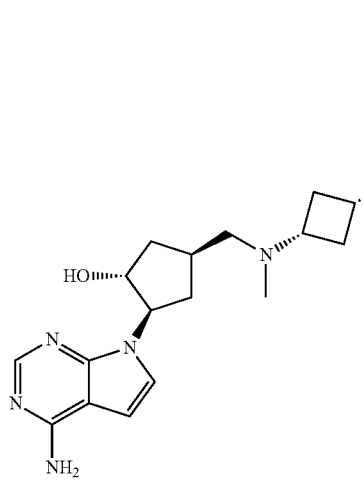
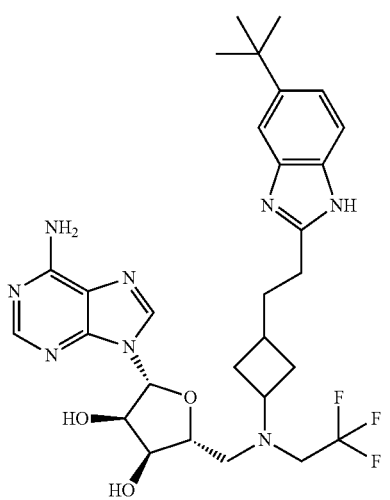

147
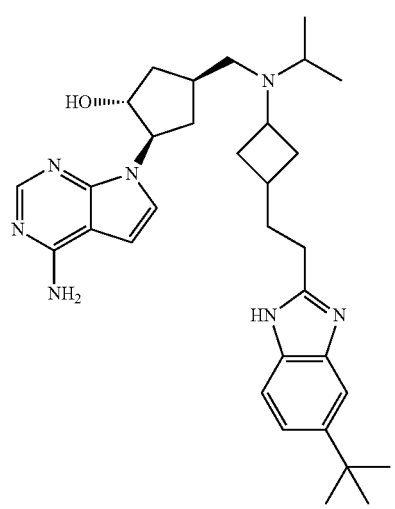
148
-continued
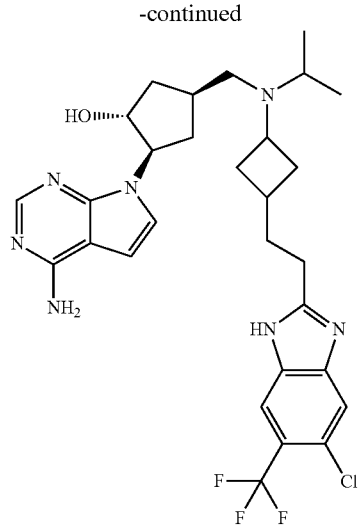
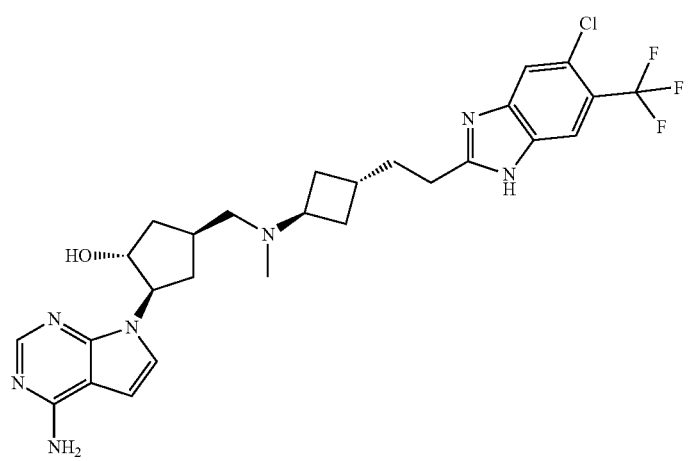
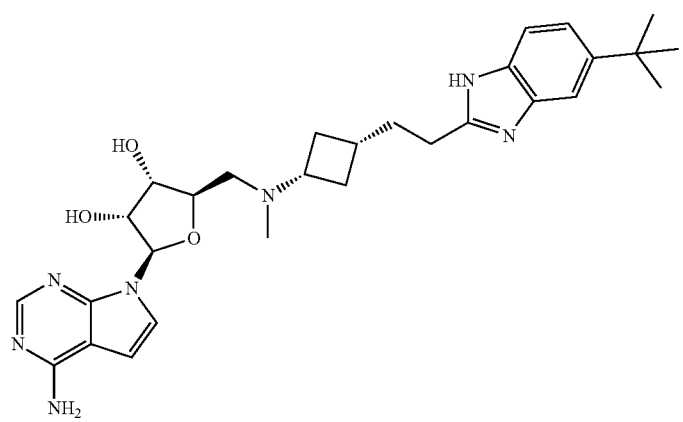

-continued
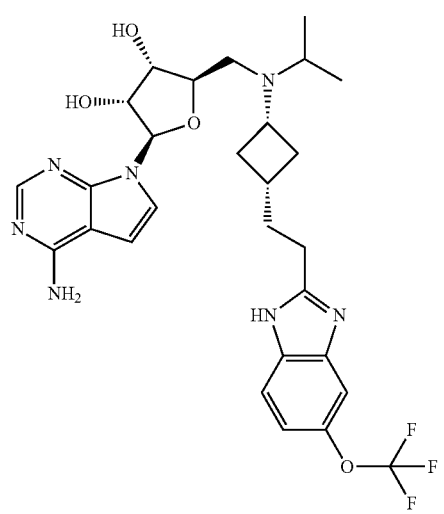
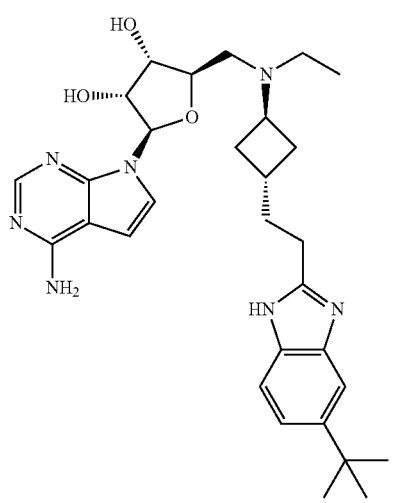
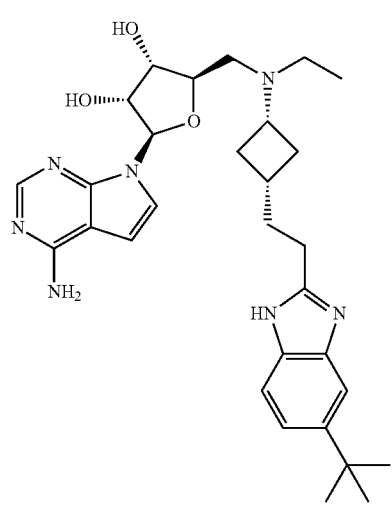
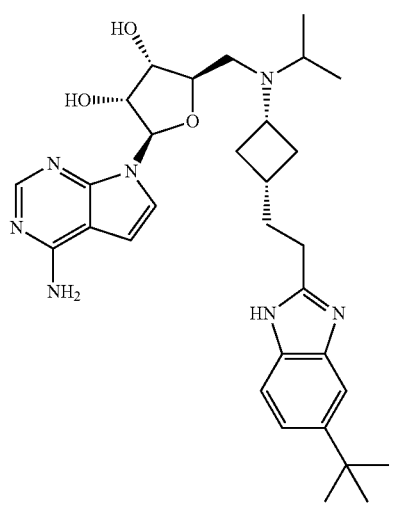
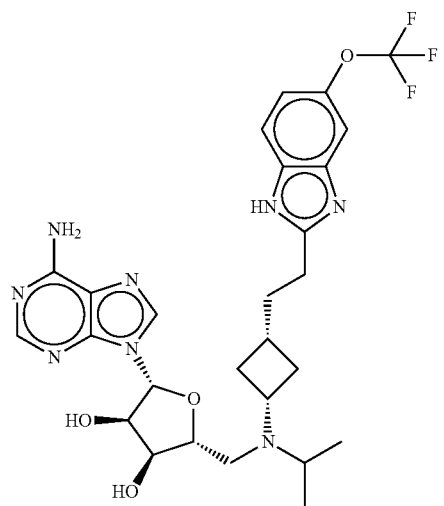

151
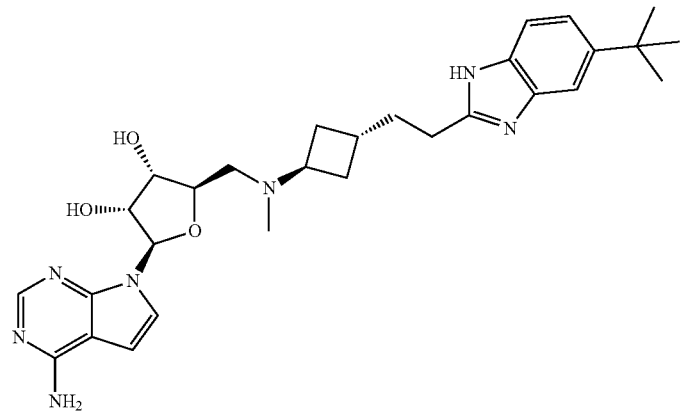
152
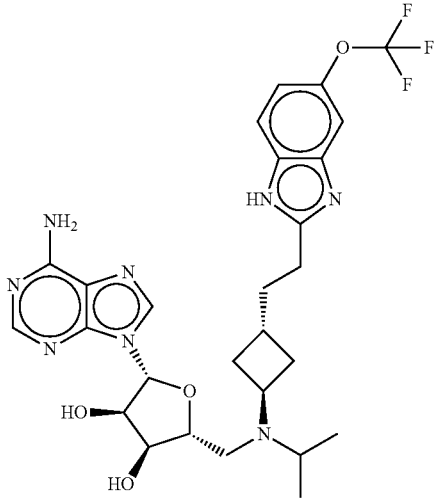
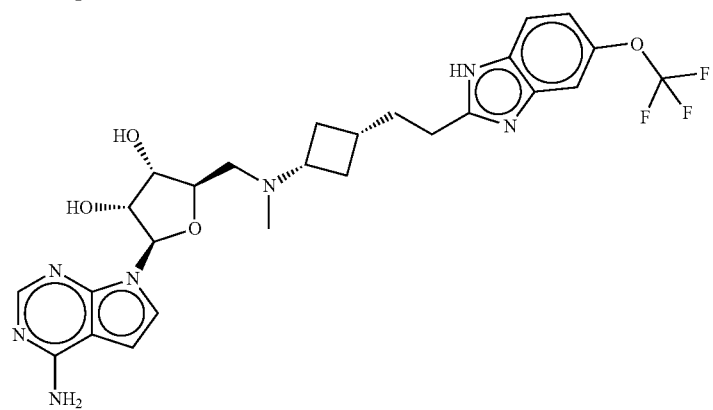
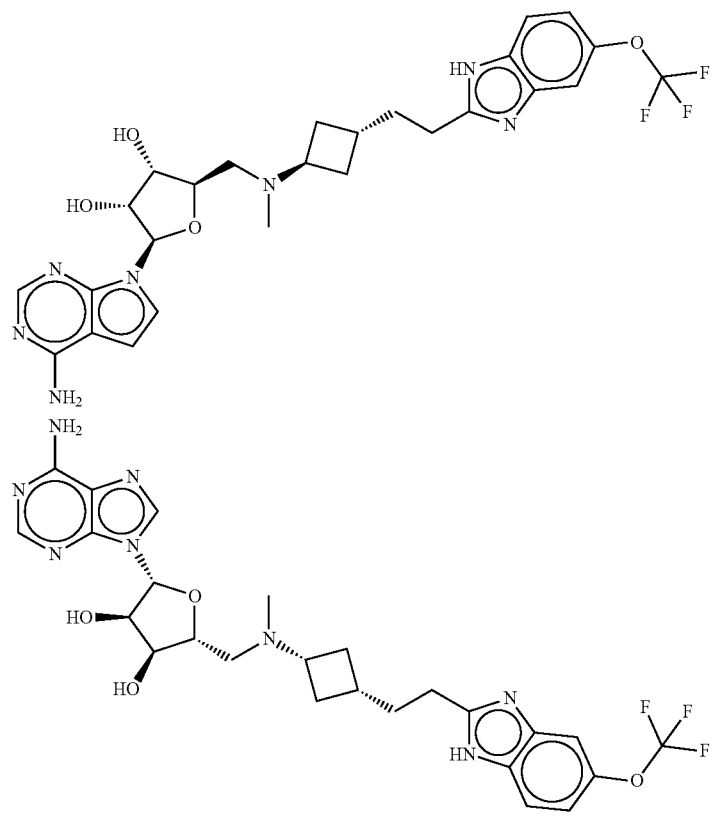

153
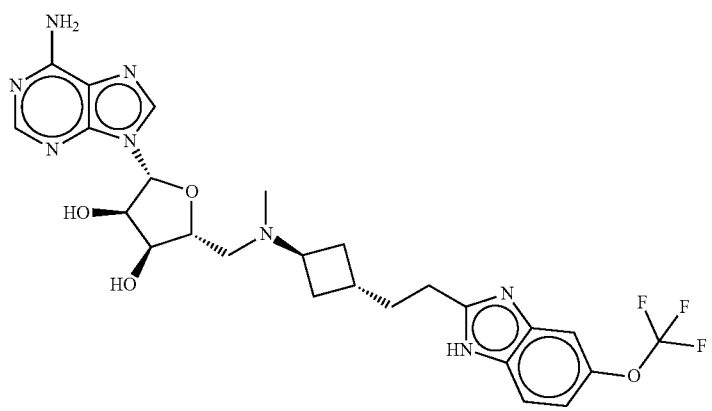
-continued
154
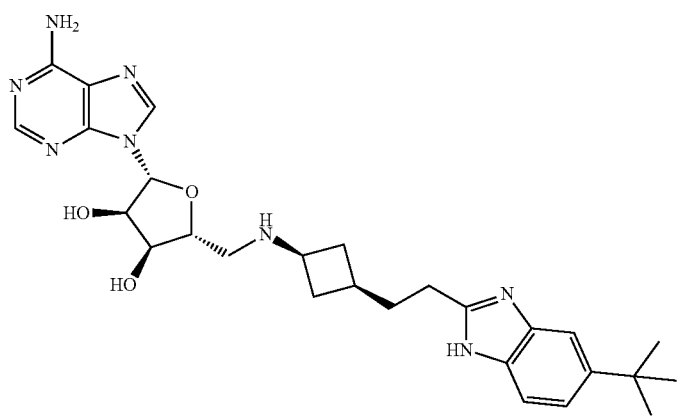
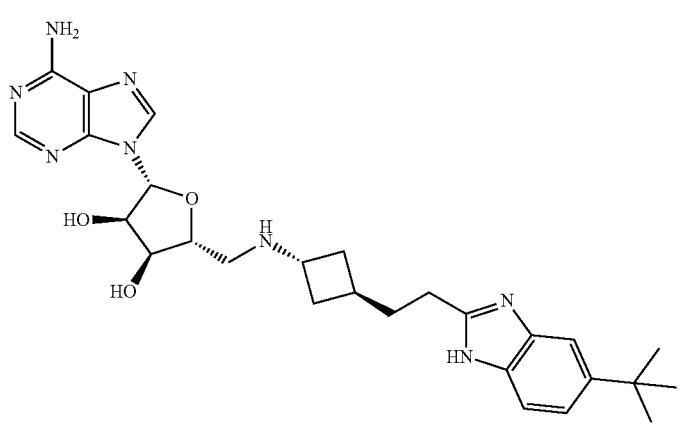
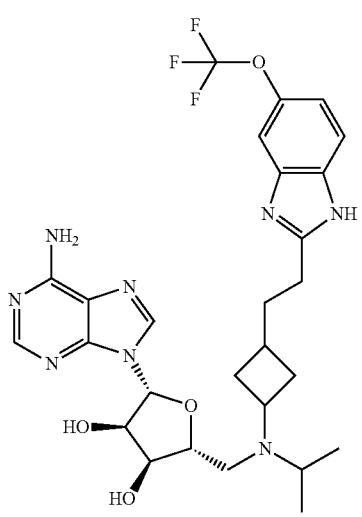

155 156
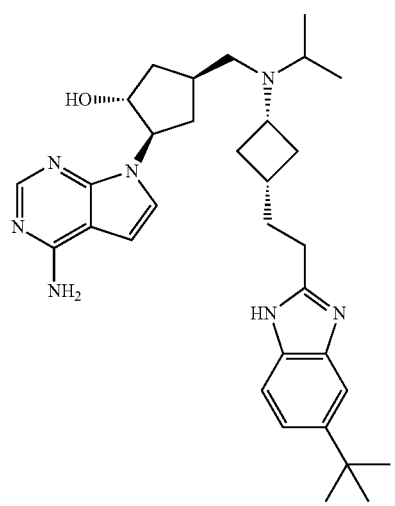
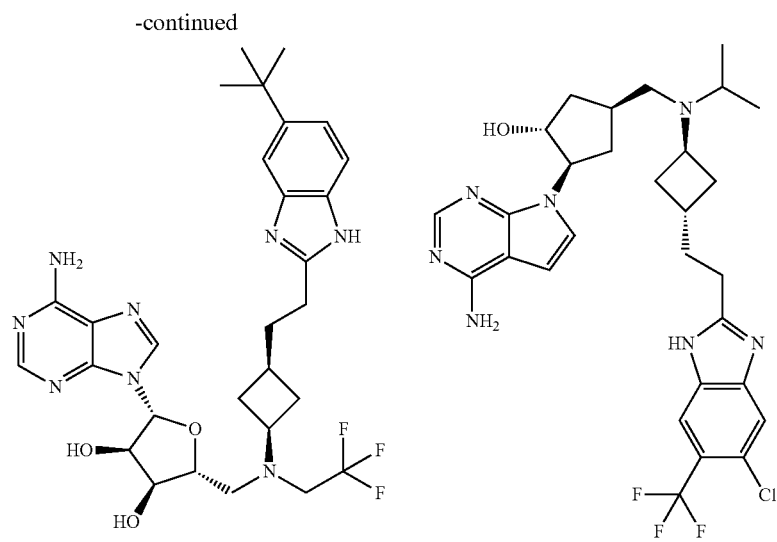
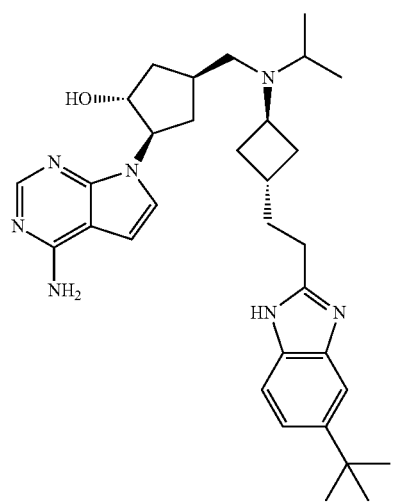
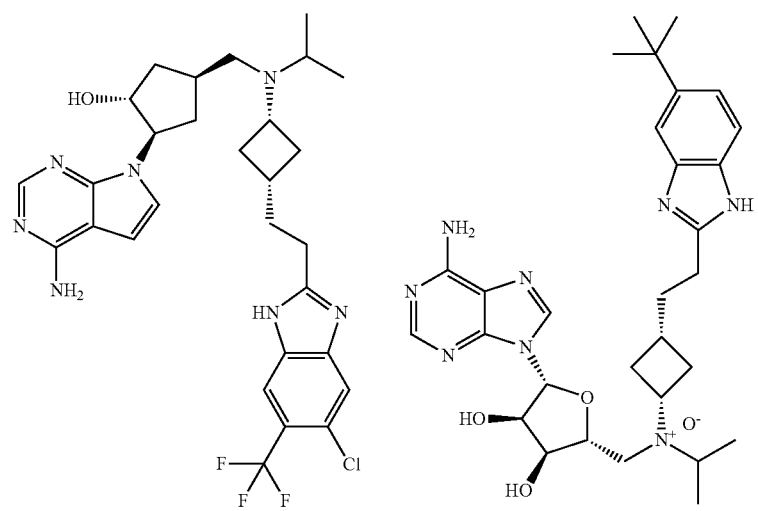
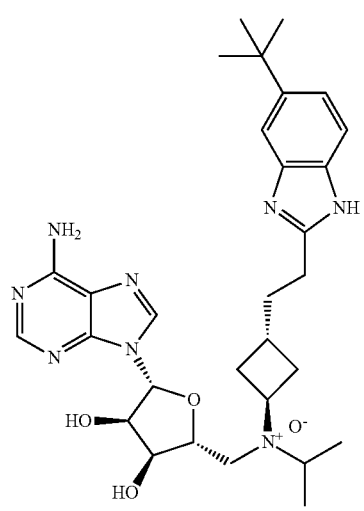
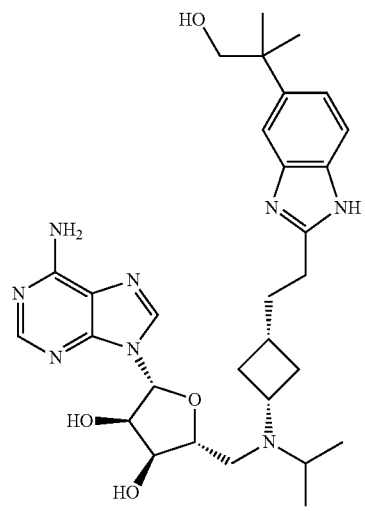
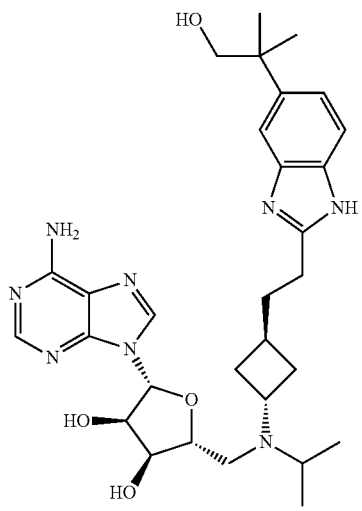

157 158
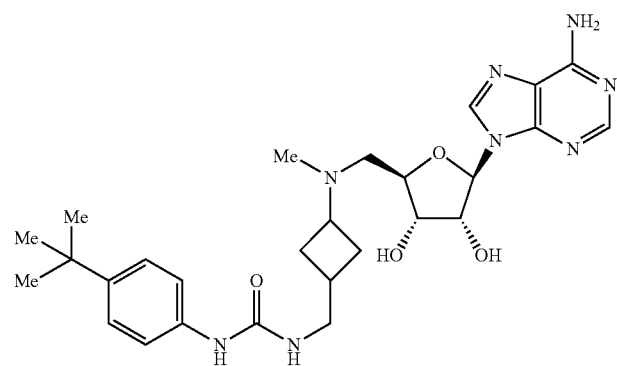
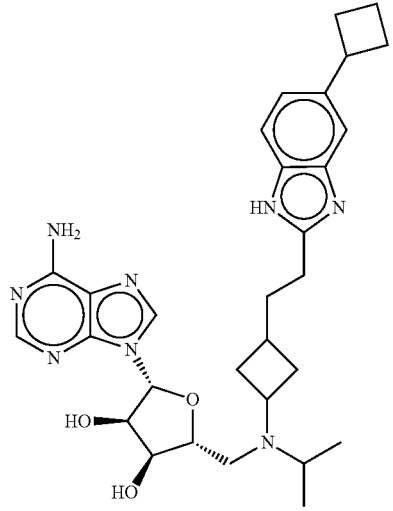
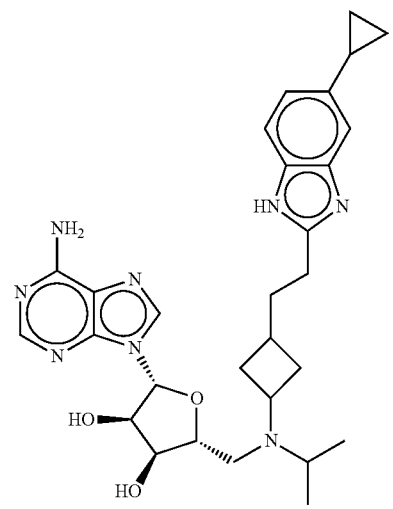
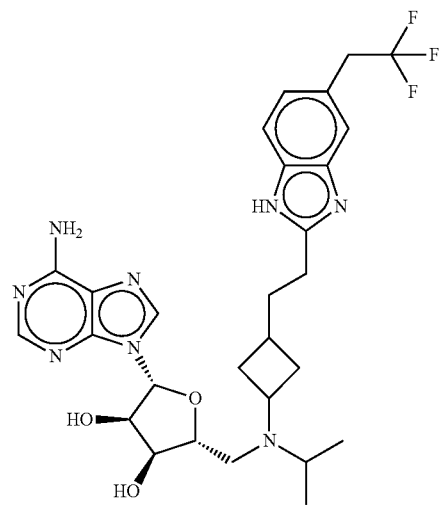
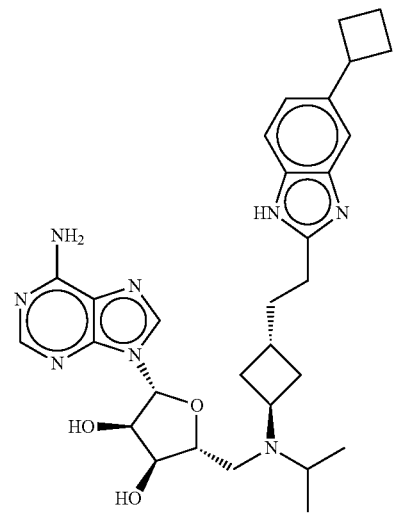
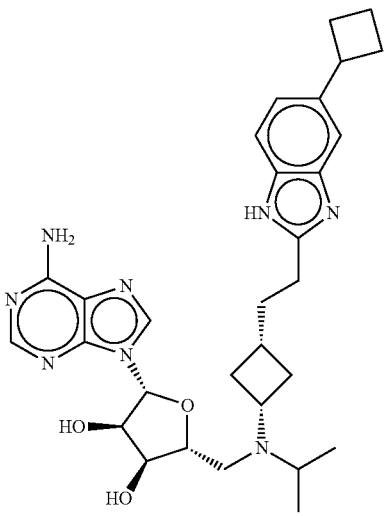
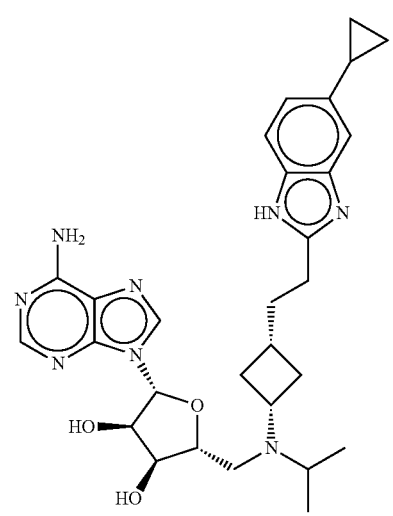

-continued
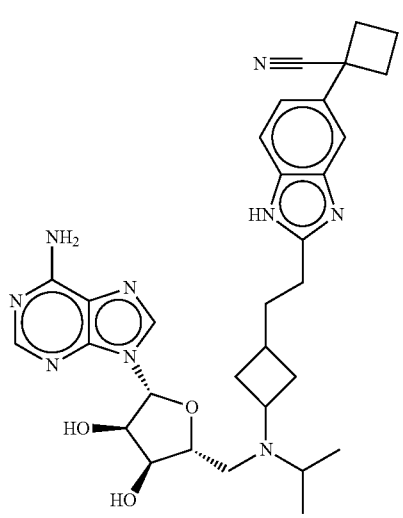 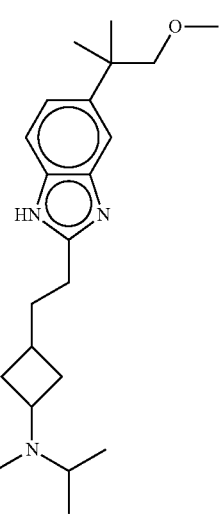
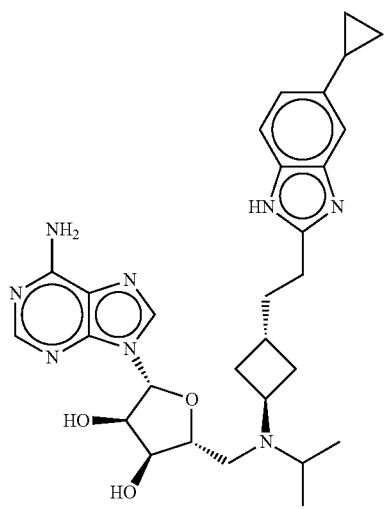 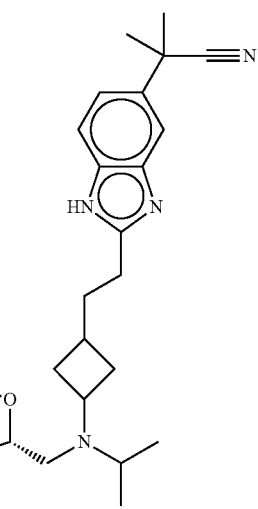
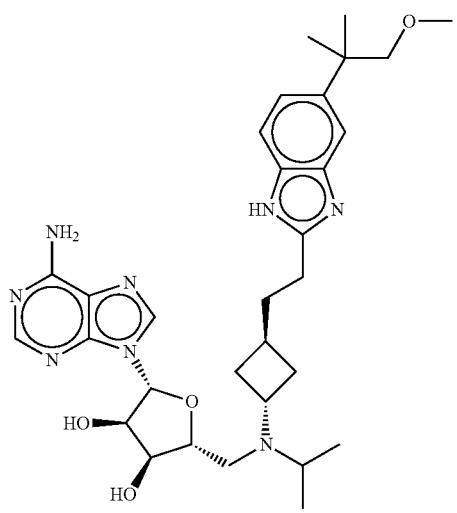 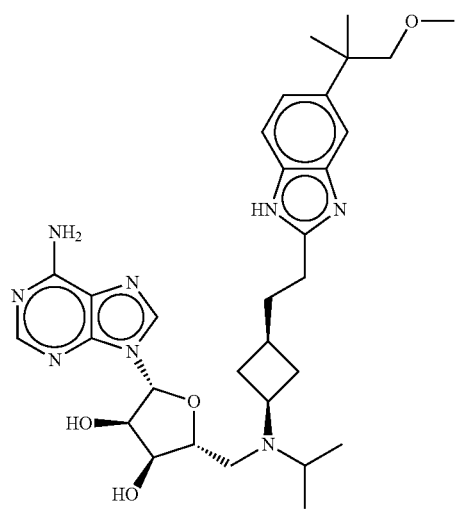

161            162
-continued
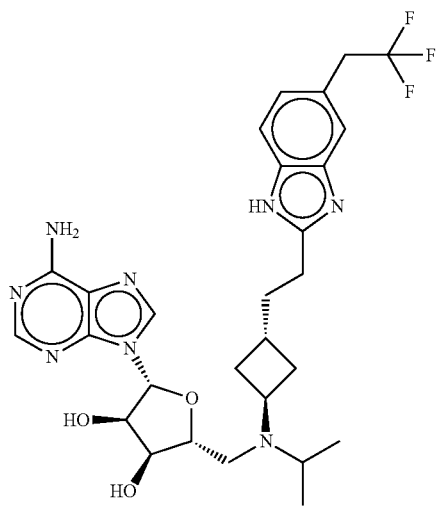
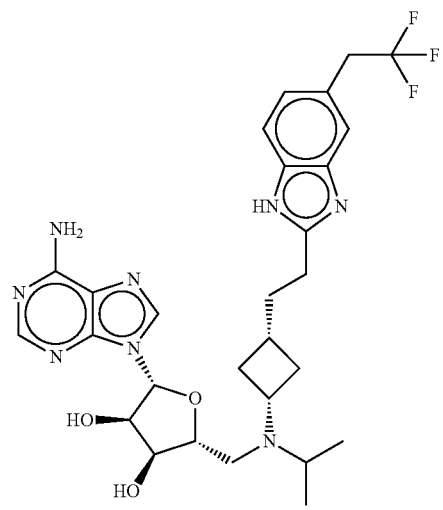
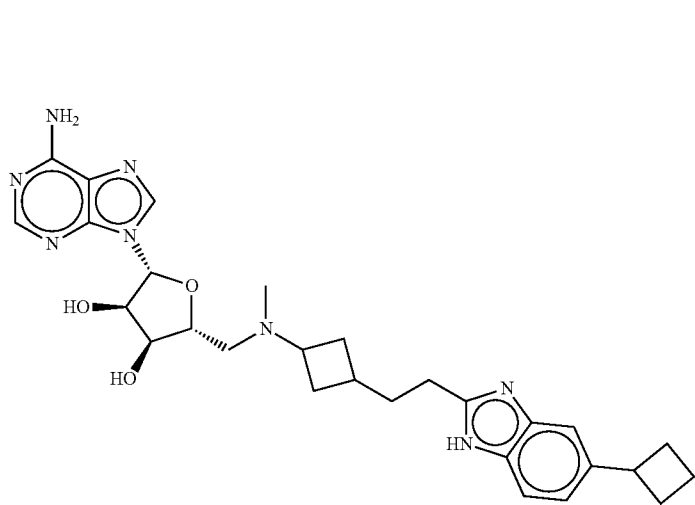
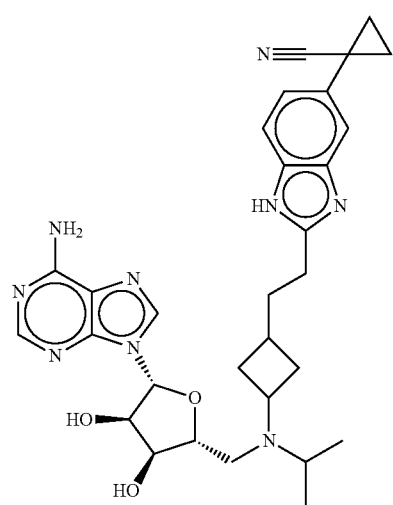
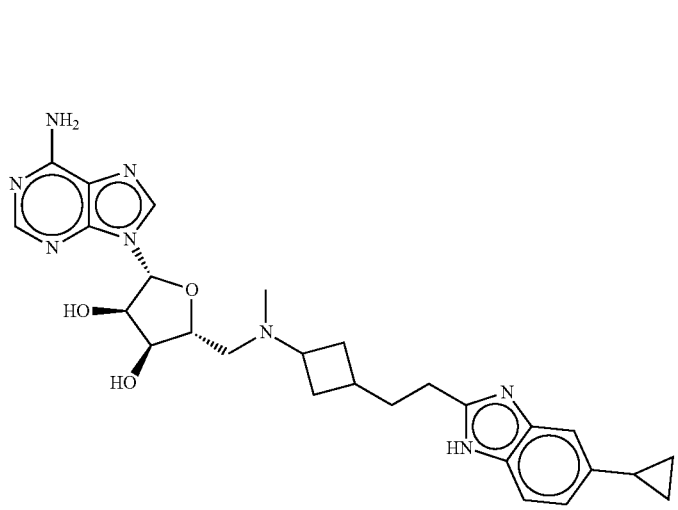
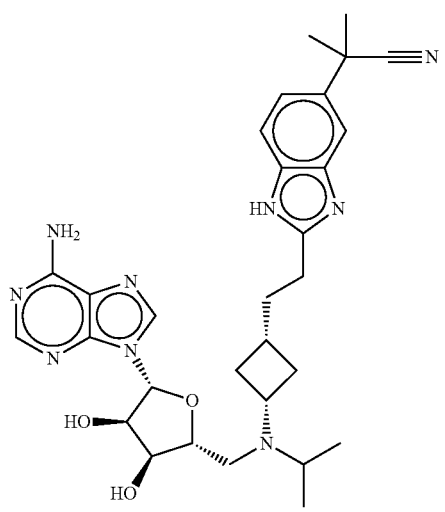

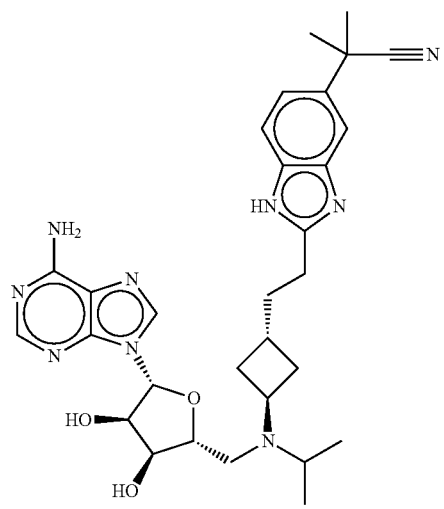
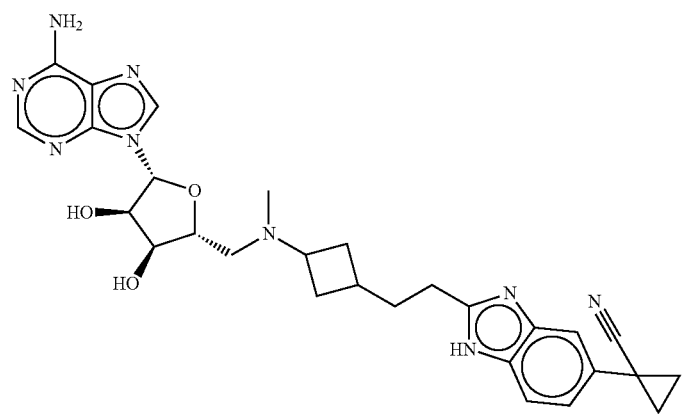
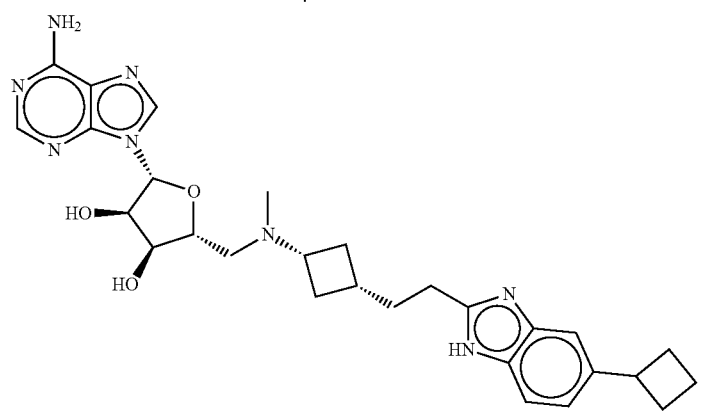
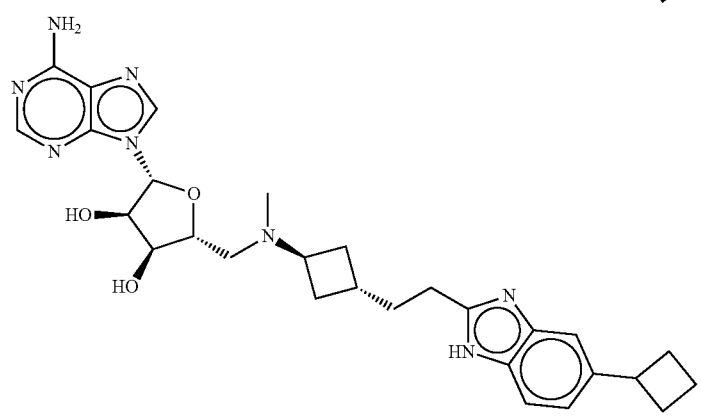
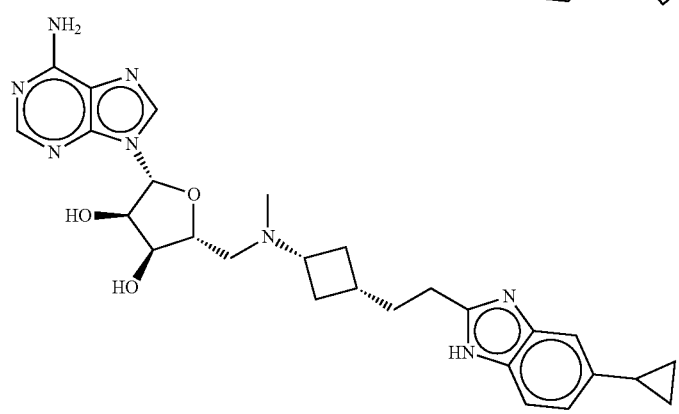

165
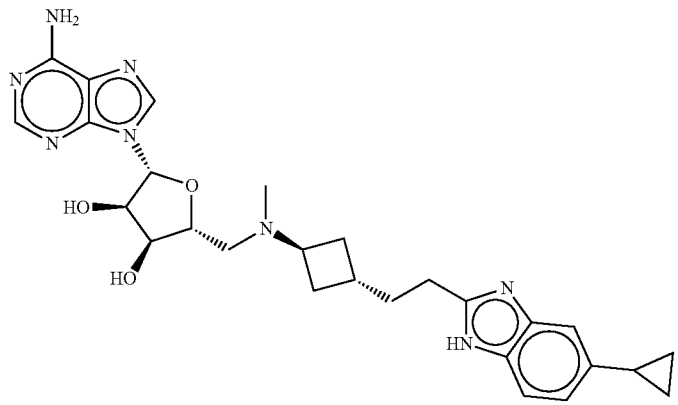
166
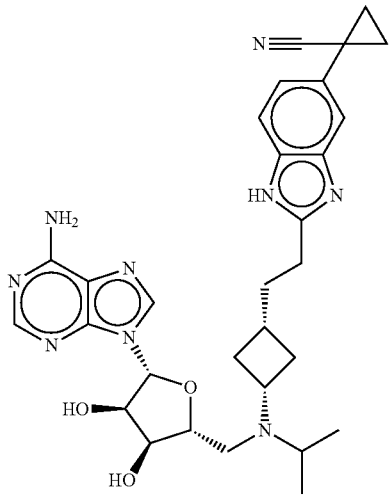
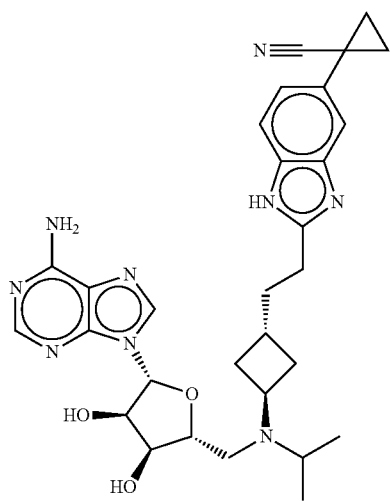
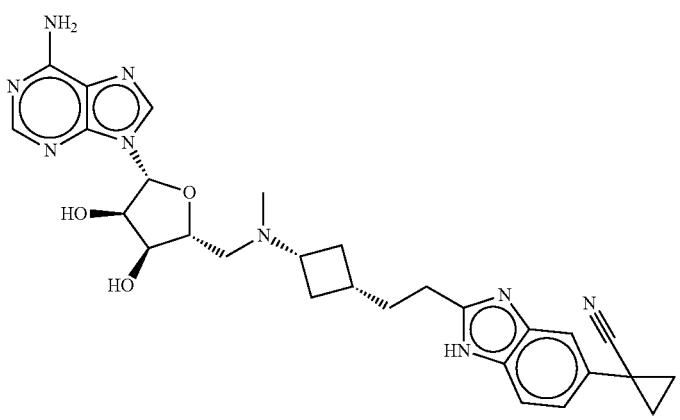
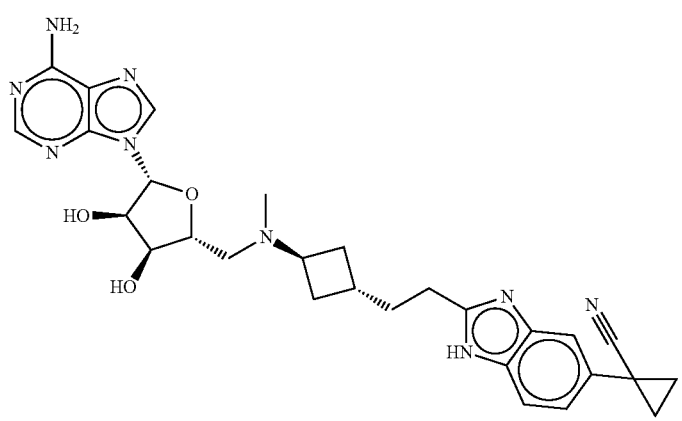
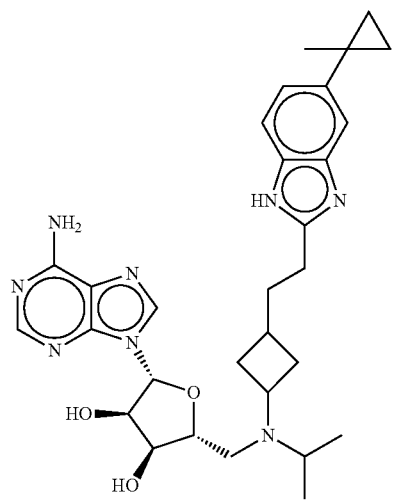

-continued
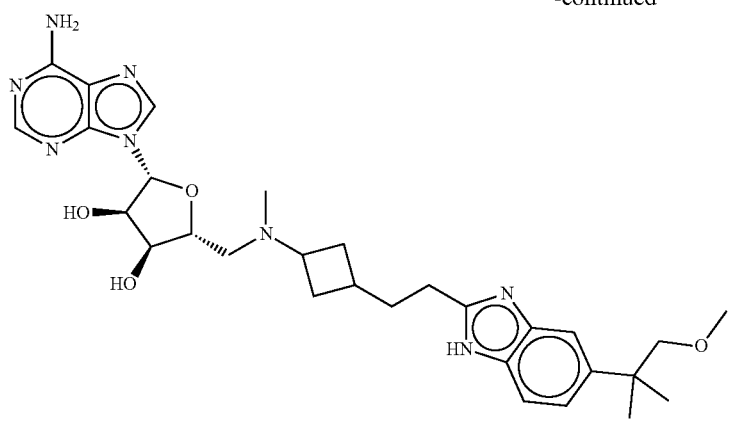
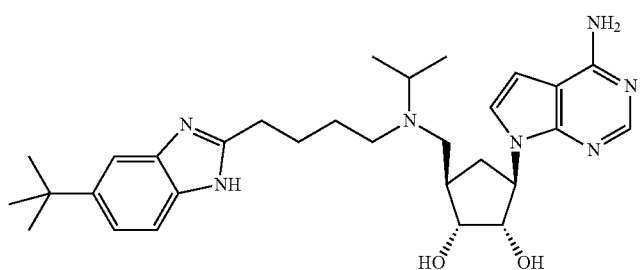
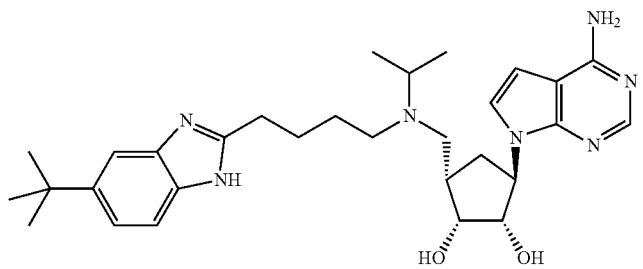
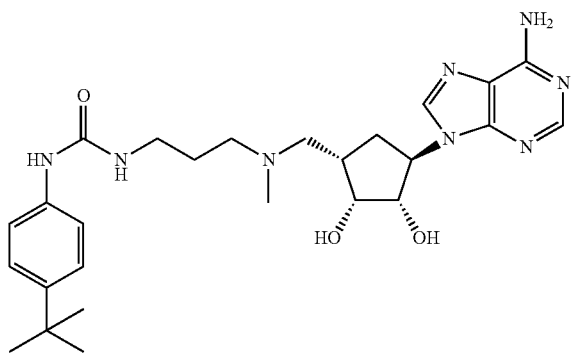
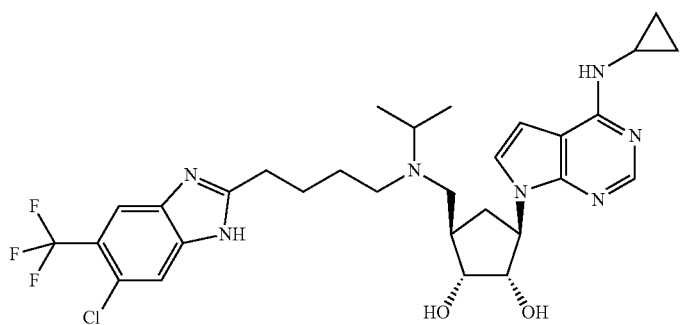

-continued
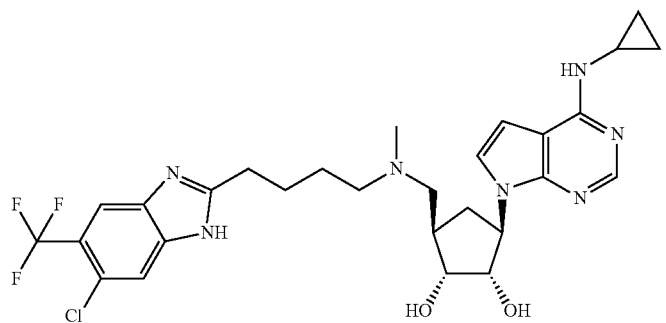
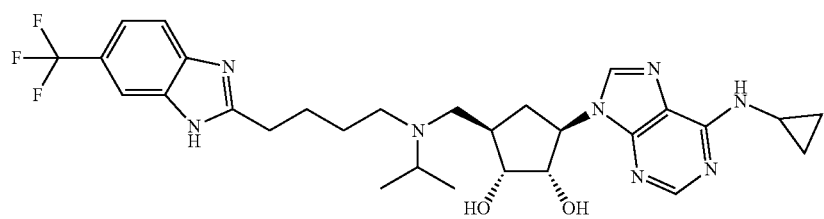
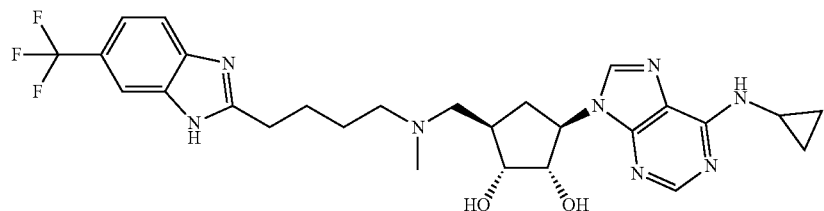
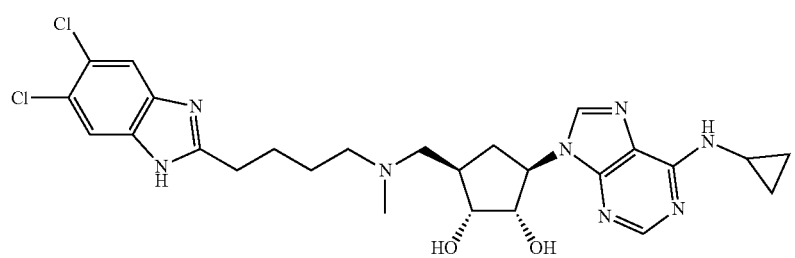
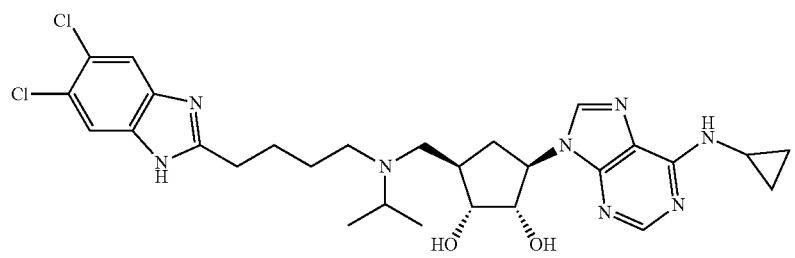
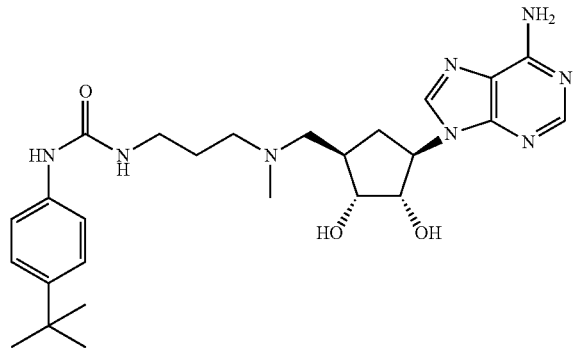

-continued
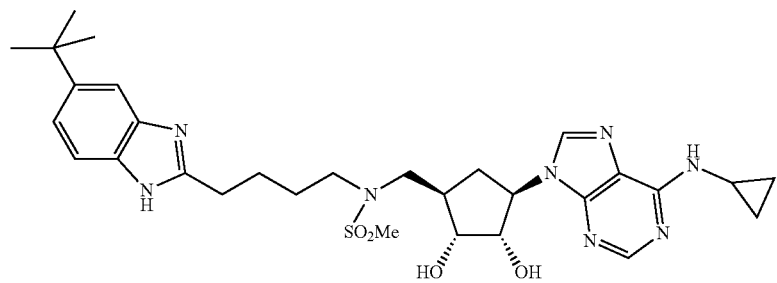
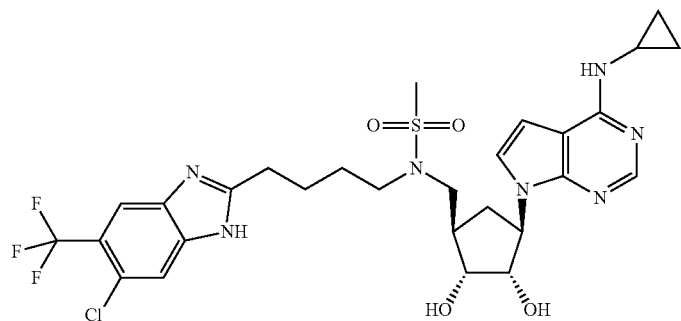
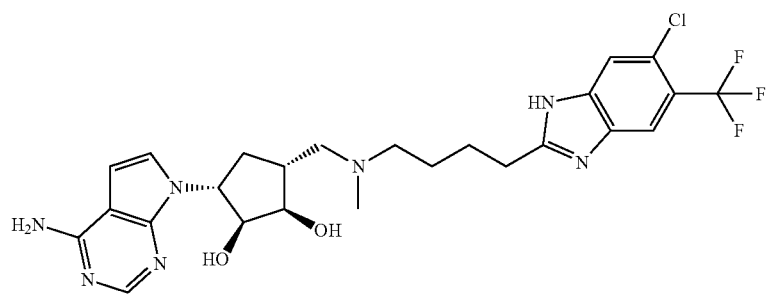
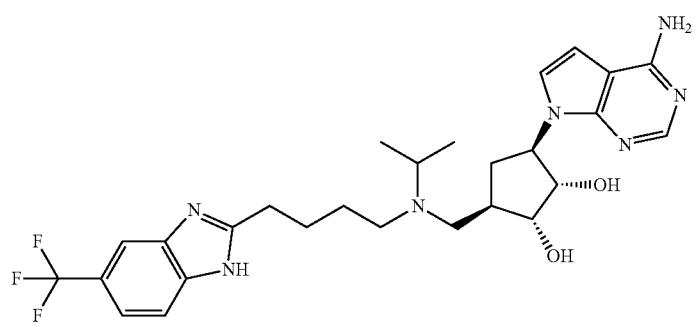
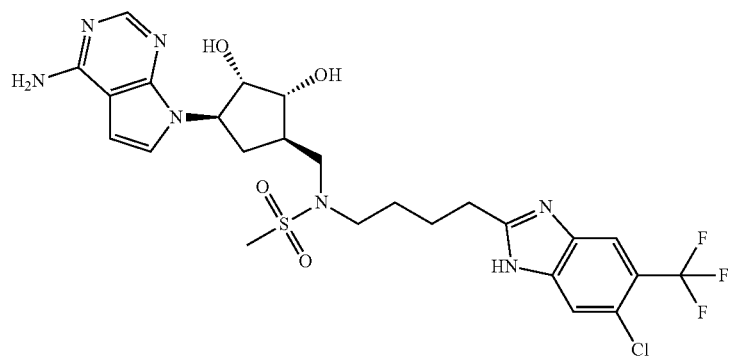

-continued

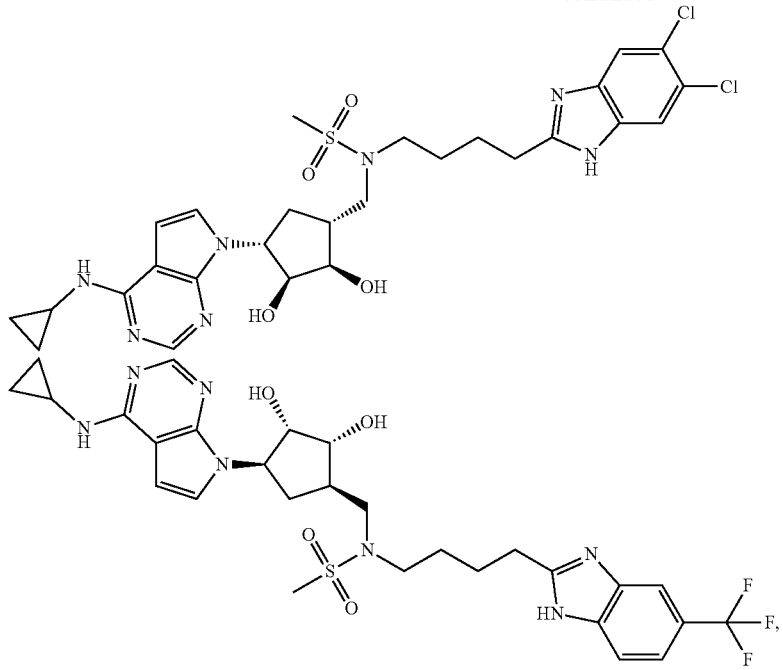

or pharmaceutically acceptable salts thereof.

In some embodiments, Dot1L is inhibited by contacting the differentiated cell with a composition comprising a compound of formula:

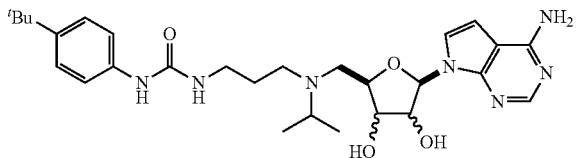

a pharmaceutically acceptable salt thereof.

In some embodiments, Dot1L is inhibited by contacting the differentiated cell with a composition comprising a compound of formula:

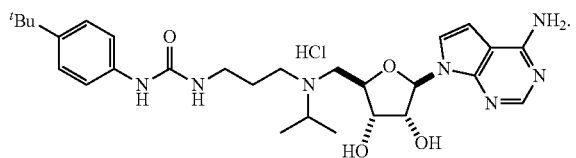

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include moieties having from one to six carbon atoms, such as, but not limited to, methyl, ethyl, n-propyl, i-propyl, n-butyl, s-butyl, t-butyl, n-pentyl, s-pentyl or n-hexyl. In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "hetero aromatic s." As used herein, the term "heteroaryl" is intended to include a stable 5- or 6-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or hetero aromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran. Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula.

Combinations of substituents and/or variables are permissible, but only if such combinations result in stable compounds.

When any variable (e.g., R*) occurs more than one time in any constituent or formula for a compound, its definition at each occurrence is independent of its definition at every other occurrence. Thus, for example, if a group is shown to be substituted with 0-2 R* moieties, then the group may optionally be substituted with up to two R* moieties and R* at each occurrence is selected independently from the definition of R*. Also, combinations of substituents and/or variables are permissible, but only if such combinations result in stable compounds.

The term "hydroxy" or "hydroxyl" includes groups with an —OH or —O".

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group.

"Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d] imidazole via tautomerization.

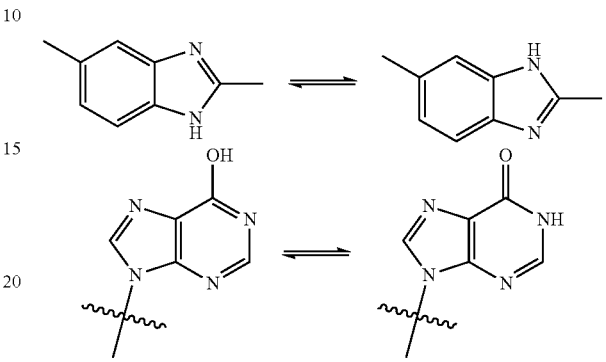

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

Compounds described herein include the compounds themselves, as well as their N-oxides, salts, their solvates, and their prodrugs, if applicable. A salt, for example, can be formed between an anion and a positively charged group (e.g., amino) on a substituted purine or 7-deazapurine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate.

Likewise, a salt can also be formed between a cation and a negatively charged group (e.g., carboxylate) on a substituted purine or 7-deazapurine compound. Suitable cations include sodium ion, potassium ion, magnesium ion, calcium ion, and an ammonium cation such as tetramethylammonium ion. The substituted purine or 7-deazapurine compounds also include those salts containing quaternary nitrogen atoms. Examples of prodrugs include esters and other pharmaceutically acceptable derivatives, which, upon administration to a subject, are capable of providing active substituted purine or 7-deazapurine compounds.

Additionally, the compounds described herein, for example, the salts of the compounds, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

All isotopes of atoms occurring in the compounds described herein are intended to be encompassed. Isotopes include those atoms having the same atomic number but different mass numbers. By way of general example and without limitation, isotopes of hydrogen include tritium and deuterium, and isotopes of carbon include C-13 and C-14.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Materials and Methods:
shRNA Cloning
shRNAs were designed using the RNAi Codex26. 97-mer oligos (Table 2) These were amplified with the following primer pair (SEQ ID NOs: 1 and 2)

Forward: GATGGCTGCTCGAGAAGGTATATTGCTGTTGACAGTGAGCG

Reverse: GTCTAGAGGAATTCCGAGGCAGTAGGC.

PCR products were gel purified, digested with EcoRI and XHoI and ligated into the MSCV-PM (Openbiosystems) vector. Clones were verified by sequencing. shRNA targeting the firefly luciferase was used as a control27. Nanog shRNA was previously described28.
Production of Viral Supernatants
293T cells were plated at a density of 2.5×106 cells per 10-cm dish. The next day, cells were transfected with 2 μg viral vector, 2 μg Gag-Pol vector and 0.22 μg VSV-G plasmid using 20 μl Fugene 6 (Roche Applied Science #1181509001) in 400 μl DMEM per plate. Supernatant was collected 48 h and 72 h post-transfection and filtered through 45 μm pore size filters. For concentration, viral supernatants were mixed with PEG3350 solution (Sigma P3640, dissolved in PBS, 10% final concentration) and left overnight at 4 C. The next day, supernatants were centrifuged at 2500 rpm for 20 minutes, and the pellets were resuspended in PBS. Titering was performed on 293 Ts. For shRNA infections, 500 ul of viral supernatant was used to infect 25,000 cells in the presence of 10 ug/ml protamine sulfate. For fluorescent labeling of dh1fs, we used lentiviruses PRRL-GFP (Addgene #12252) and FUdGW-Tomato (Addgene #22771).
Reprogramming Assays
dH1f cells were first infected with shRNA viruses at high MOI to ensure all cells received at least one vector (Gauged by puromycin resistance of parallel infected wells). 25,000 shRNA-infected dH1f cells were then plated per well in 12-well plates and infected overnight with either retroviral (MOI 2.5) 7 or lentiviral (Addgene #21162, 21164; 100-200 μl supernatant)29 reprogramming factors. For 2-factor reprogramming, Oct4 and Sox2 viruses were used at an MOI of 5. 6 days later, cells were trypsinized and re-plated 1:4 to 1:6 onto 6-well plates. Medium was changed to hES medium daily until Day 21 when plates were fixed. Small molecule inhibitor of Dot1L, EPZ004777 (a gift from Epizyme, Inc., Cambridge, Mass.) was dissolved in DMSO as a 10 mM stock and was added at the indicated concentrations. For Dot1L rescue experiments, an MSCV-based retroviral vector encoding human Dot1L with or without mutations in the SAM binding site (gifts of Y. Zhang) were mutagenized at the shRNA target site using QuikChange II XL Site-Directed Mutagenesis Kit (Agilent Technologies). In certain experiments, Nanog and Lin28 expression was achieved using lentivirus (Addgene #21163). IMR-90 and MRC5 human diploid fibroblasts were purchased from ATCC and 50000 cells were used in reprogramming experiments. Statistical analysis was performed using a Student's t-test.
Microarray Analysis
Total RNA was extracted from three independent culture plates for each conditions with an RNeasy Mini kit (Qiagen). Synthesis of cRNA from total RNA and hybridization/scanning of microarrays were performed with Affymetrix GeneChip products (HGU133A) as described in the GeneChip manual. Normalization of the raw gene expression data, quality control checks, and subsequent analyses were done with the open-source R-project statistical software (R Development Core Team, 2007)(http://www.r-project.org/) together with Bioconductor packages. Raw data files (.CEL) were converted into probe set values by RMA normalization. Genes were selected at a threshold of Log Ratio 0.4. The microarray data have been deposited in National Center for Biotechnology Information Gene Expression Omnibus (GEO) and are accessible through GEO Series accession number GSE29253.

SYBR-Green Real-Time RT-PCR

Total RNA was extracted using RNeasy Mini kit coupled with RNase-free DNase set (Qiagen) and reverse transcribed with Hexanucleotide Mix (Roche). The resulting cDNAs were used for PCR using SYBR-Green Master PCR mix (Applied Biosystem) in triplicates. All quantitations were normalized to an endogenous Beta-Actin control. The relative quantitation value for each target gene compared to the calibrator for that target is expressed as 2-(Ct-Cc) (Ct and Cc are the mean threshold cycle differences after normalizing to Beta-Actin). List of primers can be found in Table 3.

Immunostaining

Immunostaining of reprogramming plates were performed as described[8]. Briefly, cells were fixed with 4% p-formaldehyde and stained with biotin-anti-Tra-1-60 (eBioscience, #13-8863-82, 1:250) and streptavidin horseradish peroxidase (Biolegend, #405210, 1:500) diluted in PBS (3%), FCS (0.3%) Triton X-100. Staining was developed with the Vector labs DAB kit (#SK-4100), and iPSC colonies quantified with ImageJ software. For the characterization of shDot11-iPS cells, single colonies were put onto MEF coated 96-well plates. The plates were fixed for 20 min with 4% p-formaldehyde/PBS (+/+), washed several times with PBS (+/+) and incubated overnight at 4° C. with primary antibody and Hoechst diluted in 3% donkey serum/3% BSA Fraction VII/0.01% Triton X-100/PBS (+/+); Hoechst, Invitrogen #H3570 (1:20,000), Tra-1-81/A488 (BD #560174), SSEA-4/A647 (BD #560219), Tra-1-60/A647 (BD #560122), Nanog, rabbit polyclonal (Abcam #ab21624), Oct4, rabbit polyclonal (Abcam #ab19857). For Nanog and Oct4, donkey anti-rabbit IgG/A555 (Molecular Probes #A31572) secondary antibody was used. After several washes with PBS (+/+), images were acquired using a BD Pathway 435 imager equipped with a ×10 objective.

Teratoma Formation Assay iPSCs grown on MEFs were harvested with Collagenase IV (1 mg/ml in DMEM/F12). Cell clumps from one 6-well plate were resuspended in 50 μl DMEM/F12, 100 μl collagen I (Invitrogen-#A1064401) and 150 μl hESC-qualified matrigel (BD Biosciences-#354277). Cell clumps were then injected into the hind limb femoral muscles (100 μl suspension per leg) of Rag2 γ/c mice. After 6-8 weeks, teratomas were harvested and fixed in Bouin's solution overnight. Samples were then embedded in paraffin, and sections were stained with hematoxylin/eosin (Rodent Histopathology Core, Harvard Medical School, Boston, Mass., USA).

Characterization of iPS Cells

Embryoid body differentiation was performed as described (Loewer). To check for the presence of the reprogramming transgenes, genomic DNA was isolated using DNeasy Blood & Tissue Kit (Qiagen) and PCR was performed with specific primers to the endogenous or the viral trangenes[3].

ChIP Assays

ChIP-seq was performed as described with slight modifications[25]. 300 000 cells were fixed at room temperature in PBS 1% formalin (v/v) for 10 minutes with gentle agitations. Fixation was stopped by the addition of glycine (125 mM final concentration) and agitation for 5 min at room temperature. Fixed cells were washed twice in ice-cold PBS, resuspended in 100 ul of SDS lysis buffer (1% SDS, 10 mM EDTA, 50 mM Tris-HCl, pH 8.1). Chromatin was sheared by sonication to about 100-500 bp fragments using bioruptor (diagenode, Denville, N.J.) and diluted tenfold with dilution buffer (0.01% SDS, 1.1% Triton-X100, 1.2 mM EDTA, 16.7 mM Tris-HCl, pH 8.1, 167 mM NaCl). Antibodies against specific histone modifications was added to sonicated chromatin solution and incubated at 4 degree overnight with gentle agitation. The antibodies used were anti-H3K27me3 (Millipore 07-449) and anti-H3K79me2 (abcam 3594). Immune complexes were collected by incubation with 20 ul of Protein A/G agarose beads (Millipore) for an hour at 4 degree with gentle agitation. Precipitates were washed sequentially with ice cold low salt wash (0.1% SDS, 1% Triton-X-100, 2 mM EDTA, 20 mM Tris-HCl, pH8.1, 150 mM NaCl), high salt wash (0.1% SDS, 1% Triton-X-100, 2 mM EDTA, 20 mM Tris-HCl, pH 8.1, 500 mM NaCl), LiCl wash (0.25M LiCl, 1% IGEPAL CA-630, 1% deoxycholic acid, 1 mM EDTA, 10 mM Tris-HCl, pH 8.1) and TE wash (1 mM EDTA, 10 mM Tris-HCl, pH 8.1) for 5 mins each at 4 degree with gentle agitation. Samples were centrifuged briefly in between washes to collect the beads. Immunoprecipitated DNA was eluted by incubating beads with 150 ul elution buffer (1% SDS, 0.1 M NaHCO3) with gentle agitation for 15 mins at room temperature. Elution was repeated once and eluates were combined, sodium chloride (final concentration of 0.2M) were added to the eluate and eluates were incubated at 65 degree overnight to reverse crosslinking. DNA was purified using PCR purification spin column (Qiagen). For ChIP sequencing, ChIP DNA libraries were made following Illumina ChIP-seq library preparation kit and subjected to Solexa sequencing (Illumina) at Center for Cancer Computational Biology, Dana Faber Cancer Institute.

TABLE 2 shRNA Sequences evaluated

| Hairpin |
|---|
| TGCTGTTGACAGTGAGCGAGCGATTGCTCCAGGAATTTAATAGTGAAGCCACAGATGTATTAAATTCCTGGAGCAATCGCCTGCCTACTGCCTCGGA (SEQ ID NO: 3) |
| TGCTGTTGACAGTGAGCGCCGTGCCCATTCCCTGTGTCAATAGTGAAGCCACAGATGTATTGACACAGGGAATGGGCACGTTGCCTACTGCCTCGGA (SEQ ID NO: 4) |
| TGCTGTTGACAGTGAGCGAGGTGATGACTTCAGTCTCTACTAGTGAAGCCACAGATGTAGTAGAGACTGAAGTCATCACCCTGCCTACTGCCTCGGA (SEQ ID NO: 5) |

TABLE 2-continued shRNA Sequences evaluated
Hairpin

TGCTGTTGACAGTGAGCGCGGATGGAGAGGTGTACTGCATTAGTGAAGCCACAGATGTAATGCAGTACACC
TCTCCATCCTTGCCTACTGCCTCGGA (SEQ ID NO: 6)

TGCTGTTGACAGTGAGCGACGATGCCAGCAGTCATGCAAATAGTGAAGCCACAGATGTATTTGCATGACTGC
TGGCATCGCTGCCTACTGCCTCGGA(SEQ ID NO: 7)

TGCTGTTGACAGTGAGCGAGCAGCAACGGATACATCTTAATAGTGAAGCCACAGATGTATTAAGATGTATCC
GTTGCTGCCTGCCTACTGCCTCGGA (SEQ ID NO: 8)

TGCTGTTGACAGTGAGCGACGATGCCAGCAGTCATGCAAATAGTGAAGCCACAGATGTATTTGCATGACTGC
TGGCATCGCTGCCTACTGCCTCGGA (SEQ ID NO: 9)

TGCTGTTGACAGTGAGCGAGGGATTCAGATGTCACCTTAATAGTGAAGCCACAGATGTATTAAGGTGACATC
TGAATCCCGTGCCTACTGCCTCGGA (SEQ ID NO: 10)

TGCTGTTGACAGTGAGCGCCGAGTGTTATATTTGTGAATATAGTGAAGCCACAGATGTATATICACAAATATA
ACACTCGTTGCCTACTGCCTCGGA (SEQ ID NO: 11)

TGCTGTTGACAGTGAGCGCGCACCTCTGAACTTCAGAATATAGTGAAGCCACAGATGTATATTCTGAAGTTC
AGAGGTGCATGCCTACTGCCTCGGA (SEQ ID NO: 12)

TGCTGTTGACAGTGAGCGAGGACGGGAGCTCCACTGTGAATAGTGAAGCCACAGATGTATTCACAGTGGAG
CTCCCGTCCGTGCCTACTGCCTCGGA (SEQ ID NO: 13)

TGCTGTTGACAGTGAGCGCGGAGCTCACCTTTGATTACAATAGTGAAGCCACAGATGTATTGTAATCAAAGG
TGAGCTCCTTGCCTACTGCCTCGGA (SEQ ID NO: 14)

TGCTGTTGACAGTGAGCGACCTCGGTATCTCTAAGAGGAATAGTGAAGCCACAGATGTATTCCTCTTAGAGA
TACCGAGGGTGCCTACTGCCTCGGA (SEQ ID NO: 15)

TGCTGTTGACAGTGAGCGACGGGCCTTCGTGTACATCAATTAGTGAAGCCACAGATGTAATTGATGTACACG
AAGGCCCGCTGCCTACTGCCTCGGA (SEQ ID NO: 16)

TGCTGTTGACAGTGAGCGCGCCCGTTACTGCTTCAGCAATTAGTGAAGCCACAGATGTAATTGCTGAAGCAG
TAACGGGCATGCCTACTGCCTCGGA (SEQ ID NO: 17)

TGCTGTTGACAGTGAGCGCGCTTAGTATATGTGTACTTAATAGTGAAGCCACAGATGTATTAAGTACACATAT
ACTAAGCTTGCCTACTGCCTCGGA (SEQ ID NO: 18)

TGCTGTTGACAGTGAGCGACCAAATCTTCAGGTGTTCAATTAGTGAAGCCACAGATGTAATTGAACACCTGA
AGATTTGGGTGCCTACTGCCTCGGA (SEQ ID NO: 19)

TGCTGTTGACAGTGAGCGCCCTGATAGTCAGCATGCGAATTAGTGAAGCCACAGATGTAATTCGCATGCTGA
CTATCAGGTTGCCTACTGCCTCGGA (SEQ ID NO: 20)

TGCTGTTGACAGTGAGCGCGGGCTTTCATGTTATCTATAATAGTGAAGCCACAGATGTATTATAGATAACATG
AAAGCCCATGCCTACTGCCTCGGA (SEQ ID NO: 21)

TGCTGTTGACAGTGAGCGACCTGAAGAGTCCAATGATGATTAGTGAAGCCACAGATGTAATCATCATTGGAC
TCTTCAGGGTGCCTACTGCCTCGGA (SEQ ID NO: 22)

TGCTGTTGACAGTGAGCGCAGGATTCTGGCCAAACAGAAATAGTGAAGCCACAGATGTATTTCTGTTTGGCC
AGAATCCTTTGCCTACTGCCTCGGA (SEQ ID NO: 23)

TGCTGTTGACAGTGAGCGACGGAGGGCCAAGCACTATAAATAGTGAAGCCACAGATGTATTTATAGTGCTTG
GCCCTCCGGTGCCTACTGCCTCGGA (SEQ ID NO: 24)

TGCTGTTGACAGTGAGCGAACCGGTTAAGAGATTCTTATTTAGTGAAGCCACAGATGTAAATAAGAATCTCT
TAACCGGTCTGCCTACTGCCTCGGA (SEQ ID NO: 25)

TGCTGTTGACAGTGAGCGCGGCATTATGCTTGTTGTACAATAGTGAAGCCACAGATGTATTGTACAACAAGC
ATAATGCCATGCCTACTGCCTCGGA (SEQ ID NO: 26)

TGCTGTTGACAGTGAGCGACCATTGTAAGTGTTGTTTCTATAGTGAAGCCACAGATGTATAGAAACAACACTT
ACAATGGGTGCCTACTGCCTCGGA (SEQ ID NO: 27)

TGCTGTTGACAGTGAGCGAGGAAAGAATATGCATAGAATATAGTGAAGCCACAGATGTATATTCTATGCATA
TTCTTTCCGTGCCTACTGCCTCGGA (SEQ ID NO: 28)

TGCTGTTGACAGTGAGCGCCGGAACTCAACCATTAAGCAATAGTGAAGCCACAGATGTATTGCTTAATGGTT
GAGTTCCGTTGCCTACTGCCTCGGA (SEQ ID NO: 29)

TGCTGTTGACAGTGAGCGCGGGACTGCAATTATTCAGTATTAGTGAAGCCACAGATGTAATACTGAATAATT
GCAGTCCCTTGCCTACTGCCTCGGA (SEQ ID NO: 30)

TABLE 2-continued shRNA Sequences evaluated
Hairpin

TGCTGTTGACAGTGAGCGACCAGTGGCCAGTTCACTGTATTAGTGAAGCCACAGATGTAATACAGTGAACTG
GCCACTGGCTGCCTACTGCCTCGGA (SEQ ID NO: 31)

TGCTGTTGACAGTGAGCGAGCAGTTACATGCATACTTCAATAGTGAAGCCACAGATGTATTGAAGTATGCAT
GTAACTGCCTGCCTACTGCCTCGGA (SEQ ID NO: 32)

TGCTGTTGACAGTGAGCGCGCTCTGTAATCTCGTTTCAAATAGTGAAGCCACAGATGTATTTGAAACGAGATT
ACAGAGCATGCCTACTGCCTCGGA (SEQ ID NO: 33)

TGCTGTTGACAGTGAGCGCCCTCCTGATTATTCAGAATATTAGTGAAGCCACAGATGTAATATTCTGAATAAT
CAGGAGGTTGCCTACTGCCTCGGA (SEQ ID NO: 34)

TGCTGTTGACAGTGAGCGACGAAGAGCTCTTCTTTGATTATAGTGAAGCCACAGATGTATAATCAAAGAAGA
GCTCTTCGCTGCCTACTGCCTCGGA (SEQ ID NO: 35)

TGCTGTTGACAGTGAGCGCGCCAGTAACAAGAAAGAGAAATAGTGAAGCCACAGATGTATTTCTCTTTCTTG
TTACTGGCATGCCTACTGCCTCGGA (SEQ ID NO: 36)

TGCTGTTGACAGTGAGCGACCTGCATCATGACTCAGAATTTAGTGAAGCCACAGATGTAAATTCTGAGTCAT
GATGCAGGGTGCCTACTGCCTCGGA (SEQ ID NO: 37)

TGCTGTTGACAGTGAGCGCCAACATTATGGGCATCGAGAATAGTGAAGCCACAGATGTATTCTCGATGCCCA
TAATGTTGTTGCCTACTGCCTCGGA (SEQ ID NO: 38)

TGCTGTTGACAGTGAGCGACGAGCTACAAAGCATGGGAAATAGTGAAGCCACAGATGTATTTCCCATGCTTT
GTAGCTCGGTGCCTACTGCCTCGGA (SEQ ID NO: 39)

TGCTGTTGACAGTGAGCGACGTCCGCAGGAACTTAACTTATAGTGAAGCCACAGATGTATAAGTTAAGTTCC
TGCGGACGCTGCCTACTGCCTCGGA (SEQ ID NO: 40)

TGCTGTTGACAGTGAGCGCCCTGAGGATAACTCAATATAATAGTGAAGCCACAGATGTATTATATTGAGTTA
TCCTCAGGTTGCCTACTGCCTCGGA (SEQ ID NO: 41)

TGCTGTTGACAGTGAGCGCCCGGGAACAGAGAATGTTTAATAGTGAAGCCACAGATGTATTAAACATTCTCT
GTTCCCGGTTGCCTACTGCCTCGGA (SEQ ID NO: 42)

TGCTGTTGACAGTGAGCGCGGTCTCAGGCGCCAGTGGAAATAGTGAAGCCACAGATGTATTTCCACTGGCG
CCTGAGACCATGCCTACTGCCTCGGA (SEQ ID NO: 43)

TGCTGTTGACAGTGAGCGCGCCTAGTAAATTACAGAAGAATAGTGAAGCCACAGATGTATTCTTCTGTAATTT
ACTAGGCATGCCTACTGCCTCGGA (SEQ ID NO: 44)

TGCTGTTGACAGTGAGCGCGCTTCTAGGCAGAGTTGCTTATAGTGAAGCCACAGATGTATAAGCAACTCTGC
CTAGAAGCTTGCCTACTGCCTCGGA (SEQ ID NO: 45)

TGCTGTTGACAGTGAGCGACGCATATATTTGCAGTATGAATAGTGAAGCCACAGATGTATTCATACTGCAAA
TATATGCGCTGCCTACTGCCTCGGA (SEQ ID NO: 46)

TGCTGTTGACAGTGAGCGACCGTCCCGTGGAGTCGCTAAATAGTGAAGCCACAGATGTATTTAGCGACTCCA
CGGGACGGGTGCCTACTGCCTCGGA (SEQ ID NO: 47)

TGCTGTTGACAGTGAGCGCGCCCTCCCTGTCCTTTCCAGATAGTGAAGCCACAGATGTATCTGGAAAGGACA
GGGAGGGCTTGCCTACTGCCTCGGA (SEQ ID NO: 48)

TGCTGTTGACAGTGAGCGCCGCCAGCCTTCGCTTCTGAAATAGTGAAGCCACAGATGTATTTCAGAAGCGAA
GGCTGGCGTTGCCTACTGCCTCGGA (SEQ ID NO: 49)

TGCTGTTGACAGTGAGCGCGAGCTTCATGGGATTGGTAAATAGTGAAGCCACAGATGTATTTACCAATCCCA
TGAAGCTCATGCCTACTGCCTCGGA (SEQ ID NO: 50)

TGCTGTTGACAGTGAGCGAACCTTTCCAGCCATAGAGATTTAGTGAAGCCACAGATGTAAATCTCTATGGCT
GGAAAGGTGTGCCTACTGCCTCGGA (SEQ ID NO: 51)

TGCTGTrGACAGTGAGCGCGCTTTCAAGCTCATCTGTTATTAGTGAAGCCACAGATGTAATAACAGATGAGC
TTGAAAGCTTGCCTACTGCCTCGGA (SEQ ID NO: 52)

TGCTGTTGACAGTGAGCGAACAGTTGGATTCTTTAGAGAATAGTGAAGCCACAGATGTATTCTCTAAAGAAT
CCAACTGTCTGCCTACTGCCTCGGA (SEQ ID NO: 53)

TGCTGTTGACAGTGAGCGACGAGAGAGTTAGCTGACTTTATAGTGAAGCCACAGATGTATAAAGTCAGCTAA
CTCTCTCGGTGCCTACTGCCTCGGA (SEQ ID NO: 54)

TGCTGTTGACAGTGAGCGACCTGATTATATCCAGTAACACTAGTGAAGCCACAGATGTAGTGTTACTGGATA
TAATCAGGGTGCCTACTGCCTCGGA (SEQ ID NO: 55)

TABLE 2-continued shRNA Sequences evaluated
Hairpin

TGCTGTTGACAGTGAGCGCGCCCAAGGTCAAGGAGATTATTAGTGAAGCCACAGATGTAATAATCTCCTTGA
CCTTGGGCTTGCCTACTGCCTCGGA (SEQ ID NO: 56)

TGCTGTTGACAGTGAGCGCGGCATCCACTGTGAATGATAATAGTGAAGCCACAGATGTATTATCATTCACAG
TGGATGCCATGCCTACTGCCTCGGA (SEQ ID NO: 57)

TGCTGTTGACAGTGAGCGCGCTGTCTCTCTTTGATGGAATTAGTGAAGCCACAGATGTAATTCCATCAAAGA
GAGACAGCATGCCTACTGCCTCGGA (SEQ ID NO: 58)

TGCTGTTGACAGTGAGCGCCTGCAAGGACATGGTTAAATAGTGAAGCCACAGATGTATTTAACCATGTCC
TTGCAGGCTTGCCTACTGCCTCGGA (SEQ ID NO: 59)

TGCTGTTGACAGTGAGCGACGCACCTACTCCAAGTTCAAATAGTGAAGCCACAGATGTATTTGAACTTGGAG
TAGGTGCGCTGCCTACTGCCTCGGA (SEQ ID NO: 60)

TGCTGTTGACAGTGAGCGCCGAGTCTGGCTTTGAGAGTTATAGTGAAGCCACAGATGTATAACTCTCAAAGC
CAGACTCGTTGCCTACTGCCTCGGA (SEQ ID NO: 61)

TGCTGTTGACAGTGAGCGAGCCATGGAAATGCTATCAATGTAGTGAAGCCACAGATGTACATTGATAGCATT
TCCATGGCCTGCCTACTGCCTCGGA (SEQ ID NO: 62)

TGCTGTTGACAGTGAGCGCAGATGGAAGATGATATAGATATAGTGAAGCCACAGATGTATATCTATATCATC
TTCCATCTTTGCCTACTGCCTCGGA (SEQ ID NO: 63)

TGCTGTTGACAGTGAGCGCCCAAATCTTCTCCTGTCAGTATAGTGAAGCCACAGATGTATACTGACAGGAGA
AGATTTGGATGCCTACTGCCTCGGA (SEQ ID NO: 64)

TGCTGTTGACAGTGAGCGAAGAGATTATTTCTCAAGATGATAGTGAAGCCACAGATGTATCATCTTGAGAAA
TAATCTCTCTGCCTACTGCCTCGGA (SEQ ID NO: 65)

TGCTGTTGACAGTGAGCGCAGAGGGAAAGTGTATGATAAATAGTGAAGCCACAGATGTATTTATCATACACT
TTCCCTCTTTGCCTACTGCCTCGGA (SEQ ID NO: 66)

TGCTGTTGACAGTGAGCGCGGAAAGAACGGAAATCTTAAATAGTGAAGCCACAGATGTATTTAAGATTTCCG
TTCTTTCCATGCCTACTGCCTCGGA (SEQ ID NO: 67)

TGCTGTTGACAGTGAGCGCGCAGTTATGCTCTIAATGCTTTAGTGAAGCCACAGATGTAAAGCATTAAGAGC
ATAACTGCTTGCCTACTGCCTCGGA (SEQ ID NO: 68)

TGCTGTTGACAGTGAGCGCGCATGCATGACTTTAATCTTATAGTGAAGCCACAGATGTATAAGATTAAAGTC
ATGCATGCTTGCCTACTGCCTCGGA (SEQ ID NO: 69)

TGCTGTTGACAGTGAGCGAAACATGTGTAAGCTGCGGCCCTAGTGAAGCCACAGATGTAGGGCCGCAGCTT
ACACATGTTCTGCCTACTGCCTCGGA (SEQ ID NO: 70)

TGCTGTTGACAGTGAGCGAAAGGATGTGGTCCGAGTGTGGTAGTGAAGCCACAGATGTACCACACTCGGAC
CACATCCTTCTGCCTACTGCCTCGGA (SEQ ID NO: 71)

TABLE 3 qRT PCR primers used

| qRT-PCR primers | Forward | SEQ ID | SEQ ID | Reverse |
|---|---|---|---|---|
| ActB | TGAAGTGTGACGTGGACATC | 72 | 73 | GGAGGAGCAATGATCTTGAT |
| DNMT1 | GAATCTCTTGCACGAATTTCTGC | 74 | 75 | CATGAGCACCGTTCTCCAAGG |
| DNMT3A | CCGATGCTGGGGACAAGAAT | 76 | 77 | CCCGTCATCCACCAAGACAC |
| Eed | GCGGAGGAATATGTCCGAGAG | 78 | 79 | AGAGGTCTGGATTGCTGTTCT |
| ezh2 | ATGGGCCAGACTGGGAAGAA | 80 | 81 | TGGAAAATCCAAGTCACTGGTC |
| suz12 | AGTTGTCCAATAAGGCAAGTTCC | 82 | 83 | ACGAGTCACTCTAAATAGCAACG |
| hG9a | CATTTCCGCATGAGTGATGATGT | 84 | 85 | CAGGCCACCTCCTGAGTTC |
| MBD1 | TTACCCCAGGTGAAGCAAGAG | 86 | 87 | CCAATACGGGAGAAGTCAGGAC |
| MBD2 | CCCACAACGAATGAATGAACAGC | 88 | 89 | TGAAGACCTTTGGGTAGTTCCA |

TABLE 3-continued qRT PCR primers used

| qRT-PCR primers | Forward | SEQ ID | SEQ ID | Reverse |
|---|---|---|---|---|
| MBD3 | CTGGGAGAGGGAAGAAGTGC | 90 | 91 | CGGAAGTCGAAGGTGCTCAG |
| MeCP2 | AGCAGAGACATCAGAAGGGTC | 92 | 93 | CGGCCAGATTTCCTTTGCTT |
| Dot1L | GCTGCCGGTCTACGATAAACA | 94 | 95 | AGCTTGAGATCCGGGATTTCT |
| Suv39h1 | ATATCCAGACTCAGAGAGCACC | 96 | 97 | CAGCTCCCTTTCTAAGTCCTTG |
| Setdb1 | TGGATGACAAAAGATGTGAGTGG | 98 | 99 | CCATATTTGGACGTGTCCTGAG |
| smyd2 | GCCCTACAGTAAGCACTATCCT | 100 | 101 | AGTCTCCCTAGCTTCAACCAC |
| bmi1 | CCACCTGATGTGTGTGCTTTG | 102 | 103 | TTCAGTAGTGGTCTGGTCTTGT |
| ring1 | TCAGAACTCATGTGCCCTATCT | 104 | 105 | GCAGGTAGGACACTCCTTGT |
| yy1 | AGAAGAGCGGCAAGAAGAGTT | 106 | 107 | CAACCACTGTCTCATGGTCAATA |
| ezh1 | TCAATGAAGCCTGTGAGTGGA | 108 | 109 | CAATGCAACTGTGTTCAGTGAC |
| Nr2f1 | CAGGCCAGTACGCACTCAC | 110 | 111 | TGTTCTCGATGCCCATAATGTTG |
| MBD4 | CCCCACCGTCACCTCTAGT | 112 | 113 | GTAGCACCAAACTGAGCAGAA |
| suv39h2 | GGCTAAACAAAGGATAGCTCTGC | 114 | 115 | TGAAAGAAGCAATCTGTGCATGA |
| ehmt1 | CAACGCCGTAGACAGCGAG | 116 | 117 | CTCCCCGTCCTTATTGTCGAG |
| RunX1 | CCCTAGGGGATGTTCCAGAT | 118 | 119 | TGAAGCTTTTCCCTCTTCCA |
| AFP | AGCTTGGTGGTGGATGAAAC | 120 | 121 | CCCTCTTCAGCAAAGCAGAC |
| GATA4 | CTAGACCGTGGGTTTTGCAT | 122 | 123 | TGGGTTAAGTGCCCCTGTAG |
| Brachury | ACCCAGTTCATAGCGGTGAC | 124 | 125 | CAATTGTCATGGGATTGCAG |
| Ncam | ATGGAAACTCTATTAAAGTGAACCTG | 126 | 127 | TAGACCTCATACTCAGCATTCCAGT |

Example 2: Screening for Inhibitors and Enhancers of Reprogramming

To examine the influence of modifiers on somatic cell reprogramming, a loss-of-function approach was employed to interrogate the role of 22 select genes in DNA and histone methylation pathways. FIG. 1 shows a non-limiting outline of a screen for inhibitors and enhancers of reprogramming. FIG. 1A illustrates a protocol for screening shRNA pools in iPS cell generation.

Figure 6:
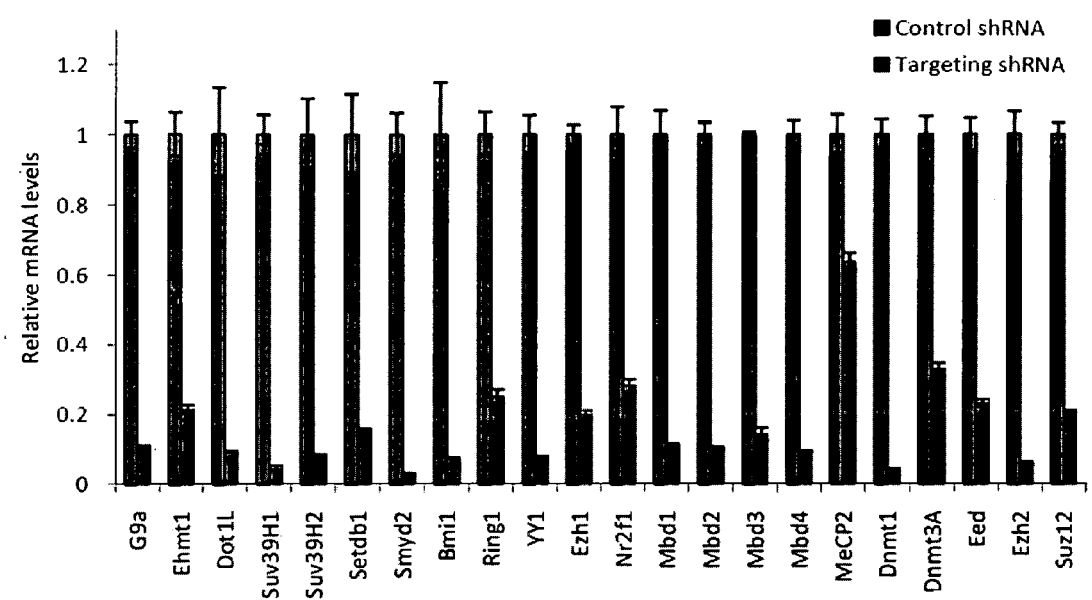
FIG. 6 shows a non-limiting example of knockdown efficiency by shRNA in dH1f cells.

In one example, a pool of 3 hairpins was tested for each of 22 target genes and knockdown efficiencies were observed of >60% for 21 out of 22 targets by qRT-PCR (FIG. 6). FIG. 6 shows the measurement of knockdown efficiency of the indicated shRNA pools in dH1f cells measured by quantitative reverse transcription PCR (qRT-PCR). Expression values for each gene were normalized to those measured in control shRNA fibroblasts. Human fibroblasts were used as a system in which to study reprogramming. Human fibroblasts were differentiated from H1 human embryonic stem cells (dH1fs), which have a higher reprogramming efficiency than primary adult dermal fibroblasts, thus yielding a reproducible baseline[7,8]. dH1fs were infected with shRNA pools (at high multiplicity of infection to ensure all cells received an shRNA vector) followed by super-infection with reprogramming vectors expressing Oct4, Sox2, Klf4 and c-Myc (OSKM), and identified the resulting iPSCs by Tra-1-60 staining (FIG. 1A).

Figure 7:
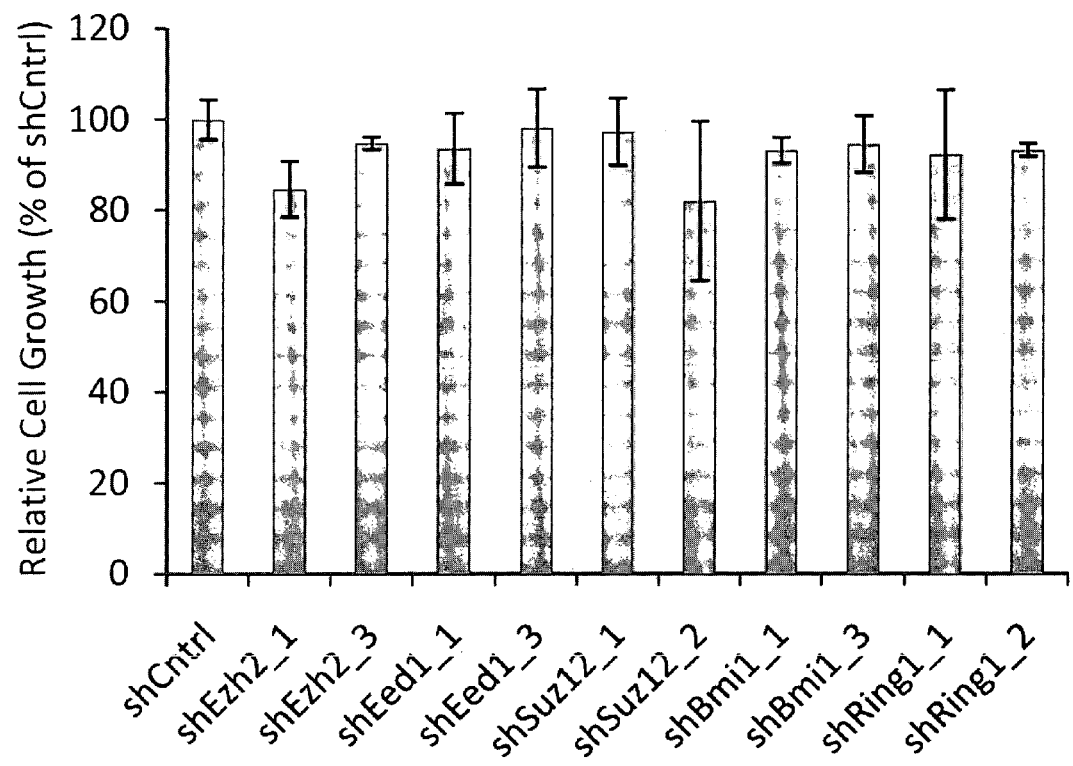
FIG. 7 shows a non-limiting example of cell proliferation upon PRC1/2 knockdown.

Eight shRNA pools negatively affected reprogramming (FIG. 1B). FIG. 1B shows the number of Tra-1-60+ colonies, as quantified by ImageJ, 21 days after OSKM transduction of 25,000 dH1f cells previously infected with pools of shRNAs against the indicated genes (3 vectors per gene). Corresponding images of representative Tra-1-60-stained reprogramming wells are shown in the lower panel. The dotted lines indicate 3 standard deviations from the mean number of colonies detected in control shRNA wells. Among the target genes were Pou5F1 (Oct4, included as a control), and Ehmt1 and SetDB1, two H3K9 methyltransferases whose histone mark was associated with transcriptional repression. The remaining five shRNA pools all targeted components of polycomb repressive complexes (PRC), which are major mediators of gene silencing and heterochromatin formation. Inhibition of PRC1 (Bmi1, Ring1) and PRC2 components (Ezh2, Eed, Suz12) did not have a significant effect on fibroblast proliferation but resulted in significantly fewer iPSC colonies than the control shRNA (FIG. 1C, FIG. 7). FIG. 1C shows the validation of primary screen hits that decrease reprogramming efficiency. Quantification of Tra-1-60+ iPSC colonies expressed as fold-change relative to control shRNA. Data correspond to the average and s.e.m. *P<0.05, **P<0.01 compared to control shRNA-expressing fibroblasts. Representative Tra-1-60-stained reprogramming wells are shown in the lower panel. FIG. 7 shows cell proliferation upon PRC1/2 knockdown. Depicted are relative cell growth rates of fibroblasts infected with the indicated shRNA vectors targeting PRC1 and PRC2 components. Relative control shRNA infected fibroblasts 5 days after shRNA transduction (n=3; error bars, +s.e.m).

This is of particular significance given the recent finding that PRC2 component Ezh2 is necessary for fusion-based reprogramming[9]. Thus, interference with chromatin-modifying enzymes that mediate repressive chromatin domains reduces reprogramming and is consistent with the importance of gene silencing of the somatic cell program during generation of iPSC.

Figure 8:
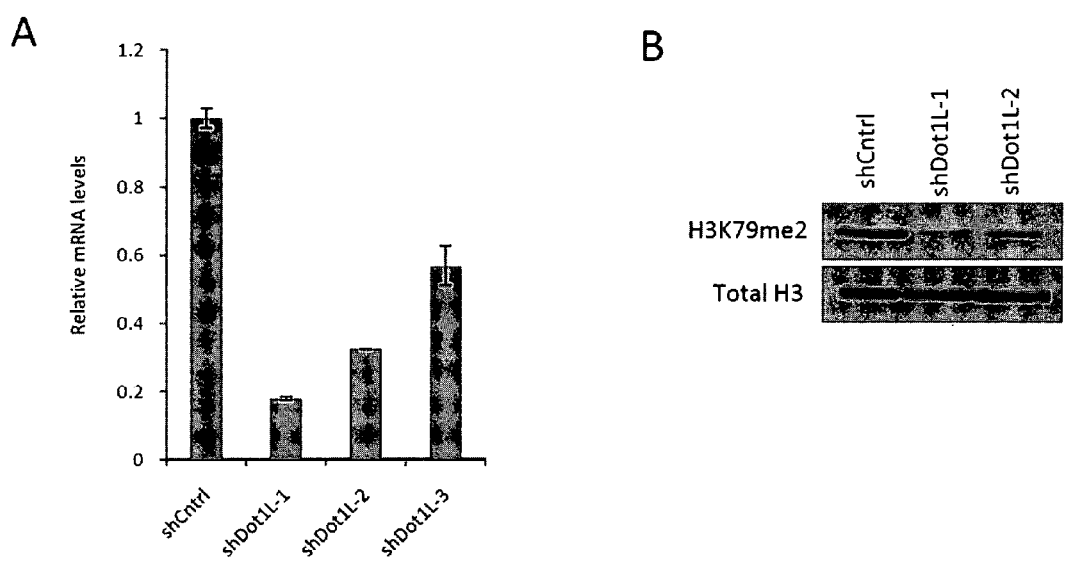
FIG. 8 shows a non-limiting example of Dot1L mRNA and total H3K79me2 levels under knock-down conditions.

Example 3: Suppression of Dot1L Expression Enhances Reprogramming Efficiency and Substitutes for Klf4 and Myc In contrast to genes whose functions appear to be required for reprogramming, inhibition of three genes enhanced reprogramming: YY1, Suv39H1, and Dot1L (FIG. 1D). FIG. 1D shows the validation of primary screen hits that increase reprogramming efficiency. Quantification of Tra-1-60+ iPSC colonies expressed as fold-change relative to control shRNA. Data correspond to the average and s.e.m. *P<0.05, **P<0.01 compared to control shRNA-expressing fibroblasts. Representative Tra-1-60-stained reprogramming wells are shown in the lower panel. YY1 is a transcription factor that activates or represses transcription in a context-dependent manner[10,11], whereas Suv39H1 is a histone H3K9 methyltransferase implicated in heterochromatin formation[12]. Enzymes that modify H3K9 were associated with both inhibition and enhancement of reprogramming in this study, which suggested that unraveling the precise mechanisms for their effects might be challenging. The studies focused on Dot1L, a histone H3 Lysine 79 methyltransferase whose role in reprogramming has not been previously studied[13]. Three Dot1L-targeting hairpin vectors were evaluated independently for knockdown efficiency and utilized the two shRNAs that resulted in the most significant downregulation of Dot1L and concomitant decrease in global H3K79 levels (FIG. 8). FIG. 8 shows Dot1L mRNA and total H3K79me2 levels under knock-down conditions. FIG. 8A shows the knock-down efficiency of individual hairpins targeting Dot1L as measured by qRT-PCR. FIG. 8B shows the total H3K79me2 levels in control and shDot1L infected fibroblasts assessed by western blotting 6 days after shRNA transduction.

Figure 2:
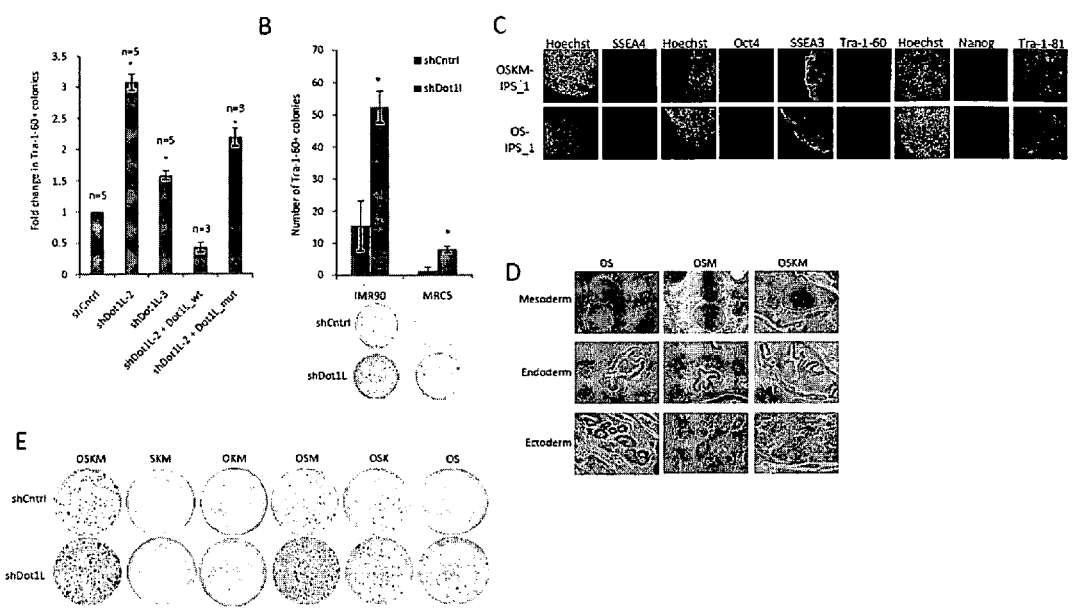
FIG. 2 shows a non-limiting example of cellular reprogramming enhanced by Dot1L inhibition.

Following infection with OSKM, fibroblasts expressing Dot1L shRNA formed significantly more iPSC colonies than control fibroblasts, and the degree of enhancement in reprogramming correlated with the degree of Dot1L knockdown (FIG. 2A, FIG. 7A). In addition, the enhanced reprogramming phenotype elicited by Dot1L knockdown could be reversed by overexpressing an shRNA-resistant wildtype Dot1L, but not by a catalytically-inactive Dot1L, indicating that inhibition of catalytic activity of Dot1L is key to reprogramming[14] (FIG. 2A). FIG. 2 shows that Dot1L inhibition enhances reprogramming efficiency and substitutes for Klf4 and Myc. FIG. 2A shows the fold change in the reprogramming efficiency of dH1f cells infected with 2 independent Dot1L shRNAs or co-infected with shRNA-2 and a vector expressing an shRNA-resistant wild-type or catalytically dead mutant Dot1L. Data correspond to the average and s.e.m.; n=independent experiments. *P<0.01 control shRNA-expressing fibroblasts.

Figure 9:
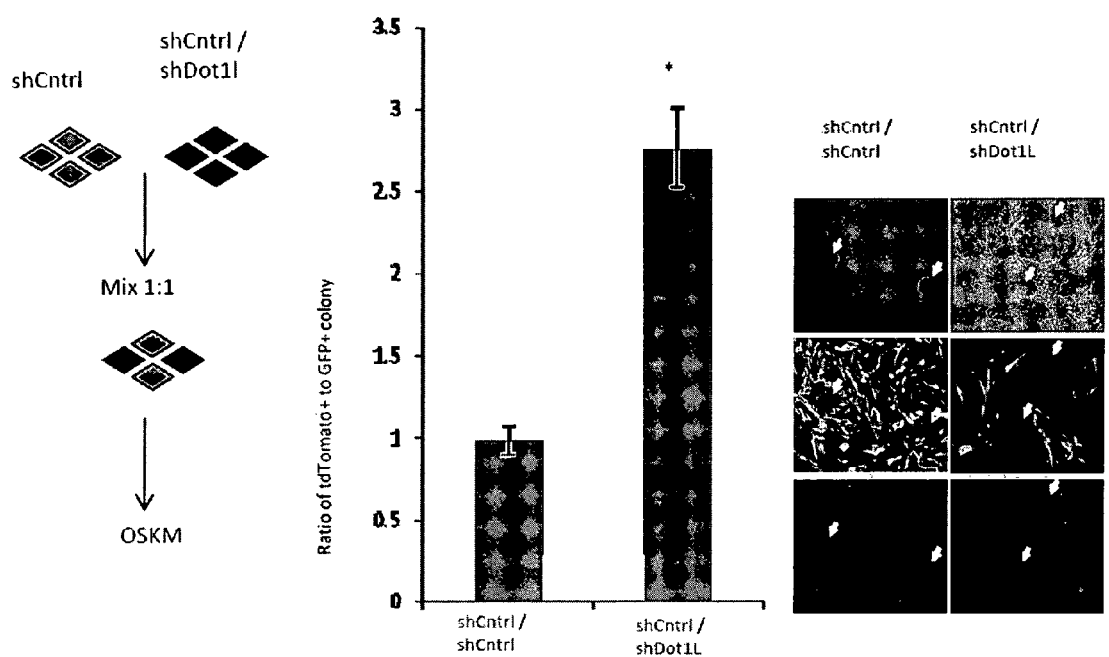
FIG. 9 shows a non-limiting example of same-well reprogramming of admixed control and Dot1L inhibited cell populations.

To further document the competitive advantage of Dot1L shRNA-expressing fibroblasts (shDot1L) during reprogramming, experiments were performed in which fibroblasts infected with Dot1L shRNA or a control vector were differentially labeled with either tdTomato or GFP and co-cultured prior to superinfection with OSKM (FIG. 9). FIG. 9 shows same-well reprogramming of admixed control and Dot1L inhibited cell populations. Control and shDot1L dH1f cells were infected with either a GFP- or tdTomato-expressing lentivirus, and mixed in a 1:1 ratio prior to OSKM infection. The middle panel shows a quantification of morphologically discernible iPS-like colonies that were scored on the basis of the fluorescent protein expression. Data correspond to the mean ratio of GFP+ colonies to Tomato+ colonies in each co-mixture and s.d. (n=2). Lower panels show representative images of either GFP or tdTomato expressing iPSC colonies (arrowheads) derived from the indicated co-mixed cell populations.

The emerging iPSC colonies were then scored for tdTomato or GFP fluorescence, which indicated their cell of origin. Co-mixture of tdTomato- and GFP-labeled control cells resulted in a 1:1 ratio of red and green iPSC colonies indicating that labeling per se did not affect relative reprogramming efficiency. In contrast, wells containing co-mixtures of tdTomato-shDot1L and GFP-shCntrl cells generated 3-fold more red colonies than green colonies, indicating that Dot1L-inhibited cells reprogram more efficiently under identical conditions (FIG. 9). The experiments were repeated with additional strains of human fibroblasts, and a 3-fold and 6-fold increases in reprogramming efficiency for IMR-90 and MRC-5 cells was observed, respectively, indicating that findings with dH1fs were broadly applicable to other human fibroblast strains (FIG. 2B). FIG. 2B shows the number of Tra-1-60+ colonies derived from 50,000 control and Dot1L shRNA-expressing IMR-90 and MRC5 human diploid fibroblasts. Data correspond to the average and s.d. *P<0.05 compared to control shRNA-expressing fibroblasts (n=2). Lower panels show representative Tra-1-60-stained wells from the indicated conditions. iPS cells generated through Dot1L inhibition exhibited a morphology characteristic of embryonic stem cells and stained positively for SSEA4, SSEA3, Tra-1-81, Oct4 and Nanog (FIG. 2C). FIG. 2C shows immunohistochemistry expression analysis of pluripotency markers, SSEA4, SSEA3, Oct4, Nanog and Tra-1-81 in expanded shDot1L-iPS colonies derived from 4-factor (OSKM) and 2-factor (OS) reprogramming.

Figure 10:
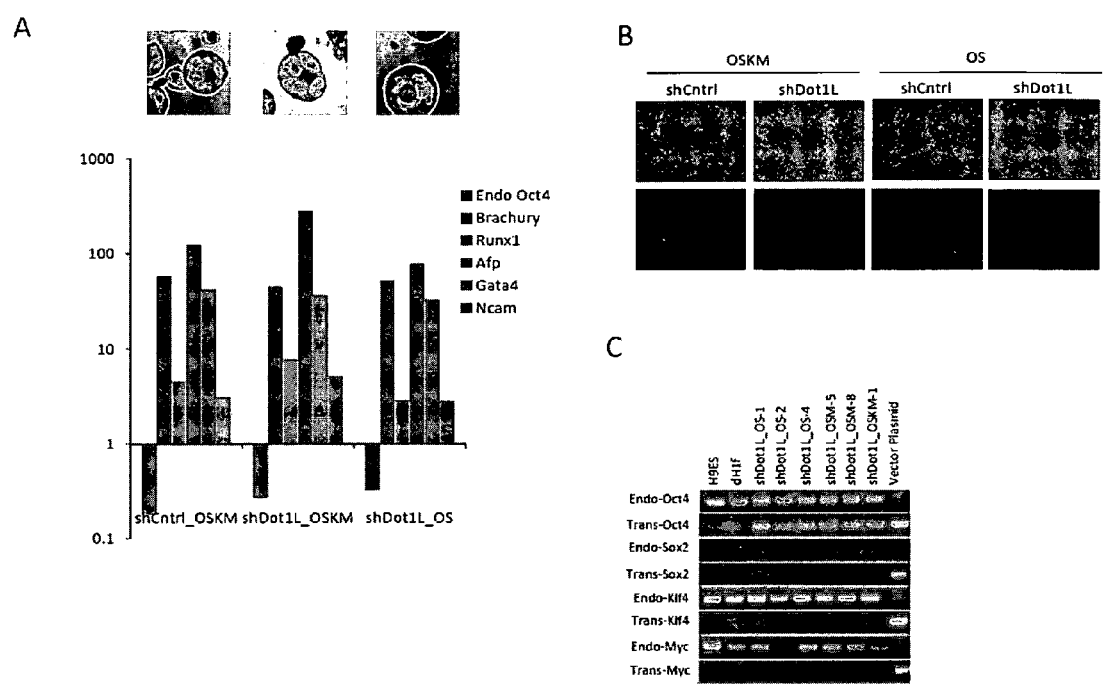
FIG. 10 shows a non-limiting characterization of shDot1L iPS cells.

Additionally, these cells were able to differentiate into all three embryonic germ layers in vitro and in teratomas (FIG. 2D and FIG. 10A), indicating that iPSCs generated following Dot1L inhibition display all of the hallmarks of pluripotency. FIG. 2D shows hematoxylin and eosin staining of representative OS-, OSM-, OSKM-shDot1L-iPS teratomas exhibiting ectoderm (neural rosettes), mesoderm (cartilage), and endoderm (gut-like endothelium) differentiation. FIG. 10 shows a characterization of shDot1L iPS cells. FIG. 10A shows the downregulation of endogenous OCT4 mRNA, as well as the upregulation of differentiation markers GATA4 and AFP (endoderm), RUNX1 and Brachury (mesoderm), and NCAM (ectoderm) in day 8 EBs derived from shCntrl-OSKM, shDot1L-OSKM, and shDot1L-OS iPS cells as judged by qRT-pCR. Expression values are represented relative to undifferentiated controls.

To assess whether Dot1L inhibition could replace any of the 4 exogenous reprogramming factors, shDot1L and shCntrl fibroblasts were infected with 3 factors, omitting one factor at a time. In the absence of Oct4 or Sox2 no iPSC colonies emerged in both types of fibroblasts. When either Klf4 or Myc was omitted, shDot1L fibroblasts were able to give rise to robust numbers of Tra-1-60 positive colonies while control cells yielded very few colonies as reported previously[3]. It was examined whether Dot1L suppression would suffice to reprogram fibroblasts in the absence of both Klf4 and c-Myc. Indeed, shDot1L fibroblasts infected with only Oct4 and Sox2 gave rise to Tra-1-60-positive colonies, whereas control fibroblasts did not (FIG. 2E). FIG. 2E shows Tra-1-60 staining of whole plates of shCntrl and shDot1L fibroblasts 21 days after reprogramming in the absence of each factor or both Klf4 and c-Myc. Two-factor iPSCs derived by Dot1L inhibition exhibited a typical ES cell morphology and had silenced GFP expression from the exogenous reprogramming vectors (FIG. 10B). FIG. 10B shows the morphology changes and retroviral silencing in colonies emerging in 4-factor (OSKM) and 2-factor (OS) reprogramming of control and Dot1L-inhibited cells. Green fluorescence indicates persistent GFP expression derived from the pMIG reprogramming vectors. Note that after 2-factor (OS) transduction, colonies arising from only shDot1L or iDot1L-treated fibroblasts silence the transgenes as indicated by the absence of GFP expression, whereas shCntrl fibroblasts yield transformed cell clusters that retain factor expression. PCR on genomic DNA isolated from expanded colonies indicated the presence of Oct4 and Sox2, but not the Klf4 and c-Myc transgenes (FIG. 10C). FIG. 10C shows PCR-based detection of transgenes in the genomic DNA of 2- and 3-factor iPSC lines derived from shDot1L cells with primers designed to amplify either endogenous loci or the virally-encoded transgenes. H9ES and dH1f cells served as negative controls for the transgenes and vector plasmids and OKSM-derived iPSC lines were used as positive controls.

The OS-shDot1L-iPS cells had all of the hallmarks of pluripotency as gauged by endogenous pluripotency factor expression and the ability to form all three embryonic germ layers in vitro and in teratomas (FIG. 2C, 2D and FIG. 10A). These findings indicate that Dot1L inhibition can reprogram cells to pluripotency in the presence of only Oct4 and Sox2.

It was examined whether the cellular mechanisms by which Dot1L inhibition promotes reprogramming. It was observed that in established human iPS clones derived from shDot1L fibroblasts, Dot1L inhibition was no longer evident, reflecting the known silencing of retroviruses that occurs during reprogramming (FIG. 11A).

Figure 11:
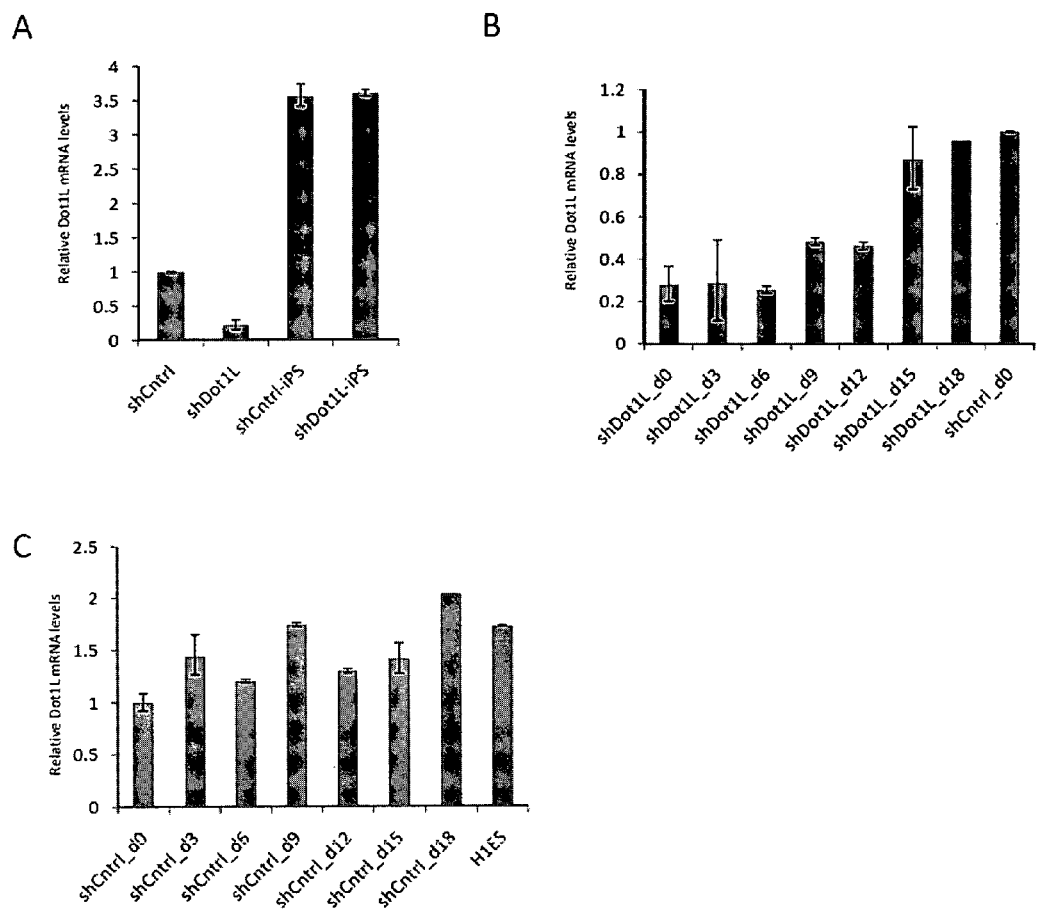
FIG. 11 shows a non-limiting example of Dot1L knockdown dynamics during reprogramming.

FIG. 11 shows Dot1L knockdown dynamics during reprogramming. FIG. 11A shows Dot1L mRNA levels in iPSCs derived from shCntrl and shDot1L iPSCs relative to levels in the starting control dh1F cells as measured by qRT-PCR. FIG. 11B shows Dot1L mRNA levels in shDot1L cells measured by qRT-PCR every 3 days after OSKM expression normalized to levels observed in control cells prior to OSKM expression. FIG. 1C shows Dot1L mRNA levels in control cells measured by qRT-PCR every 3 days after OSKM expression normalized to levels observed in control cells prior to OSKM expression.

Figure 12:
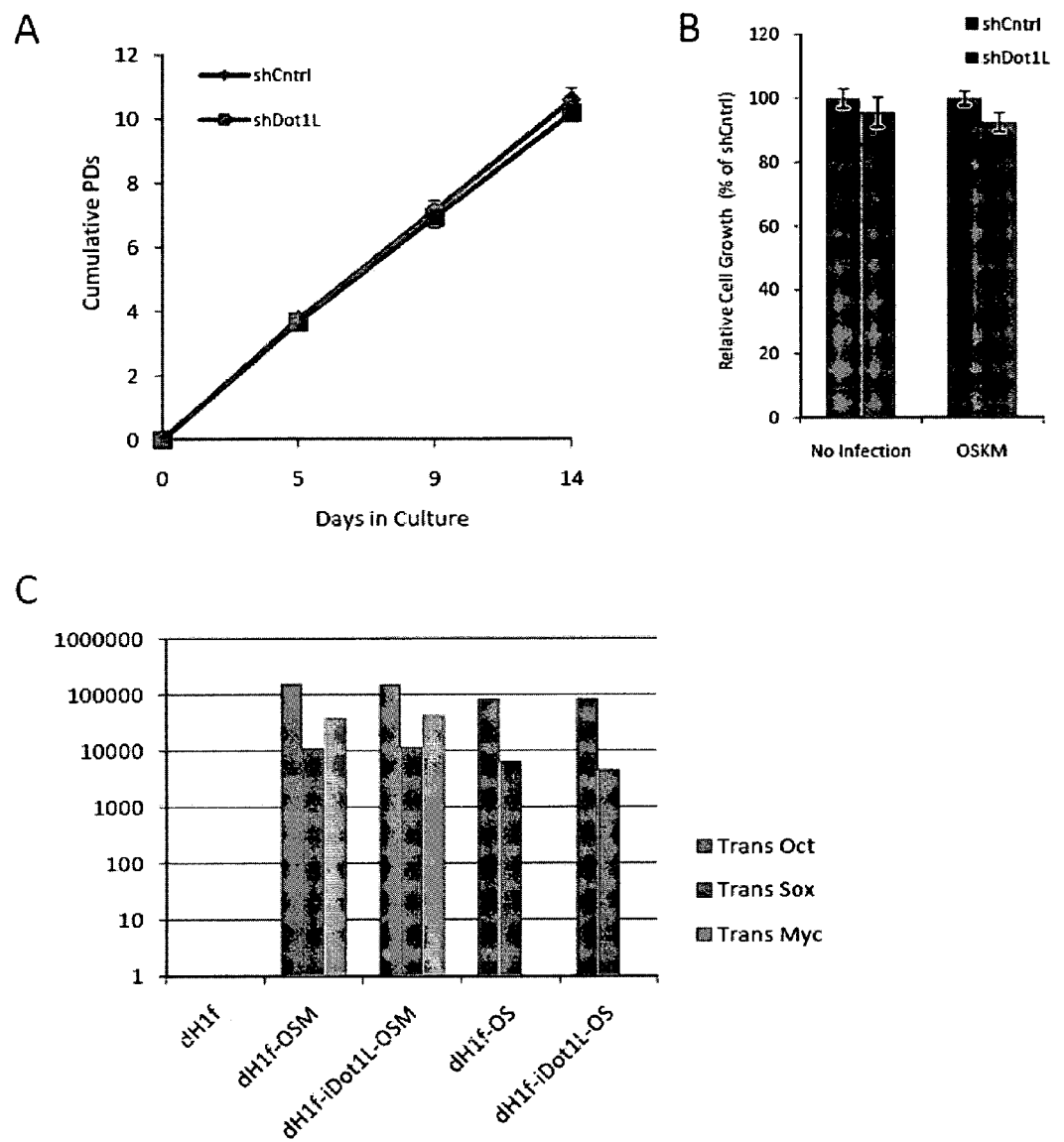
FIG. 12 shows a non-limiting example of the Growth dynamics of shDot1L cells pre- and post-OSKM transduction.

Examination of Dot1L knockdown levels during the course of reprogramming revealed that silencing occurred by day 15 after OSKM transduction (FIGS. 11B, C). Since Dot1L inhibition seemed to work in the initial phases of reprogramming, it was examined if the proliferation rates of shDot1L and shCntrl cells before and after infection with the OSKM reprogramming factors and found them to be comparable (FIGS. 12A and 12B). FIG. 12 shows the growth dynamics of shDot1L cells pre- and post-OSKM transduction. FIG. 12A shows the cumulative population doubling rates of shCntrl and shDot1L cells over a period of 14 days prior to reprogramming (n=3; error bars, +s.e.m). FIG. 12B shows the relative cell growth rates of shCntrl and shDot1L cells prior to and 6 days after OSKM transduction (n=3; error bars, ±s.e.m).

There was also no difference in the number of senescent cells, as gauged by senescence-associated β-gal staining following OSKM infection (FIG. 12C, data not shown). In addition, the level of retroviral reprogramming factor expression was similar between control and Dot1L-inhibited cells (FIG. 12C). FIG. 12C shows qRT-PCR quantification of viral transcript levels using transgene-specific primers in control or iDot1L treated dH1f cells 3 days after infection with OSM or OS expressing retroviruses.

Figure 13:
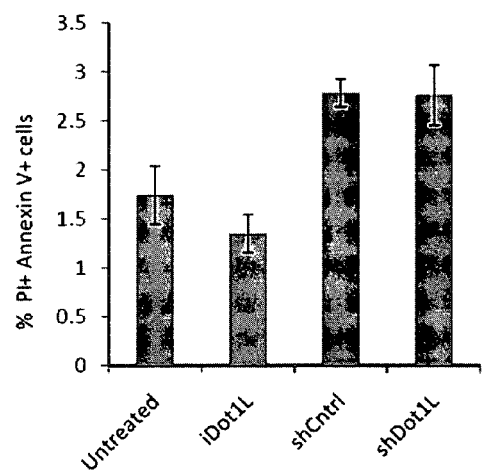
FIG. 13 shows a non-limiting example apoptosis and cell cycle profile of Dot1L-inhibited cells.
Figure 13:
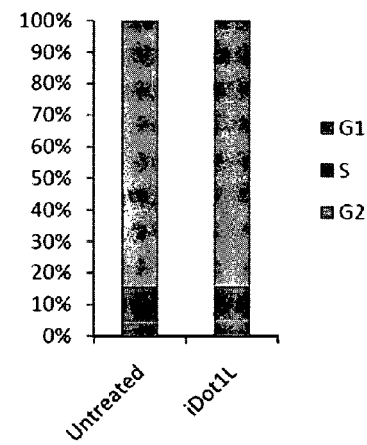

Previous studies indicated that Dot1L null cells have increased apoptosis and accumulation of cells in G2 phase[13]. However, a significant increase in apoptosis or change in the cell cycle profile of Dot1L knock-down fibroblasts was not observed (FIG. 13). FIG. 13 shows apoptosis and a cell cycle profile of Dot1L-inhibited cells. FIG. 13A shows the percentage of apoptotic cells in the indicated cell populations 5 days after treatment (iDot1L-10 um) or shRNA infection measured by PI/Annexin staining (n=3; error bars, +s.d.). FIG. 13B shows a cell cycle profile of untreated or iDot1L (10 uM for 5 days) treated fibroblasts as measured by PI staining.

Figure 14:
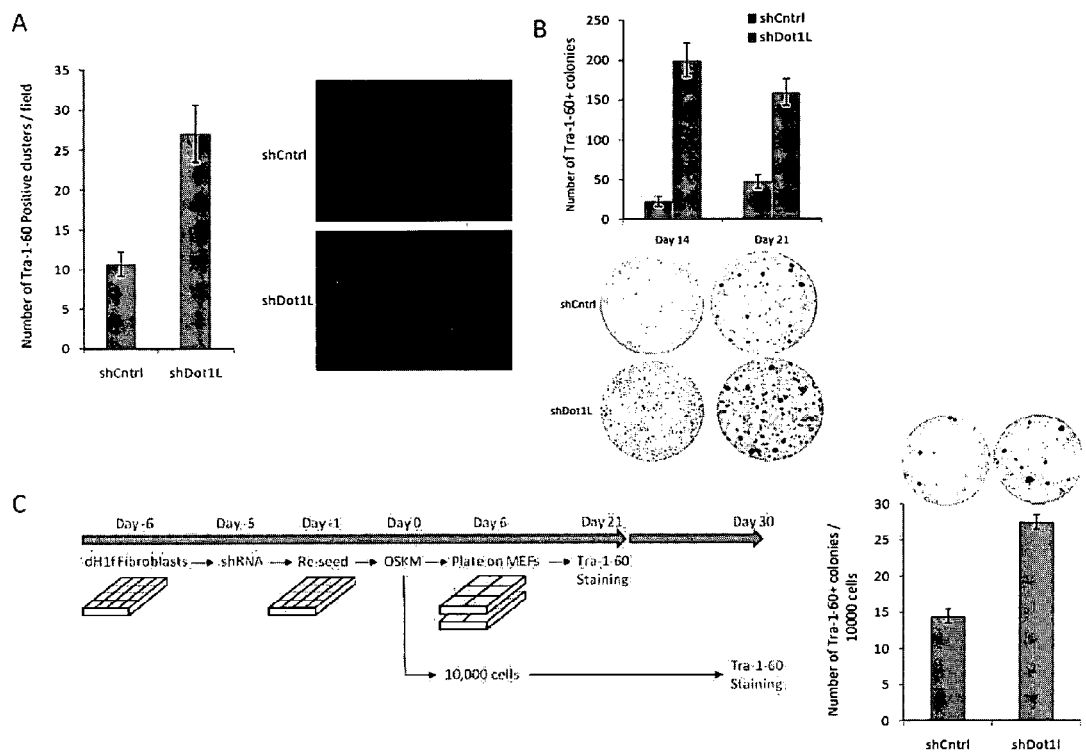
FIG. 14 shows a non-limiting example of the kinetics of iPSC colony formation upon Dot1L knockdown.

It was also examined whether Dot1L knockdown, in addition to increasing reprogramming efficiency, accelerated the kinetics of reprogramming. FIG. 14 shows the kinetics of iPSC colony formation upon Dot1L knockdown. FIG. 14A shows the number of Tra-1-60+ iPSC colonies generated by shCntrl and shDot1L dH1f cells on Day 14 and Day 21 of reprogramming (n=3; error bars, ±s.e.m). FIG. 14B shows the number of Tra-1-60+ cell clusters per field as judged by live-staining and imaging on Day 10 after OSKM transduction (n=12 fields, ±s.e.m). Immunofluorescence analysis during reprogramming revealed significantly greater numbers of Tra-1-60-positive cell clusters on day 10 (FIG. 14A) and recognizable Tra-1-60-positive colonies on days 14 and 21 in shDot1L cultures (FIG. 14B), indicating that the emergence of iPSC colonies is accelerated upon Dot1L inhibition. FIG. 12C shows qRT-PCR quantification of viral transcript levels using transgene-specific primers in control or iDot1L treated dH1f cells 3 days after infection with OSM or OS expressing retroviruses.

When the reprogramming experiments were extended by 10 more days (at which time the already-formed iPSC colonies begin to differentiate), shDot1L cells still yielded more iPSC colonies than controls (FIG. 14C). FIG. 14C shows a modified schema for testing the reprogramming efficiency of 10,000 OSKM infected dH1f cells without replating onto MEFs and a longer incubation period of 30 days. The graph on the right shows the number of Tra-1-60+ iPSC colonies generated through this modified protocol (n=2; error bars, +s.e.m) When the reprogramming experiments were extended by 10 more days (at which time the already-formed iPSC colonies begin to differentiate), shDot1L cells still yielded more iPSC colonies than controls (FIG. 14C). Taken together, Dot1L inhibition both accelerates the emergence of iPSCs and increases the total yield of the reprogramming process.

Figure 15:
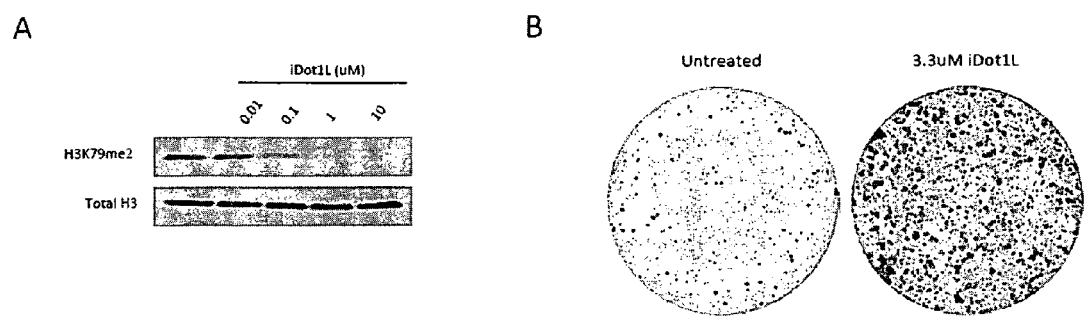
FIG. 15 shows a non-limiting example of increased reprogramming efficiency using small molecule inhibitor of Dot1L.

Example 4: Small Molecule Inhibitor of Dot1L Enhances Reprogramming and Replaces Klf4 and Myc In addition to the shRNA mediated knockdown of Dot1L, a small molecule inhibitor of Dot1L catalytic activity was used to further validate the findings[15]. This inhibitor (EPZ004777, referred to as iDot1L and shown below) abrogated H3K79 methylation robustly at 1 uM to 10 uM concentration range and led to 3-4 fold enhancement of reprogramming of human fibroblasts (FIG. 3A, FIG. 15).

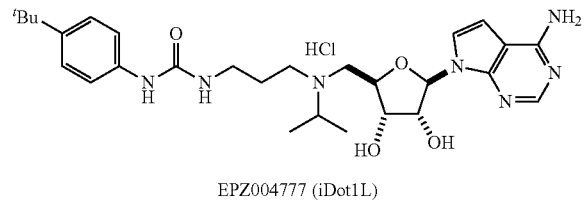

EPZ004777 (iDot1L)

Figure 3:
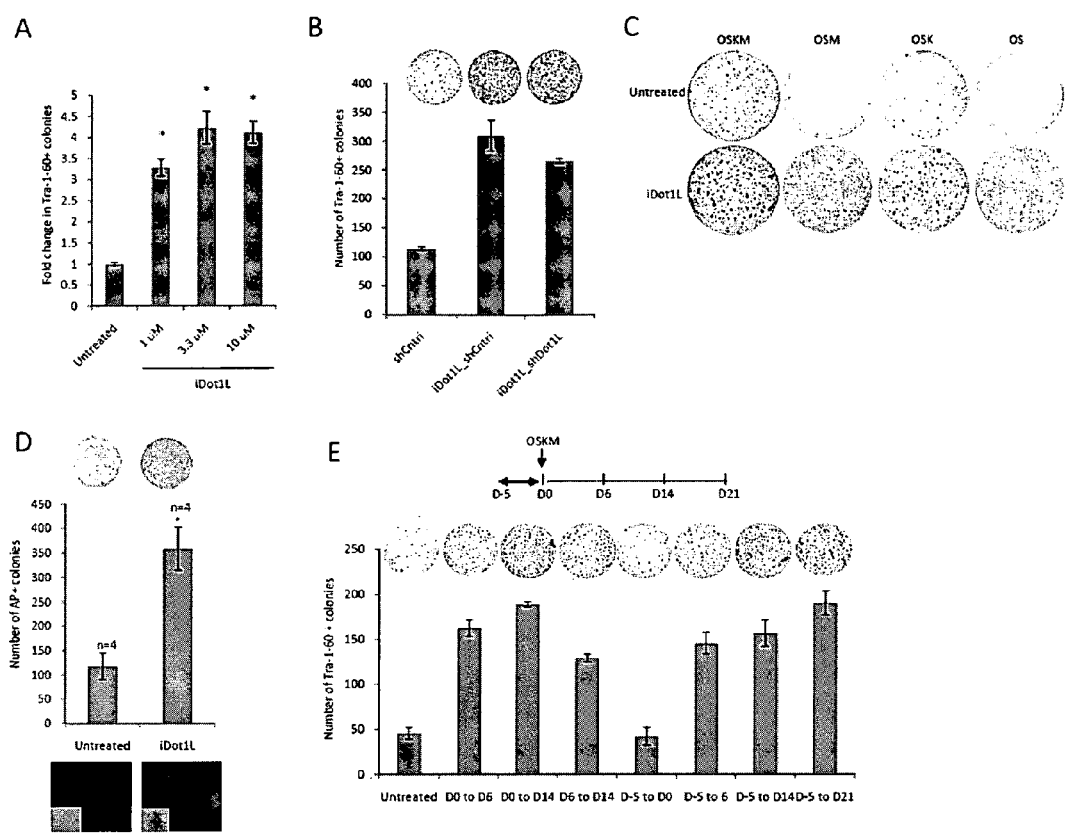
FIG. 3 shows a non-limiting example of Dot1L inhibition using a small molecule.

FIG. 3 shows that the small molecule inhibitor of Dot1L increases efficiency and substitutes for Klf4 and Myc. FIG. 3A shows the fold change in the reprogramming efficiency of dH1f cells treated with iDot1L at the indicated concentrations for 21 days. Data correspond to the average and s.d.; n=3. *P<0.001 compared untreated fibroblasts. FIG. 15 shows that the small molecule inhibitor of Dot1L increases reprogramming efficiency. FIG. 15A shows total H3K79me2 levels in fibroblasts treated with EPZ004777 (iDot1L) at the indicated concentrations for 5 days as assessed by western blotting. FIG. 15B shows representative images of control or iDot1L treated reprogramming plates stained with Tra-1-60 on day 21.

Knockdown of Dot1L protein in combination with inhibitor treatment did not result in a further increase of reprogramming efficiency thereby reinforcing the previous observation that inhibition of catalytic activity of Dot1L is key to reprogramming (FIG. 3B). FIG. 3B shows the number of Tra-1-60+ colonies 21 days after OSKM transduction of 25,000 control fibroblasts, iDot1L treated fibroblasts (10 uM) and iDot1L treated fibroblasts expressing the Dot1L shRNA. Data correspond to average and s.d (n=2). Representative Tra-1-60-stained reprogramming wells are in the lower panel. Similar to shRNA mediated suppression of Dot1L, chemical inhibition of Dot1L allowed reprogramming in the absence of either Klf4 or Myc and was able to replace both of these exogenous factors during reprogramming (FIG. 3C). FIG. 3C shows Tra-1-60 staining of whole plates of untreated or iDot1L (10 uM) fibroblasts 21 days after reprogramming in the absence of Klf4, c-Myc or both. Thus, it was possible to generate two-factor iPSCs robustly and reproducibly either by shRNA mediated suppression of Dot1L or chemical inhibition of its methyl transferase activity.

It was assessed whether these observations can be extended to the murine system. It was observed that, similar to human fibroblasts, iDot1L treatment led to 3-fold enhancement of reprogramming of Oct4-GFP MEFs (FIG. 3D). FIG. 3D shows the number of AP+ colonies derived from OSKM transduced untreated or iDot1L treated (10 um) Oct4-GFP Mefs. Data correspond to the average and s.d.; n=4. *P<0.001 compared untreated MEFs. Representative AP-stained wells and GFP-positive iPS colonies derived from each condition are shown in the lower panel.

Figure 16:
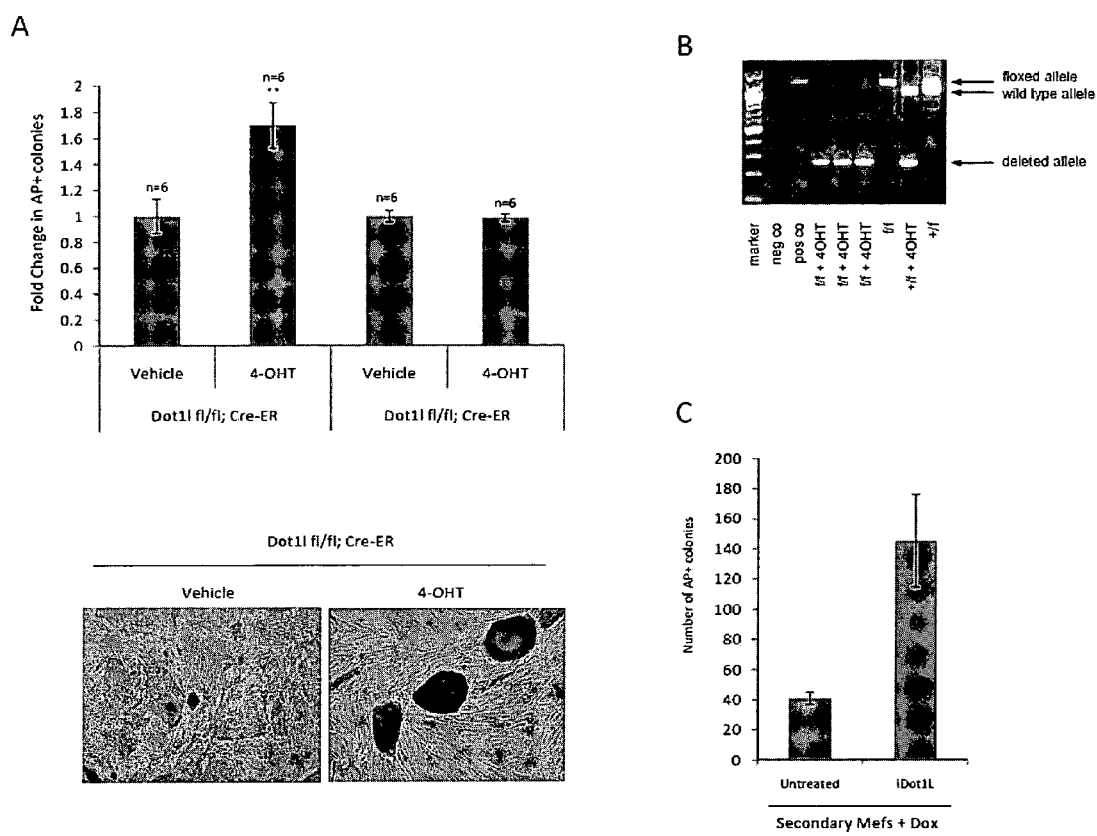
FIG. 16 shows a non-limiting example of reprogramming of Dot1L conditional knockout tail-tip fibroblasts TTFs.

The colonies resulting from Dot1L inhibition were GFP-positive indicating the activation of the endogenous Oct4 gene. Furthermore, reprogramming of tail-tip fibroblasts (TTFs) derived from a conditional knockout Dot1L mouse strain yielded significantly more iPS colonies upon Cre mediated excision of Dot1L (FIG. 16A). FIG. 16 shows the reprogramming of Dot1L conditional knockout tail-tip fibroblasts TTFs. FIG. 16A shows an example of fold change in Alkaline Phosphatase positive (AP+) colonies upon OSKM transduction of TTFs derived from Dot1L fl/fl mice. TTFs were first infected with a MSCV-CRE-ER vector. Vehicle (Ethanol) or 4-OHT was added to cultures at the same time as OSKM infection. Data correspond to average and s.e.m. (n=6). The complete excision of both floxed Dot1L alleles in iPSC clones derived from homozygous TTFs was confirmed by genomic PCR (FIG. 16B). FIG. 16B shows genomic PCR to detect wildtype, floxed or deleted Dot1L alleles in iPS colonies derived from reprogramming of the indicated starting Cre-expressing TTFs in the presence or absence of 4OHT. Dot1L inhibition also increased reprogramming efficiency of inducible iPS-derived "secondary" MEFs (FIG. 16C). FIG. 16C shows the number of AP+ colonies upon doxycycline addition to iPS-derived secondary MEFs in the presence of iDot1L (10 um). Data correspond to average and s.d (n=2).

Taken together these results demonstrate that Dot1L inhibition enhances reprogramming of mouse cells as well.

To further dissect out the crucial time window for Dot1L inhibition, human fibroblasts undergoing reprogramming were treated with iDot1L at 1 week intervals. It was observed that Dot1L inhibition either in the first or the second week was sufficient to enhance reprogramming whereas pretreatment for 5 days prior to OSKM transduction had no effect (FIG. 3E). FIG. 3E shows the number of Tra-1-60+ colonies 21 days after OSKM transduction of 25,000 untreated fibroblasts, and fibroblasts treated with iDot1L (10 uM) for the indicated time periods during reprogramming. Data correspond to average and s.d (n=3). Representative Tra-1-60-stained reprogramming wells are shown in the upper panel. These findings indicate that Dot1L inhibition at early to middle stages in the reprogramming process facilitates the acquisition of pluripotency.

Example 5: Dot1L Inhibition During Reprogramming Induces Nanog and Lin28 Expression Since the effects of Dot1L inhibition were evident early in the reprogramming process, it was investigate if gene expression changes in Dot1L-inhibited cells soon after transduction with reprogramming factors could reveal insights into the molecular mechanisms involved. A global gene-expression analyses on control and shDot1L fibroblasts prior to and 6 days after OSKM transduction was performed along with cells that were treated with iDot1L. Although thousands of genes were induced or repressed upon OSKM expression, relatively few genes were differentially expressed in shDot1L cells on Day 6 of reprogramming (22 up, 23 down;). At this time point, inhibitor treated cells exhibited broader gene expression changes (405 up and 175 down), presumably due to more complete inhibition of K79me2 levels.

To understand the mechanism by which Dot1L inhibition substitutes for Klf4, gene expression analyses on control and shDot1L cells were performed upon 3-factor infection with OSM. While 94 genes were differentially upregulated in shDot1L cells in the absence of Klf4, the intersection of this set of genes with the set differentially upregulated in 4-factor reprogramming of shDot1L and inhibitor treated cells yielded only 5 common genes (FIG. 4A, 4B). These five genes were Lefty1, Lin28A, Lum, Upp1 and Nanog. Nanog and Lin28 were upregulated in all three instances of Dot1L inhibition. These two genes are part of the core pluripotency network of human ES cells[16,17,18] and have previously been shown to be sufficient for reprogramming human fibroblasts into iPSC when used in combination with Oct4 and Sox2[4].

Figure 4:
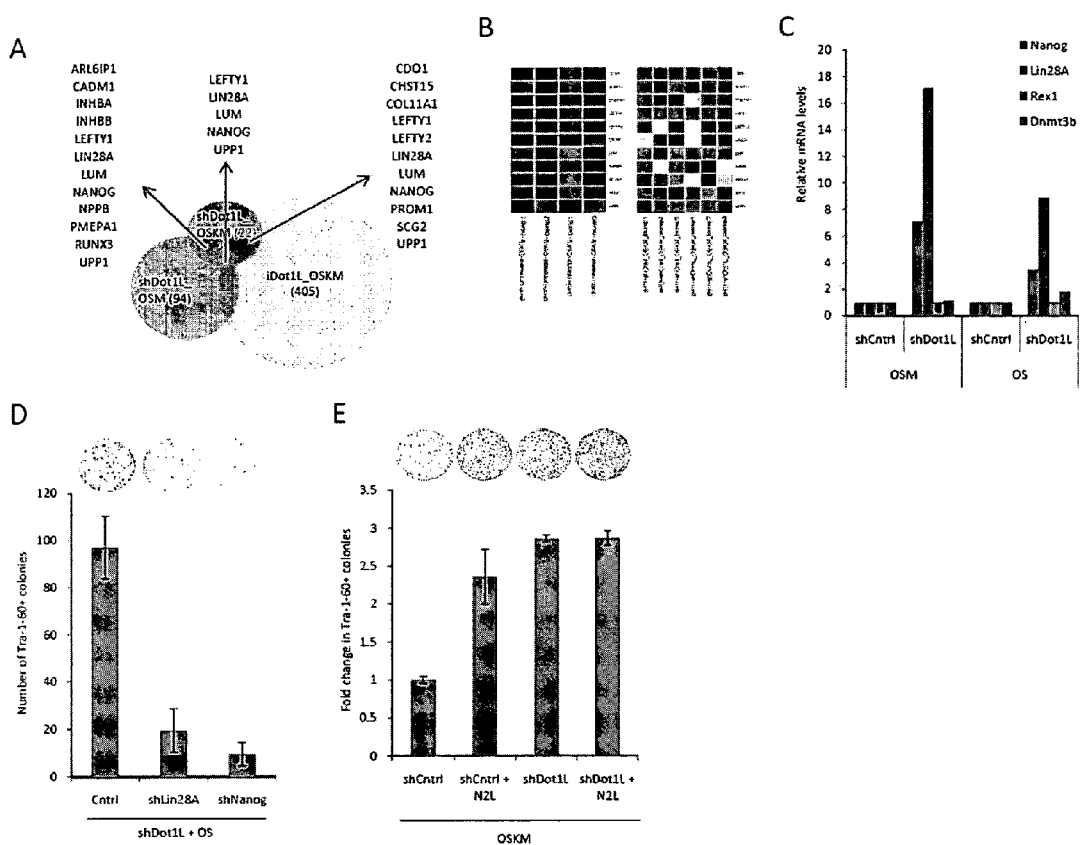
FIG. 4 shows a non-limiting example of Nanog and Lin28 associated with reprogramming by Dot1L inhibition.

FIG. 4 shows that Nanog and Lin28 are important for the enhancement of reprogramming by Dot1L inhibition. FIG. 4A shows the overlap of differentially upregulated genes in shDot1L cells 6 Days post-OSKM and OSM transduction with the genes upregulated in OSKM transduced iDotL-treated cells. FIG. 4B shows heat maps showing differential expression levels of commonly upregulated genes in OSKM transduced Dot1L-inhibited cells.

Figure 17:
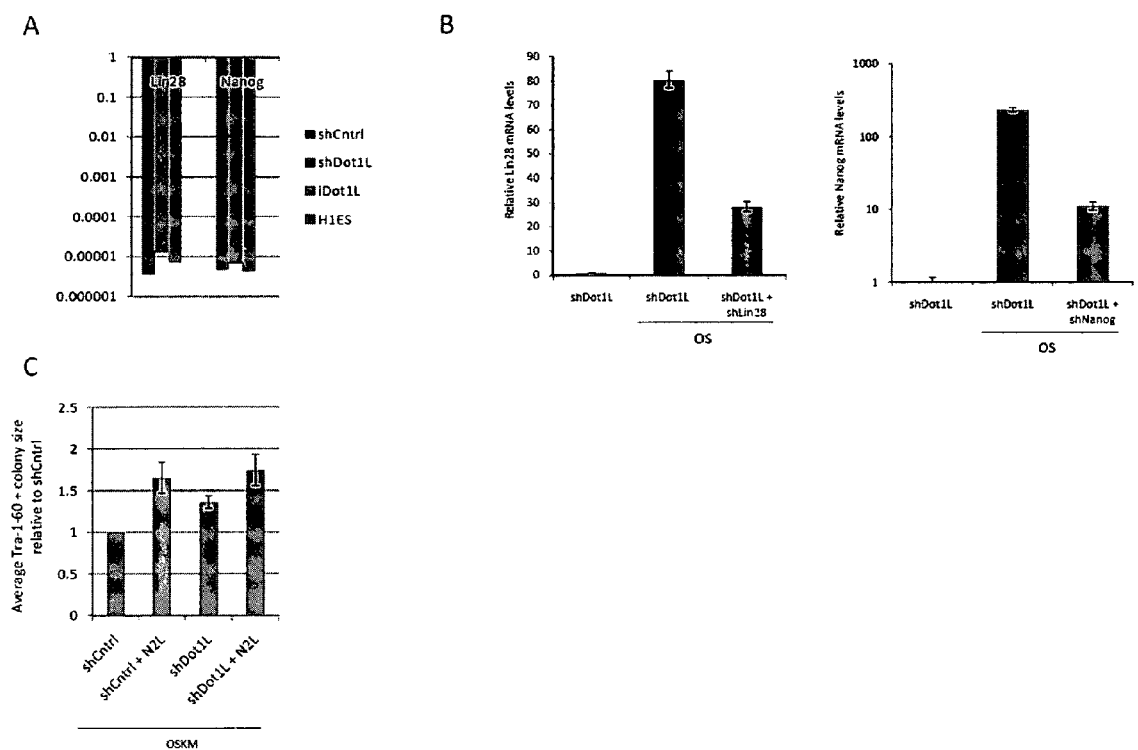
FIG. 17 shows a non-limiting example of knockdown efficiency of Nanog and Lin28 during 2-factor reprogramming.

The possibility was explored that Nanog and Lin28 upregulation was responsible for the enhanced reprogramming observed following Dot1L inhibition and validated their upregulation in shDot1L fibroblasts compared to control fibroblasts 6 days after transduction with reprogramming factors (FIG. 4C). FIG. 4C shows the expression levels of Nanog, Lin28, Rex1, and Dnmt3b in shDot1L cells 6 days post-OSM or -OS transduction relative to shCntrl cells as measured by qRT-PCR. Interestingly at this early time-point, no upregulation of Rex1 and Dnmt3b was observed, two other well-characterized pluripotency genes, suggesting that Dot1L inhibition does not broadly upregulate the pluripotency network. Suppression of either Nanog or Lin28 expression using lentiviral shRNAs abrogated the 2-factor reprogramming of shDot1L fibroblasts, indicating the essential roles of Nanog and Lin28 in this process (FIG. 4D, FIG. 17B). FIG. 4D shows the number of Tra-1-60+ iPSC colonies upon knockdown of Nanog or Lin28 in 2-factor reprogramming of shDot1L cells (n=2; error bars, ±s.e.m). FIG. 17 shows an example of the knockdown efficiency of Nanog and Lin28 during 2-factor reprogramming. FIG. 17A shows Lin28 and Nanog mRNA levels in shCntrl, shDot1L or iDot1L-treated cells prior to reprogramming. Expression values are represented relative to HIES cells. FIG. 17B shows Lin28 and Nanog mRNA levels in shDot1L cells expressing Lin28 shRNA or Nanog shRNA 6-days after OS transduction. Expression values are represented relative to shDot1L cells prior to OS infection.

It was hypothesized that if Nanog and Lin28 upregulation is the major mechanism by which Dot1L inhibition enhances reprogramming, then inclusion of Nanog and Lin28 in the OSKM reprogramming cocktail would not confer any additional enhancement to shDot1L cells. In fact, no significant difference in the number of colonies generated between 4-factor (OSKM) and 6-factor (OSKMNL) reprogramming of shDot1L cells was observed, although the colonies were larger in the latter conditions (FIG. 4E, FIG. 17C). FIG. 4E shows the fold-change in Tra-1-60+ iPSC colonies in 4-factor (OSKM) and 6-factor (OSKM+Nanog+Lin28) reprogramming of shCntrl and shDot1L fibroblasts relative to control 4-factor reprogramming of shCntrl cells. Plates were stained on Day 20 of reprogramming. Corresponding images of representative Tra-1-60 stained reprogramming wells are shown above (n=2; error bars, +s.e.m). FIG. 17C shows the average Tra-1-60 positive colony size in 4-factor (OSKM) and 6-factor (OSKM+Nanog+Lin28) reprogramming of shCntrl and shDot1L fibroblasts relative to control 4-factor reprogramming of shCntrl cells as shown in FIG. 4C. In control fibroblasts, Nanog and Lin28 expression did enhance 4-factor reprogramming by 2.4 fold, and thus significantly phenocopied Dot1L inhibition (FIG. 4E). Taken together, these data indicate that Dot1L inhibition requires the action of both Nanog and Lin28 to substitute for Klf4 and c-Myc and enhance reprogramming.

Example 6: Genome-Wide Analysis of H3K79me2 Marks During Reprogramming

Figure 5:
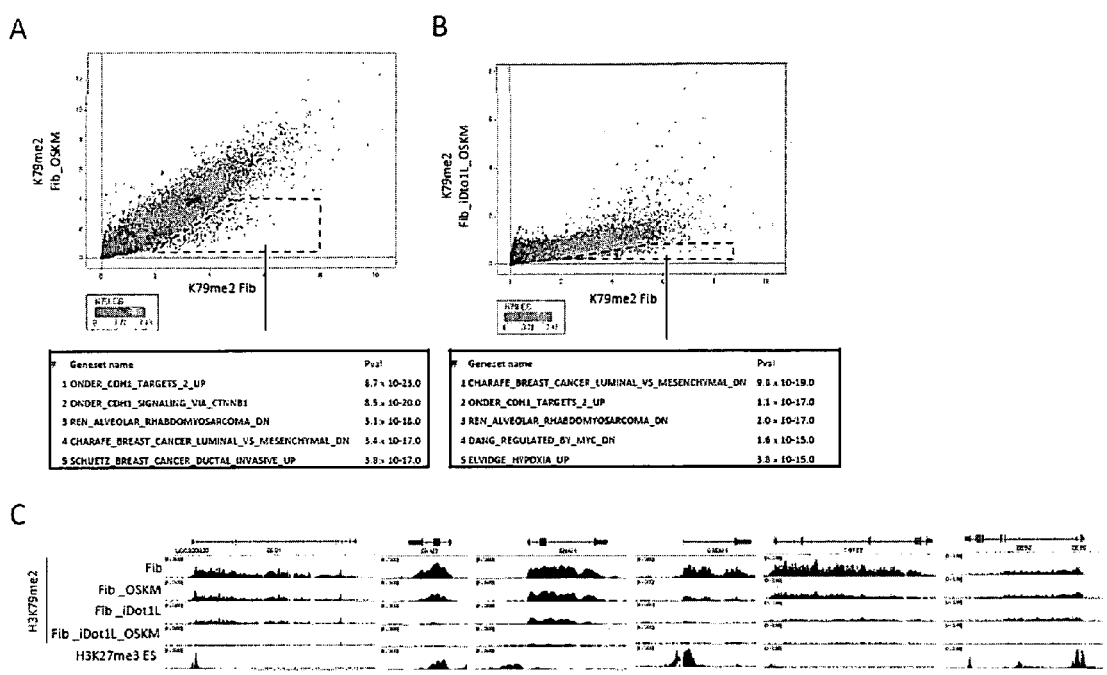
FIG. 5 shows a non-limiting example of H3K79me2 marks during reprogramming.
Figure 18:
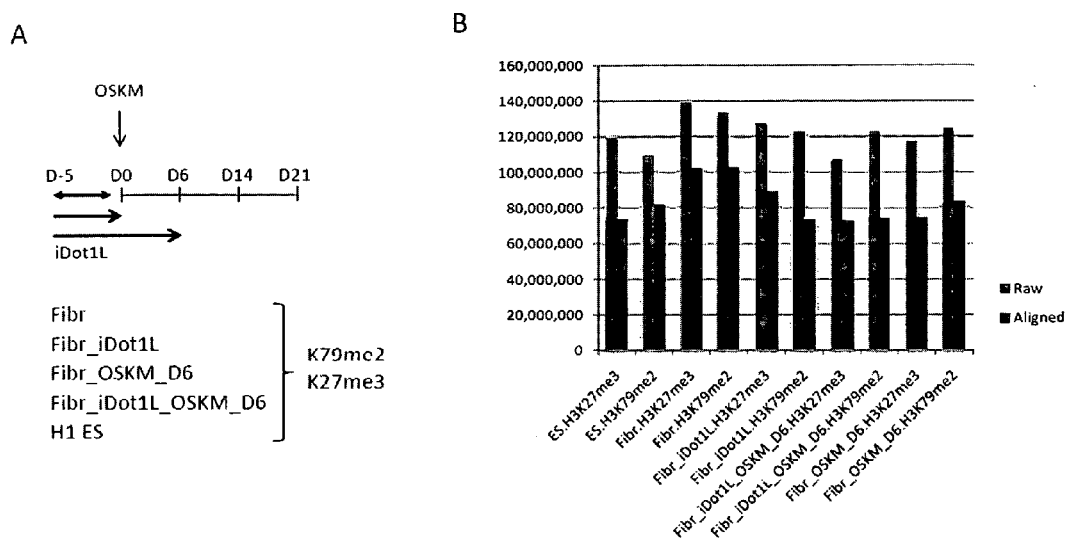
FIG. 18 illustrates a non-limiting example of Chip-seq experimental design.
Figure 19:
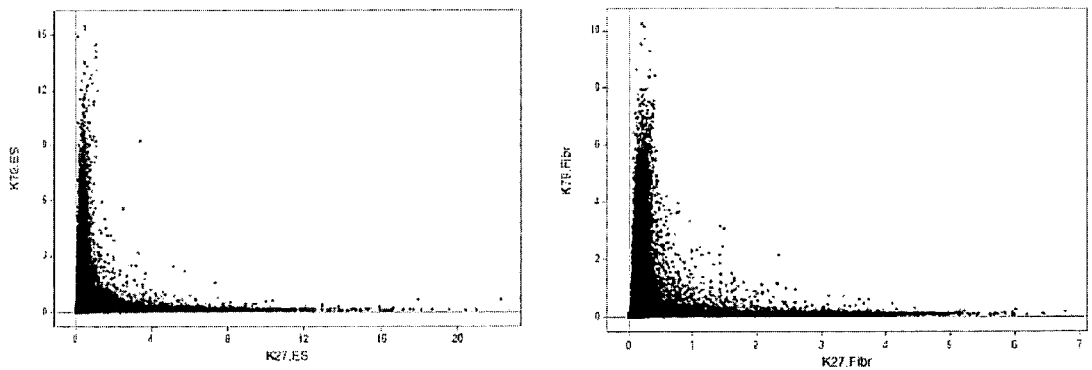
FIG. 19 shows a non-limiting example of the relationship between H3K79me2 and H3K27me3; and, FIG. 20 shows a non-limiting example of genes marked with K79me2 specifically in fibroblasts, in ESCs and in both cell types.
Figure 20:
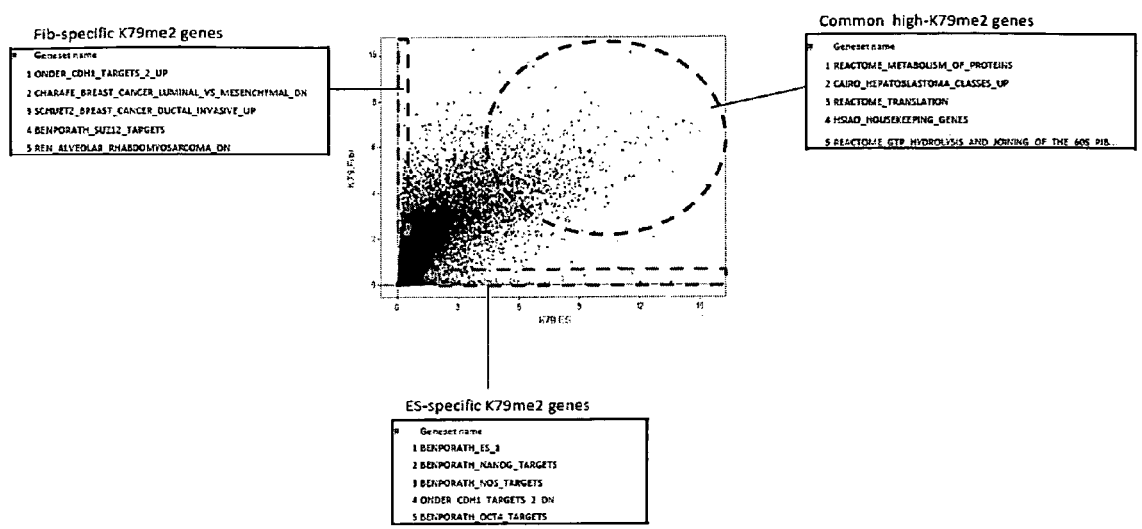

To gain insight into the genome-wide chromatin changes that are facilitated by Dot1L inhibition during reprogramming, ChIP-seq for H3K79me2 and H3K27me3 in human ES cells as well as fibroblasts undergoing reprogramming with or without the iDot1L treatment were performed (FIG. 18). FIG. 18 shows a Chip-seq experimental design. FIG. 18A shows dH1f fibroblasts that were pre-treated with iDot1L for 5 days at 10 uM (Day 0) and then infected with OSKM. 6 days later, cells were harvested for the ChIP (Day 6). FIG. 18B shows the number of raw and aligned reads from Illumina sequencing for each ChIP sample. In both ES cells and fibroblasts, the presence H3K27me3 and H3K79me2 was mutually exclusive (FIG. 19). FIG. 19 shows the relationship between H3K79me2 and H3K27me3. FIG. 19A shows a genome-wide representation of the relation between H3K79me2 and H3K27me3 in ES cells. FIG. 19B shows a genome-wide representation of the relation between H3K79me2 and H3K27me3 in Fibroblasts. Genes marked by H3K79me2 specifically in ES cells were pluripotency factors, their downstream targets and genes involved in epithelial cell adhesion such as CDH1 (165 genes, FIG. 20). In contrast, genes marked by H3K79me2 specifically in fibroblasts were significantly enriched in gene sets associated with epithelial to mesenchymal transitions (EMTs) (119 genes, FIG. 20). FIG. 20 shows genes marked with K79me2 specifically in fibroblasts, in ESCs and in both cell types. Genes that have 10-fold or more H3K79me2 in fibroblasts than in ES cells were designated as Fibroblasts-specific K79me2 marked genes (upper left dotted line). Genes that have 10-fold or more H3K79me2 in ES cells than in fibroblasts were designated as ES-specific K79me2 marked genes (lower right dotted line). Top 5 gene sets that overlap with these set of genes are indicated in the boxes. Interestingly, it was observed that 6 Days after OSKM expression, 143 genes had lost H3K79me2 2-fold or more (FIG. 5A). FIG. 5 shows genome-wide analysis of H3K79me2 marks during reprogramming. FIG. 5A shows genome-wide representation of H3K79me2 marked genes in fibroblasts and in fibroblasts 6 days into reprogramming. Each dot represents a gene and the shade indicates the H3K79me2 enrichment of that gene in ES cells. The dotted line indicates the set of genes that lose K79me2 2-fold or more upon OSKM transduction. The top 5 gene sets that overlap with these genes are indicated in the box below. Gene set overlap analysis indicated that these 143 genes were also highly significantly represented in gene sets associated with EMT phenotypes. Only a few of these genes had already decreased in expression at Day 6 (9 out of 143), but a majority of them would lose this mark in the pluripotent state (115 out of 143 devoid of H3K79me2 in ES cells). This finding lead to the question whether Dot1L inhibition promotes the removal of K79me2 from such fibroblast specific, EMT-associated genes. To explore this notion, ChIP-seq for K79me2 on OSKM expressing fibroblasts treated with iDot1L was performed. It was observed that upon inhibitor treatment, K79me2 levels were reduced on almost all genes with the exception of a subset that comprised mostly of housekeeping genes. This subset of genes also had high levels of K79me2 in ES cells indicating that these active loci turnover H3K79me2 slowly (FIG. 5B). FIG. 5B shows genome-wide representation of H3K79me2 marked genes in fibroblasts and in fibroblasts treated with iDot1L 6 days into reprogramming. Each dot represents a gene and the shade indicates the H3K79me2 enrichment of that gene in ES cells. Note that genes that have high K79me2 in ES cells retain this mark despite Dot1L inhibition. The dotted line indicates the set of genes that lose K79me2 10-fold or more in iDot1L-treated fibroblasts. The top 5 gene sets that overlap with these genes are indicated in the box below. Strikingly, the genes that lost proportionally the most K79me2 in inhibitor-treated fibroblasts during reprogramming compared to the initial fibroblasts were again highly significantly represented in gene sets associated with EMTs (FIG. 5B). In fact, master regulators of mesenchymal states such as Zeb1/2, Snai1/2, Grem1 and TGFB2, were among these genes (FIG. 5C)[19]. FIG. 5C shows H3K79me2 ChIP-sequencing tracks for select EMT-associated genes in fibroblasts and H3K27me3 in ES cells.

These observations support the notion that Dot1L inhibition collaborates with OSKM in facilitating the loss of K79me2 from fibroblast specific regulators.

Methods Summary shRNAs were designed using the RNAi Codex[26]. 97-mer oligonucleotides (Table 2) were PCR amplified and cloned into MSCV-PM[27] vector. Control shRNA targeting the firefly luciferase[27] and the Nanog shRNA were previously described[28]. Reprogramming assays were carried out with either retroviral[7] or lentiviral[29] reprogramming factors. dH1f cells were previously described[3]. IMR-90 and MRC5 human diploid fibroblasts were purchased from ATCC. Immunostaining of reprogramming plates were performed as described[8]. For gene expression analyses, total RNA was extracted from three independent culture plates for each condition and transcriptional profiling was performed using Affymetrix U133A microarrays. Primers used for quantitative real-time PCR can be found in Table 3. ChIP-seq was performed as described with slight modifications[25].

REFERENCES

1. Hemberger, M., Dean, W. & Reik, W. Epigenetic dynamics of stem cells and cell lineage commitment: digging Waddington's canal. *Nature reviews. Molecular cell biology* 10, 526-37(2009).
2. Takahashi, K. et al. Induction of pluripotent stem cells from adult human fibroblasts by defined factors. *Cell* 131, 861-72(2007).
3. Park, I.-H. et al. Reprogramming of human somatic cells to pluripotency with defined factors. *Nature* 451, 141-6 (2008).
4. Yu, J. et al. Induced pluripotent stem cell lines derived from human somatic cells. *Science* (New York, N.Y.) 318, 1917-20(2007).
5. Hawkins, R. D. et al. Distinct Epigenomic Landscapes of Pluripotent and Lineage-Committed Human Cells. *Cell Stem Cell* 6, 479-491(2010).
6. Mikkelsen, T. S. et al. Genome-wide maps of chromatin state in pluripotent and lineage-committed cells. *Nature* 448, 553-60(2007).
7. Park, I.-H. et al. Generation of human-induced pluripotent stem cells. *Nature protocols* 3, 1180-6(2008).
8. Chan, E. M. et al. Live cell imaging distinguishes bona fide human iPS cells from partially reprogrammed cells. *Nature biotechnology* 27, 1033-7(2009).
9. Pereira, C. F. et al. ESCs Require PRC2 to Direct the Successful Reprogramming of Differentiated Cells toward Pluripotency. *Cell Stem Cell* 6, 547-556(2010).
10. Cai, Y. et al. YY1 functions with INO80 to activate transcription. *Nature structural & molecular biology* 14, 872-4(2007).
11. Ko, C.-Y. et al. Epigenetic silencing of CCAAT/enhancer-binding protein delta activity by YY1/polycomb group/DNA methyltransferase complex. *The Journal of biological chemistry* 283, 30919-32(2008).
12. Schotta, G., Ebert, A. & Reuter, G. SU(VAR)3-9 is a conserved key function in heterochromatic gene silencing. *Genetica* 117, 149-58(2003).
13. Jones, B. et al. The histone H3K79 methyltransferase Dot1L is essential for mammalian development and heterochromatin structure. *PLoS genetics* 4, e1000190 (2008).
14. Okada, Y. et al. hDOT1L links histone methylation to leukemogenesis. *Cell* 121, 167-78(2005).
15. Daigle, S. R. et al. Selective Killing of Mixed Lineage Leukemia Cells by a Potent Small-Molecule DOT1L Inhibitor. *Cancer cell* 20, 53-65(2011).
16. Boyer, L. a et al. Core transcriptional regulatory circuitry in human embryonic stem cells. *Cell* 122, 947-56(2005).
17. Marson, A. et al. Connecting microRNA genes to the core transcriptional regulatory circuitry of embryonic stem cells. *Cell* 134, 521-33(2008).
18. Mikkelsen, T. S. et al. Dissecting direct reprogramming through integrative genomic analysis. *Nature* 454, 49-55 (2008).
19. Taube, J. H. et al. Core epithelial-to-mesenchymal transition interactome gene-expression signature is associated with claudin-low and metaplastic breast cancer subtypes. *Proceedings of the National Academy of Sciences of the United States of America* 107, 15449-54 (2010).
20. Samavarchi-Tehrani, P. et al. Functional Genomics Reveals a BMP-Driven Mesenchymal-to-Epithelial Transition in the Initiation of Somatic Cell Reprogramming. *Cell Stem Cell* 7, 64-77(2010).
21. Plath, K. & Lowry, W. E. Progress in understanding reprogramming to the induced pluripotent state. *Nature Reviews Genetics* 12, 253-265(2011).
22. Hanna, J. et al. Direct cell reprogramming is a stochastic process amenable to acceleration. *Nature* 462, 595-601 (2009).
23. Stadtfeld, M. et al. Defining molecular cornerstones during fibroblast to iPS cell reprogramming in mouse. *Cell stem cell* 2, 230-40(2008).
24. Li, R. et al. A Mesenchymal-to-Epithelial Transition Initiates and Is Required for the Nuclear Reprogramming of Mouse Fibroblasts. *Cell Stem Cell* 1-13(2010).doi: 10.1016/j.stem.2010.04.014
25. Bernt, K. M. et al. MLL-Rearranged Leukemia Is Dependent on Aberrant H3K79 Methylation by DOT1L. *Cancer cell* 20, 66-78(2011).
26. Olson, A. et al. RNAi Codex: a portal/database for short-hairpin RNA (shRNA) gene-silencing constructs. *Nucleic acids research* 34, D 153-7(2006).
27. Schlabach, M. R. et al. Cancer proliferation gene discovery through functional genomics. *Science* (New York, N.Y.) 319, 620-4(2008).
28. Zaehres, H. et al. High-efficiency RNA interference in human embryonic stem cells. *Stem cells* (Dayton, Ohio) 23, 299-305(2005).
29. Yu, J. et al. Human induced pluripotent stem cells free of vector and transgene sequences. *Science* (New York, N.Y.) 324, 797-801(2009).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method of producing induced pluripotent stem cells, the method comprising
   inhibiting Dot1L in a differentiated cell and culturing the differentiated cell under reprogramming conditions to produce induced pluripotent stem cells,
   wherein the reprogramming conditions comprise a reprogramming cocktail comprising a transcription factor, and
   wherein the reprogramming cocktail does not include Klf4 or c-Myc.

2. The method of claim 1, wherein Dot1L is inhibited when the cell is cultured with the reprogramming cocktail.

3. The method of claim 1, wherein the differentiated cell is a fibroblast.

4. The method of claim 1, wherein inhibiting Dot1L comprises inhibiting the methyltransferase activity of Dot1L.

5. The method of claim 1, wherein Dot1L is inhibited by contacting the differentiated cell with a composition comprising a compound of formula I, I, II, or IV.

6. The method of claim 1, wherein Dot1L is inhibited by contacting the differentiated cell with a composition comprising a compound of formula:

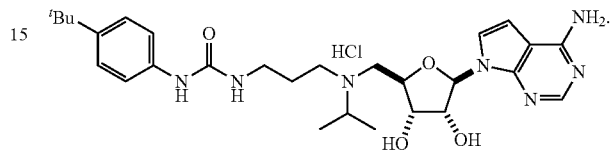

7. The method of claim 1, wherein Dot1L is inhibited by contacting the differentiated cell with an shRNA that knocks down Dot1L expression.

8. The method of claim 1, wherein the reprogramming cocktail comprises Oct4 and Sox2.

9. The method of claim 1, wherein the reprogramming cocktail consists essentially of Oct4 and Sox2.

10. A method of producing induced pluripotent stem cells, the method comprising
    inhibiting SUV39H1 in a differentiated cell and culturing the differentiated cell under reprogramming conditions to produce induced pluripotent stem cells,
    wherein the reprogramming conditions comprise a reprogramming cocktail that does not include Klf4 or c-Myc.

* * * * *

UNITED STATES PATENT AND TRADEMARK OFFICE
CERTIFICATE OF CORRECTION

PATENT NO. : 9,670,463 B2
APPLICATION NO. : 14/351717
DATED : June 6, 2017
INVENTOR(S) : Tamer T. Onder et al.

Page 1 of 1

It is certified that error appears in the above-identified patent and that said Letters Patent is hereby corrected as shown below:

In the Claims

At Column 247, Claim 5, Line 33 "prising a compound of formula I, I, II, or IV" should be --prising a compound of formula I, II, III, or IV--.

Signed and Sealed this
Sixth Day of November, 2018

Andrei Iancu
*Director of the United States Patent and Trademark Office*